US009549973B2

(12) United States Patent
Paterson et al.

(10) Patent No.: US 9,549,973 B2
(45) Date of Patent: Jan. 24, 2017

(54) COMPOSITIONS AND METHODS COMPRISING KLK3 OR FOLH1 ANTIGEN

(71) Applicants: The Trustees of the University of Pennsylvania, Philadelphia, PA (US); Advaxis, Inc., Princeton, NJ (US)

(72) Inventors: Yvonne Paterson, Philadelphia, PA (US); John Rothman, Lebanon, PA (US); Vafa Shahabi, Valley Forge, PA (US)

(73) Assignees: THE TRUSTEES OF THE UNIVERSITY OF PENNSYLVANIA, Philadelphia, PA (US); ADVAXIS, INC., Princeton, NJ (US)

( * ) Notice: Subject to any disclaimer, the term of this patent is extended or adjusted under 35 U.S.C. 154(b) by 92 days.

(21) Appl. No.: 14/581,217

(22) Filed: Dec. 23, 2014

(65) Prior Publication Data

US 2015/0335721 A1 Nov. 26, 2015

Related U.S. Application Data

(60) Division of application No. 11/798,177, filed on May 10, 2007, now Pat. No. 9,012,141, which is a continuation-in-part of application No. 11/727,889, filed on Mar. 28, 2007, now abandoned, which is a continuation-in-part of application No. 11/223,945, filed on Sep. 13, 2005, now Pat. No. 7,820,180, which is a continuation-in-part of application No. 10/949,667, filed on Sep. 24, 2004, now Pat. No. 7,794,729, which is a continuation-in-part of application No. 10/441,851, filed on May 20, 2003, now Pat. No. 7,135,188, which is a continuation of application No. 09/535,212, filed on Mar. 27, 2000, now Pat. No. 6,565,852.

(51) Int. Cl.

| | |
|---|---|
| ***C07K 1/00*** | (2006.01) |
| ***A61K 39/00*** | (2006.01) |
| ***A61K 39/02*** | (2006.01) |
| ***C12N 9/64*** | (2006.01) |
| ***C07K 14/195*** | (2006.01) |

(52) U.S. Cl.

CPC ........... *A61K 39/02* (2013.01); *A61K 39/0011* (2013.01); *C07K 14/195* (2013.01); *C12N 9/6445* (2013.01); *A61K 2039/523* (2013.01); *A61K 2039/53* (2013.01); *C07K 2319/00* (2013.01); *C07K 2319/40* (2013.01); *C12Y 304/21077* (2013.01)

(58) Field of Classification Search

None

See application file for complete search history.

(56) References Cited

U.S. PATENT DOCUMENTS 4,458,066 A 7/1984 Caruthers et al.
4,521,382 A 6/1985 Kessick
4,777,239 A 10/1988 Schoolnik
5,262,177 A 11/1993 Brown et al.
5,342,774 A 8/1994 Boon et al.
5,643,599 A 7/1997 Lee et al.
5,681,570 A 10/1997 Yang et al.
5,824,538 A 10/1998 Branstrom et al.
5,830,702 A 11/1998 Portnoy et al.
5,858,682 A 1/1999 Gruenwald et al.
5,877,159 A 3/1999 Powell et al.
5,922,583 A 7/1999 Morsey et al.
6,004,815 A 12/1999 Portnoy et al.
6,015,567 A 1/2000 Hudziak et al.
6,017,705 A 1/2000 Lurquin et al.
6,051,237 A 4/2000 Paterson
6,099,848 A 8/2000 Frankel et al.
6,287,556 B1 9/2001 Portnoy et al.
6,306,404 B1 10/2001 LaPosta et al.
6,479,258 B1 11/2002 Short
6,521,449 B1 2/2003 Polack et al.
6,565,852 B1 5/2003 Paterson
6,599,502 B2 7/2003 Portnoy et al.
6,740,516 B2 5/2004 Savitzky et al.
6,767,542 B2 7/2004 Paterson et al.
7,135,188 B2 11/2006 Paterson
7,375,091 B2 5/2008 Cheever et al.
7,425,449 B2 9/2008 Portnoy et al.
7,488,487 B2 2/2009 Frankel et al.
7,588,930 B2 9/2009 Paterson et al.
7,691,393 B2 4/2010 Dubensky, Jr. et al.
7,794,728 B2 9/2010 Portnoy et al.

(Continued)

FOREIGN PATENT DOCUMENTS

EP 0902086 3/1999
WO WO 90/12594 11/1990

(Continued)

OTHER PUBLICATIONS

Abachin et al. "Formation of D-alanyl-lipoteichoic acid is required for adhesion and virulence of Listeria monocytogenes" Molecular Microbiology 43(1), 1-14, (2002).

Adams et al., 1992, "Cre-lox recombination in *Escherichia coli* cells Mechanistic differences from the in vitro reaction", J. Mol. Biol. 226:661-673.

Ahmadzadeh et al. Tumor Antigen-Specific CD8 T Cells Infiltrating the Tumor Express High Levels of PD-1 and Are Functionally Impaired. Blood (2009) 114: 1537-1544.

Ahmed, Nabil et al., "Immunotherapy for Osteosarcoma: Genetic Modification of T cells Overcomes Low Levels of Tumor Antigen Expression", Molecular Therapy, vol. 17, No. 10, Jun. 16, 2009 (Jun. 16, 2009), pp. 1779-1787.

Alexander et al. "Characterization of an Aromatic Amino Acid-Dependent Listeria monocytogenes Mutant: Attenuation, Persistence, and Ability to Induce Protective Immunity in Mice", Infection and Immunity, vol. 61, No. 5, p. 2245-2248. May 1993.

(Continued)

*Primary Examiner* — Sean Aeder

(74) *Attorney, Agent, or Firm* — Mark Cohen; Pearl Cohen; Zedek Latzer Baratz LLP

(57) ABSTRACT

The present invention provides KLK3 peptides, FOLH1 peptides, recombinant polypeptides comprising same, recombinant nucleotide molecules encoding same, recombinant *Listeria* strains comprising same, and immunogenic and therapeutic methods utilizing same.

31 Claims, 13 Drawing Sheets

(56) References Cited

U.S. PATENT DOCUMENTS

| | | | |
|---|---|---|---|
| 7,794,729 B2 | 9/2010 | Paterson et al. | |
| 7,820,180 B2 | 10/2010 | Paterson et al. | |
| 7,842,289 B2 | 11/2010 | Dubensky et al. | |
| 7,855,064 B2 | 12/2010 | Paterson et al. | |
| 7,858,097 B2 | 12/2010 | Paterson et al. | |
| 7,871,604 B1 | 1/2011 | Curtiss, III et al. | |
| 7,887,822 B2 | 2/2011 | Ferrone et al. | |
| 7,935,804 B2 | 5/2011 | Dubensky, Jr. et al. | |
| 9,012,141 B2 * | 4/2015 | Paterson ............ | A61K 39/0011 435/6.1 |
| 9,017,660 B2 | 4/2015 | Shahabi et al. | |
| 2002/0025323 A1 | 2/2002 | Paterson et al. | |
| 2002/0136737 A1 | 9/2002 | Frankel | |
| 2003/0028206 A1 | 2/2003 | Shiser | |
| 2003/0202985 A1 | 10/2003 | Paterson | |
| 2003/0219802 A1 | 11/2003 | Dhaini | |
| 2003/0220239 A1 | 11/2003 | Simard et al. | |
| 2004/0013690 A1 | 1/2004 | Portnoy et al. | |
| 2004/0058342 A1 | 3/2004 | Yousef | |
| 2004/0228877 A1 | 11/2004 | Dubensky et al. | |
| 2005/0048081 A1 | 3/2005 | Frankel et al. | |
| 2005/0118184 A1 | 6/2005 | Paterson et al. | |
| 2005/0129715 A1 | 6/2005 | Paterson et al. | |
| 2005/0281783 A1 | 12/2005 | Kinch et al. | |
| 2006/0051380 A1 | 3/2006 | Schulick et al. | |
| 2006/0093582 A1 | 5/2006 | Paterson et al. | |
| 2006/0104991 A1 | 5/2006 | Paterson et al. | |
| 2006/0121053 A1 | 6/2006 | Sweeney et al. | |
| 2006/0205067 A1 | 9/2006 | Paterson et al. | |
| 2006/0210540 A1 | 9/2006 | Paterson et al. | |
| 2006/0233835 A1 | 10/2006 | Paterson et al. | |
| 2007/0207170 A1 | 9/2007 | Dubensky et al. | |
| 2007/0207171 A1 | 9/2007 | Dubensky et al. | |
| 2007/0253976 A1 | 11/2007 | Paterson et al. | |
| 2007/0264279 A1 | 11/2007 | Patterson et al. | |
| 2008/0124354 A1 | 5/2008 | Paterson et al. | |
| 2008/0131456 A1 | 6/2008 | Paterson et al. | |
| 2008/0213295 A1 | 9/2008 | Cheever et al. | |
| 2009/0202587 A1 | 8/2009 | Paterson et al. | |
| 2010/0189739 A1 | 7/2010 | Frankel et al. | |
| 2011/0129499 A1 | 6/2011 | Maciag et al. | |
| 2011/0142791 A1 | 6/2011 | Shahabi | |
| 2011/0223187 A1 | 9/2011 | Shahabi et al. | |
| 2012/0014984 A1 | 1/2012 | Shahabi | |
| 2012/0135033 A1 | 5/2012 | Wallecha | |
| 2014/0314708 A1 | 10/2014 | Maciag et al. | |

FOREIGN PATENT DOCUMENTS

| | | |
|---|---|---|
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 98/48026 | 10/1998 |
| WO | WO 99/06544 | 2/1999 |
| WO | WO 99/07861 | 2/1999 |
| WO | WO 99/10496 | 3/1999 |
| WO | WO 99/25376 | 5/1999 |
| WO | WO 01/27295 | 3/2001 |
| WO | WO 01/72329 | 10/2001 |
| WO | WO 03/045318 | 6/2003 |
| WO | WO 03/092600 | 11/2003 |
| WO | WO 03/102168 | 12/2003 |
| WO | WO 2004/006837 | 1/2004 |
| WO | WO 2005/037233 | 4/2005 |
| WO | WO 2005/071088 | 8/2005 |
| WO | WO 2006/017856 | 2/2006 |
| WO | WO 2006/036550 | 4/2006 |
| WO | WO 2007/061848 | 5/2007 |
| WO | WO 2007/103225 | 9/2007 |
| WO | WO 2007/137258 | 11/2007 |
| WO | WO 2008/045148 | 4/2008 |
| WO | WO 2008/130551 | 10/2008 |
| WO | WO 2008/140812 | 11/2008 |
| WO | WO 2009/110950 | 9/2009 |
| WO | WO 2009/143167 | 11/2009 |
| WO | WO 2010/011870 | 1/2010 |
| WO | WO 2011/060260 A2 | 5/2011 |
| WO | WO 2011/100754 A1 | 8/2011 |
| WO | WO 2012/125551 | 9/2012 |

OTHER PUBLICATIONS

Al-Lazikani et al. JMB Standard Conformations for the Canonical Structures of Immunoglobulins., J. Mol. Biol. 273:927-948 (1997).

Allision et al., 1997, "Cloning and characterization of a Prevotella melaninogenica hemolysin", Infect. Immun. 65(7):2765-71.

Altschul "Amino Acid Substitution Matrices from an Information Theoretic Perspective", J. Mol. Biol. 219:555-565 (1991).

Altschul et al. Basic Local Alignment Search Tool Basic Local Alignment Search Tool; J. Mol. Biol. 215:403-410 (1990).

Altschul et al. "Gapped BLAST and PSI-BLAST: A New Generation of Protein Database Search Programs" (1997) Nucleic Acids Res. 25:3389-3402.

Altschul et al. A Protein Alignment Scoring System Sensitive at all Evolutionary Distances; J. Mol. Evol. 36:290-300 (1993).

Amersham. Introduction to Glutathione S-transferase (GST) Gene Fusion System , Pharmacia Biotech; BioDirectory, Piscataway, N.J., ( pp. 384-391) (2001).

An et al., 1996, "A recombinant minigene vaccine containing a nonameric cytotoxic-T-Lymphocyte epitope confers limited protection against Listeria monocytogenes infection", Infect. Immun., vol. 64, No. 5, p. 1685-1693.

Anderson, 1998, "Human gene therapy", Nature, Apr. 30; 392 (6679 Suppl):25-30.

Angelakopoulos et al., 2002, "Safety and shedding of an attenuated strain of Listeria monocytogenes with a deletion of actA/plcB in adult volunteers: a dose escalation study of oral inoculation" Infect Immun. 70(7):3592-601.

Anthony "Precursor Lesions for Liver Cancer in Humans" Cancer Res. (1976) 36:2579-2583.

Attwood et al., "The Babel of Bioinformatics", Science, vol. 290, No. 5491: 471-473, 2000.

Auerbuch, et al. "Development of a Competitive Index Assay to Evaluate the Virulence of Listeria Monocytogenes Acta Mutants During Primary and Secondary Infection of Mice" (2001) Infect. Immunity 69:5953-5957.

Awwad, 1989, "Cyclophosphamide-induced immunologically mediated regression of a cyclophosphamide-resistant murine tumor: a consequence of eliminating precursor L3T4+ suppresor T-cells", Cancer Res., 49(7):1649-1654.

Baca et al. "Protein Chemistry and Structure: Antibody Humanization Using Monovalent Phage Display", (1997) J. Biol. Chem. 272:10678-10684.

Baert et al. "Influence of Immunogenicity on the Long-Term Efficacy of Infliximab in Crohn's Disease" (2003) New Engl. J. Med. 348:601-608.

Baloglu et al. "Immune Responses of Mice to Vaccinia Virus Recombinants Expressing Either Listeria Monocytogenes Partial Listeriolysin or *Brucella abortus* Ribosomal L7/L12 Protein", Vet Microbiol 2005, 109(1-2): 11-7.

Barbas Synthetic Human Antibodies ; Nature Medicine, 1:837-839 (1995).

Bargmann et al. "The neu oncogene encodes an epidermal growth factor receptor-related protein" Nature 319, 226-230, Jan. 16, 1986.

Barry et al (1992) "Pathogenicity and immunogenicity of Listeria monocytogenes smallplaque mutants defective for intracellular growth and cell-ta-cell spread. Infection and mutants defective for intracellular growth and cell-ta-cell spread."Infection and Immunity 60 (4): 1625-32.

Bast. et al (1975) "Antitumor activity of bacterial infection. II. effect of Listeria. monocytogenes on growth of a guinea pig hepatoma." J Natl. Cancer Inst., 54(3): 757-761.

Bear, 1986, "Tumor-specific suppressor T-cells which inhibit the in vitro generation of cytolytic T-cells from immune and early tumor-bearing host spleens", Cancer Res., Apr.; 46(4 Pt 1):1805-12.

(56) References Cited

OTHER PUBLICATIONS

Beatly, Dissertation Abstracts Interntational, 2000, 61/10B: 5224 Abstract Only.
Beattie et al. "Cloning and charcterization of T-cell-reactive protein antogens from Listeria monocytogenes", infect. Immune. Sep. 1990, 58(9):2792-803.
Beattie IA, Swaminathan B, Ziegler HK, Cloning and charcterization of T-cell-reactive protein antogens from Listeria monocytogenes, infect. Immune. Sep. 1990, 58(9):2792-803.
Beatty et al. "IFN-gamma-dependent inhibition of tumor angiogenesis by tumor-infiltrating CD4+ T cells requires tumor responsiveness to IFN-gamma", J Immunol. Feb. 15, 2001;166(4): 2276-82.
Beaucage et al., "Deoxynucelotide phosphoramidites—a new class of key intermediates for deoxypolynucleotide synthesis", 1981, Tetra. Lett., 22:1859-1862.
Becker at al., The changes in the T helper 1 (Th1) and T helper 2 (Th2) cytokine balance 3,4during HIV-1 infection are indicative of an allergic response to viral proteins that may be reversed by Th2 cytokine inhibitors and immune response modifiers—a review and hypothesis; Viruses Genes 28:5-18 (2004).
Beniaminovitz et al. "Prevention of Rejection in Cardiac Transplantation by Blockade of the Interleukin-2 Receptor With a Monoclonal Antibody " (2000) New Engl. J. Med. 342:613-619.
Benvegnu, et al. Space Occupying lesions of the liver detected by ultrasonography and their relation to hypatocellular Carcinoma in Cirrhosis; Liver 12:80-83 (1992).
Bernhard et al., 2002, "Vaccination against the HER-2/neu oncogenic protein", Endocrine-Related Cancer, 9:33-44.
Bielecki et al., "Bacillus subtilis expressing a haemolysin gene from Lesteria monocytogenes can grow in mammalian cells", Nature 1990, 354:175-176.
Billaut-Mulot, O. et al. Interleukin-18 modulates immune responses induced by HIV-1 Nef DNA prime/protein boost vaccine; Vaccine 19:95-102 (2000).
Billington et al., 1997, "The Arcanobacterium (Actinomyces) pyogenes hemolysin, pyolysin, is a novel member of the thiol-activated cytolysin family", J. Bacteriol. Oct; 179(19):6100-6.
Bird et al. "An autologous dendritic cell canine mammary tumor hybrid-cell fusion vaccine", Cancer Immunol Immunother. Jan. 2011;60(1):87-97.
Bishop et al. "Adoptive Transfer of Immunity to Listeria Monocytogenes the Influence of in Vitro Stimulation on Lymphocyte Subset Requirements", J. Immunol. 139: 2005-2009 (1987).
Bodmer et al., 1988, "Enhanced recognition of a modified peptide antigen by cytotoxic T cells specific for influenza nucleoprotein", Cell 52:253-258.
Boon et al., 2006, "Human T-cell responses against melanoma" Annu. Rev. Immunol. 24:175-208.
Bourquin et al., 2000, "Myelin oligodendrocyte glycoprotein-DNA vaccination induces antibody-mediated autoaggression in experimental autoimmune encephalomyelitis"Eur. J. Immunol. 30:3663-3671.
Bouwer HG, Barry RA, Hinrichs DJ, Acquired immunity to an intracellular pathogen: immunologic recognition of L. monocytogenes-infected cells, Immunol. Rev. Aug. 1997; 158:137-46.
Bouwer HG, Hinrichs DJ, Cytotoxic-T-lymphocyte responses to epitopes of listeriolysin O and p60 following infection with Listeria monocytogenes, Infect. Immune. Jul. 1996; 64(7):2515-22.
Boyer et al., 2005, "DNA prime Listeria boost induces a cellular immune response to SIV antigens in the rhesus macaque model that is capable of limited suppression of SIV239 viral replication", Virology, Mar. 1; 333(1):88-101.
Brantl et al. "Molecular Analysis of the Replication Region of the Conjugative *Streptococcus agalactiae* Plasmid PIP501 in Bacillus Subtilis. Comparison With Plasmids PAM Beta 1 and PSM19035", Nucleic Acid Res 18: 4783-4790, 1990.
Brasseur, et al (1992) "Human gene MAGE-1, which codes for a tumor-rejection antigen, is expressed by some breast tumors."Int. J Cancer 52(5):839-841.
Braun et al. "INLB: An Invasion Protein of Listeria Monocytogenes With a Novel Type of Surface Association", Mol Microbiol. Jul. 1997;25(2):285-94.
Brett et al. "Comparison of Antigen Presentation of Influenza A Nucleoprotein Expressed in Attenuated Aroa-*Salmonella Typhimurium* With That of Live Virus", J Immunol. Apr. 1, 1993;150(7):2869-84.
Brockstedt et al., 2004, "Listeria-based cancer vaccines that segregate immunogenicity from toxicity", Proc. Natl. Acad. Sci. USA 101(38):13832-7.
Bron et al., 2004, "Identification of Lactobacillus plantarum genes that are induced in the gastrointestinal tract of mice", J. Bacteriol. Sep.; 186(17):5721-9.
Brown et al., "Chemical synthesis and cloning of a tyrosine tRNA gene" 1979, Meth. Enzymol. 68:109-151.
Brown et al., 1988, "Site-specific integration in Saccharopolyspora erthraea and multisite integration in Streptomyces lividans of actinomycete plasmid pSE101", J. Bacteriology 170:2287-2295.
Bruder D, Darji A, Gakamsky DM, Chakraborty T, Pecht I, Wehland J, Wehland J, Weiss S, Efficient induction of cytotoxic CD8+ T cells against exogenous proteins: establishment and characterization of a T cell line specific for the membrane protein ActA of Listeria monocytogenes, Eur. J. Immunol. Sep. 1998; 28(9):2630-9.
Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.
Brundage et al., 1993, "Expression and phosphorylation of the Listeria monocytogenes ActA protein in mammalian cells", Proc. Natl. Acad. Sci. USA 90:11890-11894.
Bubert et al., 1997, "The Listeria monocytogenes iap gene as an indicator gene for the study of PrfA-dependent regulation", Mol. Gen. Genet. Sep.; 256(1):54-62.
Burnham, Drug Discovery Today, Jan. 2003, 8/2:54-55.
Calendar et al., Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.
Camilli et al. "Insertional Mutagenesis of Listeria Monocytogenes With a Novel TN917 Derivative That Allows Direct Cloning of DNA Flanking Transposon Insertions", J Bacteriol, Jul. 1990;172(7):3738-44.
Camilli et al. "Listeria Monocytogenes Mutants Lacking Phosphatidylinositol-Specific Phospholipase C Area Virulent" J Exp Med 173:751-754, (1991).
Camilli et al., 1993, "Daul roles of plcA in Listeria monocytogenes pathogenesis", Mol. Microbiol. 8:143-157.
Carbone, 1989, "Induction of ovalbumin-specific cytotoxic T cells by in vivo peptide immunization" J. Exp. Med. 169:603-612.
Carbone, 1990, "Class I-restricted processing and presentation of exogenous cell-associated antigen in vivo" J. Exp. Med. 171:377-387.
Carpenter et al. Non-Fc Receptor-Binding Humanized Anti-CD3 Antibodies Induce Apoptosis of Activated Human T Cells; J. Immunol. 165:6205-6213 (2000).
Catic A, Dietrich G, Gentschev I, Goebel W, Kaufmann SH, Hess J., Introduction of protein or DNA delivered via recombinant *Salmonella typhimurium* into the major histocompatibility complex class I presentation pathway of macrophages, Microbes Infect., Feb. 1999, 1(2):113-21.
Cenatiempo, "Prokaryotic gene expression in vitro: transcription-translation coupled systems." 1986, Biochimie 68:505-516.
Chamberlain, et al (2000) "I nnovations and strategies for the development of anticancer vaccines."Expert Opinion on Pharmacotherapy. 1(4): 603-614.
Chen et al. "Episomal Expression of Truncated Listeriolysin O in LmddA-LLO-E7 Vaccine Enhances Antitumor Efficacy by Preferentially Inducing Expansions of CD4FoxP3_ andCD8 T Cells", Cancer Immunol Res; 2(9) Sep. 2014, pp. 911-922.

(56) References Cited

OTHER PUBLICATIONS

Chen et al., "PD-L1 Expression Is Characteristic of a Subset of Aggressive B-Cell Lymphomas and Virus-Associated Malignancies" Clin Cancer Res 19: 3462-3473 (2013).
Chothia et al. Canonical Structures for the Hypervariable Regions of Immunoglobulins; J Mol. Biol. 196:901-917 (1987).
Chothia et al. Confirmations of immunoglobulin hypervariable Regions; Nature 342:878-883 (1989).
Ciesielski et al. "Therapeutic Effect of a T Helper Cell Supported CTL Response Induced by a Survivin Peptide Vaccine against Murine Cerebral Glioma"; Cancer Immunol Immunother; 57(12): 1827-1835 (2008).
Clackson et al. Making Antibody Fragments Using Phage Display Libraries; Nature 352: 624-628 (1991).
Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.
Clifton et al., "Overcoming Cancer Immune Tolerance and Escape", Clinical Cancer Research: An Official Journal of the American Association for Cancer Research 2009, vol. 15, No. 3, pp. 749-751.
Collins et al. "Directional cloning of DNA fragments at a large distance from an initial probe: a circularization method", Proc Natl Acad Sci U S A. Nov. 1984;81(21):6812-6.
Courvalin et al., 1995, "Gene transfer from bacteria to mammalian cells", C R Acad Sci III, Dec; 318(12):1207-12.
Coussens, et al (1985)"Tyrosine Kinase Receptor with Extensive Homology to EGF Receptor Shares Chromosomal Location with neu Oncogene." Science. vol. 230, 1132-1139.
Coynault et al. "Virulence and vaccine potential of *Salmonella typhimurium* mutants deficient in the expression of the RpoS (sigma S) regulon", Mol Microbiol. Oct. 1996;22(1):149-60.
Cunto-Amesty et al., 2003, "Strategies in cancer vaccines development", Int. J. Parasitol. 33(5-6):597-613.
Da'Dara et al. Elimination of helminth infection restores HIV-1C vaccine-specific T cell responses independent of helminth-induced IL-10; Vaccine; 3;28(5):1310-7 (2010).
Dakappagari et al., 2000, "Prevention of mammary tumors with a chimeric HER-2 B-cell epitope peptide vaccine", Cancer Res. Jul. 15; 60(14):3782-9.
Darji A, Bruder D, Zur Lage S, Gerstel B, Chakraborty T, Wehland J, Weiss S, The role of the bacterial membrane protein ActA in immunity and protection against Listeria monocytogenes, J. Immunol. Sep. 1, 1998, 161(5):2414-20.
Darji A, Stockinger B, Wehland J, Chakraborty T, Weiss S, Antigen-specific T cell receptor antagonism by antigen-presenting cells treated with the hemolysin of Listeria monocytogenes: a noval type of immune escape, Eur. J. Immunol. Jul. 1997; 27(7):1696-703.
Darji A, Stockinger B, Wehland J, Chakraborty T, Weiss S, T-cell anergy induced by antigen presenting cells treated with the hemolysin of Listeria monocytogenes, Immunol. Lett. Jun. 1, 1997, 57(1-3):33-7.
Darji et al., 1995, "Hyperexpression of listeriolysin in the nonpathogenic species *Listeria innocua* and high yield purification", J. Biotechnol. Dec. 15; 43(3):205-12.
Darji et al., 1995, "Listeriolysin generates a route for the presentation of exogenous antigens by major histocompatibility complex class I", Eur. J. Immunol. Oct.; 25(10):2967-71.
Darji et al., 1997, "Oral somatic transgene vaccination using attenuated *S. typhimurium*" Cell 91:765-775.
Darji et al., 1997, "TAP-dependent major histocompatibility complex class I presentation of soluble proteins using listeriolysin", Eur. J. Immunol. Jun; 27(6):1353-9.
Darji et al., 2003, "Induction of immune responses by attenuated isogenic mutant strains of Listeria monocytoge" Vaccine 1; 21 Suppl. 2:S102-9.
De Boer et al., "A division inhibitor and a topological specificity factor coded for by the minicell locus determine proper placement of the division septum in *E. coli*." 1989, Cell 56:641-649.
De Bruin et al. Selection of high-affinity phage antibodies from phage display libraries; Nature Biotechnol. 17:397-399 (1999).
De Las Mulas et al. "Oncogene HER-2 in canine mammary gland carcinomas." Breast cancer research and treatment 80.3 (2003): 363-367.
De Maria, Raffaella, et al. "Spontaneous feline mammary carcinoma is a model of HER2 overexpressing poor prognosis human breast cancer." Cancer research 65.3 D (2005): 907-912.
Decatur A.L. et al., "A PEST-Like Sequence in Listeriolysin O Essential for Listeria monocytogenes Pathogenicity", Science 2000, 290:992-995.
Dembo, A et al. Limit Distribution of Maximal Non-Aligned Two-Sequence Segmental Score Ann. Prob. 22:2022-2039; (1994).
Dermime et al., 2004, "Vaccine and antibody-directed T cell tumour immunotherapy" Biochim Biophys Acta. 1704(1):11-35.
Deshpande et al., 1997, "Isolation of a contact-dependent haemolysin from *Mycobacterium tuberculosis*", J. Med. Microbiol. Mar.; 46(3):233-8.
Dietrich et al., 1998, "Delivery of antigen-encoding plasmid DNA into the cytosol of macrophages by attenuated suicide Listeria monocytogenes" Nature Biotechnology 15:181-185.
Dietrich et al., 2001, "From evil to good: a cytolysin in vaccine development", Trends Microbiol. Jan.; 9(1):23-8.
Disis "Generation of immunity to the HER-2/neu oncogenic protein in patients with breast and ovarian cancer using a peptide-based vaccine", Clin Cancer Res. 5(6):1289-97, Jun. 1999.
Disis, et al (1996) Peptide-Based, but Not Whole Protein, Vaccines Elicit Immunity to HER-2/neu, an Oncogenic Self Protein. The Journal of Immunology, vol. 156,3151-3158.
Doling AM, Ballard JD, Shen H, Krishna KM, Ahmed R, Collier RJ, Starnbach MN, Cytotoxic T-lymphocyte epitopes fused to anthrax toxin induce protective antiviral immunity, Infect. Immun. Jul. 1999; 67(7):3290-6.
Dons et al. "Cloning and characterization of a gene encoding flagellin of Listeria monocytogenes", Mol Microbiol. Oct. 1992;6(20):2919-29.
Dramsi et al., 1995, "Entry of Listeria monocytogenes into hepatocytes requires expression of inIB, a surface protein of the internalin multigene family", Mol. Microbiol. 16(2):251-61.
Dunn et al., 1991, "Selective radiation resistance of immunologically induced T cells as the basis for irradiation-induced T-cell-mediated regression of immunogenic tumor", J. Leukoc Biol. 49(4):388-396.
Dustoor, "Antitumor activity of listeria monocytogenes on a guinea pig fibrosarcoma", Infection and Immunity, 1979, vol. 23, No. 1, pp. 54-60.
Ebbeson et al. "Rhabdomyolysis, acute renal failure, and compartment syndrome in a child with parainfluenza type 1 infection", The Pediatric Infectious Disease Journal vol. 28, No. 9, Sep. 2009.
Ebert et al., 1990, "Selective immunosuppressive action of a factor produced by colon cancer cells", Cancer Res. 50(19):6158-6161.
Edman et al. A Protein Sequenator; Eur. J. Biochem . 80: 116-132, (1967).
Eisenhauer et al. New response evaluation criteria in solid tumours: Revised RECIST guideline (version 1.1), Eur. J Cancer 45:228-247 (2009).
Emond et al. "A ribosomal DNA fragment of Listeria monocytogenes and its use as a genus-specific probe in an aqueous-phase hybridization assay", Appl Environ Microbiol. Aug. 1993;59(8):2690-7.
Ercolini et al., "Identification and characterization of the immunodominant rat HER-2/neu MHC class I epitope presented by spontaneous mammary tumors from Her-2/neu transgenic mice", Journal of Immunology, 2003, vol. 170, No. 8, pp. 4273-4280.
European Search Report for European Application No. 14190388.0 dated Mar. 2, 2015.
European Search Report for European Application No. 14195065.9 dated Mar. 12, 2015.
European Search Report for European Application No. 15182979.3 dated Oct. 26, 2015.
Everts et al. Selective Intracellular Delivery of Dexamethasone into Activated Endothelial Cells Using an E-Selectin-Directed Immunoconjugate; J. Immunol. 168:883-889 (2002).

(56) References Cited

OTHER PUBLICATIONS

Ezzel, 1995, "Cancer Vaccines: An Idea Whose Time Has Come?" J. NIH Res., 7:46-49.
Falk et al., 1991, "Identification of naturally processed viral nonapeptides allows their quantification in infected cells and suggests an allele-specific T cell epitope forecast" J. Exp. Med. 174(2):425-434.
Ferrari et al. "Isolation of an Alanine Racemase Gene from Bacillus subtilis and its Use for Plasmid Maintenance in B. subtilis", Nature Biotechnology 3, 1003-1007 (1985).
Finn et al., 2003, "Cancer vaccines: between the idea and the reality" Nature Reviews Immunology 3:630-641.
Flint et al. "Overexpression of the erbB-2 proto-oncogene in canine osteosarcoma cell lines and tumors", Vet. Pathol. 41: 291-296, 2004.
Foote et al. "Antibody Framework Residues Affecting the Conformation of the Hypervariable Loops", J. Mol. Biol. 224:487-499 (1992).
Fouts et al. "Construction and immunogenicity of *Salmonella typhimurium* vaccine vectors that express HIV-1 gp120", Vaccine. Dec. 1995;13(17):1697-705.
Frankel et al., 1995, "Induction of cell-mediated immune responses to human immunodeficiency virus type 1 Gag protein by using Listeria monocytogenes as a live vaccine vector" J. Immunol. 155:4775-4782.
Frey, 1993, "Rat adenocarcinoma 13762 expresses tumor rejection antigens but tumor-bearing animals exhibit tumor-specific immunosuppression", Clin. Immunol. Immunopathol. 69(2):223-233.
Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.
Fu et al., 1990, "Expansion of Immunoregulatory macrophages by granulocyte-macrophage colony-stimulating factor derived from a murine mammary tumor", Cancer Res. 50(2):227-234.
Fuji, 1987, "Significance of suppressor macrophages for immunosurveillance of tumor-bearing mice" J. Natl. Cancer Inst. 78(3):509-517.
Furukawa, 1993, "Nude mouse metastatic models of human stomach cancer constructed using orthotopic implantation of histologically intact tissue" Cancer Res. 53(5):1204-1208.
Gadiot et al., "Overall Survival and PD-L1 Expression in Metastasized Malignant Melanoma" Cancer 117:2192-2201 (2011).
Galakatos et al. "Biosynthetic alr alanine racemase from *Salmonella typhimurium*: DNA and protein sequence determination", Biochemistry. Jun. 3, 1986;25(11):3255-60.
Galen et al., 2001, "Can a 'flawless' live vector vaccine strain be engineered?", Trends Microbiol. 9(8):372-6.
Gao et al. Overexpression of PD-L1 Significantly Associates With Tumor Aggressiveness and Postoperative Recurrence in Human Hepatocellular Carcinoma. Clinical Cancer Research (2009) 15: 971-979.
Garay-Malparticla HM, et al., "CaSPredictor: a new computer-based tool for caspase substrate prediction", Bioinformatics Jun. 2005; 21 Suppl. 1: i169-76.
GenBank Acc. No. NC_003210 dated Dec. 17, 2014.
Genbank Accession No. AF103807 dated Nov. 1, 1999.
GenBank Accession No. AY878649 dated Feb. 6, 2005.
GenBank Accession No. DQ054588 dated Aug. 21, 2006.
GenBank Accession No. DQ054589 dated Aug. 21, 2006.
GenBank Accession No. U25452 dated Jul. 16, 2001.
Gentschev et al., "*Salmonella* Strain Secreting Active Listeriolysin Changes Its Intracellular Localization", Infect. Immun., 1995, 63:4202-4205.
Gentschev et al., 1996, "Development of antigen-delivery systems, based on the *Escherichia coli* hemolysin secreatiohn pathway" Gene 179:133-140.
Ghebeh "FOXP3+ TREGS and B7-H1+/Pd-1+ T Lymphocytes Co-Infiltrate the Tumor Tissues of High-Risk Breast Cancer Patients: Implication for Immunotherapy", BMC Cancer. Feb. 23, 2008;8:57.
Ghebeh et al. The B7-H1 (Pd-L1) T Lymphocyte-Inhibitory Molecule Is Expressed in Breast Cancer Patients With Infiltrating Ductal Carcinoma: Correlation With Important High-Risk Propgnostic Factors. Neoplasia (2006) 8: 190-198.
Ghosh et al. "Natalizumab for Active Crohn's Disease" (2003) New Engl. J. Med. 348:24-32.
Giannini et al. Morphological Precursors of Hepatocellular Carcinoma: A Morphometrical Analysis; Hepatogastroenterol. 34:95-97 (1987).
Gibellini et al. Extracellular HIV-1 Tat Protein Induces the Rapid Ser 133 Phosphorylation and Activation of CREB Transcription Factor in Both Jurkat Lymphoblastoid T Cells and Primary Peripheral Blood Mononuclear Cells; J. Immunol. 160:3891-3898 (1998).
Gilbert et al. Enhanced CD8 T cell immunogenicity and protective efficacyin a mouse malaria model using a recombinant adenoviral vaccine in heterologous prime-boost immunization regimes; Vaccine 20:1039-45 (2002).
Gilman et al., "Isolation of sigma-28-specific promoters from Bacillus subtilis DNA" 1984, Gene 32:11-20.
Gilmore et al., 1989, "A Bacillus cereus cytolytic determinant, cereolysin AB, which comprises the phospholipase C and sphingomyelinase genes: nucleotide sequenc and genetic linkage", J. Bacteriol. Feb.; 171(2):744-53.
Gish, W et al. Identification of protein coding regions by database similarity search; Nature Genet. 3:266-272 (1993).
Glaser et al. "Comparative genomics of *Listeria* species", Science. Oct. 26, 2001;294(5543):849-52.
Glick, "Factors affecting the expression of foreign proteins in *Escherichia coli*" 1987, J. Ind. Microbiol. 1:277-282.
Glomski et al., 2002, "The Listeria monocytogenes hemolysin has an acidic pH optimum to compartmentalize activity and pevent damage to infected host cells" J. Cell Biol. Mar. 18; 156(6):1029-38.
Goebel et al., 1993, "Listeria monocytogenes—a model system for studying the pathomechanisms of an intracellular microorganism", Zbl. Bakt. 278:334-347.
Gold L. et al., "Translational initiation in prokaryotes." 1981, Ann. Rev. Microbiol. 35:365-404.
Gonzalo et al. a heterologous prime-boost regime using DNA and recombinant vaccinia virus expressing the Leishmania infantum P36/LACK antigen protects BALB/c mice from cutaneous leishmaniasis; Vaccine 20:1226-31 (2002).
Goossens et al., 1992, "Induction of protective CD8+ T lymphocytes by an attenuated Listeria monocytogenes actA mutant" Int. Immunol. Dec.; 4(12):1413-8.
Goossens et al., 1995, "Attenuated Listeria monocytogenes as a live vector for induction of CD8+ T cells in vivo: a study with the nucleoprotein of the lymphocytic choriomeningitis virus", Int. Immunol. May; 7(5):797-805.
Gottesman, "Bacterial regulation: global regulatory networks." 1984, Ann. Rev. Genet. 18:415-442.
Gouin et al: "The Listeria monocytogenes InIC protein interferes with innate immune responses by targeting the I B kinase subunit IKK ", Proceedings of the National Academy of Sciences, vol. 107, No. 40, Sep. 20, 2010 (Sep. 20, 2010), pp. 17333-17338.
Graham et al. "Candidate AIDS vaccines", N Engl J Med. Nov. 16, 1995;333(20):1331-9.
Gregory et al., 1997, "Internalin B promotes the replication of Listeria monocytogenes in mouse hepatocytes" Infect. Immun. 65(12):5137-41.
Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK 314-348.
Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.
Gunn et al., Trends in Microbiology, Apr. 2001, 9/4: 161-162.
Gunn, Dissertation Abstracts International, 2001, 62/5B: 2244 Abstract Only.
Gunn, George R., et al. "Two Listeria monocytogenes vaccine vectors that express different molecular forms of human papilloma virus-16 (HPV-16) E7 induce qualitatively different T cell immunity

(56) References Cited

OTHER PUBLICATIONS that correlates with their ability to induce regression of established tumors immortalized by HPV-16." The Journal of Immunology 167.11 (2001): 6471-6479.

Guzman Carlos A et al.: "Attenuated Listeria monocytogenes carrier strains can deliver an HIV-1 gp120 T helper epitope to MHC class II-restricted human CD4+ T cells", European Journal of Immunology, vol. 28, No. 6, Jun. 1998, pp. 1807-1814.

Hamanishi et al. Programmed Cell Death 1 Ligand 1 and Tumor-Infiltrating CD8+ T Lymphocytes Are Prognostic Factors of Human Ovarian Cancer. Proceeding of the National Academy of Sciences (2007): 104: 3360-3365.

Hancock et al. SIMPLE34: An Improved and Enhanced Implementation for VAX and Sun computers of the Simple algorithm for analysis of clustered repetitive motifs in nucleotide sequences; Comput. Appl. Biosci. 10:67-70 (1994).

Harty et al. "CD8 T lymphocytes specific for the secreted p60 antigen protect against Listeria monocytogenes infection", J. Immunol. May 1, 1995; 154(9):4642-50.

Harty et al. "CD8+ T cells specific for a single nonamer epitope of Listeria monocytogenes are protective in vivo", J Exp Med. Jun. 1, 1992;175(6):1531-8.

Harty JT, Pamer EG, CD8 T lymphocytes specific for the secreted p60 antigen protect against Listeria monocytogenes infection, J. Immunol. May 1, 1995; 154(9):4642-50.

Harty, et al., Current Opinion in Immunology, 1996, 8: 526-530.

Hassan et al., 2004, "Mesothelin: a new target for immunotherapy" Clin. Cancer Res. 10(12 Pt 1):3937-42.

Hauf et al., 1997, "Listeria monocytogenes infection of P388D1 macrophages results in a biphasic NF-kappaB (RelA/p50) activation induced by lipoteichoic acid and Bacterial phospholipases and mediated by IkappaBalpha and IkappaBbeta degradation", Proc. Nat. Acad. Sci. U.S.A. Aug. 19; 94(17):9394-9.

Haynes et al. "Scientific and social issues of human immunodeficiency virus vaccine development", Science. May 28, 1993;260(5112):1279-86.

Haynes et al. "Update on the issues of HIV vaccine development", Ann Med. Feb. 1996;28(1):39-41.

He et al. Humanization and Pharmacokinetics of a Monoclonal Antibody with Specificity for Both E- and P-Selectin; J. Immunol. 160:1029 (1998).

Henikoff et al. "Amino acid substitution matrices from protein blocks" (1992) Proc. Natl. Acad. Sci. USA 89:10915-10919.

Herold et al. "Anti-Cd3 Monoclonal Antibody in New-Onset Type 1 Diabetes Mellitus" (2002) New Engl. J. Med. 346:1692-1698.

Hess et al., 1995, "Listeria monocytogenes p60 supports host cell invasion by and in vivo survival of attenuated *Salmonella typhimurium*" Infect. Immun. May; 63(5):2047-53.

Hess et al., 1996, "*Salmonella typhimurium* aroA-infection in gene-targeted immunodeficient mice: major role of CD4+ TCR-alpha beta cells and IFN-gamma in bacterial clearance independent of intracellular location" J. Immunol. May 1; 156(9):3321-6.

Hess et al., 1996, "Superior efficacy of secreted over somatic antigen display in recombinant *Salmonella* vaccine induced protection against listeriosis" Proc. Nat. Acad. Sci. 93:1458-1463.

Hess et al., 1997, "Protection against murine listeriosis by an attenuated recombinant *Salmonella typhimurium* vaccine strain that secretes the naturally somatic antigen superoxide dismutase", Infect. Immun. Apr.; 65(4):1286-92.

Hess J, et al, "*Mycobacterium bovis* Bacille Calmette-Guerin strains secreting listeriolysin of Listeria monocytogenes", Proc. Natl. Acad. Sci. U.S.A. Apr. 28, 1998; 95(9):5299-304.

Hess J., Kaufmann SH, Abstract, Live antigen carriers as tools for improved anti-tuberculosis vaccines, FEMS Immunol. Med. Microbiol. Feb. 1999; 23(2):165-73.

Higgins DE, Shastri N, Portnoy DA, Abstract, Delivery of protein to the cytosol of macrophages using *Escherichia coli* K-12, Mol. Microbiol. Mar. 1999 31(6):1631-41.

Higgins et al., 1998, "Bacterial delivery of DNA evolves" Nat. Biotechnol. Feb.; 16(2):138-9.

Hiltbold EM, Safley SA, Ziegler HK, The presentation of class I and class II epitopes of listeriolysin O is regulated by intracellular localization and by intracelluar spread of Listeria monocytogenes, J. Immunol. Aug. 1, 1996; 157(3):1163-75.

Hiltbold EM, Ziegler HK, Mechanisms of processing and presentation of the antigens of Listeria monocytogenes, Infect. Agents Dis. Oct. 1993; 2(5):314-23.

Hino et al. Tumor cell expression of programmed cell death-1 is a prognostic factor for malignant melanoma. Cancer (2010 116(7):1757-66.

Hodgson, 2000, "Generalized transduction of serotype 1/2 and serotype 4b strains of Listeria monocytogenes", Mol. Microbiol. 35(2):312-23.

Hoogenboom et al. "Natural and designer binding sites made by phage display technology", Immunol. Today 21:371-377 (2000).

Hsing et al. "Requirement for Nuclear Factor-kB Activation by a Distinct Subset of CD40-Mediated Effector Functions in B Lymphocytes", J. Immunol. 162:2804-2811 (1999).

Hu et al., J. Immunology, 2004, 172: 1595-1601.

Huang et al., 1994, "Role of bone marrow-derived cells in presenting MHC class I-restricted tumor antigens" Science 264:961-965.

Hussain et al., 2004, "CD4+CD25+ regulatory T cells that secrete TGFbeta and IL-10 are preferentially induced by a vaccine vector" J. Immunother. Sep.-Oct.; 27(5):339-46.

Hussein et al., "What is needed for effective antitumor immunotherapy? Lessons learned using Listeria Monocytogenes as a live vector for HPV-associated tumors", Cancer Immunology, Immunotherapy, vol. 54, No. 6, 2005, pp. 577-586.

Ikonomidis et al. "Delivery of a viral antigen to the class I processing and presentation pathway by Listeria monocytogenes", J Exp Med. Dec. 1, 1994;180(6):2209-18.

Ikonomidis et al., "Influenze-specific immunity induced by recombinant Listeria monocytogenese vaccines", Vaccine, vol. 15, No. 4, 1997, pp. 433-440.

Ikonomidis et al., 1994, Abstract E-90, Abstracts, 94th General Meeting of the American society for Microbiology, May 23-27.

Inman et al. PD-L1 (B7-H1) expression by urothelial carcinoma of the bladder and BCG-induced granulomata: associations with localized stage progression. Cancer (2007): 109: 1499-1505.

International Search Report for PCT Application No. PCT/US15/40855 mailed Dec. 18, 2015.

International Search Report for PCT Application No. PCT/US15/040911 mailed Nov. 2, 2015.

International Search Report of Application No. PCT/US07/06292 issued on Jun. 17, 2008.

International Search Reports of Application No. PCT/US07/10635.

International Search Reports of Application No. PCT/US08/03067.

Jensen et al., 1997, "Recombinant Listeria monocytogenes as a live vaccine vehicle and a probe for studying-cell-mediated immunity" Immunological Review 158:147-157.

Jensen, 1997, "Recombinant Listeria monocytogenes vaccination eliminates papillomavirus-induced tumors and prevents papilloma formation from viral DNA", J. Virol. 71(11):8467-8474.

Jiang et al. "Characterization of a mutant Listeria monocytogenes strain expressing green fluorescent protein" Acta. Biochim. Biophys Sin (Shanghai), 37(1): 19-24, (2005).

Johnson et al., "Kabat database and its applications: 30 years after the first variability plot", Nucleic Acids Research, 2000, vol. 28, No. 1, pp. 214-218.

Jones et al., 1994, "Characterization of Listeria monocytogenes pathogenesis in a strain expressing perfingolysin O in place of listeriolysin O", Infect. Immun. 62:5608-5613.

Kabat "The Structural Basis of Antibody Complementarity", Adv. Prot. Chem. 32:1-75 (1978).

Kabat et al., "Unusual distributions of amino acids in complementarity-determining (hypervariable) segments of heavy and light chains of immunoglobulins and their possible roles in specificity of antibody-combining sites" (1977) J. Biol. Chem. 252:6609-6616.

Kaithamana et al. Induction of Experimental Autoimmune Graves' Disease in BALB/c Mice; J. Immunol. 163:5157-5164 (1999).

Karlin et al. "Methods for assessing the statistical significance of molecular sequence features by using general scoring schemes" (1990) Proc. Natl. Acad. Sci. USA 87:2264-2268.

(56) References Cited

OTHER PUBLICATIONS

Karlin et al., "Applications and statistics for multiple high-scoring segments in molecular sequences " (1993) Proc. Natl. Acad. Sci. USA 90:5873-5877.
Kaufman S.H. et al., "Impact of intracellular location of and antigen display by intracellular bacteria:implications for vaccine development", J. Immunol. Lett. 1999, 65(1-2):81-84.
Kaufmann "Immunity to intracellular bacteria", Annu Rev Immunol. 1993;11:129-63.
Kerksiek et al., Current Opinion in Immunology, 1999, 11:40-405.
Kim, Myoung-Dong, et al. "Coexpression of BiP increased antithrombotic hirudin production in recombinant *Saccharomyces cerevisiae*." Journal of biotechnology 101.1 (2003): 81-87.
King et al. "Amplification of a novel v-erbB-related gene in a human mammary carcinoma" Science. 229:974-976, (1985).
Knutson K. L. et al., "Immunization with a HER-2/neu helper peptide vaccine generates HER-2/neu CD8 T-cell immunity in cancer patients." The Journal of Clinical Investegation, 107:477-484, 2001.
Kocks et al., 1992, "L monocytogenes-induced act in assembly requires the actA gene product", Cell, vol. 68, No. 3, p. 521-531.
Kohler et al. "Expression of the iap gene coding for protein p60 of Listeria monocytogenes is controlled on the posttranscriptional level", J Bacteriol. Aug. 1991;173(15):4668-74.
Kohler et al. Continuous Cultures of Fused Cells Secreting Antibody of Predefined Specificity; Nature 256: 495 (1975).
Kovacsovics-Bankowski et al., 1993, "Efficient major histocompatibility complex class I peresentation of exogenous antigen upon phagocytosis by macrophages", Proc. Natl. Acad. Sci. USA 90:4942-4946.
Kyte J. and Dootlittle RF, "A simple method for displaying the hydropathic character of a protein" J. Mol. Biol. 157, 105, 1982.
Lamikanra et al., J. Virology. Oct. 2001, 75/20:9654-9664.
Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.
Lara-Tejero et al., Current Opinion in Immunology, 2004, 7: 45-50.
Lasa et al., 1997, "Identification of two regions in the N-terminal domain of ActA involved in the actin comet tail formation by Listeria monocytogenes" EMBO 16(7):1531-40.
Lauer et al., " Characterization of the Attachment Site of Bacteriophage U153 within the Listeria monocytogenes comK Gene" ASM Meeting, Abstract 1999.
Lauer et al., "Systematic mutational analysis of the amino-terminal domain of the Listeria monocytogenes ActA protein reveals novel functions in actin-based motility" Molecular Microbiology 42(5):1163-1177, 2001.
Lauer et al., 2002, "Construction, characterization, and use of two Listeria monocytogenes site-specific phage integration vectors" J. Bacteriology 184:4177-4186.
Le Doussal et al. Enhanced in Vivo Targeting of an Asymmetric Bivalent Hapten Antibody Conjugate CocktailsTo Double-Antigen-Positive Mouse B Cells With Monoclonal ; J. Immunol. 146:169-175 (1991).
Leao et al., 1995, "A species-specific nucleotide sequence of *Mycobacterium tuberculosis* encodes a protein that exhibts hemolytic activity when expressed in *Escherichia coli*" Infect. Immun. Nov.; 63(11):4301-6.
Lebrun M. et al., Aug. 1996, "Intemallan must be on the Bacterial Surface to mediate Entry of Listeria monocytogenes into Epilhalial Cells", Molecullar Microbiology 21:579-592.
Lee et al., 1991, "Construction of single-copy integration vectors for *Staphylococcus aureus*", Gene 103:101-5.
Lee KD, Oh YK, Portnoy DA, Swanson JA, Delivery of macromolecules into cytosol using liposomes containig hemolysin from Listeria monocytogenes, J. Biol. Chem., Mar. 29, 1996, 271(13):7249-52.
Lehner et al., 1996, "Processing and delivery of peptides presented by MHC class I molecules", Curr. Opin. Immunol. 8(1):59-67.
Lejeune, 1994, "Nitric oxide involvement in tumor-induced immunosuppression" J. Immunol. 152(10):5077-5083.
Lenz "Stable integration vector for nutrient broth-based selection of attenuated Listeria monocytogenes strains with recombinant antigen expression", Clin Vaccine Immunol. 15(9):1414-1419. Sep. 2008.
Li et al., "Conditional lethality yields a new vaccine strain of listeria monocytogenes for the induction of cell-mediated immunity", Infection and Immunity, 2005, 73(8): 5065-5073.
Liau et al., 2002, "Tumor immunity within the central nervous system stimulated by recombinant Listeria monocytogenes vaccination", Cancer Res., 62(8):2287-93.
Lieberman et al., "Engineered listeria monocytogenes as an Aids vaccine", Vaccine 2002, , 20: 2007-2010.
Lin et al., "Treatment of Established Tumors with a Novel Vaccine that Enhances Major Histocompatibility Class II Presentation of Tumor Antigen", Cancer Res. 1996, 56:21-26.
Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.
Lingnau et al., 1995, "Expression of the Listeria monocytogenes EGD inIA and inIB genes, whose products mediate bacterial entry into tissue culture cell lines, by PrfA-dependent and independent mechanisms" Infect. Immun. Oct.; 63(10):3896-903.
Lipford GB, Wagner H, Heeg K, Vaccination with immunodominant peptides encapsulated in Quil A-containing liposomes induces peptide-specific primary CD8+ cytotoxic T cells, Vaccine Jan. 1994; 12(1):73-80.
Lipsky et al. "Infliximab and Methotrexate in the Treatment of Rheumatoid Arthritis" (2000) New Engl. J. Med. 343:1594-1602.
Liu et al. "Randomised, double blind, placebo controlled study of interferon beta-1 a in relapsing-remitting multiple sclerosis analysed by area under disability/time curves" (1999) J. Neurol. Neurosurg. Psych. 67:451-456.
Lobocka et al. "Organization and expression of the *Escherichia coli* K-12 dad operon encoding the smaller subunit of D-amino acid dehydrogenase and the catabolic alanine racemase", J Bacteriol. Mar. 1994;176(5):1500-10.
Loeffler et al., 2006, "Comparison of different live vaccine strategies in vivo for delivery of protein antigen or antigen-encoding DNA and mRNA by virulence-attenuated Listeria monocytogenes" Infect. Immun. Jul; 74(7):3946-57.
Loessner et al., 1995, "Heterogeneous endolysins in Listeria monocytogenes bacteriophages: a new class of enzymes and evidence for conserved holin genes within the siphoviral lysis cassettes", Mol. Microbiol. Jun.; 16(6):1231-41.
Loessner et al., 2000, "Complete nucleotide sequence, molecular analysis and genome structure of bacteriophage A118 of Listeria monocytogenes: implications for phage evolution", Molecular Microbiology 35(2):324-40.
Maciag et al. "The first clinical use of a live-attenuated Listeria monocytogenes vaccine: a Phase I safety study of Lm-LLO-E7 in patients with advanced carcinoma of the cervix", Vaccine. Jun. 19, 2009;27(30):3975-83.
Madden et al. Applications of Network BLAST Server; Meth. Enzymol. 266:131-141 (1996).
Makela et al., Hand book of Experimental Immunology vol. 1, Chapter 3—"Haptens and carriers", pp. 3.1-3.13; 1987.
Mandal et al., BBA, 2002,1563: 7-17.
Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.
Marks et al. By-passing Immunization Human Antibodies from V-gene Libraries Displayed on Phage; J. Mol. Biol. 222: 581-597 (1991).
Marquis et al. "Intracytoplasmic growth and virulence of Listeria monocytogenes auxotrophic mutants", Infect Immun. Sep. 1993;61(9):3756-60.

(56) References Cited

OTHER PUBLICATIONS

Marquis et al., 1997, "Proteolytic pathways of activation and degradation of a bacterial phospholipase C during intracellular infection by Listeria monocytogenes" J. Cell Biol. 137:1381-1392.
Martin et al., 1986, "Nucleotide sequence of the tetM tetracycline resistance determinant of the streptococcal conjugative shuttle transposon Tn1545", Nucleic Acid Res. 14:7047-7058.
Marx et al., 2002, "Broad-host-range cre-lox system for antibiotic marker recycling in gramnegativ bacteria" Biotechniques, Nov.; 33(5):1062-7.
Mata et al. Th1 T.cell responses to HIV•1 Gag protein delivered by Listeria monocytogenes vaccine are similar to those induced by endogenous listerial antigen's; J. Immunol 163:1449-1456. (1999).
Mazzaccaro RJ, Gedde M, Jensen ER, Van Santen HM, Polegh HL, Rock KL, Bloom BR, Major histocompatibility class I presentation of soluble antigen facilitated by *Mycobacterium tuberculosis* infection, Proc. Natl. Acad. Sci. U.S.A. Oct. 15, 1996; 93(21):11786-91.
McLaughlan et al., 1998, "Molecular characterization of an autolytic amidase of Listeria monocytogenes EGD", Microbiology, May; 144(Pt 5):1359-67.
Mendez et al. Functional Transplant of Megabase Human immunoglobulin Loci Recapitulates Human Antibody Response in Mice; Nature Genetics 15:146-156 (1997).
Mengaud et al. "Transcriptional mapping and nucleotide sequence of the Listeria monocytogenes hlyA region reveal structural features that may be involved in regulation", Infect Immun. Dec. 1989;57(12):3695-701.
Mengaud et al., 1988, "Expression in *Escherichia coli* and sequence analysis of the listeriolysin O determinant of listeria monocytogenes", Infect. Immun., vol. 56, No. 4, 766-772.
Menne et al. "A comparison of signal sequence predition methods using a test set of signal peptides" (2000) Bioinformatics 16: 741-742.
Merrifiled et al., "Solid phase peptide synthesis. 1. The synthesis of a tetrapeptide" J. Am. Chem. Soc., 85:2149-2156 (1963).
Meyaard et al. "LAIR-1, a Novel Inhibitory Receptor Expressed on Human Mononuclear Leukocytes" (1997) Immunity 7:283-290.
Mikayama et al., Molecular cloning and functional expression of a cDNA encoding gycosylation-inhibiting factor, Nov. 1993, Pro Natl. Acad. Sci., USA, vol. 90:10056-10060.
Milgrom et al. "Treatment of Allergic Asthma With Monoclonal Anti-Ige Antibody" (1999) New Engl. J. Med. 341:1966-1973.
Miller et al., "Targeted vectors for gene therapy" 1995, FASEB J., 9:190-199.
Mitchell et al. "Avoidance of autophagy mediated by PIcA or ActA is required for Listeria monocytogenes growth in macrophages", Infect Immun. May 2015;83(5):2175-84.
Mkrtichyan et al. "Anti-PD-1 antibody significantly increases therapeutic efficacy of Listeria monocytogenes (Lm)-LLO immunotherapy", Journal for ImmunoTherapy of Cancer 2013, 1:15.
Mlynarova et al., 2002, "The promiscuity of heterospecific lox sites increases dramatically in the presence of palindromic DNA", Gene, Aug. 21; 296(1-2):129-37.
Mollet et al., 1993, "Directed genomic integratoin, gene replacement, and integrative gene expression in *Streptococcus thermophilus*" J. Bacteriology 175:4315-4324.
Moriishi et al., 1998, "Sequence analysis of the actA gene of Listeria monocytogenes isolated from human", Microbiol. Immunol., vol. 42, No. 2, p. 129-132.
Nagai et al 1991 Isolation and partial characterization of major protein antigens in the culture fluid of *Mycobacterium tuberculosis*. Infect Immun. Jan. 1991;59(1):372-82.
Nakanuma, et al. Anatomic and molecular pathology of intrahepatic cholangiocarcinoma, J. Hepatobiliary Pancreat. Surg. 10:265-281 (2003).
Narang et al., "Improved phosphotriester method for the synthesis of gene fragments" 1979, Meth. Enzymol. 68:90-99.
Naz NK et al., "Novel human prostate-specific cDNA: molecular cloning, expression, and immunobiology of the recombinant protein" Biochem Biophys Res. Commun. 297:1075-84.
Ngo et al., 1994, The Protein Folding Problem and Tertiary Structure Prediction, pp. 492-495.
Nielsen PE, "Peptide nucleic acids as therapeutic agents" Curr. Opin. Struct Biol. 9:353-57.
Nitcheu-Tefit et al. "Listeriolysin O Expressed in a Bacterial Vaccine Suppresses CD4_CD25high Regulatory T Cell Function in Vivo", J Immunol. Aug. 1, 2007;179(3):1532-41.
Nomi et al. Clinical significance and therapeutic potential of the programmed death-1 ligand/programmed death-1 pathway in human pancreatic cancer. Clinical Cancer Research (2007);13:2151-2157.
Noriega et al. "Engineered deltaguaB-A deltavirG Shigella flexneri 2a strain CVD 1205: construction, safety, immunogenicity, and potential efficacy as a mucosal vaccine", Infect Immun. Aug. 1996;64(8):3055-61.
Ochsenbein et al., 1999, "A comparison of T cell memory against the same antigen induced by virus versus intracellular bacteria" Proc. Natl. Acad Sci U.S.A. Aug. 3; 96(16):9293-8.
Offit et al. "Addressing Parents' Concerns: Do Multiple Vaccines Overwhelm or Weaken the Infant's Immune System?", Pediatrics vol. 109 No. 1 Jan. 2002.
Ohigashi et al. Clinical significance of programmed death-1 ligand-1 and programmed death-1 ligand 2 expression in human esophageal cancer. Clin. Cancer Research (2005): 11: 2947-2953.
O'Riordan, et al. Listeria Intracellular Growth and Virulence Require Host-Derived Lipoic Acid, Science 302: 462-464(2003).
Oscarsson et al., 1996, "Induction of haemolytic activity in *Escherichia coli* by the slyA gene product" Mol. Microbiol. Apr.; 20(1):191-9.
Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.
Palmeros et al., 2000, "A family of removable cassettes designed to obtain antibiotic-resistance-free genomic modifications of *Escherichia coli* and other bacteria" Gene, Apr. 18; 247(1-2):255-64.
Pamer et al. "Precise prediction of a dominant class I MHC-restricted epitope of Listeria monocytogenes", Nature. Oct. 31, 1991;353(6347):852-5.
Pan et al., "Regression of Established Tumors in Mice Mediated by the Oral Administration of a Recombinant Listeria monocytogenes Vaccine", Cancer Res., 1995, 55:4776-4779.
Pan et al., 1995, "A recombinant Listeria monocytogenes vaccine expressing a model tumour antigen protects mice against lethal tumour cell challenge and causes regression of established tumours" Nature Med. 1:471-477.
Pan et al., Cancer Research, 1999, 59: 5264-5269.
Parida et al., 1998, "Internalin B is essential for adhesion and mediates the invasion of Listeria monocytogenes into human endothelial cells" Mol. Microbiol. Apr.; 28(1):81-93.
Parsa, Saba, and Blaine Pfeifer. "Engineering bacterial vectors for delivery of genes and proteins to antigen-presenting cells." Molecular pharmaceutics 4.1 (2007): 4-17.
Passos et al. Recombinant Leishmania Antigens for Serodiagnosis of Visceral Leishmaniasis Clinical and Diagnostic Laboratory Immunology, Oct. 2005, p. 1164-1167, vol. 12, No. 10.
Paterson et al. "Recombinant Listeria monocytogenes cancer vaccines", Curr Opin Immunol. Oct. 1996;8(5):664-9.
Paterson, "Rational approaches to immune regulation", Immunologic Research, 2003; 27/2-3:451-462.
Paterson, Yvonne, and Paulo Cesar Maciag. "Listeria-based vaccines for cancer treatment." Current opinion in molecular therapeutics 7.5 (2005): 454-460.
Paul et al. An IL-4 Receptor Region Containing an Insulin Receptor Motif Is Important for IL+Mediated IRS-1 Phosphorylation and Cell Growth, Cell 76 241-251 (1994).
Paul et al. Frequent associations between CTI and T-Helper epitopes in HIV-1 genomes and 12, 13 implications for multi-epitope vaccine designs. BMC Microbiology 10:1-16 (2010).

(56) References Cited

OTHER PUBLICATIONS

Paul et al., 1989, "Fundamental Immunology", Second Edition, Raven Press, 987-988.
Pawelek et al. "Tumor-targeted *Salmonella* as a novel anticancer vector", Cancer Res. Oct. 15, 1997;57(20):4537-44.
Peng et al. "Adjuvant properties of listeriolysin O in a DNA vaccine strategy", Cancer Immunol Immunother, Jun. 2007;56(6):797-806.
Peng et al., J. Immunology, 2004,172: 6030-6038.
Penichet et al., 2001, "Antibody-cytokine fusion proteins for the therapy of cancer" J. Immunological Methods 248:91-101.
Peters et al. The Induction of HIV Gag-Specific CD8+ T Cells in the Spleen and Gut-Associated Lymphoid Tissue by Parenteral or Mucosal monocytogenes HIV Gag Immunization with Recombinant Listeria; J Immunol; 170:5176-5187 ( 2003).
Peters et al., "Enhancing the immunogenicity of bioengineered listeria monocytogenes by passing through olive animal hosts", Vaccine 2003, 21: 1187-1194.
Peters et al., 2003, "Tailoring host immune responses to Listeria by manipulation of virulence genes—the interface between innate and acquired immunity" FEMS Immunol. Med. Microbiol. Apr. 1; 35(3):243-53.
Pfeifer et al., 1993, "Phagocytic processing of bacterial antigens for class I MHC presentation to T cells" Nature, Jan. 28; 361(6410):359-62.
Portielji et al. IL-12: a promising adjuvant for cancer vaccination, Cancer Immunol. Immunother. 52:133-144 (2003).
Portnoy et al. "Molecular determinants of Listeria monocytogenes pathogenesis", Infect Immun. Apr. 1992;60(4):1263-7.
Presta "Selection, design, and engineering of therapeutic antibodies" (2005) J. Allergy Clin. Immunol. 116:731.
Pupa et al., 2001, "Prevention of spontaneous neu-expressing mammary tumor development in mice transgenic for rat proto-neu by DNA vaccination" Gene Ther. Jan.; 8(1):75-9.
Purchio et al. "Methods in Enzymology: Methods for molecular cloning in eukaryotic cells", (2003).
Quenee et al., 2005, "Combined sacB-based negative selection and cre-lox antibiotic marker recycling for efficient gene deletion in pseudomonas aeruginosa", Biotechniques, Jan.; 38(1):63-7.
Radford et al., Gene Therapy, 2002, 9: 1455-1463.
Radford et al., Int. J. Cancer, 2003,105: 811-819.
Raveneau et al., 1992, "Reduced virulence of a Listeria monocytogenes phospholipase-deficient mutant obtained by transposon insertion into the zinc metalloproteas gene" Infect. Immune., 60:916-921.
Realini et al., "Proposed roles in protein-protein association and presentation of peptides by MHC Class I receptors", FEBS Lett., 1994, 348:109-113.
Rechsteiner and Rogers, "PEST sequences and regulation by proteolysis", TIBS, 1996, 21:267-271.
Reiter et al., 1989, "Transfer RNA genes frequently serve as integration sites for porkaryotic genetic elements", Nucleic Acids Research 17(5):1907-14.
Renard V. et al., "HER-2 DNA and protein vaccines containing potent Th cell epitopes induce distinct protective and therapeutic antitumor responses in HER-2 transgenic mice", The Journal of Immunology, 171(3):1588-1595, 2003.
Repique, 1992, "Immunosuppression derived from human B-lymphoblastoid and melanoma cell lines" Cancer Invest. 10(3):201-208.
Riegler. Preneoplastic Conditions of the Liver; Seminars in Gastrointestinal Disease vol. 7, No. 2:pp. 74-87 (1996).
Riera et al. Evaluation of a latex agglutination test (KAtex) for detection of Leishmania antigen in urine of patients with HIV-Leishmania coinfection: value in diagnosis and post-treatment follow-up. Eur J Clin Microbiol Infect Dis. Dec;23 (12):899-904 (2004).
Robinson et al. "New Hope for an Aids Vaccine", Nat. Rev. Immunol. 2:239-50 (2002).
Rocken et al. "Pathalogy and Pathogenesis of Hepatocellular", Digestive Diseases 19:269-278 (2001).
Roden et al., 2004, "Vaccination to prevent and treat cervical cancer", Hum. Pathol. 35(8):971-82.
Rogers et al., "Amino acid sequences common to rapidly degraded proteins: The pest hypothesis", Science, vol. 234, 1986, pp. 364-368.
Rongcun et al. "Identification of new HER2/neu-derived peptide epitopes that can elicit specific CTL against autologous and allogeneic carcinomas and melanomas." The Journal of Immunology 163.2 (1999): 1037-1044.
Rothman et. al. "The use of living listeria monocytogenes as an active immunotherapy for the treatment of cancer", Emerging Cancer Therapy: Microbial Approaches and Biotechnological Tools, Edited by Arsénio M. Fialho and Ananda M. Chakrabarty Copyright © 2010 John Wiley & Sons, Inc.
Rubin et al. "Cloning, sequence determination, and regulation of the ribonucleotide reductase subunits from Plasmodium falciparum: a target for antimalarial therapy", Proc Natl Acad Sci U S A. Oct. 15, 1993;90(20):9280-4.
Russmann et al., 1998, "Delivery of epitopes by the *Salmonella* type III secretion system for vaccine system for vaccine development", Science, Jul. 24; 281(5376):565-8.
Safley et al., "Role of listeriolysin-O (LLO) in the T lymphocyte response to infection with Listeria monocytogenes. Identification of T cell epitopes of LLO" J. Immunology 146(10):3604-3616; May 1991.
Sambrook et al. "Molecular cloning: a laboratory manual", Cold Spring Harbor Laboratory Press, Cold Spring Harbor, New York 2 (2001).
Scardino, et al (2002) "HER-2/neu and hTERT Cryptic Epitopes as Novel Targets for Broad Spectrum Tumor Immunotherapy." The Journal of Immunology, vol. 168,5900-5906.
Schafer, et al (1992) Induction of a cellular immune response to a foreign antigen by a recombinant Listeria monocytogenes vaccine . . . J Immunology, 149(1) 53-59.
Scheirlinck et al., 1989, "Integration and expression of alpha-amylase and endoglucanase genes in the Lactobacillus plantarum chromosome", Appl. Environ Microbiol. 55(9):2130-7.
Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159.
Schmidt et al., 1995, "Molecular Analysis of the Plasmid-Encoded Hemolysin of *Escherichia coli* O157:H7 Strain EDL 933", Infection and Immunity, 63(3):1055-1061.
Schneider et al. Induction of CD8+ T cells using heterologous prime-boost immunisation strategies, Immunol.Rev. 170:29-38 (1999).
Schnupf et al. "ListeriolysinO: a phagosome-specific lysine", Microbes & Infect. 2007, 9:1176-1187.
Schnupf et al., "Phosphorylation, ubiquitination and degradation of listeriolysic O in mammalian cells: role of the PEST-like sequence" Cellular microbiology 8(2):353-364, 2006.
Scortti et al., 2007, "The PrfA virulence regulon", Microbes Infect. Aug.; 9(10):1196-207.
Seavey "A novel human Her-2/neu chimeric molecule expressed by Listeria monocytogenes can elicit potent HLA-A2 restricted CD8-positive T cell responses and impact the growth and spread of Her-2/neu-positive breast tumors" Clin Cancer Res. 15(3):924-32, Feb. 1, 2009.
Sewell D. A., Regression of HPV-Positive Tumors Treated with a New Listeria monocytogenes Vaccine Arch Otolaryngol., Head Neck Surg., Jan. 2004, vol. 130, pp. 92-97.
Sewell et al., "Recombinant Listeria vaccines containing PEST sequences are potent immune adjuvants for the tumor-associated antigen human papillomavirus-16 E7", Cancer Research 64(24):8821-8825, 2004.
Shahabi et al. "A live, attenuated Listeria-based immunotherapeutic for the treatment of breast cancer", 2009 ASCO Breast cancer Symposium, Oct. 8, 2009, abstract.
Shahabi et al. "Development of a live and highly attentuated Listeria monocytogenes-based vaccine for the treatment of Her2/neu-overexpressing cancers in human", Cancer Gene Therapy, vol. 18, No. 1, Jan. 1, 2011, pp. 53-62.

(56) References Cited

OTHER PUBLICATIONS

Shahabi et al. "Live, attenuated strains of Listeria and *Salmonella* as vaccine vectors in cancer treatment", Bioeng. Bugs, 2010, vol. 1, No. 4, pp. 235-243.
Shahabi et al., "Development of a Listeria Monocytogenes based vaccine against prostate cancer", Cancer Immunology, Immunotherapy, vol. 57, No. 9, 2008, pp. 1301-1313.
Sharpe et al. "The function of programmed cell death 1 and its ligands in regulating autoimmunity and infection", Nature Immunology ; 8:239-245 (2007).
Shaw et al. "Complete nucleotide sequence of macrolide-lincosamide-streptogramin B-resistance transposon Tn917 in *Streptococcus faecalis*", J Bacteriol. Nov. 1985; 164(2):782-96.
Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.
Shen et al., 1998, "Compartmentalization of bacterial antigens: diffrential effects on priming of CD8 T cells and protective immunity" Cell., Feb. 20; 92(4):535-45.
Shen et al., Current Opinion in Immunology, 1998, 10: 450-458.
Shetron-Rama et al., 2002, "Intracellular induction of Listeria monocytogenes actA expression" Infect. Immun. 70:1087-1096.
Shimauchi et al. Augmented expression of programmed death-1 in both neoplasmatic and nonneoplastic CD4+ T-cells in adult T-cell Leukemia/ Lymphoma. Int. J. Cancer (2007): 121:2585-2590.
Shimizu et al., 1994, "Effects of CD4+ and CD8+ T cells in tumor-bearing mice on antibody production" Cancer Immunol. Immunother 38(4):272-276.
Shiver et al., Replication-incompetent adenoviral vaccine vector elicits effective anti-immunodeficiency-virus immunity, Nature 415: 331-5 (2002).
Sin et al. DNA Priming-Protein Boosting Enhances Both Antigen-Specific Antibody and Th1-Type Cellular Immune Responses in a Murine Herpes Simplex Virus-2 gD Vaccine Model, DNA Cell Biol. 18:771-9 (1999).
Singh et al. "Immunoediting sculpts tumor epitopes during immunotherapy", Cancer Res.67(5):1887-92. Mar. 1, 2007.
Singh et al. "Cancer immunotherapy using recombinant Listeria monocytogenes transition from bench to clinic", Human Vaccines, 2011, vol. 7(5), pp. 497-505.
Singh, R. Fusion to Listeriolysin O and Delivery by Listeria monocytogenes Enhances the Immunogenicity of HER-2/neu and Reveals Subdominant Epitope in the FVB/N Mouse, J. Immunology, Sep. 15, 2005, vol. 175, pp. 3663-3673.
Sirard et al., 1997, "Intrtracytoplasmic delivery of Lidteriolysin O by vaccinal strain of Bacillus anthracis induces CD8-mediated protection against listeria monocytogenes", J. Immunology, vol. 159, p. 4435-4443.
Skoble J. et al., Aug. 7, 2000, "Three Regions within ActA Promote Atp2/3 Complex-mediated Actin Nucleation and Listeria monocytogenes Motility", The Journal of cell Biology 150(3):527-537.
Skolnick et al., Form genes to protein structure and function: novel applications of computational approaches in the genomic era, Jan. 2000, Trends in Biotech., 18(1):34-39.
Slamon et al. "Use of Chemotherapy Plus a Monoclonal Antibody Against Her2 for Metastatic Breast Cancer That Overexpresses Her2" 2001, New Engl. J. Med. 344:783-792.
Slifka et al., 1996, "Antiviral cytotoxic T-cell memory by vaccination with recombinant Listeria monocytogenes" J. Virol. 70(5):2902-10.
Smith et al., 1995, "The two distinct phospholipases C of Listeria monocytogenes have overlapping roles in escape from a vacuole and cell-to-cell spread", Infect. Immun. 63:4231-4237.
Smith G.A. et al., Sep. 1995, "Asymmetric Distribution of the Listeria monocytogenes ActA Protein is Required and Sufficient to Direct Actin-Based Motility", Molecular Microbiology 17:945-951.
Souders et al., 2006, "In vivo bactofection: listeriacan function as a DNA-cancer vaccine" DNA Cell Biol. Mar.; 25(3):142-51.
Soussi, Neirouz, et al. "Effect of intragastric and intraperitoneal immunisation with attenuated and wild-type LACK-expressing Listeria monocytogenes on control of murine Leishmania major infection." Vaccine 20.21 (2002): 2702-2712.
Soussi, Neirouz, et al. "Listeria monocytogenes as a short-lived delivery system for the induction of type 1 cell-mediated immunity against the p36/LACK antigen of Leishmania major." Infection and immunity 68.3 (2000): 1498-1506.
Stahl et al., 1984, "Replacement of the Bacillus subtilisin structural gene with an in vitro-derived deletion mutation" J. Bacteriol. 158:411-418.
Starks et al., 2004, "Listeria monocytogenes as a vaccine vector: virulence attenuation or existing antivector immunity does not diminish therapeutic efficacy", J. Immunology 173:420-427.
States, D.J. et al. Improved Sensitivity of Nucleic Acid Database Searches Using Application-Specific Scoring Matrices, Methods 3:66-70 (1991).
Stitz et al., 1990, "Characterization and immunological properties of influenza A virus nucleoprotein (NP): cell-associated NP isolated from infected cells or viral NP expressed by vaccinia recombinant virus do not confer protection" J. Gen. Virol., 71(Pt 5):1169-1179.
Strungnell et al., 1990, "Stable expression of forgein antigens from the chromosome of *Salmonella typhimurium* vaccine strains" Gene 88:57-63.
Strych et al. "Characterization of the alanine racemases from two mycobacteria", FEMS Microbiol Lett. Mar. 15, 2001;196(2):93-8.
Stryer et al., "Levels of structure in protein architecture" Biochemistry, Third Edition, W H Freeman Company, New York, pp. 31-33, 1998.
Su et al. "Relevance of Hepatic Preneoplasia for Human Hepatocarcinogenesis" (2003) Toxicol. Pathol. 31:126-133.
Sun et al., 1990, "Isolation of Listeria monocytogenes small-plaque mutants defective for intracellular growth and cell-to-cell speard" Infect. Immun. 58:3770-3778.
Szalay G, Hess J, Kaufmann SH, Presentation of Listeria monocytogenes antigenes by major histocompatibility complex class I molecules to CD8 cytotoxic T lymphocytes independent of listeriolysin secretion and virulence, Eur. J. Immunol. Jul. 1994; 24(7):1471-7.
Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun., 1999, 67(2):568-575.
Tang et al. "Protein Chemistry and Structure: Use of a Peptide Mimotope to Guide the Humanization of MRK-16, an Anti-P-glycoprotein Monoclonal Antibody", 1999 J. Biol. Chem. 274:27371-27378.
Tanghe "Improved Immunogenicity and Protective Efficacy of a Tuberculosis DNA Vaccine Encoding Ag85 by Protein Boosting" Infect. Immun. 69:3041-7 (2001).
Tanizawa et al. "The primary structure of thermostable D-amino acid aminotransferase from a thermophilic *Bacillus* species and its correlation with L-amino acid aminotransferases", J Biol Chem. Feb. 15, 1989;264(5):2450-4.
Tanizawa et al. "Thermostable alanine racemase from Bacillus stearothermophilus: DNA and protein sequence determination and secondary structure prediction", Biochemistry. Feb. 23, 1988;27(4):1311-6.
Taube, J. M. et al. Colocalization of Inflammatory Response with B7-H1 Expression in Human Melanocytic Lesions Supports an Adaptive Resistance Mechanism of Immune Escape, Sci Transl Med 4, 127ra37 (2012).
Teitelbaum R, Cammer M, Maitland ML, Freitag NE, Condeelis J., Bloom BR, Mycobacterial infection of macrophages results in membrane-permeable phagosomes, Proc. Natl. Acad. Sci. U.S.A, Dec. 21, 1999, 96(26):15190-5.
Terracciano et al. "Cytogenetic alterations in liver cell tumors as detected by Comparitive Genomic Hybridization", Pathologica 95:71-82 (2003).
Thompson et al. "Costimulatory B7-H1 in renal cell carcinoma patients: Indicator of tumor aggressiveness and potential therapeutic target" PNAS 101 (49); 17174-17179 (2004).

(56) References Cited

OTHER PUBLICATIONS

Thompson et al. "Overall Survival and PD-L1 Expression in Metastasized Malignant Melanoma" Cancer Res. 66:3381-3385 (2006).
Thompson et al. "Pathogenicity and immunogenicity of a Listeria monocytogenes strain that requires D-alanine for growth", Infect Immun. Aug. 1998;66(8):3552-61.
Thompson et al. "PD-1 is expressed by tumor infiltrating cells and is associated with poor outcome for patients with renal carcinoma" Clinical Cancer Research (2007) 15:1757-1761.
Tilney et al., 1989, "Actin filaments and the growth, momvement, and speard of the intracellular bacterial parasite, *Listeria monocytogenes*" J. Cell Biol., Oct.; 109(4 Pt 1):1597-608.
TopAlian et al., "Safety, Activity, and Immune Correlates of Anti-PD-1 Antibody in Cancer" New Eng. J Med. 366 (26): 2443-2454 (2012).
Triglia et al. "A procedure for in vitro amplification of DNA segments that lie outside the boundaries of known sequences", Nucleic Acids Res. Aug. 25, 1988;16(16):8186.
Ulmanen et al., "Transcription and translation of foreign genes in Bacillus Subtilis by the aid of a secretion vector" 1985, J. Bacteriol. 162:176-182.
Vasil et al., 1982, "Cloning of a phosphate-regulated hemolysin gene (phospholipase C) from Pseudomonas aeruginosa" J. Bacteriol. Oct.; 152(1):431-40.
Vaughan et al. Human Antibodies with Sub-nanomolar Affinities Isolated from a Large Non-immunized Phage Display Library, Nature Biotechnol. 14:309-314 (1996).
Vazquez et al. Differential regulation of la expression and antigen presentation by listeriolysin-producing versus non-producing strains of Listeria monocytogenes, J. Leukoc Biol. May 1996; 59(5):683-90.
Vazquez MA, Sicher SC, Proctor ML, Crowley JC, Lu CY, Differential regulation of la expression and antigen presentation by listeriolysin-producing versus non-producing strains of Listeria monocytogenes, J. Leukoc Biol. May 1996; 59(5):683-90.
Vazquez-Boland et al., 1992, "Nucleotide sequence of the lecithinase operon of Listeria monocytogenes and possible role of lecithinase in cell-to-cell spread" Infect. Immun. 60:219-230.
Verch et al., 2004, "Listeria monocytogenes-based antibiotic resistance gene-free antigen delivery system applicable to other bacterial vectors and DNA vaccines" Infect. Immun. Nov.; 72(1 1):6418-25.
Verma et al., 1995, "Delivery of class I and class II MHC-restricted T-cell epitopes of listeriolysin of listeria monocytogenes by attenuated *salmonella*", Vacine, vol. 13, No. 2, p. 142-150.
Villanueva MS, Sijts AJ, Pamer EG, Listeriolysin is processed efficiently into an MHC class I-associated epitope in Listeria monocytogenes-infected cells, J. Immunol. Dec. 1, 1995; 155(11):5227-33.
Vines A. et al., "Identfication and characterization of nucleotide sequence difference in three virulence-associate genes of listeria monocytogenes strains representing clinically important serotypes", Current Microbiology, May 1998, vol. 36, No. 5, pp. 309-318.
von Heijne "A new method for predicting signal sequence cleavage sites" (1986) Nucleic Acids Res. 14:4683-4690.
Von Heijne. Patterns of Amino Acids near Signal-Sequence Cleavage Sites Eur. J. Biochem. 133:17-21 (1983).
Wada, The Journal of the Japanese Orthopaedic Association, vol. 78(8), S950, English Translation.
Walker et al., 1994, "Tumor growth Alters T cell and macrophage production of and responsiveness to granulocyte-macrophage colony-stimulating factor: partial dysregulation through interleukin-10" Cell Immunol. 154(1):342-357.
Wallecha et al. "Multiple effector mechanisms induced by recombinant listeria monocytogenes anticancer immunotherapeutics", Advances in Applied Microbiology, vol. 66, 2009, pp. 1-27.
Wallecha et al., "Construction and characterization of an attenuated Listeria Monocytogenes strain for clinical use in cancer immunotherapy", Clinical and Vaccine Immunology, vol. 16, No. 1, Jan. 2009, pp. 96-103.
Ward et al., "Construction and characterisation of a series of multi-copy promoter-probe plasmid vectors for Streptomyces using the aminoglycoside phosphotransferase gene from Tn5 as indicator" 1986, Mol. Gen. Genet. 203:468-478.
Wasserman et al. "Catabolic alanine racemase from *Salmonella typhimurium*: DNA sequence, enzyme purification, and characterization", Biochemistry. Oct. 23, 1984;23(22):5182-7.
Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.
Weber "Assessing Tumor Response to Therapy" Nucl. Med. 50:1S-10S (2009).
Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.
Weidt et al., 1994, "CD8+ T lymphocyte-mediated antiviral immunity in mice as a result of injection of recombinant viral proteins", J. Immunol. Sep. 15; 153(6):2554-61.
Weiskirch LM, Paterson Y: "Listeria monocytogenes: a potent vaccine vector for neoplastic and infectious disease" Immunol. Rev., vol. 158, Aug. 1997, p. 159-169.
Welch M.D. et al., Jul. 3, 1998, "Interaction of Human Arp2/3 Complex and the Listeria monocytogenes ActA Protein in Actin Filament Nucleation" Science 281:105-108; pa-998020.
Wilson RL, White DW, Harty JT, Transient expression of bacterial gene fragments in eukaryotic cells: implications for CD8(+) T cell epitope analaysis, J. Immunol. Methods, Feb. 3, 2000; 234 (1-2):137-47.
Wipke et al. "Variable binding affinities of listeriolysin O peptides for the H-2Kd class I molecule", Eur J Immunol. Aug. 1993;23(8):2005-10.
Wirth et al., 1986, "Highly efficient protoplast transformation system for *Streptococcus faecalis* and a new *Escherichia coli*-S faecalis shuttle vector", J. Bacteriol. 165(3):831-6.
Wolff et. al. "Direct Gene Transfer into Mouse Muscle in Vivo", Science 247:1465(1990).
Wood et al. "Cancer immunotherapy using Listeria monocytogenes and listerial virulence factors" Immunol Res. ; 42(1-3):233-45. (2008).
Wootton et al. Statistics of Local Complexity in Amino Acid Sequences and Sequence Databases, Comput. Chem. 17:149-163 (1993).
Wright et al. "Lymphoid/Neuronal Cell Surface OX2 Glycoprotein Recognizes a Novel Receptor on Macrophages Implicated in the Control of Their Function ", (2000) Immunity 13:233-242.
Wu et al., "Engineering an itracellular pathway for major histrocompatibility complex class II presentation of antigens", Proc. Natl. Acad. Sci. USA, 1995, 92:11671-5.
Yamamoto et al., Listeriolysin O derived from Listeria monocytogenes inhibits the effector phase of an experimental allergic rhinitis induced by ovalbumin in mice:, Clin Exp Immunol. Jun. 2006;144(3):475-84.
Yang et al. "A Randomized Trial of Bevacizumab, an Anti-Vascular Endothelial Growth Factor Antibody, for Metastatic Renal Cancer " (2003) New Engl. J. Med. 349:427-434.
Young et al., 1992, "Tumor-derived cytokines induce bone marrow suppressor cells that mediate immunosuppression through transforming growth factor beta", Cancer Immunol. Immunother. 35(1):14-18.
Young et al., 1995, "Holins: form and function in bacteriophage lysis" FEMS Microbiol Rev., Aug.; 17 (1-2):191-205.
Zhang et al. "PowerBLAST: A New Network BLAST Application for Interactive or Automated Sequence Analysis and Annotation" (1997) Genome Res. 7:649-656.
Zhang et al., 1993, "Functional replacement of the hemolysin A transport signal by a different primary sequence" Proc. Natl. Acad. Sci. U.S.A May 1; 90(9):4211-5.
Zhao et al., "Pathogenecity and immunogenicity of a vaccine strain of Listeria monocytogenes that relies on a suicide plasmid to supply essential gene product", Infection and Immunity 2005, 73(9): 5789-5798.

(56) References Cited

OTHER PUBLICATIONS

Zwickey HL, Potter TA, "Peptide epitopes from noncytosolic Listeria monocytogenes can be presented by major histocompatibility complex class I molecules", Infect. Immun. May 1996; 64(5):1870-2.

Zwickey HL, Potter TA, Antigen secreted from noncytosolic Listeria monocytogenes is processed by the classical MHC class I processing pathway, J. Immunol. Jun. 1, 1999; 162(11):6341-50.

* cited by examiner

SEQUENCE LISTING

```
<160> NUMBER OF SEQ ID NOS: 60

<210> SEQ ID NO 1
<211> LENGTH: 32
<212> TYPE: PRT
<213> ORGANISM: Listeria monocytogenes

<400> SEQUENCE: 1
```

```
Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30


<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
1               5                   10


<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25


<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Pro Thr Asp
1               5                   10                  15

Glu Glu Leu Arg
            20


<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg


<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
1               5                   10                  15

Lys


<210> SEQ ID NO 7
<211> LENGTH: 17
<212> TYPE: PRT
<213> ORGANISM: Streptococcus equisimilis
```

<400> SEQUENCE: 7

```
Lys Gln Asn Thr Ala Asn Thr Glu Thr Thr Thr Thr Asn Glu Gln Pro
1               5                   10                  15

Lys
```

<210> SEQ ID NO 8
<211> LENGTH: 22
<212> TYPE: DNA
<213> ORGANISM: Artificial
<220> FEATURE:
<223> OTHER INFORMATION: chemically synthesized

<400> SEQUENCE: 8
ggctcgagca tggagataca cc 22

<210> SEQ ID NO 9
<211> LENGTH: 28
<212> TYPE: DNA
<213> ORGANISM: Artificial
<220> FEATURE:
<223> OTHER INFORMATION: chemically synthesized

<400> SEQUENCE: 9
ggggactagt ttatggtttc tgagaaca 28

<210> SEQ ID NO 10
<211> LENGTH: 31
<212> TYPE: DNA
<213> ORGANISM: Artificial
<220> FEATURE:
<223> OTHER INFORMATION: chemically synthesized

<400> SEQUENCE: 10
gggggctagc cctcctttga ttagtatatt c 31

<210> SEQ ID NO 11
<211> LENGTH: 28
<212> TYPE: DNA
<213> ORGANISM: Artificial
<220> FEATURE:
<223> OTHER INFORMATION: chemically synthesized

<400> SEQUENCE: 11
ctccctcgag atcataattt acttcatc 28

<210> SEQ ID NO 12
<211> LENGTH: 55
<212> TYPE: DNA
<213> ORGANISM: Artificial
<220> FEATURE:
<223> OTHER INFORMATION: chemically synthesized

<400> SEQUENCE: 12
gactacaagg acgatgaccg acaagtgata acccgggatc taaataaatc cgttt 55

<210> SEQ ID NO 13
<211> LENGTH: 27
<212> TYPE: DNA
<213> ORGANISM: Artificial
<220> FEATURE:
<223> OTHER INFORMATION: chemically synthesized

<400> SEQUENCE: 13
cccgtcgacc agctcttctt ggtgaag 27

<210> SEQ ID NO 14
<211> LENGTH: 100
<212> TYPE: PRT
<213> ORGANISM: Listeria monocytogenes

<400> SEQUENCE: 14

```
Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn
            100
```

<210> SEQ ID NO 15
<211> LENGTH: 390
<212> TYPE: PRT
<213> ORGANISM: Listeria monocytogenes

<400> SEQUENCE: 15

```
Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220
```

```
Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Glu Leu Asn
    370                 375                 380

Gly Arg Gly Gly Arg Pro
385                 390
```

<210> SEQ ID NO 16
<211> LENGTH: 1170
<212> TYPE: DNA
<213> ORGANISM: Listeria monocytogenes

<400> SEQUENCE: 16

```
atgcgtgcga tgatggtggt tttcattact gccaattgca ttacgattaa ccccgacata      60

atatttgcag cgacagatag cgaagattct agtctaaaca cagatgaatg ggaagaagaa     120

aaaacagaag agcaaccaag cgaggtaaat acgggaccaa gatacgaaac tgcacgtgaa     180

gtaagttcac gtgatattaa agaactagaa aaatcgaata aagtgagaaa tacgaacaaa     240

gcagacctaa tagcaatgtt gaaagaaaaa gcagaaaaag gtccaaatat caataataac     300

aacagtgaac aaactgagaa tgcggctata aatgaagagg cttcaggagc cgaccgacca     360

gctatacaag tggagcgtcg tcatccagga ttgccatcgg atagcgcagc ggaaattaaa     420

aaaagaagga aagccatagc atcatcggat agtgagcttg aaagccttac ttatccggat     480

aaaccaacaa aagtaaataa gaaaaaagtg gcgaaagagt cagttgcgga tgcttctgaa     540

agtgacttag attctagcat gcagtcagca gatgagtctt caccacaacc tttaaaagca     600

aaccaacaac catttttccc taaagtattt aaaaaaataa aagatgcggg gaaatgggta     660

cgtgataaaa tcgacgaaaa tcctgaagta aagaaagcga ttgttgataa aagtgcaggg     720

ttaattgacc aattattaac caaaaagaaa agtgaagagg taaatgcttc ggacttcccg     780

ccaccaccta cggatgaaga gttaagactt gctttgccag agacaccaat gcttcttggt     840

tttaatgctc ctgctacatc agaaccgagc tcattcgaat ttccaccacc acctacggat     900

gaagagttaa gacttgcttt gccagagacg ccaatgcttc ttggttttaa tgctcctgct     960

acatcggaac cgagctcgtt cgaatttcca ccgcctccaa cagaagatga actagaaatc    1020

atccgggaaa cagcatcctc gctagattct agttttacaa gaggggattt agctagtttg    1080

agaaatgcta ttaatcgcca tagtcaaaat ttctctgatt tcccaccaat cccaacagaa    1140
```

gaagagttga acgggagagg cggtagacca 1170

<210> SEQ ID NO 17
<211> LENGTH: 529
<212> TYPE: PRT
<213> ORGANISM: Listeria monocytogenes

<400> SEQUENCE: 17

Met Lys Lys Ile Met Leu Val Phe Ile Thr Leu Ile Leu Val Ser Leu
1 5 10 15

Pro Ile Ala Gln Gln Thr Glu Ala Lys Asp Ala Ser Ala Phe Asn Lys
20 25 30

Glu Asn Ser Ile Ser Ser Met Ala Pro Pro Ala Ser Pro Pro Ala Ser
35 40 45

Pro Lys Thr Pro Ile Glu Lys Lys His Ala Asp Glu Ile Asp Lys Tyr
50 55 60

Ile Gln Gly Leu Asp Tyr Asn Lys Asn Asn Val Leu Val Tyr His Gly
65 70 75 80

Asp Ala Val Thr Asn Val Pro Pro Arg Lys Gly Tyr Lys Asp Gly Asn
85 90 95

Glu Tyr Ile Val Val Glu Lys Lys Lys Lys Ser Ile Asn Gln Asn Asn
100 105 110

Ala Asp Ile Gln Val Val Asn Ala Ile Ser Ser Leu Thr Tyr Pro Gly
115 120 125

Ala Leu Val Lys Ala Asn Ser Glu Leu Val Glu Asn Gln Pro Asp Val
130 135 140

Leu Pro Val Lys Arg Asp Ser Leu Thr Leu Ser Ile Asp Leu Pro Gly
145 150 155 160

Met Thr Asn Gln Asp Asn Lys Ile Val Val Lys Asn Ala Thr Lys Ser
165 170 175

Asn Val Asn Asn Ala Val Asn Thr Leu Val Glu Arg Trp Asn Glu Lys
180 185 190

Tyr Ala Gln Ala Tyr Pro Asn Val Ser Ala Lys Ile Asp Tyr Asp Asp
195 200 205

Glu Met Ala Tyr Ser Glu Ser Gln Leu Ile Ala Lys Phe Gly Thr Ala
210 215 220

Phe Lys Ala Val Asn Asn Ser Leu Asn Val Asn Phe Gly Ala Ile Ser
225 230 235 240

Glu Gly Lys Met Gln Glu Glu Val Ile Ser Phe Lys Gln Ile Tyr Tyr
245 250 255

Asn Val Asn Val Asn Glu Pro Thr Arg Pro Ser Arg Phe Phe Gly Lys
260 265 270

Ala Val Thr Lys Glu Gln Leu Gln Ala Leu Gly Val Asn Ala Glu Asn
275 280 285

Pro Pro Ala Tyr Ile Ser Ser Val Ala Tyr Gly Arg Gln Val Tyr Leu
290 295 300

Lys Leu Ser Thr Asn Ser His Ser Thr Lys Val Lys Ala Ala Phe Asp
305 310 315 320

Ala Ala Val Ser Gly Lys Ser Val Ser Gly Asp Val Glu Leu Thr Asn
325 330 335

Ile Ile Lys Asn Ser Ser Phe Lys Ala Val Ile Tyr Gly Gly Ser Ala
340 345 350

Lys Asp Glu Val Gln Ile Ile Asp Gly Asn Leu Gly Asp Leu Arg Asp
355 360 365

```
Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu


<210> SEQ ID NO 18
<211> LENGTH: 441
<212> TYPE: PRT
<213> ORGANISM: Listeria monocytogenes

<400> SEQUENCE: 18

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205
```

```
Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
            245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440


<210> SEQ ID NO 19
<211> LENGTH: 416
<212> TYPE: PRT
<213> ORGANISM: Listeria monocytogenes

<400> SEQUENCE: 19

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
```

```
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415


<210> SEQ ID NO 20
<211> LENGTH: 19
<212> TYPE: PRT
<213> ORGANISM: Listeria seeligeri

<400> SEQUENCE: 20

Arg Ser Glu Val Thr Ile Ser Pro Ala Glu Thr Pro Glu Ser Pro Pro
1               5                   10                  15

Ala Thr Pro


<210> SEQ ID NO 21
<211> LENGTH: 19
<212> TYPE: PRT
<213> ORGANISM: Listeria monocytogenes

<400> SEQUENCE: 21

Lys Glu Asn Ser Ile Ser Ser Met Ala Pro Pro Ala Ser Pro Pro Ala
1               5                   10                  15

Ser Pro Lys
```

<210> SEQ ID NO 22
<211> LENGTH: 25
<212> TYPE: DNA
<213> ORGANISM: Artificial
<220> FEATURE:
<223> OTHER INFORMATION: chemically synthesized

<400> SEQUENCE: 22
gcggatccca tggagataca cctac 25

<210> SEQ ID NO 23
<211> LENGTH: 25
<212> TYPE: DNA
<213> ORGANISM: Artificial
<220> FEATURE:
<223> OTHER INFORMATION: chemically synthesized

<400> SEQUENCE: 23
gcggatccca tggagataca cctac 25

<210> SEQ ID NO 24
<211> LENGTH: 9
<212> TYPE: PRT
<213> ORGANISM: Human papillomavirus

<400> SEQUENCE: 24

```
Arg Ala His Tyr Asn Ile Val Thr Phe
1               5
```

<210> SEQ ID NO 25
<211> LENGTH: 261
<212> TYPE: PRT
<213> ORGANISM: Homo sapiens

<400> SEQUENCE: 25

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190
```

```
Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260
```

<210> SEQ ID NO 26
<211> LENGTH: 5873
<212> TYPE: DNA
<213> ORGANISM: Homo sapiens

<400> SEQUENCE: 26

```
ggtgtcttag gcacactggt cttggagtgc aaaggatcta ggcacgtgag gctttgtatg     60

aagaatcggg gatcgtaccc accccctgtt tctgtttcat cctgggcatg tctcctctgc    120

ctttgtcccc tagatgaagt ctccatgagc tacaagggcc tggtgcatcc agggtgatct    180

agtaattgca gaacagcaag tgctagctct ccctcccctt ccacagctct gggtgtggga    240

gggggttgtc cagcctccag cagcatgggg agggccttgg tcagcctctg ggtgccagca    300

gggcaggggc ggagtcctgg ggaatgaagg ttttataggg ctcctggggg aggctcccca    360

gccccaagct taccacctgc acccggagag ctgtgtcacc atgtgggtcc cggttgtctt    420

cctcaccctg tccgtgacgt ggattggtga gaggggccat ggttgggggg atgcaggaga    480

gggagccagc cctgactgtc aagctgaggc tctttccccc ccaacccagc accccagccc    540

agacagggag ctgggctctt ttctgtctct cccagcccca cttcaagccc ataccccccag    600

tcccctccat attgcaacag tcctcactcc cacaccaggt ccccgctccc tcccacttac    660

cccagaactt tcttcccatt tgcccagcca gctccctgct cccagctgct ttactaaagg    720

ggaagttcct gggcatctcc gtgtttctct ttgtggggct caaaacctcc aaggacctct    780

ctcaatgcca ttggttcctt ggaccgtatc actggtccat ctcctgagcc cctcaatcct    840

atcacagtct actgactttt cccattcagc tgtgagtgtc caaccctatc ccagagacct    900

tgatgcttgg cctcccaatc ttgccctagg atacccagat gccaaccaga cacctccttc    960

tttcctagcc aggctatctg gcctgagaca acaaatgggt ccctcagtct ggcaatggga   1020

ctctgagaac tcctcattcc ctgactctta gccccagact cttcattcag tggcccacat   1080

tttccttagg aaaaacatga gcatccccag ccacaactgc cagctctctg agtccccaaa   1140

tctgcatcct tttcaaaacc taaaaacaaa aagaaaaaca aataaaacaa aaccaactca   1200

gaccagaact gttttctcaa cctgggactt cctaaacttt ccaaaacctt cctcttccag   1260

caactgaacc tcgccataag gcacttatcc ctggttccta gcacccctta tcccctcaga   1320

atccacaact tgtaccaagt ttcccttctc ccagtccaag accccaaatc accacaaagg   1380

acccaatccc cagactcaag atatggtctg ggcgctgtct tgtgtctcct accctgatcc   1440

ctgggttcaa ctctgctccc agagcatgaa gcctctccac cagcaccagc caccaacctg   1500

caaacctagg gaagattgac agaattccca gcctttccca gctcccccctg cccatgtccc   1560

aggactccca gccttggttc tctgcccccg tgtcttttca aacccacatc ctaaatccat   1620

ctcctatccg agtcccccag ttccccctgt caaccctgat tcccctgatc tagcaccccc   1680
```

```
tctgcaggcg ctgcgcccct catcctgtct cggattgtgg gaggctggga gtgcgagaag   1740
cattcccaac cctggcaggt gcttgtggcc tctcgtggca gggcagtctg cggcggtgtt   1800
ctggtgcacc cccagtgggt cctcacagct gcccactgca tcaggaagtg agtaggggcc   1860
tggggtctgg ggagcaggtg tctgtgtccc agaggaataa cagctgggca ttttccccag   1920
gataacctct aaggccagcc ttgggactgg gggagagagg gaaagttctg gttcaggtca   1980
catggggagg cagggttggg gctggaccac cctccccatg gctgcctggg tctccatctg   2040
tgtccctcta tgtctctttg tgtcgctttc attatgtctc ttggtaactg gcttcggttg   2100
tgtctctccg tgtgactatt ttgttctctc tctccctctc ttctctgtct tcagtctcca   2160
tatctccccc tctctctgtc cttctctggt ccctctctag ccagtgtgtc tcaccctgta   2220
tctctctgcc aggctctgtc tctcggtctc tgtctcacct gtgccttctc cctactgaac   2280
acacgcacgg gatgggcctg ggggaccctg agaaaaggaa gggctttggc tgggcgcggt   2340
ggctcacacc tgtaatccca gcactttggg aggccaaggc aggtagatca cctgaggtca   2400
ggagttcgag accagcctgg ccaactggtg aaaccccatc tctactaaaa atacaaaaaa   2460
ttagccaggc gtggtggcgc atgcctgtag tcccagctac tcaggagctg agggaggaga   2520
attgcattga acctggaggt tgaggttgca gtgagccgag accgtgccac tgcactccag   2580
cctgggtgac agagtgagac tccgcctcaa aaaaaaaaaa aaaaaaaaaa aaaaaaaaga   2640
aaagaaaaga aaagaaaagg aagtgtttta tccctgatgt gtgtgggtat gagggtatga   2700
gagggcccct ctcactccat tccttctcca ggacatccct ccactcttgg gagacacaga   2760
gaagggctgg ttccagctgg agctgggagg ggcaattgag ggaggaggaa ggagaagggg   2820
gaaggaaaac agggtatggg ggaaaggacc ctggggagcg aagtggagga tacaaccttg   2880
ggcctgcagg caggctacct acccacttgg aaacccacgc caaagccgca tctacagctg   2940
agccactctg aggcctcccc tccccggcgg tccccactca gctccaaagt ctctctccct   3000
tttctctccc acactttatc atcccccgga ttcctctcta cttggttctc attcttcctt   3060
tgacttcctg cttccctttc tcattcatct gtttctcact ttctgcctgg ttttgttctt   3120
ctctctctct ttctctggcc catgtctgtt tctctatgtt tctgtctttt ctttctcatc   3180
ctgtgtattt tcggctcacc ttgtttgtca ctgttctccc ctctgccctt tcattctctc   3240
tgccctttta ccctcttcct tttcccttgg ttctctcagt tctgtatctg cccttcaccc   3300
tctcacactg ctgtttccca actcgttgtc tgtattttgg cctgaactgt gtcttcccaa   3360
ccctgtgttt tctcactgtt tctttttctc ttttggagcc tcctccttgc tcctctgtcc   3420
cttctctctt tccttatcat cctcgctcct cattcctgcg tctgcttcct ccccagcaaa   3480
agcgtgatct tgctgggtcg gcacagcctg tttcatcctg aagacacagg ccaggtattt   3540
caggtcagcc acagcttccc acacccgctc tacgatatga gcctcctgaa gaatcgattc   3600
ctcaggccag gtgatgactc cagccacgac ctcatgctgc tccgcctgtc agagcctgcc   3660
gagctcacgg atgctgtgaa ggtcatggac ctgcccaccc aggagccagc actggggacc   3720
acctgctacg cctcaggctg gggcagcatt gaaccagagg agtgtacgcc tgggccagat   3780
ggtgcagccg ggagcccaga tgcctgggtc tgagggagga ggggacagga ctcctgggtc   3840
tgagggagga gggccaagga accaggtggg gtccagccca caacagtgtt tttgcctggc   3900
ccgtagtctt gaccccaaag aaacttcagt gtgtggacct ccatgttatt tccaatgacg   3960
tgtgtgcgca agttcaccct cagaaggtga ccaagttcat gctgtgtgct ggacgctgga   4020
cagggggcaa aagcacctgc tcggtgagtc atccctactc ccaagatctt gagggaaagg   4080
```

```
tgagtgggac cttaattctg ggctggggtc tagaagccaa caaggcgtct gcctcccctg   4140

ctccccagct gtagccatgc cacctccccg tgtctcatct cattccctcc ttccctcttc   4200

tttgactccc tcaaggcaat aggttattct tacagcacaa ctcatctgtt cctgcgttca   4260

gcacacggtt actaggcacc tgctatgcac ccagcactgc cctagagcct gggacatagc   4320

agtgaacaga cagagagcag cccctccctt ctgtagcccc caagccagtg aggggcacag   4380

gcaggaacag ggaccacaac acagaaaagc tggagggtgt caggaggtga tcaggctctc   4440

ggggagggag aaggggtggg gagtgtgact gggaggagac atcctgcaga aggtgggagt   4500

gagcaaacac ctgcgcaggg gaggggaggg cctgcggcac ctgggggagc agagggaaca   4560

gcatctggcc aggcctggga ggaggggcct agagggcgtc aggagcagag aggaggttgc   4620

ctggctggag tgaaggatcg gggcagggtg cgagagggaa caaaggaccc ctcctgcagg   4680

gcctcacctg ggccacagga ggacactgct tttcctctga ggagtcagga actgtggatg   4740

gtgctggaca gaagcaggac agggcctggc tcaggtgtcc agaggctgcg ctggcctcct   4800

atgggatcag actgcaggga gggagggcag cagggatgtg gagggagtga tgatggggct   4860

gacctggggg tggctccagg cattgtcccc acctgggccc ttacccagcc tccctcacag   4920

gctcctggcc ctcagtctct cccctccact ccattctcca cctacccaca gtgggtcatt   4980

ctgatcaccg aactgaccat gccagccctg ccgatggtcc tccatggctc cctagtgccc   5040

tggagaggag gtgtctagtc agagagtagt cctggaaggt ggcctctgtg aggagccacg   5100

gggacagcat cctgcagatg gtcctggccc ttgtcccacc gacctgtcta caaggactgt   5160

cctcgtggac cctcccctct gcacaggagc tggaccctga agtcccttcc taccggccag   5220

gactggagcc cctacccctc tgttggaatc cctgcccacc ttcttctgga agtcggctct   5280

ggagacattt ctctcttctt ccaaagctgg gaactgctat ctgttatctg cctgtccagg   5340

tctgaaagat aggattgccc aggcagaaac tgggactgac ctatctcact ctctccctgc   5400

ttttaccctt agggtgattc tgggggccca cttgtctgta atggtgtgct tcaaggtatc   5460

acgtcatggg gcagtgaacc atgtgccctg cccgaaaggc cttccctgta caccaaggtg   5520

gtgcattacc ggaagtggat caaggacacc atcgtggcca acccctgagc acccctatca   5580

agtccctatt gtagtaaact tggaaccttg gaaatgacca ggccaagact caagcctccc   5640

cagttctact gacctttgtc cttaggtgtg aggtccaggg ttgctaggaa aagaaatcag   5700

cagacacagg tgtagaccag agtgtttctt aaatggtgta attttgtcct ctctgtgtcc   5760

tggggaatac tggccatgcc tggagacata tcactcaatt tctctgagga cacagttagg   5820

atggggtgtc tgtgttattt gtgggataca gagatgaaag aggggtggga tcc          5873
```

```
<210> SEQ ID NO 27
<211> LENGTH: 238
<212> TYPE: PRT
<213> ORGANISM: Homo sapiens

<400> SEQUENCE: 27

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
```

```
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Trp Val Ile Leu Ile Thr Glu Leu Thr Met Pro Ala Leu Pro
    210                 215                 220

Met Val Leu His Gly Ser Leu Val Pro Trp Arg Gly Gly Val
225                 230                 235


<210> SEQ ID NO 28
<211> LENGTH: 1906
<212> TYPE: DNA
<213> ORGANISM: Homo sapiens

<400> SEQUENCE: 28

agccccaagc ttaccacctg cacccggaga gctgtgtcac catgtgggtc ccggttgtct     60

tcctcaccct gtccgtgacg tggattggtg ctgcacccct catcctgtct cggattgtgg    120

gaggctggga gtgcgagaag cattcccaac cctggcaggt gcttgtggcc tctcgtggca    180

gggcagtctg cggcggtgtt ctggtgcacc cccagtgggt cctcacagct gcccactgca    240

tcaggaacaa aagcgtgatc ttgctgggtc ggcacagcct gtttcatcct gaagacacag    300

gccaggtatt tcaggtcagc cacagcttcc cacacccgct ctacgatatg agcctcctga    360

agaatcgatt cctcaggcca ggtgatgact ccagccacga cctcatgctg ctccgcctgt    420

cagagcctgc cgagctcacg gatgctgtga aggtcatgga cctgcccacc caggagccag    480

cactggggac cacctgctac gcctcaggct ggggcagcat tgaaccagag gagttcttga    540

ccccaaagaa acttcagtgt gtggacctcc atgttatttc caatgacgtg tgtgcgcaag    600

ttcaccctca gaaggtgacc aagttcatgc tgtgtgctgg acgctggaca gggggcaaaa    660

gcacctgctc gtgggtcatt ctgatcaccg aactgaccat gccagccctg ccgatggtcc    720

tccatggctc cctagtgccc tggagaggag gtgtctagtc agagagtagt cctggaaggt    780

ggcctctgtg aggagccacg gggacagcat cctgcagatg gtcctggccc ttgtcccacc    840

gacctgtcta caaggactgt cctcgtggac cctcccctct gcacaggagc tggaccctga    900

agtcccttcc ccaccggcca ggactggagc ccctacccct ctgttggaat ccctgcccac    960

cttcttctgg aagtcggctc tggagacatt tctctcttct tccaaagctg ggaactgcta   1020

tctgttatct gcctgtccag gtctgaaaga taggattgcc caggcagaaa ctggactga   1080
```

```
cctatctcac tctctccctg cttttaccct tagggtgatt ctgggggccc acttgtctgt   1140

aatggtgtgc ttcaaggtat cacgtcatgg ggcagtgaac catgtgccct gcccgaaagg   1200

ccttccctgt acaccaaggt ggtgcattac cggaagtgga tcaaggacac catcgtggcc   1260

aacccctgag cacccctatc aacccctat tgtagtaaac ttggaacctt ggaaatgacc   1320

aggccaagac tcaagcctcc ccagttctac tgacctttgt ccttaggtgt gaggtccagg   1380

gttgctagga aaagaaatca gcagacacag gtgtagacca gagtgtttct taaatggtgt   1440

aattttgtcc tctctgtgtc ctggggaata ctggccatgc ctggagacat atcactcaat   1500

ttctctgagg acacagatag gatggggtgt ctgtgttatt tgtggggtac agagatgaaa   1560

gaggggtggg atccacactg agagagtgga gagtgacatg tgctggacac tgtccatgaa   1620

gcactgagca gaagctggag gcacaacgca ccagacactc acagcaagga tggagctgaa   1680

aacataaccc actctgtcct ggaggcactg ggaagcctag agaaggctgt gagccaagga   1740

gggagggtct tcctttggca tgggatgggg atgaagtaag gagagggact ggacccctg    1800

gaagctgatt cactatgggg ggaggtgtat tgaagtcctc cagacaaccc tcagatttga   1860

tgatttccta gtagaactca cagaaataaa gagctgttat actgtg                  1906
```

<210> SEQ ID NO 29
<211> LENGTH: 69
<212> TYPE: PRT
<213> ORGANISM: Homo sapiens

<400> SEQUENCE: 29

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65
```

<210> SEQ ID NO 30
<211> LENGTH: 220
<212> TYPE: PRT
<213> ORGANISM: Homo sapiens

<400> SEQUENCE: 30

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110
```

```
Pro Gly Asp Asp Ser Ser Ile Glu Pro Glu Glu Phe Leu Thr Pro Lys
        115                 120                 125

Lys Leu Gln Cys Val Asp Leu His Val Ile Ser Asn Asp Val Cys Ala
    130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

Cys Ala Leu Pro Glu Arg Pro Ser Leu Tyr Thr Lys Val Val His Tyr
        195                 200                 205

Arg Lys Trp Ile Lys Asp Thr Ile Val Ala Asn Pro
    210                 215                 220


<210> SEQ ID NO 31
<211> LENGTH: 218
<212> TYPE: PRT
<213> ORGANISM: Homo sapiens

<400> SEQUENCE: 31

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys Pro Gly Asp Asp Ser Ser His Asp Leu Met Leu
65                  70                  75                  80

Leu Arg Leu Ser Glu Pro Ala Glu Leu Thr Asp Ala Val Lys Val Met
                85                  90                  95

Asp Leu Pro Thr Gln Glu Pro Ala Leu Gly Thr Thr Cys Tyr Ala Ser
            100                 105                 110

Gly Trp Gly Ser Ile Glu Pro Glu Glu Phe Leu Thr Pro Lys Lys Leu
        115                 120                 125

Gln Cys Val Asp Leu His Val Ile Ser Asn Asp Val Cys Ala Gln Val
    130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
    210                 215


<210> SEQ ID NO 32
<211> LENGTH: 261
<212> TYPE: PRT
<213> ORGANISM: Homo sapiens

<400> SEQUENCE: 32
```

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260
```

<210> SEQ ID NO 33
<211> LENGTH: 1464
<212> TYPE: DNA
<213> ORGANISM: Homo sapiens

<400> SEQUENCE: 33

```
agccccaagc ttaccacctg cacccggaga gctgtgtcac catgtgggtc ccggttgtct      60

tcctcaccct gtccgtgacg tggattggtg ctgcacccct catcctgtct cggattgtgg     120

gaggctggga gtgcgagaag cattcccaac cctggcaggt gcttgtggcc tctcgtggca     180

gggcagtctg cggcggtgtt ctggtgcacc cccagtgggt cctcacagct gcccactgca     240

tcaggaacaa aagcgtgatc ttgctgggtc ggcacagcct gtttcatcct gaagacacag     300

gccaggtatt tcaggtcagc cacagcttcc cacacccgct ctacgatatg agcctcctga     360

agaatcgatt cctcaggcca ggtgatgact ccagccacga cctcatgctg ctccgcctgt     420

cagagcctgc cgagctcacg gatgctgtga aggtcatgga cctgcccacc caggagccag     480

cactggggac cacctgctac gcctcaggct ggggcagcat tgaaccagag gagttcttga     540

ccccaaagaa acttcagtgt gtggacctcc atgttatttc caatgacgtg tgtgcgcaag     600
```

```
ttcaccctca gaaggtgacc aagttcatgc tgtgtgctgg acgctggaca gggggcaaaa    660

gcacctgctc gggtgattct gggggcccac ttgtctgtaa tggtgtgctt caaggtatca    720

cgtcatgggg cagtgaacca tgtgccctgc ccgaaaggcc ttccctgtac accaaggtgg    780

tgcattaccg gaagtggatc aaggacacca tcgtggccaa cccctgagca cccctatcaa    840

ccccctattg tagtaaactt ggaaccttgg aaatgaccag gccaagactc aagcctcccc    900

agttctactg acctttgtcc ttaggtgtga ggtccagggt tgctaggaaa agaaatcagc    960

agacacaggt gtagaccaga gtgtttctta aatggtgtaa ttttgtcctc tctgtgtcct   1020

ggggaatact ggccatgcct ggagacatat cactcaattt ctctgaggac acagatagga   1080

tggggtgtct gtgttatttg tggggtacag agatgaaaga ggggtgggat ccacactgag   1140

agagtggaga gtgacatgtg ctggacactg tccatgaagc actgagcaga agctggaggc   1200

acaacgcacc agacactcac agcaaggatg gagctgaaaa cataacccac tctgtcctgg   1260

aggcactggg aagcctagag aaggctgtga gccaaggagg gagggtcttc ctttggcatg   1320

ggatggggat gaagtaagga gagggactgg accccctgga agctgattca ctatgggggg   1380

aggtgtattg aagtcctcca gacaaccctc agatttgatg atttcctagt agaactcaca   1440

gaaataaaga gctgttatac tgtg                                          1464
```

```
<210> SEQ ID NO 34
<211> LENGTH: 261
<212> TYPE: PRT
<213> ORGANISM: Homo sapiens

<400> SEQUENCE: 34

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
```

```
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260


<210> SEQ ID NO 35
<211> LENGTH: 1495
<212> TYPE: DNA
<213> ORGANISM: Homo sapiens

<400> SEQUENCE: 35

gggggagccc caagcttacc acctgcaccc ggagagctgt gtcaccatgt gggtcccggt      60

tgtcttcctc accctgtccg tgacgtggat tggtgctgca cccctcatcc tgtctcggat     120

tgtgggaggc tgggagtgcg agaagcattc ccaaccctgg caggtgcttg tggcctctcg     180

tggcagggca gtctgcggcg gtgttctggt gcacccccag tgggtcctca cagctgccca     240

ctgcatcagg aacaaaagcg tgatcttgct gggtcggcac agcctgtttc atcctgaaga     300

cacaggccag gtatttcagg tcagccacag cttcccacac ccgctctacg atatgagcct     360

cctgaagaat cgattcctca ggccaggtga tgactccagc cacgacctca tgctgctccg     420

cctgtcagag cctgccgagc tcacggatgc tgtgaaggtc atggacctgc ccacccagga     480

gccagcactg gggaccacct gctacgcctc aggctggggc agcattgaac cagaggagtt     540

cttgacccca aagaaacttc agtgtgtgga cctccatgtt atttccaatg acgtgtgtgc     600

gcaagttcac cctcagaagg tgaccaagtt catgctgtgt gctggacgct ggacaggggg     660

caaaagcacc tgctcgggtg attctggggg cccacttgtc tgtaatggtg tgcttcaagg     720

tatcacgtca tggggcagtg aaccatgtgc cctgcccgaa aggccttccc tgtacaccaa     780

ggtggtgcat taccggaagt ggatcaagga caccatcgtg gccaacccct gagcacccct     840

atcaactccc tattgtagta aacttggaac cttggaaatg accaggccaa gactcaggcc     900

tccccagttc tactgacctt tgtccttagg tgtgaggtcc agggttgcta ggaaaagaaa     960

tcagcagaca caggtgtaga ccagagtgtt tcttaaatgg tgtaattttg tcctctctgt    1020

gtcctgggga atactggcca tgcctggaga catatcactc aatttctctg aggacacaga    1080

taggatgggg tgtctgtgtt atttgtgggg tacagagatg aaagaggggt gggatccaca    1140

ctgagagagt ggagagtgac atgtgctgga cactgtccat gaagcactga gcagaagctg    1200

gaggcacaac gcaccagaca ctcacagcaa ggatggagct gaaaacataa cccactctgt    1260

cctggaggca ctgggaagcc tagagaaggc tgtgagccaa ggagggaggg tcttcctttg    1320

gcatgggatg ggatgaagt agggagaggg actggacccc ctggaagctg attcactatg    1380

gggggaggtg tattgaagtc ctccagacaa ccctcagatt tgatgatttc ctagtagaac    1440

tcacagaaat aaagagctgt tatactgcga aaaaaaaaaa aaaaaaaaaa aaaaa         1495


<210> SEQ ID NO 36
<211> LENGTH: 218
<212> TYPE: PRT
<213> ORGANISM: Homo sapiens

<400> SEQUENCE: 36

Met Trp Val Pro Val Val Phe Leu Thr Leu Ser Val Thr Trp Ile Gly
1               5                   10                  15
```

```
Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser Ile Glu Pro Glu Glu Phe Leu Thr Pro Lys
        115                 120                 125

Lys Leu Gln Cys Val Asp Leu His Val Ile Ser Asn Asp Val Cys Ala
    130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

Cys Ala Leu Pro Glu Arg Pro Ser Leu Tyr Thr Lys Val Val His Tyr
        195                 200                 205

Arg Lys Trp Ile Lys Asp Thr Ile Val Ala
    210                 215


<210> SEQ ID NO 37
<211> LENGTH: 227
<212> TYPE: PRT
<213> ORGANISM: Homo sapiens

<400> SEQUENCE: 37

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
```

```
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Val Ser His Pro Tyr Ser Gln Asp Leu Glu Gly Lys Gly Glu
    210                 215                 220

Trp Gly Pro
225


<210> SEQ ID NO 38
<211> LENGTH: 104
<212> TYPE: PRT
<213> ORGANISM: Homo sapiens

<400> SEQUENCE: 38

Met Trp Val Pro Val Val Phe Leu Thr Leu Ser Val Thr Trp Ile Gly
1               5                   10                  15

Glu Arg Gly His Gly Trp Gly Asp Ala Gly Glu Gly Ala Ser Pro Asp
            20                  25                  30

Cys Gln Ala Glu Ala Leu Ser Pro Pro Thr Gln His Pro Ser Pro Asp
        35                  40                  45

Arg Glu Leu Gly Ser Phe Leu Ser Leu Pro Ala Pro Leu Gln Ala His
    50                  55                  60

Thr Pro Ser Pro Ser Ile Leu Gln Gln Ser Ser Leu Pro His Gln Val
65                  70                  75                  80

Pro Ala Pro Ser His Leu Pro Gln Asn Phe Leu Pro Ile Ala Gln Pro
                85                  90                  95

Ala Pro Cys Ser Gln Leu Leu Tyr
            100


<210> SEQ ID NO 39
<211> LENGTH: 261
<212> TYPE: PRT
<213> ORGANISM: Homo sapiens

<400> SEQUENCE: 39

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
```

```
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260


<210> SEQ ID NO 40
<211> LENGTH: 1729
<212> TYPE: DNA
<213> ORGANISM: Homo sapiens

<400> SEQUENCE: 40

aagtttccct tctcccagtc caagacccca aatcaccaca aaggacccaa tccccagact     60

caagatatgg tctgggcgct gtcttgtgtc tcctaccctg atccctgggt tcaactctgc    120

tcccagagca tgaagcctct ccaccagcac cagccaccaa cctgcaaacc tagggaagat    180

tgacagaatt cccagccttt cccagctccc cctgcccatg tcccaggact cccagccttg    240

gttctctgcc cccgtgtctt ttcaaaccca catcctaaat ccatctccta tccgagtccc    300

ccagttcctc ctgtcaaccc tgattcccct gatctagcac cccctctgca ggtgctgcac    360

ccctcatcct gtctcggatt gtgggaggct gggagtgcga gaagcattcc caaccctggc    420

aggtgcttgt agcctctcgt ggcagggcag tctgcggcgg tgttctggtg cacccccagt    480

gggtcctcac agctacccac tgcatcagga acaaaagcgt gatcttgctg ggtcggcaca    540

gcctgtttca tcctgaagac acaggccagg tatttcaggt cagccacagc ttcccacacc    600

cgctctacga tatgagcctc ctgaagaatc gattcctcag gccaggtgat gactccagcc    660

acgacctcat gctgctccgc ctgtcagagc ctgccgagct cacggatgct atgaaggtca    720

tggacctgcc cacccaggag ccagcactgg ggaccacctg ctacgcctca ggctggggca    780

gcattgaacc agaggagttc ttgaccccaa agaaacttca gtgtgtggac ctccatgtta    840

tttccaatga cgtgtgtgcg caagttcacc ctcagaaggt gaccaagttc atgctgtgtg    900

ctggacgctg gacagggggc aaaagcacct gctcgggtga ttctgggggc ccacttgtct    960

gtaatggtgt gcttcaaggt atcacgtcat ggggcagtga accatgtgcc ctgcccgaaa   1020

ggccttccct gtacaccaag gtggtgcatt accggaagtg gatcaaggac accatcgtgg   1080

ccaacccctg agcaccccta tcaactccct attgtagtaa acttggaacc ttggaaatga   1140

ccaggccaag actcaggcct ccccagttct actgaccttt gtccttaggt gtgaggtcca   1200

gggttgctag gaaaagaaat cagcagacac aggtgtagac cagagtgttt cttaaatggt   1260

gtaattttgt cctctctgtg tcctggggaa tactggccat gcctggagac atatcactca   1320

atttctctga ggacacagat aggatggggt gtctgtgtta tttgtggggt acagagatga   1380

aagaggggtg ggatccacac tgagagagtg gagagtgaca tgtgctggac actgtccatg   1440
```

```
aagcactgag cagaagctgg aggcacaacg caccagacac tcacagcaag gatggagctg   1500

aaaacataac ccactctgtc ctggaggcac tgggaagcct agagaaggct gtgaaccaag   1560

gagggagggt cttcctttgg catgggatgg ggatgaagta aggagaggga ctgacccccct  1620

ggaagctgat tcactatggg gggaggtgta ttgaagtcct ccagacaacc ctcagatttg   1680

atgatttcct agtagaactc acagaaataa agagctgtta tactgtgaa               1729


<210> SEQ ID NO 41
<211> LENGTH: 719
<212> TYPE: PRT
<213> ORGANISM: Homo sapiens

<400> SEQUENCE: 41

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
```

```
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Lys His Val Ile Tyr Ala Pro Ser Ser His Asn Lys Tyr Ala Gly Glu
            660                 665                 670

Ser Phe Pro Gly Ile Tyr Asp Ala Leu Phe Asp Ile Glu Ser Lys Val
        675                 680                 685

Asp Pro Ser Lys Ala Trp Gly Glu Val Lys Arg Gln Ile Tyr Val Ala
    690                 695                 700

Ala Phe Thr Val Gln Ala Ala Ala Glu Thr Leu Ser Glu Val Ala
705                 710                 715
```

<210> SEQ ID NO 42
<211> LENGTH: 2472
<212> TYPE: DNA
<213> ORGANISM: Homo sapiens

<400> SEQUENCE: 42

```
ctggacccca ggtctggagc gaattccagc ctgcagggct gataagcgag gcattagtga     60
gattgagaga gactttaccc cgccgtggtg gttggagggc gcgcagtaga gcagcagcac    120
aggcgcgggt cccgggaggc cggctctgct cgcgccgaga tgtggaatct ccttcacgaa    180
accgactcgg ctgtggccac cgcgcgccgc ccgcgctggc tgtgcgctgg ggcgctggtg    240
ctggcgggtg gcttctttct cctcggcttc ctcttcgggt ggtttataaa atcctccaat    300
gaagctacta acattactcc aaagcataat atgaaagcat tttggatga attgaaagct     360
gagaacatca agaagttctt atataatttt acacagatac cacatttagc aggaacagaa    420
caaaactttc agcttgcaaa gcaaattcaa tcccagtgga aagaatttgg cctggattct    480
gttgagctag cacattatga tgtcctgttg tcctacccaa ataagactca tcccaactac    540
atctcaataa ttaatgaaga tggaaatgag attttcaaca catcattatt tgaaccacct    600
cctccaggat atgaaaatgt ttcggatatt gtaccacctt tcagtgcttt ctctcctcaa    660
ggaatgccag agggcgatct agtgtatgtt aactatgcac gaactgaaga cttctttaaa    720
ttggaacggg acatgaaaat caattgctct gggaaaattg taattgccag atatgggaaa    780
gttttcagag gaaataaggt taaaaatgcc cagctggcag gggccaaagg agtcattctc    840
tactccgacc ctgctgacta ctttgctcct ggggtgaagt cctatccaga tggttggaat    900
cttcctggag gtggtgtcca gcgtggaaat atcctaaatc tgaatggtgc aggagaccct    960
ctcacaccag gttacccagc aaatgaatat gcttataggc gtggaattgc agaggctgtt   1020
ggtcttccaa gtattcctgt tcatccaatt ggatactatg atgcacagaa gctcctagaa   1080
aaaatgggtg gctcagcacc accagatagc agctggagag gaagtctcaa agtgccctac   1140
aatgttggac ctggctttac tggaaacttt tctacacaaa aagtcaagat gcacatccac   1200
tctaccaatg aagtgacaag aatttacaat gtgataggta ctctcagagg agcagtggaa   1260
ccagacagat atgtcattct gggaggtcac cgggactcat gggtgtttgg tggtattgac   1320
cctcagagtg gagcagctgt tgttcatgaa attgtgagga gctttggaac actgaaaaag   1380
gaagggtgga gacctagaag aacaattttg tttgcaagct gggatgcaga agaatttggt   1440
cttcttggtt ctactgagtg ggcagaggag aattcaagac tccttcaaga gcgtggcgtg   1500
gcttatatta atgctgactc atctatagaa ggaaactaca ctctgagagt tgattgtaca   1560
ccgctgatgt acagcttggt acacaaccta acaaaagagc tgaaaagccc tgatgaaggc   1620
tttgaaggca aatctcttta tgaaagttgg actaaaaaaa gtccttcccc agagttcagt   1680
ggcatgccca ggataagcaa attgggatct ggaaatgatt ttgaggtgtt cttccaacga   1740
cttggaattg cttcaggcag agcacggtat actaaaaatt gggaaacaaa caaattcagc   1800
ggctatccac tgtatcacag tgtctatgaa acatatgagt tggtggaaaa gttttatgat   1860
ccaatgttta aatatcacct cactgtggcc caggttcgag gagggatggt gtttgagcta   1920
gccaattcca tagtgctccc ttttgattgt cgagattatg ctgtagtttt aagaaagtat   1980
gctgacaaaa tctacagtat ttctatgaaa catccacagg aaatgaagac atacagtgta   2040
tcatttgatt cactttttc tgcagtaaag aattttacag aaattgcttc caagttcagt    2100
gagagactcc aggactttga caaaagcaag catgtcatct atgctccaag cagccacaac   2160
aagtatgcag gggagtcatt cccaggaatt tatgatgctc tgtttgatat tgaaagcaaa   2220
gtggaccctt ccaaggcctg ggggagaagtg aagagacaga tttatgttgc agccttcaca  2280
```

gtgcaggcag ctgcagagac tttgagtgaa gtagcctaag aggattcttt agagaatccg 2340
tattgaattt gtgtggtatg tcactcagaa agaatcgtaa tgggtatatt gataaatttt 2400
aaaattggta tatttgaaat aaagttgaat attatatata aaaaaaaaaa aaaaaaaaaa 2460
aaaaaaaaaa aa 2472

<210> SEQ ID NO 43
<211> LENGTH: 719
<212> TYPE: PRT
<213> ORGANISM: Homo sapiens

<400> SEQUENCE: 43

Met Trp Asn Leu Leu His Glu Thr Asp Ser Ala Val Ala Thr Ala Arg
1 5 10 15

Arg Pro Arg Trp Leu Cys Ala Gly Ala Leu Val Leu Ala Gly Gly Phe
20 25 30

Phe Leu Leu Gly Phe Leu Phe Gly Trp Phe Ile Lys Ser Ser Asn Glu
35 40 45

Ala Thr Asn Ile Thr Pro Lys His Asn Met Lys Ala Phe Leu Asp Glu
50 55 60

Leu Lys Ala Glu Asn Ile Lys Lys Phe Leu Tyr Asn Phe Thr Gln Ile
65 70 75 80

Pro His Leu Ala Gly Thr Glu Gln Asn Phe Gln Leu Ala Lys Gln Ile
85 90 95

Gln Ser Gln Trp Lys Glu Phe Gly Leu Asp Ser Val Glu Leu Ala His
100 105 110

Tyr Asp Val Leu Leu Ser Tyr Pro Asn Lys Thr His Pro Asn Tyr Ile
115 120 125

Ser Ile Ile Asn Glu Asp Gly Asn Glu Ile Phe Asn Thr Ser Leu Phe
130 135 140

Glu Pro Pro Pro Pro Gly Tyr Glu Asn Val Ser Asp Ile Val Pro Pro
145 150 155 160

Phe Ser Ala Phe Ser Pro Gln Gly Met Pro Glu Gly Asp Leu Val Tyr
165 170 175

Val Asn Tyr Ala Arg Thr Glu Asp Phe Phe Lys Leu Glu Arg Asp Met
180 185 190

Lys Ile Asn Cys Ser Gly Lys Ile Val Ile Ala Arg Tyr Gly Lys Val
195 200 205

Phe Arg Gly Asn Lys Val Lys Asn Ala Gln Leu Ala Gly Ala Lys Gly
210 215 220

Val Ile Leu Tyr Ser Asp Pro Ala Asp Tyr Phe Ala Pro Gly Val Lys
225 230 235 240

Ser Tyr Pro Asp Gly Trp Asn Leu Pro Gly Gly Gly Val Gln Arg Gly
245 250 255

Asn Ile Leu Asn Leu Asn Gly Ala Gly Asp Pro Leu Thr Pro Gly Tyr
260 265 270

Pro Ala Asn Glu Tyr Ala Tyr Arg Arg Gly Ile Ala Glu Ala Val Gly
275 280 285

Leu Pro Ser Ile Pro Val His Pro Ile Gly Tyr Tyr Asp Ala Gln Lys
290 295 300

Leu Leu Glu Lys Met Gly Gly Ser Ala Pro Pro Asp Ser Ser Trp Arg
305 310 315 320

Gly Ser Leu Lys Val Pro Tyr Asn Val Gly Pro Gly Phe Thr Gly Asn
325 330 335

```
Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Lys His Val Ile Tyr Ala Pro Ser Ser His Asn Lys Tyr Ala Gly Glu
            660                 665                 670

Ser Phe Pro Gly Ile Tyr Asp Ala Leu Phe Asp Ile Glu Ser Lys Val
        675                 680                 685

Asp Pro Ser Lys Ala Trp Gly Glu Val Lys Arg Gln Ile Tyr Val Ala
    690                 695                 700

Ala Phe Thr Val Gln Ala Ala Ala Glu Thr Leu Ser Glu Val Ala
705                 710                 715
```

<210> SEQ ID NO 44
<211> LENGTH: 750
<212> TYPE: PRT
<213> ORGANISM: Homo sapiens

<400> SEQUENCE: 44

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415
```

```
Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750


<210> SEQ ID NO 45
<211> LENGTH: 671
<212> TYPE: PRT
<213> ORGANISM: Homo sapiens

<400> SEQUENCE: 45

Ile Pro His Leu Ala Gly Thr Glu Gln Asn Phe Gln Leu Ala Lys Gln
1               5                   10                  15

Ile Gln Ser Gln Trp Lys Glu Phe Gly Leu Asp Ser Val Glu Leu Ala
            20                  25                  30

His Tyr Asp Val Leu Leu Ser Tyr Pro Asn Lys Thr His Pro Asn Tyr
        35                  40                  45
```

```
Ile Ser Ile Ile Asn Glu Asp Gly Asn Glu Ile Phe Asn Thr Ser Leu
    50                  55                  60

Phe Glu Pro Pro Pro Pro Gly Tyr Glu Asn Val Ser Asp Ile Val Pro
65                  70                  75                  80

Pro Phe Ser Ala Phe Ser Pro Gln Gly Met Pro Glu Gly Asp Leu Val
                85                  90                  95

Tyr Val Asn Tyr Ala Arg Thr Glu Asp Phe Phe Lys Leu Glu Arg Asp
            100                 105                 110

Met Lys Ile Asn Cys Ser Gly Lys Ile Val Ile Ala Arg Tyr Gly Lys
        115                 120                 125

Val Phe Arg Gly Asn Lys Val Lys Asn Ala Gln Leu Ala Gly Ala Lys
    130                 135                 140

Gly Val Ile Leu Tyr Ser Asp Pro Ala Asp Tyr Phe Ala Pro Gly Val
145                 150                 155                 160

Lys Ser Tyr Pro Asp Gly Trp Asn Leu Pro Gly Gly Gly Val Gln Arg
                165                 170                 175

Gly Asn Ile Leu Asn Leu Asn Gly Ala Gly Asp Pro Leu Thr Pro Gly
            180                 185                 190

Tyr Pro Ala Asn Glu Tyr Ala Tyr Arg Arg Gly Ile Ala Glu Ala Val
        195                 200                 205

Gly Leu Pro Ser Ile Pro Val His Pro Ile Gly Tyr Tyr Asp Ala Gln
    210                 215                 220

Lys Leu Leu Glu Lys Met Gly Gly Ser Ala Pro Pro Asp Ser Ser Trp
225                 230                 235                 240

Arg Gly Ser Leu Lys Val Pro Tyr Asn Val Gly Pro Gly Phe Thr Gly
                245                 250                 255

Asn Phe Ser Thr Gln Lys Val Lys Met His Ile His Ser Thr Asn Glu
            260                 265                 270

Val Thr Arg Ile Tyr Asn Val Ile Gly Thr Leu Arg Gly Ala Val Glu
        275                 280                 285

Pro Asp Arg Tyr Val Ile Leu Gly Gly His Arg Asp Ser Trp Val Phe
    290                 295                 300

Gly Gly Ile Asp Pro Gln Ser Gly Ala Ala Val Val His Glu Ile Val
305                 310                 315                 320

Arg Ser Phe Gly Thr Leu Lys Lys Glu Gly Trp Arg Pro Arg Arg Thr
                325                 330                 335

Ile Leu Phe Ala Ser Trp Asp Ala Glu Glu Phe Gly Leu Leu Gly Ser
            340                 345                 350

Thr Glu Trp Ala Glu Glu Asn Ser Arg Leu Leu Gln Glu Arg Gly Val
        355                 360                 365

Ala Tyr Ile Asn Ala Asp Ser Ser Ile Glu Gly Asn Tyr Thr Leu Arg
    370                 375                 380

Val Asp Cys Thr Pro Leu Met Tyr Ser Leu Val His Asn Leu Thr Lys
385                 390                 395                 400

Glu Leu Lys Ser Pro Asp Glu Gly Phe Glu Gly Lys Ser Leu Tyr Glu
                405                 410                 415

Ser Trp Thr Lys Lys Ser Pro Ser Pro Glu Phe Ser Gly Met Pro Arg
            420                 425                 430

Ile Ser Lys Leu Gly Ser Gly Asn Asp Phe Glu Val Phe Phe Gln Arg
        435                 440                 445

Leu Gly Ile Ala Ser Gly Arg Ala Arg Tyr Thr Lys Asn Trp Glu Thr
    450                 455                 460
```

```
Asn Lys Phe Ser Gly Tyr Pro Leu Tyr His Ser Val Tyr Glu Thr Tyr
465                 470                 475                 480

Glu Leu Val Glu Lys Phe Tyr Asp Pro Met Phe Lys Tyr His Leu Thr
                485                 490                 495

Val Ala Gln Val Arg Gly Gly Met Val Phe Glu Leu Ala Asn Ser Ile
            500                 505                 510

Val Leu Pro Phe Asp Cys Arg Asp Tyr Ala Val Val Leu Arg Lys Tyr
        515                 520                 525

Ala Asp Lys Ile Tyr Ser Ile Ser Met Lys His Pro Gln Glu Met Lys
    530                 535                 540

Thr Tyr Ser Val Ser Phe Asp Ser Leu Phe Ser Ala Val Lys Asn Phe
545                 550                 555                 560

Thr Glu Ile Ala Ser Lys Phe Ser Glu Arg Leu Gln Asp Phe Asp Lys
                565                 570                 575

Ser Asn Pro Ile Val Leu Arg Met Met Asn Asp Gln Leu Met Phe Leu
            580                 585                 590

Glu Arg Ala Phe Ile Asp Pro Leu Gly Leu Pro Asp Arg Pro Phe Tyr
        595                 600                 605

Arg His Val Ile Tyr Ala Pro Ser Ser His Asn Lys Tyr Ala Gly Glu
    610                 615                 620

Ser Phe Pro Gly Ile Tyr Asp Ala Leu Phe Asp Ile Glu Ser Lys Val
625                 630                 635                 640

Asp Pro Ser Lys Ala Trp Gly Glu Val Lys Arg Gln Ile Tyr Val Ala
                645                 650                 655

Ala Phe Thr Val Gln Ala Ala Ala Glu Thr Leu Ser Glu Val Ala
            660                 665                 670
```

<210> SEQ ID NO 46
<211> LENGTH: 31
<212> TYPE: DNA
<213> ORGANISM: Artificial
<220> FEATURE:
<223> OTHER INFORMATION: chemically synthesized

<400> SEQUENCE: 46
ggggtctaga cctcctttga ttagtatatt c 31

<210> SEQ ID NO 47
<211> LENGTH: 45
<212> TYPE: DNA
<213> ORGANISM: Artificial
<220> FEATURE:
<223> OTHER INFORMATION: chemically synthesized

<400> SEQUENCE: 47
atcttcgcta tctgtcgccg cggcgcgtgc ttcagtttgt tgcgc 45

<210> SEQ ID NO 48
<211> LENGTH: 45
<212> TYPE: DNA
<213> ORGANISM: Artificial
<220> FEATURE:
<223> OTHER INFORMATION: chemically synthesized

<400> SEQUENCE: 48
gcgcaacaaa ctgaagcagc ggccgcggcg acagatagcg aagat 45

<210> SEQ ID NO 49
<211> LENGTH: 42
<212> TYPE: DNA

<213> ORGANISM: Artificial
<220> FEATURE:
<223> OTHER INFORMATION: chemically synthesized

<400> SEQUENCE: 49
tgtaggtgta tctccatgct cgagagctag gcgatcaatt tc 42

<210> SEQ ID NO 50
<211> LENGTH: 42
<212> TYPE: DNA
<213> ORGANISM: Artificial
<220> FEATURE:
<223> OTHER INFORMATION: chemically synthesized

<400> SEQUENCE: 50
ggaattgatc gcctagctct cgagcatgga gatacaccta ca 42

<210> SEQ ID NO 51
<211> LENGTH: 42
<212> TYPE: DNA
<213> ORGANISM: Artificial
<220> FEATURE:
<223> OTHER INFORMATION: chemically synthesized

<400> SEQUENCE: 51
aaacggattt atttagatcc cgggttatgg tttctgagaa ca 42

<210> SEQ ID NO 52
<211> LENGTH: 42
<212> TYPE: DNA
<213> ORGANISM: Artificial
<220> FEATURE:
<223> OTHER INFORMATION: chemically synthesized

<400> SEQUENCE: 52
tgttctcaga aaccataacc cgggatctaa ataaatccgt tt 42

<210> SEQ ID NO 53
<211> LENGTH: 28
<212> TYPE: DNA
<213> ORGANISM: Artificial
<220> FEATURE:
<223> OTHER INFORMATION: chemically synthesized

<400> SEQUENCE: 53
gggggtcgac cagctcttct tggtgaag 28

<210> SEQ ID NO 54
<211> LENGTH: 680
<212> TYPE: PRT
<213> ORGANISM: Artificial
<220> FEATURE:
<223> OTHER INFORMATION: chemically synthesized

<400> SEQUENCE: 54

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
```

```
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Leu Glu Ile Val Gly Gly Trp
        435                 440                 445

Glu Cys Glu Lys His Ser Gln Pro Trp Gln Val Leu Val Ala Ser Arg
    450                 455                 460

Gly Arg Ala Val Cys Gly Gly Val Leu Val His Pro Gln Trp Val Leu
465                 470                 475                 480

Thr Ala Ala His Cys Ile Arg Asn Lys Ser Val Ile Leu Leu Gly Arg
                485                 490                 495
```

```
His Ser Leu Phe His Pro Glu Asp Thr Gly Gln Val Phe Gln Val Ser
            500                 505                 510

His Ser Phe Pro His Pro Leu Tyr Asp Met Ser Leu Leu Lys Asn Arg
        515                 520                 525

Phe Leu Arg Pro Gly Asp Asp Ser Ser His Asp Leu Met Leu Leu Arg
    530                 535                 540

Leu Ser Glu Pro Ala Glu Leu Thr Asp Ala Val Lys Val Met Asp Leu
545                 550                 555                 560

Pro Thr Gln Glu Pro Ala Leu Gly Thr Thr Cys Tyr Ala Ser Gly Trp
                565                 570                 575

Gly Ser Ile Glu Pro Glu Glu Phe Leu Thr Pro Lys Lys Leu Gln Cys
            580                 585                 590

Val Asp Leu His Val Ile Ser Asn Asp Val Cys Ala Gln Val His Pro
        595                 600                 605

Gln Lys Val Thr Lys Phe Met Leu Cys Ala Gly Arg Trp Thr Gly Gly
    610                 615                 620

Lys Ser Thr Cys Ser Gly Asp Ser Gly Gly Pro Leu Val Cys Tyr Gly
625                 630                 635                 640

Val Leu Gln Gly Ile Thr Ser Trp Gly Ser Glu Pro Cys Ala Leu Pro
                645                 650                 655

Glu Arg Pro Ser Leu Tyr Thr Lys Val Val His Tyr Arg Lys Trp Ile
            660                 665                 670

Lys Asp Thr Ile Val Ala Asn Pro
        675                 680
```

<210> SEQ ID NO 55
<211> LENGTH: 13294
<212> TYPE: DNA
<213> ORGANISM: Artificial
<220> FEATURE:
<223> OTHER INFORMATION: chemically synthesized

<400> SEQUENCE: 55

```
aattccggat gagcattcat caggcgggca agaatgtgaa taaaggccgg ataaaacttg     60

tgcttatttt tctttacggt ctttaaaaag gccgtaatat ccagctgaac ggtctggtta    120

taggtacatt gagcaactga ctgaaatgcc tcaaaatgtt ctttacgatg ccattgggat    180

atatcaacgg tggtatatcc agtgattttt ttctccattt tagcttcctt agctcctgaa    240

aatctcgata actcaaaaaa tacgcccggt agtgatctta tttcattatg gtgaaagttg    300

gaacctctta cgtgccgatc aacgtctcat tttcgccaaa agttggccca gggcttcccg    360

gtatcaacag ggacaccagg atttatttat tctgcgaagt gatcttccgt cacaggtatt    420

tattcggcgc aaagtgcgtc gggtgatgct gccaacttac tgatttagtg tatgatggtg    480

tttttgaggt gctccagtgg cttctgtttc tatcagctgt ccctcctgtt cagctactga    540

cggggtggtg cgtaacggca aaagcaccgc cggacatcag cgctagcgga gtgtatactg    600

gcttactatg ttggcactga tgagggtgtc agtgaagtgc ttcatgtggc aggagaaaaa    660

aggctgcacc ggtgcgtcag cagaatatgt gatacaggat atattccgct tcctcgctca    720

ctgactcgct acgctcggtc gttcgactgc ggcgagcgga aatggcttac gaacggggcg    780

gagatttcct ggaagatgcc aggaagatac ttaacaggga agtgagaggg ccgcggcaaa    840

gccgtttttc cataggctcc gcccccctga caagcatcac gaaatctgac gctcaaatca    900

gtggtggcga aacccgacag gactataaag ataccaggcg tttccccctg gcggctccct    960
```

```
cgtgcgctct cctgttcctg cctttcggtt taccggtgtc attccgctgt tatggccgcg   1020
tttgtctcat tccacgcctg acactcagtt ccgggtaggc agttcgctcc aagctggact   1080
gtatgcacga acccccgtt cagtccgacc gctgcgcctt atccggtaac tatcgtcttg   1140
agtccaaccc ggaaagacat gcaaaagcac cactggcagc agccactggt aattgattta   1200
gaggagttag tcttgaagtc atgcgccggt taaggctaaa ctgaaaggac aagttttggt   1260
gactgcgctc ctccaagcca gttacctcgg ttcaaagagt tggtagctca gagaaccttc   1320
gaaaaaccgc cctgcaaggc ggtttttcg ttttcagagc aagagattac gcgcagacca   1380
aaacgatctc aagaagatca tcttattaat cagataaaat atttctagcc ctcctttgat   1440
tagtatattc ctatcttaaa gttactttta tgtggaggca ttaacatttg ttaatgacgt   1500
caaaaggata gcaagactag aataaagcta taaagcaagc atataatatt gcgtttcatc   1560
tttagaagcg aatttcgcca atattataat tatcaaaaga gaggggtggc aaacggtatt   1620
tggcattatt aggttaaaaa atgtagaagg agagtgaaac ccatgaaaaa aataatgcta   1680
gtttttatta cacttatatt agttagtcta ccaattgcgc aacaaactga agcaaaggat   1740
gcatctgcat tcaataaaga aaattcaatt tcatccatgg caccaccagc atctccgcct   1800
gcaagtccta agacgccaat cgaaaagaaa cacgcggatg aaatcgataa gtatatacaa   1860
ggattggatt acaataaaaa caatgtatta gtataccacg gagatgcagt gacaaatgtg   1920
ccgccaagaa aaggttacaa agatggaaat gaatatattg ttgtggagaa aaagaagaaa   1980
tccatcaatc aaaataatgc agacattcaa gttgtgaatg caatttcgag cctaacctat   2040
ccaggtgctc tcgtaaaagc gaattcggaa ttagtagaaa atcaaccaga tgttctccct   2100
gtaaaacgtg attcattaac actcagcatt gatttgccag gtatgactaa tcaagacaat   2160
aaaatagttg taaaaaatgc cactaaatca aacgttaaca acgcagtaaa tacattagtg   2220
gaaagatgga atgaaaaata tgctcaagct tatccaaatg taagtgcaaa aattgattat   2280
gatgacgaaa tggcttacag tgaatcacaa ttaattgcga aatttggtac agcatttaaa   2340
gctgtaaata atagcttgaa tgtaaacttc ggcgcaatca gtgaagggaa aatgcaagaa   2400
gaagtcatta gttttaaaca aatttactat aacgtgaatg ttaatgaacc tacaagacct   2460
tccagatttt tcggcaaagc tgttactaaa gagcagttgc aagcgcttgg agtgaatgca   2520
gaaaatcctc ctgcatatat ctcaagtgtg gcgtatggcc gtcaagttta tttgaaatta   2580
tcaactaatt cccatagtac taaagtaaaa gctgcttttg atgctgccgt aagcggaaaa   2640
tctgtctcag gtgatgtaga actaacaaat atcatcaaaa attcttcctt caaagccgta   2700
atttacggag gttccgcaaa agatgaagtt caaatcatcg acggcaacct cggagactta   2760
cgcgatattt tgaaaaaagg cgctactttt aatcgagaaa caccaggagt tcccattgct   2820
tatacaacaa acttcctaaa agacaatgaa ttagctgtta ttaaaaacaa ctcagaatat   2880
attgaaacaa cttcaaaagc ttatacagat ggaaaaatta acatcgatca ctctggagga   2940
tacgttgctc aattcaacat ttcttgggat gaagtaaatt atgatctcga gattgtggga   3000
ggctgggagt gcgagaagca ttcccaaccc tggcaggtgc ttgtggcctc tcgtggcagg   3060
gcagtctgcg gcggtgttct ggtgcacccc cagtgggtcc tcacagctgc ccactgcatc   3120
aggaacaaaa gcgtgatctt gctgggtcgg cacagcctgt ttcatcctga agacacaggc   3180
caggtatttc aggtcagcca cagcttccca cacccgctct acgatatgag cctcctgaag   3240
aatcgattcc tcaggccagg tgatgactcc agccacgacc tcatgctgct ccgcctgtca   3300
gagcctgccg agctcacgga tgctgtgaag gtcatggacc tgcccaccca ggagccagca   3360
```

```
ctggggacca cctgctacgc ctcaggctgg ggcagcattg aaccagagga gttcttgacc   3420

ccaaagaaac ttcagtgtgt ggacctccat gttatttcca atgacgtgtg tgcgcaagtt   3480

caccctcaga aggtgaccaa gttcatgctg tgtgctggac gctggacagg gggcaaaagc   3540

acctgctcgg gtgattctgg gggcccactt gtctgttatg gtgtgcttca aggtatcacg   3600

tcatggggca gtgaaccatg tgccctgccc gaaaggcctt ccctgtacac caaggtggtg   3660

cattaccgga agtggatcaa ggacaccatc gtggccaacc cctaaactag tgactacaag   3720

gacgatgacg acaagtgata cccgggatct aaataaatcc gtttttaaat atgtatgcat   3780

ttcttttgcg aaatcaaaat ttgtataata aaatcctata tgtaaaaaac atcatttagc   3840

gtgactttct ttcaacagct aacaattgtt gttactgcct aatgttttta gggtatttta   3900

aaaaagggcg ataaaaaacg attgggggat gagacatgaa cgctcaagca gaagaattca   3960

aaaaatattt agaaactaac gggataaaac caaaacaatt tcataaaaaa gaacttattt   4020

ttaaccaatg ggatccacaa gaatattgta ttttcctata tgatggtatc acaaagctca   4080

cgagtattag cgagaacggg accatcatga atttacaata ctacaaaggg gctttcgtta   4140

taatgtctgg ctttattgat acagaaacat cggttggcta ttataattta gaagtcatta   4200

gcgagcaggc taccgcatac gttatcaaaa taaacgaact aaaagaacta ctgagcaaaa   4260

atcttacgca ctttttctat gttttccaaa ccctacaaaa acaagtttca tacagcctag   4320

ctaaatttaa tgatttttcg attaacggga agcttggctc tatttgcggt caacttttaa   4380

tcctgaccta tgtgtatggt aaagaaactc ctgatggcat caagattaca ctggataatt   4440

taacaatgca ggagttagga tattcaagtg gcatcgcaca tagctcagct gttagcagaa   4500

ttatttccaa attaaagcaa gagaaagtta tcgtgtataa aaattcatgc ttttatgtac   4560

aaaatcgtga ttatctcaaa agatatgccc ctaaattaga tgaatggttt tatttagcat   4620

gtcctgctac ttggggaaaa ttaaattaaa tcaaaaacag tattcctcaa tgaggaatac   4680

tgttttatat tttattcgaa taaagaactt acagaagcat tttcatgaac gcgtacgatt   4740

gcttcaccaa gaagagctgg tcgaccgatg cccttgagag ccttcaaccc agtcagctcc   4800

ttccggtggg cgcggggcat gactatcgtc gccgcactta tgactgtctt ctttatcatg   4860

caactcgtag gacaggtgcc ggcagcgctc tgggtcattt tcggcgagga ccgctttcgc   4920

tggagcgcga cgatgatcgg cctgtcgctt gcggtattcg gaatcttgca cgccctcgct   4980

caagccttcg tcactggtcc cgccaccaaa cgtttcggcg agaagcaggc cattatcgcc   5040

ggcatggcgg ccgacgcgct gggctacgtc ttgctggcgt tcgcgacgcg aggctggatg   5100

gccttcccca ttatgattct tctcgcttcc ggcggcatcg ggatgcccgc gttgcaggcc   5160

atgctgtcca ggcaggtaga tgacgaccat cagggacagc ttcaaggatc gctcgcggct   5220

cttaccagcc taacttcgat cattggaccg ctgatcgtca cggcgattta tgccgcctcg   5280

gcgagcacat ggaacgggtt ggcatggatt gtaggcgccg ccctatacct tgtctgcctc   5340

cccgcgttgc gtcgcggtgc atggagccgg gccacctcga cctgaatgga agccggcggc   5400

acctcgctaa cggattcacc actccaagaa ttggagccaa tcaattcttg cggagaactg   5460

tgaatgcgca aaccaaccct tggcagaaca tatccatcgc gtccgccatc tccagcagcc   5520

gcacgcggcg catctcggct ttcgatttgt ttttgaatgg tttatccgat aaagaagttg   5580

aagaacaaac tggaatcaat cgccgaacgt ttagaaggta tcgagcaaga tataacgtga   5640

cagtcgatca aagaaaaaac aatgaaaaga gggatagtta atgagtacgg ttattttagc   5700
```

```
tgaaaaacca agccaggcat tagcctacgc aagtgcttta aaacaaagca ccaaaaaaga   5760
cggttatttt gagatcaaag acccactatt tacagatgaa acgtttatca cctttggttt   5820
tgggcattta gtggaattag cagaaccagg tcattatgac gaaaagtggc aaaattggaa   5880
acttgaatct ttgccgattt ttcctgatcg atacgatttt gaagttgcaa aagataaggg   5940
aaagcagttt aaaattgttg cagaacttct caaaaaggca aatacaatta ttgttgcaac   6000
agatagcgac agagaaggtg aaaatatcgc ctggtcgatt atccataaag caaatgcctt   6060
ttcaaaagat aaaacattta aaagactatg gatcaatagc ttagaaaaag atgtaatccg   6120
aagcggtttt caaaatttgc aacctggaat gaattactat cccttttatc aagaagcgca   6180
aacacgccaa attgccgatt ggttgatcgg catgaacgca agccctttgt atacgttaaa   6240
tttacaacag aagggcgtac aaggtacatt ttcactagga cgtgttcaaa cgcccacctt   6300
ataccttatt tttcagcgcc aggaagccat agagaatttt aaaaaagaac ctttttttcga   6360
ggtggaagct agtataaaag taaaccaagg gtcgtttaag ggcgttctaa gccccacaca   6420
gcgttttaaa acccaagagg agcttttagc ttttgtttct tctaaacaag ctaaaatagg   6480
caatcaagag gggataattg ctgatgttca aaccaaagag aagaaaacga atagtccgag   6540
tttgttttct ttaagtagtt tgcaatcaaa agtcaatcag ctttataaag cgacagcgag   6600
ccaaacttta aaagctattt ctttttttaat aacttaaaaa taaacttaat gtaacagcaa   6660
gcacagtcaa ggtatacacc tttgacaaaa aatagcacat tctctatcga aaatttttgc   6720
ttattttta aattattttg ggaaattttc ccaatccctt tttctaactc aaaaaatata   6780
atcactcaaa atttaaaagg gcgcacttat acatcatttt aaaaaattga tgtaacgtgc   6840
taagttcaaa acaaagggcg cacttataca cgattttcaa tcttgtatat ttctaacgaa   6900
aagcgtgcgc caaaaaaccc ccttcgtcaa ttttgacagg gggcttttttg atgtaaaaat   6960
ttctatcgaa atttaaaaat tcgcttcact catgttataa agacttaaaa taaaataact   7020
ctttaaaatc ttttgctagt tgttcttcaa tattttttat tcggtgcatc ttccaagtaa   7080
agtataacac actagactta tttactacgt ttcataagtc attaatgcgt gtgctctgcg   7140
aggctagttt ttgtgcaagc acaaaaaatg gactgaataa atcagtccat aagttcaaaa   7200
ccaaattcaa aatcaaaacc acaagcaacc aaaaaatgtg gttgttatac gttcataaat   7260
tttatgatca cttacgtgta taaaattaaa ttcactttca aaatctaaaa actaaatcca   7320
atcatctacc ctatgaatta tatcttgaaa ttcattcata aatagtgaag catggtaacc   7380
atcacataca gaatgatgaa gttgcagagc aactggtata taaattttat tattctcact   7440
ataaaattta cctatcgtaa taataggcaa taaaaagctg ctattgttac caatatttaa   7500
attaaatgaa ctaaaatcaa tccaaggaat cattgaaatc ggtatggtgt tttcaggtat   7560
cggtttttta ggaaacattt cttctttatc tttatattca agcaagtcat ttttataatt   7620
attataaaaa gaaatgaagt ttttatcaga ttcagtccaa atgttagtaa atttttcagt   7680
ttgcttatta aaaactgtat acaaaggatt taacttatcc caataaccta atttattctc   7740
actattaatt cctgttctaa acactttatt tttatttaca acttccataa ttgcataaat   7800
taaagaggga taaatttcat atcctttctt ttttatcata tctttaaaca aagtaatatc   7860
aatttcttta gtaatgctat aagtagtttg ctgattaaaa tagtgttcaa aatattcttt   7920
tctatcccaa ttttctaatt caataatatt aaaagtcata tataacttcc tcctaaattt   7980
taaattttta tatttaggag gaataatcct ctgatttttt catacgttat gtcacctcgt   8040
aaatattaat tatactgaat tagcaatttt tatcaaataa aacttatttt acttccaaaa   8100
```

```
cctaaattca cgttgccaaa aatcaatctg cttttgcaat tgtttttcgt tcgcttttaa   8160
agtcgatttc attaattccg ttaaatcaat tggagatatt tctctaatca atttttttaaa  8220
tttagtctta gtattcttac ttagctttcc ccacatactt tcttcatgca acaaagtata   8280
aaccatagct tgctcattaa ttttttctaa agtagcccac gcaggtttca agatgtgtaa   8340
atcattaaaa caatcattcc agtaatcaac catatctctt tttaattcaa cttctacacg   8400
ccataaatgt tcagacacaa cttcaacatc tgcgttatct ttacgttctt gtttttttatt  8460
ataaattcta ataaatctat cactatcacg gacaccaaaa tattttgttt ctggcttgcc   8520
attacgacca taaaaaaacag ttttcttaac tgctttatca gtcattgcat agtaatcgct  8580
caaatcatct tcaaaatcaa aagctaagtc taatcttgta aaaccgtcat cttccatgta   8640
gtcgataata ttttgtttta accaaatcat ttcttcatgt gtgagtttat tgggattaaa   8700
ttcaacacgc atattacgtc tatcccaagt atctgctttt actttgtcat attcgatata   8760
aactttttct tgaagtgcct tagctttaaa ctttgtttga agtatatccc aaagtcgtat   8820
ttgtggctct acactcataa agtcagatag ctttttagca ttagttttgt tcaaatttcc   8880
aacgattgtc atggcatcaa aacttaatgc gggttgagat tttcccaaag tttgaccact   8940
taaccggcta ttacttaacc ggctattaga gacggaacta actcaacgct agtagtggat   9000
ttaatcccaa atgagccaac agaaccagaa ccagaaacag aacaagtaac attggagtta   9060
gaaatggaag aagaaaaaag caatgatttc gtgtgaataa tgcacgaaat cattgcttat   9120
tttttaaaa agcgatatac tagatataac gaaacaacga actgaataaa gaatacaaaa    9180
aaagagccac gaccagttaa agcctgagaa actttaactg cgagccttaa ttgattacca   9240
ccaatcaatt aaagaagtcg agacccaaaa tttggtaaag tatttaatta ctttattaat   9300
cagatactta aatatctgta aacccattat atcgggtttt tgaggggatt tcaagtcttt   9360
aagaagatac caggcaatca attaagaaaa acttagttga ttgccttttt tgttgtgatt   9420
caactttgat cgtagcttct aactaattaa ttttcgtaag aaaggagaac agctgaatga   9480
atatcccttt tgttgtagaa actgtgcttc atgacggctt gttaaagtac aaatttaaaa   9540
atagtaaaat tcgctcaatc actaccaagc caggtaaaag taaaggggct atttttgcgt   9600
atcgctcaaa aaaaagcatg attggcggac gtggcgttgt tctgacttcc gaagaagcga   9660
ttcacgaaaa tcaagataca tttacgcatt ggacaccaaa cgtttatcgt tatggtacgt   9720
atgcagacga aaaccgttca tacactaaag gacattctga aaacaattta agacaaatca   9780
ataccttctt tattgatttt gatattcaca cggaaaaaga aactatttca gcaagcgata   9840
ttttaacaac agctattgat ttaggtttta tgcctacgtt aattatcaaa tctgataaag   9900
gttatcaagc atattttgtt ttagaaacgc cagtctatgt gacttcaaaa tcagaattta   9960
aatctgtcaa agcagccaaa ataatctcgc aaaatatccg agaatatttt ggaaagtctt   10020
tgccagttga tctaacgtgc aatcattttg ggattgctcg tataccaaga acggacaatg   10080
tagaattttt tgatcccaat taccgttatt ctttcaaaga atggcaagat tggtctttca   10140
aacaaacaga taataagggc tttactcgtt caagtctaac ggttttaagc ggtacagaag   10200
gcaaaaaaca agtagatgaa ccctggttta atctcttatt gcacgaaacg aaattttcag   10260
gagaaaaggg tttagtaggg cgcaatagcg ttatgtttac cctctcttta gcctacttta   10320
gttcaggcta ttcaatcgaa acgtgcgaat ataatatgtt tgagtttaat aatcgattag   10380
atcaaccctt agaagaaaaa gaagtaatca aaattgttag aagtgcctat tcagaaaact   10440
```

```
atcaaggggc taatagggaa tacattacca ttctttgcaa agcttgggta tcaagtgatt  10500
taaccagtaa agatttattt gtccgtcaag ggtggtttaa attcaagaaa aaaagaagcg  10560
aacgtcaacg tgttcatttg tcagaatgga aagaagattt aatggcttat attagcgaaa  10620
aaagcgatgt atacaagcct tatttagcga cgaccaaaaa agagattaga gaagtgctag  10680
gcattcctga acggacatta gataaattgc tgaaggtact gaaggcgaat caggaaattt  10740
tctttaagat taaaccagga agaaatggtg gcattcaact tgctagtgtt aaatcattgt  10800
tgctatcgat cattaaatta aaaaaagaag aacgagaaag ctatataaag gcgctgacag  10860
cttcgtttaa tttagaacgt acatttattc aagaaactct aaacaaattg gcagaacgcc  10920
ccaaaacgga cccacaactc gatttgttta gctacgatac aggctgaaaa taaaacccgc  10980
actatgccat tacatttata tctatgatac gtgtttgttt ttctttgctg tttagtgaat  11040
gattagcaga aatatacaga gtaagatttt aattaattat tagggggaga aggagagagt  11100
agcccgaaaa cttttagttg gcttggactg aacgaagtga gggaaaggct actaaaacgt  11160
cgaggggcag tgagagcgaa gcgaacactt gatcttttaa gttgctatca tttataggtc  11220
aatagagtat acctatttgt cctaatatga ttttagcagt ataattgact tggtgaatag  11280
gtcatttaag ttgggcataa taggaggagt aaaatgaaaa aatttattta tcgagtttta  11340
gaaaatgacg aagtggtggc tatttttaat gagcaacaat atgcgcaaga ttttatcgct  11400
tacgaaaaga caatttctga taagcaattt gaaattgaaa aagtagatat tgctgattgg  11460
ttattgcaac cgagagaatt ttagaggttg gttgaaaatg gctaaaattg gttatgcacg  11520
tgtcagtagc aaagaacaga acttagatcg gcaattacaa gcgttacagg gcgtttctaa  11580
ggtcttttca gacaaattaa gcggtcaatc ggtcgaacgc ccacaattac aagctatgct  11640
taactatatt cgtgaagggg atattgttat tgttactgaa ttagatcgat taggacgaaa  11700
taataaagaa ttaacagaat tgatgaatca aattcaaatt aagggggcaa ccctggaagt  11760
cttaaattta ccctcaatga atggtattga agatgaaaat ttaaggcgtt tgattaatag  11820
ccttgtcatt gaattgtaca agtatcaagc agaatcagaa cgaaaaaaaa ttaaggaacg  11880
tcaggcacaa ggaatcgaaa ttgctaagaa aaaaggcaaa ttcaaaggtc gtcagcataa  11940
atttaaagaa aatgatccac gtttaaagtc gggcagcgtt gggtcctggc cacgggtgcg  12000
catgatcgtg ctcctgtcgt tgaggacccg gctaggctgg cggggttgcc ttactggtta  12060
gcagaatgaa tcaccgatac gcgagcgaac gtgaagcgac tgctgctgca aaacgtctgc  12120
gacctgagca acaacatgaa tggtcttcgg tttccgtgtt tcgtaaagtc tggaaacgcg  12180
gaagtcccct acgtgctgct gaagttgccc gcaacagaga gtggaaccaa ccggtgatac  12240
cacgatacta tgactgagag tcaacgccat gagcggcctc atttcttatt ctgagttaca  12300
acagtccgca ccgctgccgg tagctccttc cggtgggcgc ggggcatgac tatcgtcgcc  12360
gcacttatga ctgtcttctt tatcatgcaa ctcgtaggac aggtgccggc agcgcccaac  12420
agtcccccgg ccacggggcc tgccaccata cccacgccga aacaagcgcc ctgcaccatt  12480
atgttccgga tctgcatcgc aggatgctgc tggctaccct gtggaacacc tacatctgta  12540
ttaacgaagc gctaaccgtt tttatcaggc tctgggaggc agaataaatg atcatatcgt  12600
caattattac ctccacgggg agagcctgag caaactggcc tcaggcattt gagaagcaca  12660
cggtcacact gcttccggta gtcaataaac cggtaaacca gcaatagaca taagcggcta  12720
tttaacgacc ctgccctgaa ccgacgaccg ggtcgaattt gctttcgaat ttctgccatt  12780
catccgctta ttatcactta ttcaggcgta gcaaccaggc gtttaagggc accaataact  12840
```

```
gccttaaaaa aattacgccc cgccctgcca ctcatcgcag tactgttgta attcattaag  12900

cattctgccg acatggaagc catcacaaac ggcatgatga acctgaatcg ccagcggcat  12960

cagcaccttg tcgccttgcg tataatattt gcccatggtg aaaacggggg cgaagaagtt  13020

gtccatattg gccacgttta aatcaaaact ggtgaaactc acccagggat tggctgagac  13080

gaaaaacata ttctcaataa accctttagg gaaataggcc aggttttcac cgtaacacgc  13140

cacatcttgc gaatatatgt gtagaaactg ccggaaatcg tcgtggtatt cactccagag  13200

cgatgaaaac gtttcagttt gctcatggaa aacggtgtaa caagggtgaa cactatccca  13260

tatcaccagc tcaccgtctt tcattgccat acgg                              13294

<210> SEQ ID NO 56
<211> LENGTH: 368
<212> TYPE: PRT
<213> ORGANISM: Listeria monocytogenes

<400> SEQUENCE: 56

Met Val Thr Gly Trp His Arg Pro Thr Trp Ile Glu Ile Asp Arg Ala
1               5                   10                  15

Ala Ile Arg Glu Asn Ile Lys Asn Glu Gln Asn Lys Leu Pro Glu Ser
            20                  25                  30

Val Asp Leu Trp Ala Val Val Lys Ala Asn Ala Tyr Gly His Gly Ile
        35                  40                  45

Ile Glu Val Ala Arg Thr Ala Lys Glu Ala Gly Ala Lys Gly Phe Cys
    50                  55                  60

Val Ala Ile Leu Asp Glu Ala Leu Ala Leu Arg Glu Ala Gly Phe Gln
65                  70                  75                  80

Asp Asp Phe Ile Leu Val Leu Gly Ala Thr Arg Lys Glu Asp Ala Asn
                85                  90                  95

Leu Ala Ala Lys Asn His Ile Ser Leu Thr Val Phe Arg Glu Asp Trp
            100                 105                 110

Leu Glu Asn Leu Thr Leu Glu Ala Thr Leu Arg Ile His Leu Lys Val
        115                 120                 125

Asp Ser Gly Met Gly Arg Leu Gly Ile Arg Thr Thr Glu Glu Ala Arg
    130                 135                 140

Arg Ile Glu Ala Thr Ser Thr Asn Asp His Gln Leu Gln Leu Glu Gly
145                 150                 155                 160

Ile Tyr Thr His Phe Ala Thr Ala Asp Gln Leu Glu Thr Ser Tyr Phe
                165                 170                 175

Glu Gln Gln Leu Ala Lys Phe Gln Thr Ile Leu Thr Ser Leu Lys Lys
            180                 185                 190

Arg Pro Thr Tyr Val His Thr Ala Asn Ser Ala Ala Ser Leu Leu Gln
        195                 200                 205

Pro Gln Ile Gly Phe Asp Ala Ile Arg Phe Gly Ile Ser Met Tyr Gly
    210                 215                 220

Leu Thr Pro Ser Thr Glu Ile Lys Thr Ser Leu Pro Phe Glu Leu Lys
225                 230                 235                 240

Pro Ala Leu Ala Leu Tyr Thr Glu Met Val His Val Lys Glu Leu Ala
                245                 250                 255

Pro Gly Asp Ser Val Ser Tyr Gly Ala Thr Tyr Thr Ala Thr Glu Arg
            260                 265                 270

Glu Trp Val Ala Thr Leu Pro Ile Gly Tyr Ala Asp Gly Leu Ile Arg
        275                 280                 285
```

```
His Tyr Ser Gly Phe His Val Leu Val Asp Gly Glu Pro Ala Pro Ile
    290                 295                 300

Ile Gly Arg Val Cys Met Asp Gln Thr Ile Ile Lys Leu Pro Arg Glu
305                 310                 315                 320

Phe Gln Thr Gly Ser Lys Val Thr Ile Ile Gly Lys Asp His Gly Asn
                325                 330                 335

Thr Val Thr Ala Asp Asp Ala Ala Gln Tyr Leu Asp Thr Ile Asn Tyr
            340                 345                 350

Glu Val Thr Cys Leu Leu Asn Glu Arg Ile Pro Arg Lys Tyr Ile His
        355                 360                 365


<210> SEQ ID NO 57
<211> LENGTH: 289
<212> TYPE: PRT
<213> ORGANISM: Listeria monocytogenes

<400> SEQUENCE: 57

Met Lys Val Leu Val Asn Asn His Leu Val Glu Arg Glu Asp Ala Thr
1               5                   10                  15

Val Asp Ile Glu Asp Arg Gly Tyr Gln Phe Gly Asp Gly Val Tyr Glu
            20                  25                  30

Val Val Arg Leu Tyr Asn Gly Lys Phe Phe Thr Tyr Asn Glu His Ile
        35                  40                  45

Asp Arg Leu Tyr Ala Ser Ala Ala Lys Ile Asp Leu Val Ile Pro Tyr
    50                  55                  60

Ser Lys Glu Glu Leu Arg Glu Leu Leu Glu Lys Leu Val Ala Glu Asn
65                  70                  75                  80

Asn Ile Asn Thr Gly Asn Val Tyr Leu Gln Val Thr Arg Gly Val Gln
                85                  90                  95

Asn Pro Arg Asn His Val Ile Pro Asp Asp Phe Pro Leu Glu Gly Val
            100                 105                 110

Leu Thr Ala Ala Ala Arg Glu Val Pro Arg Asn Glu Arg Gln Phe Val
        115                 120                 125

Glu Gly Gly Thr Ala Ile Thr Glu Glu Asp Val Arg Trp Leu Arg Cys
    130                 135                 140

Asp Ile Lys Ser Leu Asn Leu Leu Gly Asn Ile Leu Ala Lys Asn Lys
145                 150                 155                 160

Ala His Gln Gln Asn Ala Leu Glu Ala Ile Leu His Arg Gly Glu Gln
                165                 170                 175

Val Thr Glu Cys Ser Ala Ser Asn Val Ser Ile Ile Lys Asp Gly Val
            180                 185                 190

Leu Trp Thr His Ala Ala Asp Asn Leu Ile Leu Asn Gly Ile Thr Arg
        195                 200                 205

Gln Val Ile Ile Asp Val Ala Lys Lys Asn Gly Ile Pro Val Lys Glu
    210                 215                 220

Ala Asp Phe Thr Leu Thr Asp Leu Arg Glu Ala Asp Glu Val Phe Ile
225                 230                 235                 240

Ser Ser Thr Thr Ile Glu Ile Thr Pro Ile Thr His Ile Asp Gly Val
                245                 250                 255

Gln Val Ala Asp Gly Lys Arg Gly Pro Ile Thr Ala Gln Leu His Gln
            260                 265                 270

Tyr Phe Val Glu Glu Ile Thr Arg Ala Cys Gly Glu Leu Glu Phe Ala
        275                 280                 285

Lys
```

-continued

```
<210> SEQ ID NO 58
<211> LENGTH: 29
<212> TYPE: DNA
<213> ORGANISM: Artificial
<220> FEATURE:
<223> OTHER INFORMATION: chemically synthesized

<400> SEQUENCE: 58

gtgctcgaga ttgtgggagg ctgggagtg                                     29


<210> SEQ ID NO 59
<211> LENGTH: 29
<212> TYPE: DNA
<213> ORGANISM: Artificial
<220> FEATURE:
<223> OTHER INFORMATION: chemically synthesized

<400> SEQUENCE: 59

gatactagtt taggggttgg ccacgatgg                                     29


<210> SEQ ID NO 60
<211> LENGTH: 10
<212> TYPE: PRT
<213> ORGANISM: Homo sapiens

<400> SEQUENCE: 60

His Cys Ile Arg Asn Lys Ser Val Ile Leu
1               5                   10
```

COMPOSITIONS AND METHODS COMPRISING KLK3 OR FOLH1 ANTIGEN

CROSS REFERENCE TO RELATED APPLICATIONS

This application is a divisional of U.S. application Ser. No. 11/798,177, filed May 10, 2007, which is a Continuation-in-Part of U.S. application Ser. No. 11/727,889, filed Mar. 28, 2007 now abandoned, which is a Continuation-in-Part of U.S. application Ser. No. 11/223,945, filed Sep. 13, 2005, now U.S. Pat. No. 7,820,180, which is a Continuation-in-Part of U.S. application Ser. No. 10/949,667, filed Sep. 24, 2004, now U.S. Pat. No. 7,794,729, which is a Continuation-in-Part of U.S. application Ser. No. 10/441,851, filed May 20, 2003, now U.S. Pat. No. 7,135,188, which is a Continuation of U.S. application Ser. No. 09/535,212, filed Mar. 27, 2000, now U.S. Pat. No. 6,565,852. These applications are hereby incorporated in their entirety by reference herein.

FIELD OF THE INVENTION

The present invention provides KLK3 peptides, FOLH1 peptides, recombinant polypeptides comprising same, recombinant nucleotide molecules encoding same, recombinant *Listeria* strains comprising same, and immunogenic and therapeutic methods utilizing same.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate $CD4^+$ T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism which facilitates major histocompatibility class I antigen presentation of listerial antigens. This escape is dependent upon the pore-forming sulfhydryl-activated cytolysin, listeriolysin O (LLO).

ActA is a surface-associated Listerial protein, and acts as a scaffold in infected host cells to facilitate the polymerization, assembly and activation of host actin polymers in order to propel the *Listeria* organism through the cytoplasm. Shortly after entry into the mammalian cell cytosol, *L. monocytogenes* induces the polymerization of host actin filaments and uses the force generated by actin polymerization to move, first intracellularly and then from cell to cell. A single bacterial protein, ActA is responsible for mediating actin nucleation and actin-based motility. The ActA protein provides multiple binding sites for host cytoskeletal components, thereby acting as a scaffold to assemble the cellular actin polymerization machinery. The $NH_2$ terminus of ActA binds to monomeric actin and acts as a constitutively active nucleation promoting factor by stimulating the intrinsic actin nucleation activity. ActA and hly are both members of the 10-kb gene cluster regulated by the transcriptional activator PrfA, and is upregulated approximately 226-fold in the mammalian cytosol.

Prostate cancer is the most frequent type of cancer in American men and it is the second cause of cancer related death in this population. Prostate Specific Antigen (PSA) is a marker for prostate cancer that is highly expressed by prostate tumors.

There exists a long-felt need to develop compositions and methods to enhance the immunogenicity of antigens, especially antigens useful in the prevention and treatment of tumors and intracellular pathogens.

SUMMARY OF THE INVENTION

The present invention provides KLK3 peptides, FOLH1 peptides, recombinant polypeptides comprising same, recombinant nucleotide molecules encoding same, recombinant *Listeria* strains comprising same, and immunogenic and therapeutic methods utilizing same.

In another embodiment, the present invention provides a recombinant *Listeria* strain expressing a kallikrein-related peptidase 3 (KLK3) peptide. In another embodiment, the sequence of the KLK3 peptide is selected from SEQ ID No: 25, 27, 29-32, 34, and 36-39. In another embodiment, the KLK3 peptide is an immunogenic KLK3 peptide. In another embodiment, the KLK3 peptide is any other KLK3 peptide known in the art. Each possibility represents a separate embodiment of the present invention.

In another embodiment, the present invention provides a recombinant *Listeria* strain expressing a folate hydrolase 1 (FOLH1) peptide. In another embodiment, the sequence of the FOLH1 peptide is selected from SEQ ID No: 41, 43, 44, and 45. In another embodiment, the FOLH1 peptide is an immunogenic FOLH1 peptide. In another embodiment, the FOLH1 peptide is any other FOLH1 peptide known in the art. Each possibility represents a separate embodiment of the present invention.

In another embodiment, the present invention provides a recombinant polypeptide, comprising a KLK3 peptide operatively linked to a non-KLK3 peptide. In another embodiment, the non-KLK3 peptide is an LLO peptide. In another embodiment, the non-KLK3 peptide is an ActA peptide. In another embodiment, the non-KLK3 peptide is a PEST-like sequence peptide. In another embodiment, the non-KLK3 peptide enhances the immunogenicity of the KLK3 peptide. In another embodiment, the non-KLK3 peptide is any other type of peptide known in the art. Each possibility represents a separate embodiment of the present invention.

In another embodiment, the present invention provides a recombinant polypeptide, comprising an FOLH1 peptide operatively linked to a non-FOLH1 peptide. In another embodiment, the non-FOLH1 peptide is an LLO peptide. In another embodiment, the non-FOLH1 peptide is an ActA peptide. In another embodiment, the non-FOLH1 peptide is a PEST-like sequence peptide. In another embodiment, the non-FOLH1 peptide enhances the immunogenicity of the FOLH1 peptide. In another embodiment, the non-FOLH1 peptide is any other type of peptide known in the art. Each possibility represents a separate embodiment of the present invention.

In another embodiment, the present invention provides a recombinant vaccine vector encoding a recombinant polypeptide of the present invention.

In another embodiment, the present invention provides a nucleotide molecule encoding a recombinant polypeptide of the present invention.

In another embodiment, the present invention provides a method of inducing an anti-KLK3 immune response in a subject, comprising administering to the subject a composition comprising a recombinant *Listeria* strain of the present invention, thereby inducing an anti-KLK3 immune response in a subject.

In another embodiment, the present invention provides a method of treating a KLK3 protein-expressing tumor in a subject, the method comprising the step of administering to the subject a composition comprising a recombinant *Listeria* strain of the present invention, whereby the subject mounts an immune response against the KLK3 protein-expressing tumor, thereby treating a KLK3 protein-expressing tumor in a subject. Each possibility represents a separate embodiment of the present invention.

In another embodiment, the present invention provides a method of protecting a human subject against a KLK3 protein-expressing tumor, the method comprising the step of administering to the human subject a composition comprising a recombinant *Listeria* strain of the present invention, whereby the subject mounts an immune response against the KLK3 protein, thereby protecting a human subject against a KLK3 protein-expressing tumor. Each possibility represents a separate embodiment of the present invention.

In another embodiment, the present invention provides a method of inducing an anti-FOLH1 immune response in a subject, comprising administering to the subject a composition comprising a recombinant *Listeria* strain of the present invention, thereby inducing an anti-FOLH1 immune response in a subject.

In another embodiment, the present invention provides a method of treating an FOLH1 protein-expressing tumor in a subject, the method comprising the step of administering to the subject a composition comprising a recombinant *Listeria* strain of the present invention, whereby the subject mounts an immune response against the FOLH1 protein-expressing tumor, thereby treating an FOLH1 protein-expressing tumor in a subject. Each possibility represents a separate embodiment of the present invention.

In another embodiment, the present invention provides a method of protecting a human subject against an FOLH1 protein-expressing tumor, the method comprising the step of administering to the human subject a composition comprising a recombinant *Listeria* strain of the present invention, whereby the subject mounts an immune response against the FOLH1 protein, thereby protecting a human subject against an FOLH1 protein-expressing tumor. Each possibility represents a separate embodiment of the present invention.

BRIEF DESCRIPTION OF THE DRAWINGS

FIG. 3A. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles. FIG. 3B. Tumor immunotherapeutic efficacy of LLO-Ova fusions.

FIG. 8A. schematic representation of the plasmid inserts used to create 4 LM vaccines. Lm-LLO-E7 insert contains all of the *Listeria* genes used. It contains the hly promoter, the first 1.3 kb of the hly gene (which encodes the protein LLO), and the HPV-16 E7 gene. The first 1.3 kb of hly includes the signal sequence (ss) and the PEST region. Lm-PEST-E7 includes the hly promoter, the signal sequence, and PEST and E7 sequences but excludes the remainder of the truncated LLO gene. Lm-ΔPEST-E7 excludes the PEST region, but contains the hly promoter, the signal sequence, E7, and the remainder of the truncated LLO. Lm-E7epi has only the hly promoter, the signal sequence, and E7. FIG. 8B. Schematic representation of the pActA-E7 expression system used to express and secrete E7 from recombinant *Listeria* bacteria. The hly promoter (pHLY) drives expression, the prfA gene is used to select retention of the plasmid by recombinant *Listeria* in vivo. FIG. 8C. Top panel: *Listeria* constructs containing PEST regions induce tumor regression. Solid triangles: naïve mice; Circles: Lm-LLO-E7; Squares: Lm-E7epi; +signs: Lm-ΔPEST-E7; hollow triangles: Lm-PEST-E7. FIG. 8D. Average tumor sizes at day 28 post-tumor challenge in 2 separate experiments. FIG. 8E. *Listeria* constructs containing PEST regions induce a higher percentage of E7-specific lymphocytes in the spleen. Average and SE of data from 3 experiments are depicted.

FIG. 10A. Induction of E7-specific IFN-gamma-secreting CD8$^+$ T cells in the spleens and the numbers penetrating the tumors, in mice administered TC-1 tumor cells and subsequently administered Lm-E7, Lm-LLO-E7, Lm-ActA-E7, or no vaccine (naive). FIG. 10B.

Figure 10A:
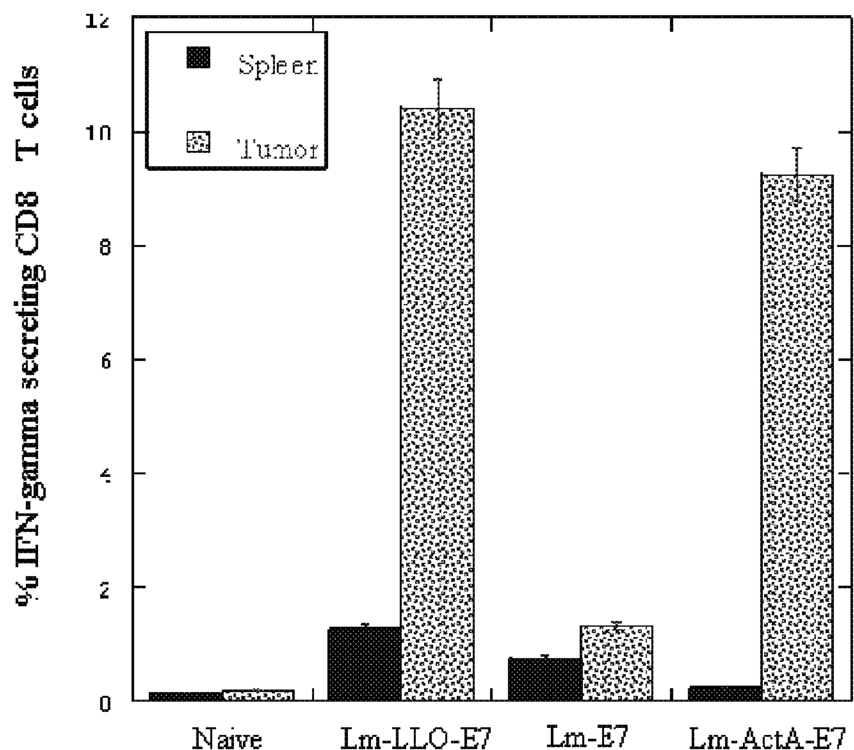
FIG. 10A-B.

Induction and penetration of E7 specific $CD8^+$ cells in the spleens and tumors of the mice described for (FIG. 10A).

Figure 11A:
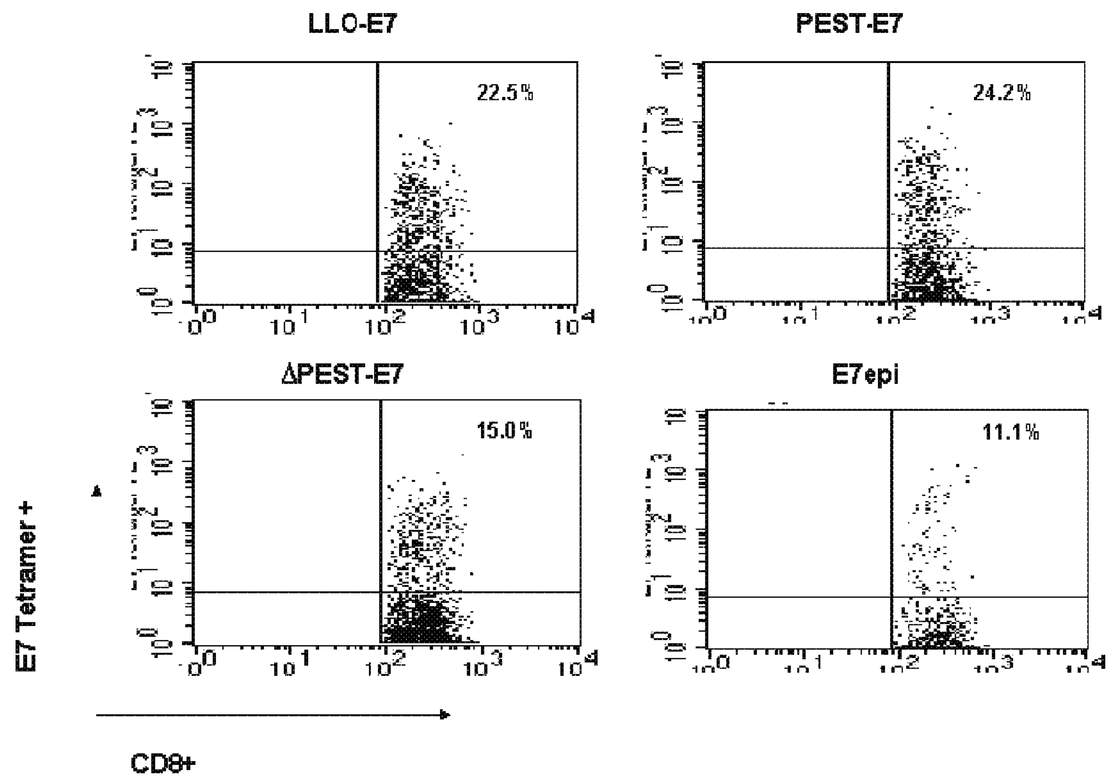
Figure 11B:
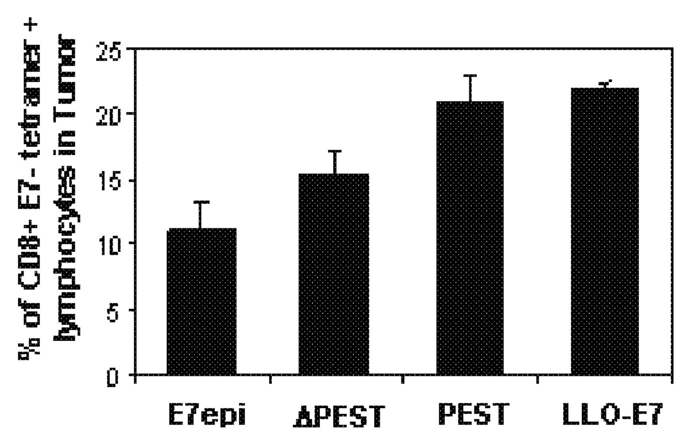

FIG. 11A-B. *Listeria* constructs containing PEST regions induce a higher percentage of E7-specific lymphocytes within the tumor. FIG. 11A. representative data from 1 experiment. FIG. 11B. average and SE of data from all 3 experiments.

Figure 12:
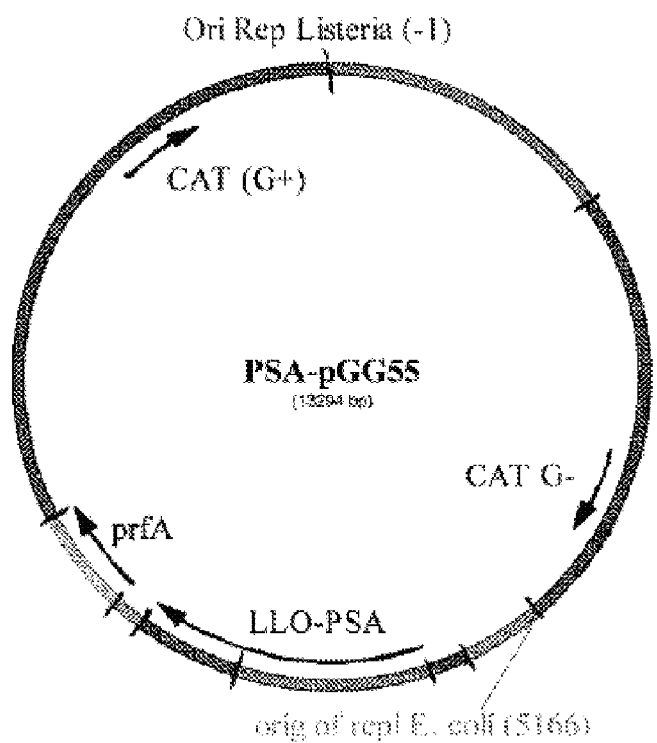

FIG. 12: Plasmid map of pAdv34 (PSA-pGG55).

Figure 13:
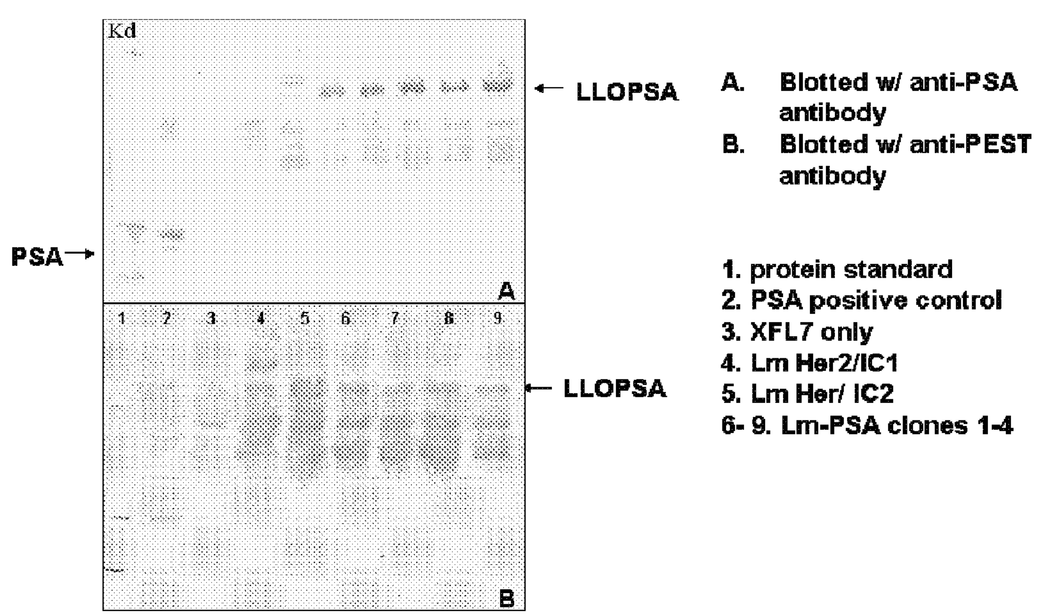

FIG. 13. Western blot analysis of the cell culture supernatants of Lm-PSA. Proteins in culture broth from 4 colonies of Lm-PSA were precipitated with 10% TCA, separated on a 4-20% SDS protein gel, transferred to PVDF membranes and then detected with either anti-PSA (A) or anti-LLO antibody (B) (Lanes 6-9). A cell lysate from PSA-vaccinia transfected BHK21 cells was used as the positive control (lane 2). Parent XFL7 *Listeria* (lane 3) and two *Listeria* construct expressing fragments of Her2/neu antigen (Lanes 4 and 5) were used as negative controls.

Figure 14A:
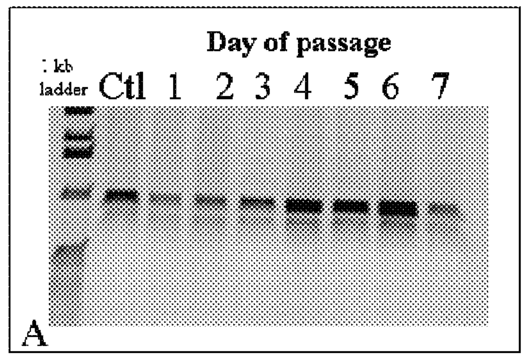
Figure 14B:
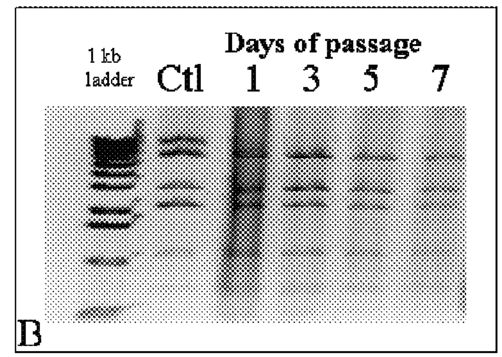

FIG. 14A-B. Stability of Lm-PSA. Lm-PSA was grown and passaged for 7 consecutive days in vitro. Plasmid DNA was purified from bacterial samples taken every day during the in vitro growth and tested by amplification of PSA gene by PCR (FIG. 14A) or EcoRI/HindIII restriction mapping of the plasmid (FIG. 14B).

Figure 15A:
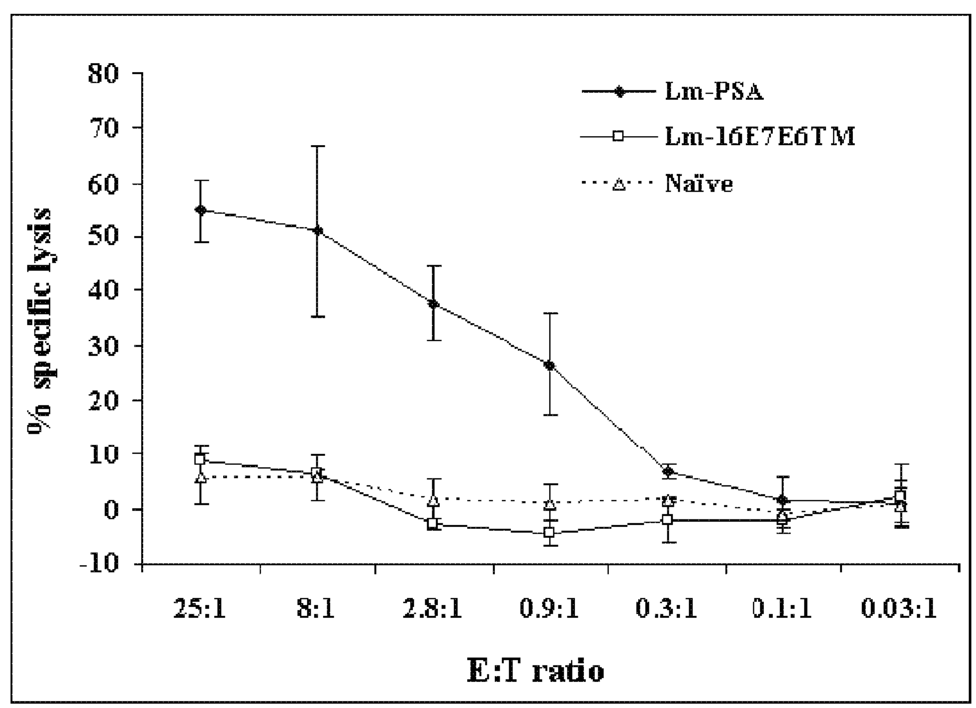
Figure 15B:
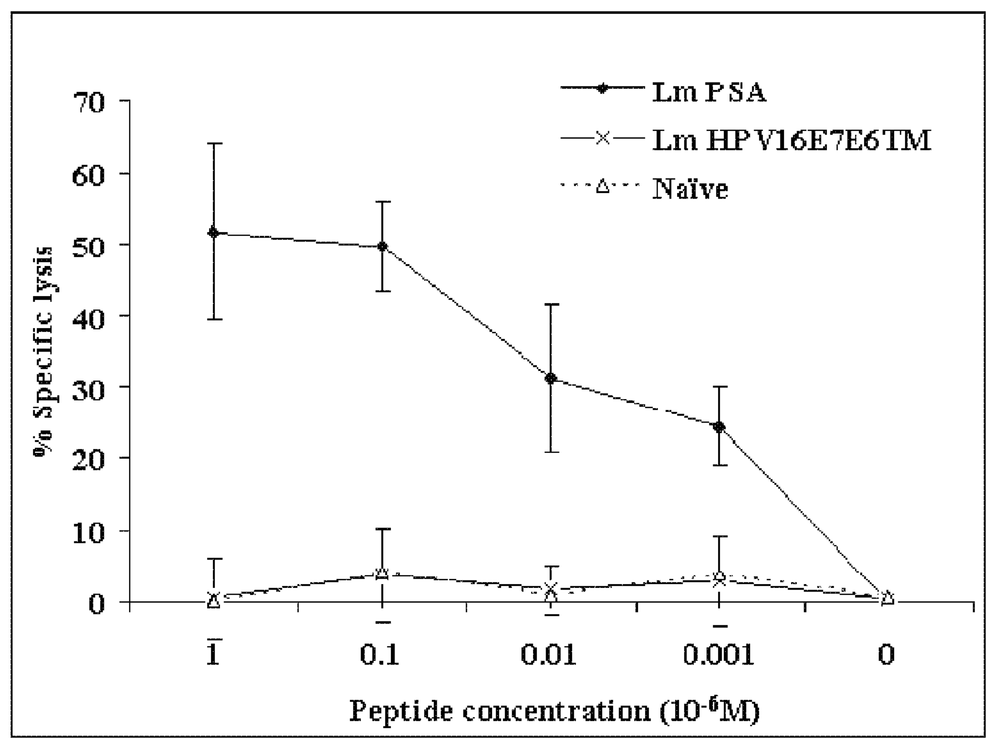

FIG. 15A-B. Immunogenicity of Lm-LLO-PSA. Mice were immunized two times with Lm-PSA and splenocytes were tested by CTL assay with (FIG. 15A) different E:T (effector to target) ratios and (FIG. 15B) different peptide concentrations. % specific lysis is defined as (Experimental release −spontaneous release)×100/(Maximum release−spontaneous release).

Figure 16:
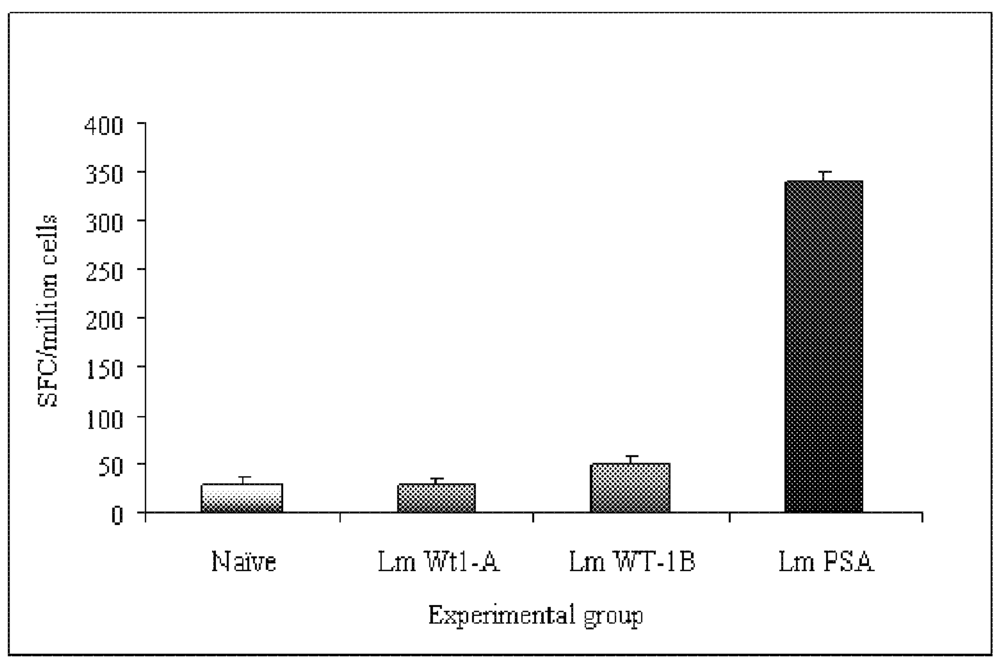

FIG. 16. IFN-γ secretion by splenocytes from immunized mice in response to peptide pulse with PSA peptide. Naïve mice were injected with PBS. LmWt1-A and B are two *Listeria* strains that express two fragments of Wilm's Tumor antigen and were used as negative controls.

DETAILED DESCRIPTION OF THE INVENTION

The present invention provides KLK3 peptides, FOLH1 peptides, recombinant polypeptides comprising same, recombinant nucleotide molecules encoding same, recombinant *Listeria* strains comprising same, and immunogenic and therapeutic methods utilizing same.

In another embodiment, the present invention provides a recombinant *Listeria* strain expressing a kallikrein-related peptidase 3 (KLK3) peptide. In another embodiment, the sequence of the KLK3 peptide is selected from SEQ ID No: 25, 27, 29-32, 34, and 36-39. In another embodiment, the sequence of the KLK3 peptide is set forth in SEQ ID No: 25. In another embodiment, the sequence of the KLK3 peptide is set forth in SEQ ID No: 27. In another embodiment, the sequence of the KLK3 peptide is set forth in SEQ ID No: 29. In another embodiment, the sequence of the KLK3 peptide is set forth in SEQ ID No: 30. In another embodiment, the sequence of the KLK3 peptide is set forth in SEQ ID No: 31. In another embodiment, the sequence of the KLK3 peptide is set forth in SEQ ID No: 32. In another embodiment, the sequence of the KLK3 peptide is set forth in SEQ ID No: 34. In another embodiment, the sequence of the KLK3 peptide is set forth in SEQ ID No: 36. In another embodiment, the sequence of the KLK3 peptide is set forth in SEQ ID No: 37. In another embodiment, the sequence of the KLK3 peptide is set forth in SEQ ID No: 38. In another embodiment, the sequence of the KLK3 peptide is set forth in SEQ ID No: 39. In another embodiment, the sequence of the KLK3 peptide is any other KLK3 protein sequence known in the art. Each possibility represents a separate embodiment of the present invention.

In another embodiment, the sequence of the KLK3 peptide comprises a sequence selected from SEQ ID No: 25, 27, 29-32, 34, and 36-39.

In another embodiment, the KLK3 peptide is an immunogenic fragment of a larger KLK3 peptide, wherein the sequence of the larger KLK3 peptide is a sequence selected from SEQ ID No: 25, 27, 29-32, 34, and 36-39. In another embodiment, the KLK3 peptide is an immunogenic fragment of a larger KLK3 peptide, wherein the sequence of the larger KLK3 peptide is set forth in SEQ ID No: 25. In another embodiment, the sequence of the larger KLK3 peptide is set forth in SEQ ID No: 27. In another embodiment, the sequence of the larger KLK3 peptide is set forth in SEQ ID No: 29. In another embodiment, the sequence of the larger KLK3 peptide is set forth in SEQ ID No: 30. In another embodiment, the sequence of the larger KLK3 peptide is set forth in SEQ ID No: 31. In another embodiment, the sequence of the larger KLK3 peptide is set forth in SEQ ID No: 32. In another embodiment, the sequence of the larger KLK3 peptide is set forth in SEQ ID No: 34. In another embodiment, the sequence of the larger KLK3 peptide is set forth in SEQ ID No: 36. In another embodiment, the sequence of the larger KLK3 peptide is set forth in SEQ ID No: 37. In another embodiment, the sequence of the larger KLK3 peptide is set forth in SEQ ID No: 38. In another embodiment, the sequence of the larger KLK3 peptide is set forth in SEQ ID No: 39. In another embodiment, the sequence of the larger KLK3 peptide is any other KLK3 protein sequence known in the art. Each possibility represents a separate embodiment of the present invention.

In another embodiment, the sequence of the KLK3 peptide comprises an immunogenic fragment of a sequence selected from SEQ ID No: 25, 27, 29-32, 34, and 36-39.

In another embodiment, the KLK3 peptide is any other KLK3 peptide known in the art. In another embodiment, the KLK3 peptide is a fragment of any other KLK3 peptide known in the art. Each type of KLK3 peptide represents a separate embodiment of the present invention.

"KLK3 peptide" refers, in another embodiment, to a full-length KLK3 protein. In another embodiment, the term refers to a fragment of a KLK3 protein. In another embodiment, the term refers to a fragment of a KLK3 protein that is lacking the KLK3 signal peptide. In another embodiment, the term refers to a KLK3 protein that contains the entire KLK3 sequence except the KLK3 signal peptide. "KLK3 signal sequence" refers, in another embodiment, to any signal sequence found in nature on a KLK3 protein. In another embodiment, a KLK3 protein of methods and compositions of the present invention does not contain any signal sequence. Each possibility represents a separate embodiment of the present invention.

In another embodiment, the kallikrein-related peptidase 3 (KLK3 protein) that is the source of a KLK3 peptide of methods and compositions of the present invention is a PSA protein. In another embodiment, the KLK3 protein is a P-30 antigen protein. In another embodiment, the KLK3 protein is a gamma-seminoprotein protein. In another embodiment, the KLK3 protein is a kallikrein 3 protein. In another embodiment, the KLK3 protein is a semenogelase protein. In another embodiment, the KLK3 protein is a seminin protein. In another embodiment, the KLK3 protein is any other type of KLK3 protein that is known in the art. Each possibility represents a separate embodiment of the present invention.

In another embodiment, the KLK3 protein is a splice variant 1 KLK3 protein. In another embodiment, the KLK3 protein is a splice variant 2 KLK3 protein. In another embodiment, the KLK3 protein is a splice variant 3 KLK3 protein. In another embodiment, the KLK3 protein is a transcript variant 1 KLK3 protein. In another embodiment, the KLK3 protein is a transcript variant 2 KLK3 protein. In another embodiment, the KLK3 protein is a transcript variant 3 KLK3 protein. In another embodiment, the KLK3 protein is a transcript variant 4 KLK3 protein. In another embodiment, the KLK3 protein is a transcript variant 5 KLK3 protein. In another embodiment, the KLK3 protein is a transcript variant 6 KLK3 protein. In another embodiment, the KLK3 protein is a splice variant RP5 KLK3 protein. In another embodiment, the KLK3 protein is any other splice variant KLK3 protein known in the art. In another embodiment, the KLK3 protein is any other transcript variant KLK3 protein known in the art. Each possibility represents a separate embodiment of the present invention.

In another embodiment, the KLK3 protein is a mature KLK3 protein. In another embodiment, the KLK3 protein is a pro-KLK3 protein. In another embodiment, the leader sequence has been removed from a mature KLK3 protein of methods and compositions of the present invention. An example of a mature KLK3 protein is encoded by 378-1088 of SEQ ID No: 40. Each possibility represents a separate embodiment of the present invention.

In another embodiment, the KLK3 protein that is the source of a KLK3 peptide of methods and compositions of the present invention is a human KLK3 protein. In another embodiment, the KLK3 protein is a primate KLK3 protein. In another embodiment, the KLK3 protein is a KLK3 protein of any other species known in the art. In another embodiment, 1 of the above KLK3 proteins is referred to in the art as a "KLK3 protein." Each possibility represents a separate embodiment of the present invention.

In another embodiment, the KLK3 protein has the sequence:

MWVPVVFLTLSVTWIGAAPLILSRIVGGWECEKH-
SQPWQVLVASRGRAVCGGVL VHPQWVLTAAH-
CIRNKSVILLGRHSLFHPEDTGQVFQVSHSFPHPLY-
DMSLLKNRFLRPG
DDSSHDLMLLRLSEPAELTDAVKVMDLPTQEPALGT-
TCYASGWGSIEPEEFLTPKKLQCV DLHVISNDV-
CAQVHPQKVTKFMLCAGRWTGGKSTCSGDSGG-
PLVCNGVLQGITSWGSEP
CALPERPSLYTKVVHYRKWIKDTIVANP (SEQ ID No: 25; GenBank Accession No. X14810). In another embodiment, the KLK3 protein is a homologue of SEQ ID No: 25. In another embodiment, the KLK3 protein is a variant of SEQ ID No: 25. In another embodiment, the KLK3 protein is an isomer of SEQ ID No: 25. In another embodiment, the KLK3 protein is a fragment of SEQ ID No: 25. Each possibility represents a separate embodiment of the present invention.

In another embodiment, the KLK3 protein is encoded by a nucleotide molecule having the sequence:

gtgtctaggcacactggtcttggagtgcaaaggatctaggcacgtgagg cttt-
gtatgaagaatcggggatcgtacccacccccct Gtttctgtttcatcctgggcat-
gtctcctctgcctttgtcccctagatgaagtctc catgagctacaagggcctggtg-
catccagggtgatctagta
Attgcagaacagcaagtgctagctctccctccccttccacagctctgggtgtg
ggagggggttgtccagcctccagcagcatggggagggcc ttggtcagc-
ctctgggtgccagcagggcaggggcggagtcctggggaatg aaggttt-
tatagggctcctgggggaggctccccagccccaa gcttaccacctgcacccg-
gagagctgtgtcaccatgtgggtcccggttgtctt
cctcaccctgtccgtgacgtggattggtgagaggggccatg Gttgggggat-
gcaggagagggagccagccctgactgtcaagctgag gctctttcccccccaac-
ccagcaccccagcccagacagggag ctgggctcttttctgtctctcccagc-
cccacttcaagcccatacccccagtc
ccctccatattgcaacagtcctcactcccacaccaggtccccg ctccctcccact-
taccccagaactttcttcccatttgcccagccagctccc tgctcccagctgctt-
tactaaaggggaagttcctgggcatctccg tgtttctctttgtggggctcaaaac-
ctccaaggacctctctcaatgccattgg
ttccttggaccgtatcactggtccatctcctgagcccctcaatcc tatcacagtc-
tactgacttttcccattcagctgtgagtgtccaaccctatccc agagaccttgatgct-
tggcctcccaatcttgccctaggatacccagatgcc aaccagacacctccttcttc-
ctagccaggctatctggcctgagacaacaaat
gggtccctcagtctggcaatgggactctgagaac tcctcattccctgactcttagc-
cccagactcttcattcagtggcccacattttcc ttaggaaaaacatgagcatcccca-
gccacaactgccagctc tctgagtccccaaatctgcatccttttcaaaac-
ctaaaaacaaaaagaaaaa
caaataaaacaaaaccaactcagaccagaactgttttctcaac ctgggacttc-
ctaaactttccaaaaccttcctcttccagcaactgaacctcgcc ataaggcact-
tatccctggttcctagcaccccttatcccctca gaatccacaacttgtaccaagtttc-
ccttctcccagtccaagaccccaaatcac
cacaaaggacccaatccccagactcaagatatggtctggg cgctgtcttgtgtctc-
ctaccctgatccctgggttcaactctgctcccagagcat gaagcctctccaccag-
caccagccaccaacctgcaaacct agggaagattgacagaattcccagcctttc-
ccagctcccccctgcccatgtccca
ggactcccagccttggttctctgcccccgtgtcttttcaaa cccacatcctaaatc-
catctcctatccgagtcccccagttcccccctgtcaaccct gattcccctgatctag-
cacccccctctgcaggcgctgcgcc cctcatcctgtctcggattgtgggag-
gctgggagtgcgagaagcattcccaac
cctggcaggtgcttgtggcctctcgtggcagggcagtctg cggcggtgttctggt-
gcacccccagtgggtcctcacagctgcccactgcatca ggaagtgag-
taggggcctggggtctggggagcaggtgt ctgtgtcccagaggaataaca-
gctgggcattttccccaggataacctctaag
gccagccttgggactgggggagagagggaaagttctggtt caggtca-
catggggaggcagggttggggctggaccaccctccccatggctgc
ctgggtctccatctgtgtccctctatgtctctttgtgtcgcttt cattatgtctcttgg-
taactggcttcggttgtgtctctccgtgtgactattttgttctct ctctccctctcttctct-
gtcttcagtctccatatctccccctct ctctgtccttctctggtccctctctagccagt-
gtgtctcaccctgtatctctctgcca
ggctctgtctctcggtctctgtctcacctgtgccttctccct actgaacacacg-
cacgggatgggcctgggggaccctgagaaaaggaaggg ctttg-
gctgggcgcggtggctcacacctgtaatcccagca ctttgggaggccaaggca-
ggtagatcacctgaggtcaggagttcgagaccag
cctggccaactggtgaaaccccatctctactaaaaataca aaaaattagccag-
gcgtggtggcgcatgcctgtagtcccagctactcaggagc tgagggagga-
gaattgcattgaacctggaggttgaggtt gcagtgagccgagaccgtgccactg-
cactccagcctgggtgacagagtg
agactccgcctcaaaaaaaaaaaaaaaaaaaaaaaaaaaa
agaaaagaaaagaaaagaaaaggaagtgttttatccctgatgtgtgtgggtatg
agggtatgagagggcccctctcactccattccttctccag gacatccctccactct-
tgggagacacagagaagggctggttccagctggagct gggaggggcaatt-
gagggaggaggaaggagaaggg ggaaggaaaacaggg-
tatgggggaaaggaccctggggagcgaagtggagg
atacaaccttgggcctgcaggcaggctacctacccactt ggaaacccacgc-
caaagccgcatctacagctgagccactctgaggcctccc ctccccggcggtc-
cccactcagctccaaagtctctctccctt ttctctcccacactttatcatcccccggat-
tcctctctacttggttctcattcttccttt
gacttcctgcttccctttctcattcatctgtttctcactttctgc ctggttttgttct-
tctctctctctttctctggcccatgtctgtttctcttttgttt tgtcttttctttctcatcctgt-
gtattttcggctcaccttgtttgtcactgt tctcccctctgccctttcattctctctgc-
ccttttaccctcttccttttcccttg
ttctctcagttctgtatctgcccttcaccctctcacactgctgtttcc caactcgtt-
gtctgtattttggcctgaactgtgtcttcccaaccctgtgttttctc act-
gtttctttttctcttttggagcctcctccttgctcctctgtccct tctctctttccttatcatc-
ctcgctcctcattcctgcgtctgcttcctccccagca
aagcgtgatcttgctgggtcggcacagcctgtttcatcctga agacacaggccaggtatttcaggtcagccacagcttcccacacccgctctac gatatgagcctcct-
gaagaatcgattcctcaggccaggtga tgactccagccacgacctcatgctgctc-
cgcctgtcagagcctgccgagctcac
ggatgctgtgaaggtcatggacctgcccacccaggagc cagcactggggac-
cacctgctacgcctcaggctggggcagcattgaacc agaggagtgtacgc-
ctgggccagatggtgcagccgggagc ccagatgcctgggtctgagggag-
gaggggacaggactcctgggtctgag
ggaggagggccaaggaaccaggtggggtccagcccacaa cagtgtttttgc-
ctggcccgtagtcttgaccccaaagaaacttcagtgtgtgga cctccatgttatttc-
caatgacgtgtgtgcgcaagttcaccct cagaaggtgaccaagttcatgctgtgt-
gctggacgctggacagggggcaaa
agcacctgctcggtgagtcatccctactcccaagatcttga gggaaaggt-
gagtgggaccttaattctgggctggggtctagaagccaacaag gcgtctgcctc-
ccctgctccccagctgtagccatgccacc tccccgtgtctcatctcattccctcct-
tccctcttctttgactccctcaaggcaata
ggttattcttacagcacaactcatctgttcctgcgttcagcac acggttactag-
gcacctgctatgcacccagcactgccctagagcctgggac atagcagtgaaca-
gacagagagcagcccctcccttctgtag cccccaagccagtgaggggcacag-
gcaggaacagggaccacaacacag
aaaagctggagggtgtcaggaggtgatcaggctctcgggg aggga-
gaaggggtggggagtgtgactgggaggagacatcctgcagaag gtgggagt-
gagcaaacacctgcgcaggggaggggagggc ctgcggcac-
ctgggggagcagagggaacagcatctggccaggcctggg
ggagggggcctagagggcgtcaggagcagagaggaggtt gcctggctggagt-
gaaggatcggggcagggtgcgagagggaacaaag gacccctcctgcagggc-
ctcacctgggccacaggaggacac tgcttttcctctgaggagtcaggaactgtg-
gatggtgctggacagaagcag
gacagggcctggctcaggtgtccagaggctgcgctggcctc ctatgggatca-
gactgcagggagggagggcagcagggatgtggagggag tgatgatggggct-
gacctgggggtggctccaggcattgtc cccacctgggcccttacccagcctccct-
cacaggctcctggccctcagtctc
tcccctccactccattctccacctacccacagtgggtcattct gatcaccgaact-
gaccatgccagccctgccgatggtcctccatggctcccta gtgccctggagag-
gaggtgtctagtcagagagtagtcctg gaaggtggcctctgtgaggagc-
cacggggacagcatcctgcagatggtcct
ggcccttgtcccaccgacctgtctacaaggactgtcctcgt ggaccctcccctctg-
cacaggagctggaccctgaagtcccttcctaccggcc aggactggagcccctac-
ccctctgttggaatccctgccca ccttcttctggaagtcggctctggaga-
catttctctcttcttccaaagctgggaa
ctgctatctgttatctgcctgtccaggtctgaaagataggatt gcccaggca-
gaaactgggactgacctatctcactctctccctgcttttaccctta ggtgat-
tctgggggcccacttgtctgtaatggtgtgcttca aggtatcacgtcatggggca-
gtgaaccatgtgccctgcccgaaaggccttccc
gtacaccaaggtggtgcattaccggaagtggatcaagg acaccatcgtggc-
caacccctgagcacccctatcaagtccctattgtagtaaac ttggaaccttg-
gaaatgaccaggccaagactcaagcctc cccagttctactgacctttgtccttag-
gtgtgaggtccagggttgctaggaaaag
aaatcagcagacacaggtgtagaccagagtgtttcttaaa tggtgtaattttgtc-
ctctctgtgtcctggggaatactggccatgcctggagacat atcactcaatttctct-
gaggacacagttaggatggggtgtc tgtgttatttgtgggatacagagat-
gaaagaggggtgggatcc (SEQ ID No: 26; GenBank Accession No. X14810). In another embodiment, the KLK3 protein is encoded by residues 401 . . . 446, 1688 . . . 1847, 3477 . . . 3763, 3907 . . . 4043, and 5413 . . . 5568 of SEQ ID No: 26. In another embodiment, the KLK3 protein is encoded by a homologue of SEQ ID No: 26. In another embodiment, the KLK3 protein is encoded by a variant of SEQ ID No: 26. In another embodiment, the KLK3 protein is encoded by an isomer of SEQ ID No: 26. In another embodiment, the KLK3 protein is encoded by a fragment of SEQ ID No: 26. Each possibility represents a separate embodiment of the present invention.

In another embodiment, the KLK3 protein has the sequence:

MWVPVVFLTLSVTWIGAAPLILSRIVGGWECEKH-
SQPWQVLVASRGRAVCGGVL VHPQWVLTAAH-
CIRNKSVILLGRHSLFHPEDTGQVFQVSHSFPHPLY-
DMSLLKNRFLRPG
DDSSHDLMLLRLSEPAELTDAVKVMDLPTQEPALGT-
TCYASGWGSIEPEEFLTPKKLQCV DLHVISNDV-
CAQVHPQKVTKFMLCAGRWTGGKSTCSWVI-
LITELTMPALPMVLHGSLVP WRGGV (SEQ ID No: 27; GenBank Accession No. NM_001030047) In another embodiment, the KLK3 protein is a homologue of SEQ ID No: 27. In another embodiment, the KLK3 protein is a variant of SEQ ID No: 27. In another embodiment, the KLK3 protein is an isomer of SEQ ID No: 27. In another embodiment, the KLK3 protein is a fragment of SEQ ID No: 27. Each possibility represents a separate embodiment of the present invention.

In another embodiment, the KLK3 protein is encoded by a nucleotide molecule having the sequence:

agccccaagcttaccacctgcacccggagagctgtgtcaccatgtgg gtc-
ccggttgtcttcctcaccctgtccgtgacgtggattg gtgctgcacccctcatcct-
gtctcggattgtgggaggctgggagtgcgagaa gcattcccaaccctggcaggt-
gcttgtggcctctcgtggca
gggcagtctgcggcggtgttctggtgcacccccagtgggtcctcacagctg
cccactgcatcaggaacaaaagcgtgatcttgctgggtcgg cacagcct-
gtttcatcctgaagacacaggccaggtatttcaggtcagccacag cttcccacac-
ccgctctacgatatgagcctcctgaagaatc gattcctcaggccaggtgatgactc-
cagccacgacctcatgctgctccgcctg
tcagagcctgccgagctcacggatgctgtgaaggtcatg gacctgcccacccag-
gagccagcactggggaccacctgctacgcctcaggc tggggcagcattgaac-
cagaggagttcttgaccccaaag aaacttcagtgtgtggacctccatgttatttc-
caatgacgtgtgtgcgcaagttca
ccctcagaaggtgaccaagttcatgctgtgtgctggacgc tggaca-
gggggcaaaagcacctgctcgtgggtcattctgatcaccgaactgac catgcca-
gccctgccgatggtcctccatggctccctagtg ccctggagaggaggt-
gtctagtcagagagtagtcctggaaggtggcctctgt
gaggagccacggggacagcatcctgcagatggtcctggc ccttgtcccac-
cgacctgtctacaaggactgtcctcgtggaccctcccctctg cacaggagctg-
gaccctgaagtcccttccccaccggccag gactggagcccctacccctctgttg-
gaatccctgcccaccttcttctggaagtc
ggctctggagacatttctctcttcttccaaagctgggaactg ctatctgttatctgcct-
gtccaggtctgaaagataggattgcccaggcagaa actgggactgacctatct-
cactctctccctgcttttacccttagg gtgattctgggggcccacttgtctgtaatg-
gtgtgcttcaaggtatcacgtcat
ggggcagtgaaccatgtgccctgcccgaaaggccttccct gtacaccaaggtg-
gtgcattaccggaagtggatcaaggacaccatcgtggc caacccctgagcac-
ccctatcaaccccctattgtagtaaact tggaaccttggaaatgaccaggc-
caagactcaagcctccccagttctactga
cctttgtccttaggtgtgaggtccagggttgctaggaaaaga aatcagcaga-
cacaggtgtagaccagagtgtttcttaaatggtgtaattttgtcc tctctgtgtc-
ctggggaatactggccatgcctggagacata tcactcaatttctctgaggacaca-
gataggatggggtgtctgtgttatttgtg
gggtacagagatgaaagaggggtgggatccacactgagaga gtggagagt-
gacatgtgctggacactgtccatgaagcactgagcagaag ctggaggca-
caacgcaccagacactcacagcaaggatggag ctgaaaacataacccactct-
gtcctggaggcactgggaagcctagagaa
ggctgtgagccaaggagggagggtcttcctttggcatgggatg gggatgaag-
taaggagagggactggaccccctggaagctgattcactatg gggggaggtgtat-
tgaagtcctccagacaaccctcagatttg atgatttcctagtagaactcaca-
gaaataaagagctgttatactgtg (SEQ ID No: 28; GenBank Accession No. NM_001030047). In another embodiment, the KLK3 protein is encoded by residues 42-758 of SEQ ID No: 28. In another embodiment, the KLK3 protein is encoded by a homologue of SEQ ID No: 28. In another embodiment, the KLK3 protein is encoded by a variant of SEQ ID No: 28. In another embodiment, the KLK3 protein is encoded by an isomer of SEQ ID No: 28. In another embodiment, the KLK3 protein is encoded by a fragment of SEQ ID No: 28. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVCGGVL VHPQWVLTAAHCIRK (SEQ ID No: 29; GenBank Accession No. NM_001030050). In another embodiment, the KLK3 protein is a homologue of SEQ ID No: 29. In another embodiment, the KLK3 protein is a variant of SEQ ID No: 29. In another embodiment, the sequence of the KLK3 protein comprises SEQ ID No: 29. In another embodiment, the KLK3 protein is an isomer of SEQ ID No: 29. In another embodiment, the KLK3 protein is a fragment of SEQ ID No: 29. Each possibility represents a separate embodiment of the present invention.

In another embodiment, the KLK3 protein that is the source of the KLK3 peptide has the sequence:

MWVPVVFLTLSVTWIGAAPLILSRIVGGWECEKHSQPWQVLVASRGRAVCGGVL VHPQWVLTAAHCIRNKSVILLGRHSLFHPEDTGQVFQVSHSFPHPLYDMSLLKNRFLRPG DDSSIEPEEFLTPKKLQCVDLHVISNDVCAQVHPQKVTKFMLCAGRWTGGKSTCSGDSG GPLVCNGVLQGITSWGSEPCALPERPSLYTKVVHYRKWIKDTIVANP (SEQ ID No: 30; GenBank Accession No. NM_001030049). In another embodiment, the KLK3 protein is a homologue of SEQ ID No: 30. In another embodiment, the KLK3 protein is a variant of SEQ ID No: 30. In another embodiment, the KLK3 protein is an isomer of SEQ ID No: 30. In another embodiment, the KLK3 protein is a fragment of SEQ ID No: 30. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVCGGVL VHPQWVLTAAHCIRKPGDDSSHDLMLLRLSEPAELTDAVKVMDLPTQEPALGTTCYASG WGSIEPEEFLTPKKLQCVDLHVISNDVCAQVHPQKVTKFMLCAGRWTGGKSTCSGDSGG PLVCNGVLQGITSWGSEPCALPERPSLYTKVVHYRKWIKDTIVANP (SEQ ID No: 31; GenBank Accession No. NM_001030048). In another embodiment, the KLK3 protein is a homologue of SEQ ID No: 31. In another embodiment, the KLK3 protein is a variant of SEQ ID No: 31. In another embodiment, the KLK3 protein is an isomer of SEQ ID No: 31. In another embodiment, the KLK3 protein is a fragment of SEQ ID No: 31. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVCGGVL VHPQWVLTAAHCIRNKSVILLGRHSLFHPEDTGQVFQVSHSFPHPLYDMSLLKNRFLRPG DDSSHDLMLLRLSEPAELTDAVKVMDLPTQEPALGTTCYASGWGSIEPEEFLTPKKLQCV DLHVISNDVCAQVHPQKVTKFMLCAGRWTGGKSTCSGDSGGPLVCNGVLQGITSWGSEP CALPERPSLYTKVVHYRKWIKDTIVANP (SEQ ID No: 32; GenBank Accession No. NM_001648). In another embodiment, the KLK3 protein is a homologue of SEQ ID No: 32. In another embodiment, the KLK3 protein is a variant of SEQ ID No: 32. In another embodiment, the KLK3 protein is an isomer of SEQ ID No: 32. In another embodiment, the KLK3 protein is a fragment of SEQ ID No: 32. Each possibility represents a separate embodiment of the present invention.

In another embodiment, the KLK3 protein is encoded by a nucleotide molecule having the sequence:

agccccaagcttaccacctgcacccggagagctgtgtcaccatgtgggt cccggttgtctcctcaccctgtccgtgacgtggattg gtgctgcacccctcatcctgtctcggattgtgggaggctgggagtgcgaga agcattcccaaccctggcaggtgcttgtggcctctcgtggca gggcagtctgcggcggtgttctggtgcacccccagtgggtcctcacagctgc ccactgcatcaggaacaaaagcgtgatcttgctgggtcgg cacagcctgtttcatcctgaagacacaggccaggtatttcaggtcagcca cagcttcccacacccgctctacgatatgagcctcctgaagaatc gattcctcaggccaggtgatgactccagccacgacctcatgctgctccgc ctgtcagagcctgccgagctcacggatgctgtgaaggtcatg gacctgcccacccaggagccagcactggggaccacctgctacgcctcag gctggggcagcattgaaccagaggagttcttgaccccaaag aaacttcagtgtgtggacctccatgttatttccaatgacgtgtgtgcgcaagtt caccctcagaaggtgaccaagttcatgctgtgtgctggacgc tggacagggggcaaaagcacctgctcgggtgattctgggggcccacttgtc tgtaatggtgtgcttcaaggtatcacgtcatggggcagtgaa ccatgtgccctgcccgaaaggccttccctgtacaccaaggtggtgcattacc ggaagtggatcaaggacaccatcgtggccaacccctgagc acccctatcaacccccctattgtagtaaacttggaaccttggaaatgaccaggcc aagactcaagcctccccagttctactgacctttgtccttagg tgtgaggtccagggttgctaggaaaagaaatcagcagacacaggtgtagac cagagtgtttcttaaatggtgtaattttgtcctctctgtgtcctg gggaatactggccatgcctggagacatatcactcaatttctctgaggacaca gataggatggggtgtctgtgttatttgtggggtacagagatga aagaggggtgggatccacactgagagagtggagagtgacatgtgctgga cactgtccatgaagcactgagcagaagctggaggcacaac gcaccagacactcacagcaaggatggagctgaaaacataacccactctgt cctggaggcactgggaagcctagagaaggctgtgagccaa ggagggagggtcttcctttggcatgggatggggatgaagtaaggagagg gactggacccccctggaagctgattcactatggggggaggtgt attgaagtcctccagacaaccctcagatttgatgatttcctagtagaactca cagaaataaagagctgttatactgtg (SEQ ID No: 33; GenBank Accession No. NM_001648). In another embodiment, the KLK3 protein is encoded by residues 42-827 of SEQ ID No: 33. In another embodiment, the KLK3 protein is encoded by a homologue of SEQ ID No: 33. In another embodiment, the KLK3 protein is encoded by a variant of SEQ ID No: 33. In another embodiment, the KLK3 protein is encoded by an isomer of SEQ ID No: 33. In another embodiment, the KLK3 protein is encoded by a fragment of SEQ ID No: 33. Each possibility represents a separate embodiment of the present invention.

In another embodiment, the KLK3 protein has the sequence:

MWVPVVFLTLSVTWIGAAPLILSRIVGGWECEKHSQPWQVLVASRGRAVCGGVL VHPQWVLTAAHCIRNKSVILLGRHSLFHPEDTGQVFQVSHSFPHPLYDMSLLKNRFLRPG DDSSHDLMLLRLSEPAELTDAVKVMDLPTQEPALGTTCYASGWGSIEPEEFLTPKKLQCV DLHVISNDVCAQVHPQKVTKFMLCAGRWTGGKSTCSGDSGGPLVCNGVLQGITSWGSEP CALPERPSLYTKVVHYRKWIKDTIVANP (SEQ ID No: 34; GenBank Accession No. BC056665). In another embodiment, the KLK3 protein is a homologue of SEQ ID No: 34. In another embodiment, the KLK3 protein is a variant of SEQ ID No: 34. In another embodiment, the KLK3 protein is an isomer of SEQ ID No: 34. In another embodiment, the KLK3 protein is a fragment of SEQ ID No: 34. Each possibility represents a separate embodiment of the present invention.

In another embodiment, the KLK3 protein is encoded by a nucleotide molecule having the sequence:

gggggagccccaagcnaccacctgcacccggagagctgtgtcaccat gtgggtcccggagtcacctcaccctgtccgtgacgt ggattggtgctgcacccctcatcctgtctcggattgtgggaggctgggagt gcgagaagcattcccaaccctggcaggtgcagtggcctctc gtggcagggcagtctgcggcggtgactggtgcac-
ccccagtgggtcctca
cagctgcccactgcatcaggaacaaaagcgtgatcagctg ggtcggcacagc-
ctgtttcatcctgaagacacaggccaggtatttcaggtca gccacagcttccca-
cacccgctctacgatatgagcctcctga agaatcgattcctcaggccaggtgat-
gactccagccacgacctcatgctgct
ccgcctgtcagagcctgccgagctcacggatgctgtgaag gtcatggacctgc-
ccacccaggagccagcactggggaccacctgctacg cctcaggctggggcag-
cattgaaccagaggagttcttgaccc caaagaaacttcagtgtgtggacctccat-
gttatttccaatgacgtgtgtgcgc
aagttcaccctcagaaggtgaccaagttcatgctgtgtgctg gacgctggaca-
gggggcaaaagcacctgctcgggtgattctgggggcccact tgtctgtaatggt-
gtgatcaaggtatcacgtcatggggc agtgaaccatgtgccctgcccgaaaggc-
cttccctgtacaccaaggtggtgc
attaccggaagtggatcaaggacaccatcgtggccaaccc ctgagcaccectat-
caactccctattgtagtaaacttggaaccttggaaatgac caggccaagactcag-
gcctccccagactactgacctagtc cnaggtgtgaggtccagggagctag-
gaaaagaaatcagcagacacaggtgt
agaccagagtgatcttaaatggtgtaattagtcctctctgt gtcctggggaatactg-
gccatgcctggagacatatcactcaatttctctgagga cacagataggatggggt-
gtctgtgttatttgtggggtacag agatgaaagaggggtgggatccacactgaga-
gagtggagagtgacatgt
gctggacactgtccatgaagcactgagcagaagctggaggc acaacgcacca-
gacactcacagcaaggatggagctgaaaacataacccac tctgtectggag-
gcactgggaagcctagagaaggctgtga gccaaggagggagggtcacctag-
gcatgggatggggatgaagtagggag
agggactggacccccctggaagctgattcactatgggggg aggtgtatt-
gaagtectccagacaaccctcagantgatgatacctagtagaac tcaca-
gaaataaagagctgaatactgcgaaaaaaaaaaa aaaaaaaaaaaaaa
(SEQ ID No: 35; GenBank Accession No. BCO56665). In another embodiment, the KLK3 protein is encoded by residues 47-832 of SEQ ID No: 35. In another embodiment, the KLK3 protein is encoded by a homologue of SEQ ID No: 35. In another embodiment, the KLK3 protein is encoded by a variant of SEQ ID No: 35. In another embodiment, the KLK3 protein is encoded by an isomer of SEQ ID No: 35. In another embodiment, the KLK3 protein is encoded by a fragment of SEQ ID No: 35. Each possibility represents a separate embodiment of the present invention.

In another embodiment, the KLK3 protein has the sequence:

MWVPVVFLTLSVTWIGAAPLILSRIVGGWECEKH-
SQPWQVLVASRGRAVCGGVL VHPQWVLTAAH-
CIRNKSVILLGRHSLFHPEDTGQVFQVSHSFPHPLY-
DMSLLKNRFLRPG
DDSSIEPEEFLTPKKLQCVDLHVISNDVCAQVHPQK-
VTKFMLCAGRWTGGKSTCSGDSG GPLVCNGV-
LQGITSWGSEPCALPERPSLYTKVVHYRKWIKDTIVA
(SEQ ID No: 36; GenBank Accession No. AJ459782). In another embodiment, the KLK3 protein is a homologue of SEQ ID No: 36. In another embodiment, the KLK3 protein is a variant of SEQ ID No: 36. In another embodiment, the KLK3 protein is an isomer of SEQ ID No: 36. In another embodiment, the KLK3 protein is a fragment of SEQ ID No: 36. Each possibility represents a separate embodiment of the present invention.

In another embodiment, the KLK3 protein has the sequence:

MWVPVVFLTLSVTWIGAAPLILSRIVGGWECEKH-
SQPWQVLVASRGRAVCGGVL VHPQWVLTAAH-
CIRNKSVILLGRHSLFHPEDTGQVFQVSHSFPHPLY-
DMSLLKNRFLRPG
DDSSHDLMLLRLSEPAELTDAVKVMDLPTQEPALGT-
TCYASGWGSIEPEEFLTPKKLQCV DLHVISNDV-
CAQVHPQKVTKFMLCAGRWTGGKSTCSVSH-
PYSQDLEGKGEWGP (SEQ ID No: 37 GenBank Accession No. AJ512346). In another embodiment, the KLK3 protein is a homologue of SEQ ID No: 37. In another embodiment, the KLK3 protein is a variant of SEQ ID No: 37. In another embodiment, the KLK3 protein is an isomer of SEQ ID No: 37. In another embodiment, the sequence of the KLK3 protein comprises SEQ ID No: 37. In another embodiment, the KLK3 protein is a fragment of SEQ ID No: 37. Each possibility represents a separate embodiment of the present invention.

In another embodiment, the KLK3 protein has the sequence:

MWVPVVFLTLSVTWIGERGHGWGDAGEGASPDC-
QAEALSPPTQHPSPDRELGSFL SLPAPLQAHTPSP-
SILQQSSLPHQVPAPSHLPQNFLPIAQPAPCSQLLY
(SEQ ID No: 38 GenBank Accession No. AJ459784). In another embodiment, the KLK3 protein is a homologue of SEQ ID No: 38. In another embodiment, the KLK3 protein is a variant of SEQ ID No: 38. In another embodiment, the sequence of the KLK3 protein comprises SEQ ID No: 38. In another embodiment, the KLK3 protein is an isomer of SEQ ID No: 38. In another embodiment, the KLK3 protein is a fragment of SEQ ID No: 38. Each possibility represents a separate embodiment of the present invention.

In another embodiment, the KLK3 protein has the sequence:

MWVPVVFLTLSVTWIGAAPLILSRIVGGWECEKH-
SQPWQVLVASRGRAVCGGVL VHPQWVLTAAH-
CIRNKSVILLGRHSLFHPEDTGQVFQVSHSFPHPLY-
DMSLLKNRFLRPG
DDSSHDLMLLRLSEPAELTDAVKVMDLPTQEPALGT-
TCYASGWGSIEPEEFLTPKKLQCV DLHVISNDV-
CAQVHPQKVTKFMLCAGRWTGGKSTCSGDSGG-
PLVCNGVLQGITSWGSEP
CALPERPSLYTKVVHYRKWIKDTIVANP (SEQ ID No: 39 GenBank Accession No. AJ459783). In another embodiment, the KLK3 protein is a homologue of SEQ ID No: 39. In another embodiment, the KLK3 protein is a variant of SEQ ID No: 39. In another embodiment, the KLK3 protein is an isomer of SEQ ID No: 39. In another embodiment, the KLK3 protein is a fragment of SEQ ID No: 39. Each possibility represents a separate embodiment of the present invention.

In another embodiment, the KLK3 protein is encoded by a nucleotide molecule having the sequence:

aagtttcccttctcccagtccaagaccccaaatcaccacaaaggaccca atc-
cccagactcaagatatggtctgggcgctgtcttgt gtctcctaccctgatc-
cctgggacaactctgctcccagagcatgaagcctct ccaccagcaccagccac-
caacctgcaaacctagggaagat
tgacagaattcccagcctttcccagctccccctgcccatgtcccaggactcc
cagccttggttctctgcccccgtgtcttttcaaacccacatcct aaatccatctc-
ctatccgagtcccccagacctcctgtcaaccctgattcccctg atctagcac-
cccctctgcaggtgctgcacccctcatcctgt ctcggattgtgggag-
gctgggagtgcgagaagcattcccaaccctggca
ggtgcttgtagcctctcgtggcagggcagtctgcggcggtgtt ctggtgcac-
ccccagtgggtcctcacagctacccactgcatcaggaacaaa agcgtgatctt-
gctgggtcggcacagcctgatcatcctgaa gacacaggccaggtatttcag-
gtcagccacagcacccacacccgctctac
gatatgagcctcctgaagaatcgattcctcaggccaggtgat gactccagccac-
gacctcatgctgctccgcctgtcagagcctgccgagct cacggatgctat-
gaaggtcatggacctgcccacccaggagc cagcactggggaccacctgc-
tacgcctcaggctggggcagcattgaa
ccagaggagttcttgaccccaaagaaacttcagtgtgtggacctc catgaatac-
caatgacgtgtgtgcgcaagacaccctcagaaggtgaccaa gacatgctgtgt-
gctggacgctggacagggggcaaaagc acctgctcgggtgattctgggggc-
ccacttgtctgtaatggtgtgcttcaag
gtatcacgtcatggggcagtgaaccatgtgccctgcccgaaa ggccttccctgta-
caccaaggtggtgcattaccggaagtggatcaaggac accatcgtggccaac-
ccctgagcacccctatcaactccctatt gtagtaaacttggaaccaggaaatgaccaggccaagactcaggcctcccca gactactgaccatgtccttaggtgtgaggtccagggagct aggaaaagaaatca-gcagacacaggtgtagaccagagtgtttcttaa atggtgtaattttgtcctctctgt-gtcctggggaatactggccatgcct ggagacatatcactcaatactctgagga-cacagataggatggggtgtctgtg aatttgtggggtacagagatgaaagaggggtgggatccac actgagagagtg-gagagtgacatgtgctggacactgtccatgaagcactgag cagaagctggag-gcacaacgcaccagacactcacagca aggatggagctgaaaacataac-ccactctgtcctggaggcactgggaagc ctagagaaggctgtgaaccaaggagggagggtatcctag gcatgggatggggatgaagtaaggagagggactgaccccctggaagctga ttcactatgggggaggtgtattgaagtcctccagacaacc ctcagatttgat-gatttcctagtagaactcacagaaataaagagctgttatactgtgaa (SEQ ID No: 40; GenBank Accession No. X07730). In another embodiment, the KLK3 protein is encoded by residues 67-1088 of SEQ ID No: 40. In another embodiment, the KLK3 protein is encoded by a homologue of SEQ ID No: 40. In another embodiment, the KLK3 protein is encoded by a variant of SEQ ID No: 40. In another embodiment, the KLK3 protein is encoded by an isomer of SEQ ID No: 40. In another embodiment, the KLK3 protein is encoded by a fragment of SEQ ID No: 40. Each possibility represents a separate embodiment of the present invention.

In another embodiment, the KLK3 protein has a sequence set forth in one of the following GenBank Accession Numbers: BC005307, AJ310938, AJ310937, AF335478, AF335477, M27274, and M26663. In another embodiment, the KLK3 protein is encoded by a sequence set forth in one of the above GenBank Accession Numbers. Each possibility represents a separate embodiment of the present invention.

In another embodiment, the KLK3 protein is encoded by a sequence set forth in one of the following GenBank Accession Numbers: NM_001030050, NM_001030049, NM_001030048, AJ459782, AJ512346, or AJ459784. Each possibility represents a separate embodiment of the present invention.

In another embodiment, the KLK3 protein has the sequence that comprises a sequence set forth in one of the following GenBank Accession Numbers: X13943, X13942, X13940, X13941, and X13944. Each possibility represents a separate embodiment of the present invention.

In another embodiment, the KLK3 protein is any other KLK3 protein known in the art. Each KLK3 protein represents a separate embodiment of the present invention.

In another embodiment, the present invention provides a recombinant *Listeria* strain expressing a folate hydrolase 1 (FOLH1) peptide. In another embodiment, the sequence of the FOLH1 peptide is selected from SEQ ID No: 41, 43, 44, and 45. In another embodiment, the sequence of the FOLH1 peptide is set forth in SEQ ID No: 41. In another embodiment, the sequence of the FOLH1 peptide is set forth in SEQ ID No: 43. In another embodiment, the sequence of the FOLH1 peptide is set forth in SEQ ID No: 44. In another embodiment, the sequence of the FOLH1 peptide is set forth in SEQ ID No: 45. In another embodiment, the sequence of the FOLH1 peptide is any other FOLH1 protein sequence known in the art. Each possibility represents a separate embodiment of the present invention.

In another embodiment, the sequence of the FOLH1 peptide comprises a sequence selected from SEQ ID No: 41, 43, 44, and 45.

In another embodiment, the FOLH1 peptide is an immunogenic fragment of a larger FOLH1 peptide, wherein the sequence of the larger FOLH1 peptide is a sequence selected from SEQ ID No: 41, 43, 44, and 45. In another embodiment, the FOLH1 peptide is an immunogenic fragment of a larger FOLH1 peptide, wherein the sequence of the larger FOLH1 peptide is set forth in SEQ ID No: 41. In another embodiment, the sequence of the larger FOLH1 peptide is set forth in SEQ ID No: 43. In another embodiment, the sequence of the larger FOLH1 peptide is set forth in SEQ ID No: 44. In another embodiment, the sequence of the larger FOLH1 peptide is set forth in SEQ ID No: 45. In another embodiment, the sequence of the larger FOLH1 peptide is any other FOLH1 protein sequence known in the art. Each possibility represents a separate embodiment of the present invention.

In another embodiment, the sequence of the FOLH1 peptide comprises an immunogenic fragment of a sequence selected from SEQ ID No: 41, 43, 44, and 45.

"FOLH1 peptide" refers, in another embodiment, to a full-length FOLH1 protein. In another embodiment, the term refers to a fragment of an FOLH1 protein. In another embodiment, the term refers to a fragment of an FOLH1 protein that is lacking the FOLH1 signal peptide. In another embodiment, the term refers to an FOLH1 protein that contains the entire FOLH1 sequence except the FOLH1 signal peptide. "FOLH1 signal sequence" refers, in another embodiment, to any signal sequence found in nature on an FOLH1 protein. In another embodiment, an FOLH1 protein of methods and compositions of the present invention does not contain any signal sequence. Each possibility represents a separate embodiment of the present invention.

In another embodiment, the FOLH1 protein that is the source of an FOLH1 peptide of methods and compositions of the present invention is a human FOLH1 protein. In another embodiment, the FOLH1 protein is a mouse FOLH1 protein. In another embodiment, the FOLH1 protein is a rodent FOLH1 protein. In another embodiment, the FOLH1 protein is an FOLH1 protein of any other species known in the art. In another embodiment, 1 of the above FOLH1 proteins is referred to in the art as a "FOLH1 protein." Each possibility represents a separate embodiment of the present invention.

The FOLH1 protein that is the source of an FOLH1 peptide of methods and compositions of the present invention is a folate hydrolase (prostate-specific membrane antigen) protein. In another embodiment, the FOLH1 protein is PSMA protein. In another embodiment, the FOLH1 protein is a N-acetylated alpha-linked acidic dipeptidase 1 protein. In another embodiment, the FOLH1 protein is a folate hydrolase 1 protein. In another embodiment, the FOLH1 protein is a folylpoly-gamma-glutamate carboxypeptidase protein. In another embodiment, the FOLH1 protein is a glutamate carboxylase II protein. In another embodiment, the FOLH1 protein is a glutamate carboxypeptidase II protein. In another embodiment, the FOLH1 protein is a membrane glutamate carboxypeptidase protein. In another embodiment, the FOLH1 protein is a pteroylpoly-gamma-glutamate carboxypeptidase protein. In another embodiment, the FOLH1 protein is any other type of FOLH1 protein that is known in the art. Each possibility represents a separate embodiment of the present invention.

In another embodiment, the FOLH1 protein has the sequence:

MWNLLHETDSAVATARRPRWLCAGALVLAGGF-FLLGFLFGWFIKSSNEATNITPK HNMKAFLDELKAE-NIKKFLYNFTQIPHLAGTEQNFQLAKQIQSQWKEF-GLDSVELAHYD VLLSYPNKTHPNYISIINEDGNEIFNTSLFEPPPPGY-ENVSDIVPPFSAFSPQGMPEGDLVYV NYARTED-FFKLERDMKINCSGKIVIARYGKVFRGNK-VKNAQLAGAKGVILYSDPADYFA PGVKSYPDGWNLPGGGVQRGNILNLNGAGDPLTP-

GYPANEYAYRRGIAEAVGLPSIPVHP IGYYDAQKLLE-KMGGSAPPDSSWRGSLKVPYNVGPGFTGNFSTQK-VKMHIHSTNEVTRI YNVIGTLRGAVEPDRYVILGGHRDSWVFGGIDPQS-GAAVVHEIVRSFGTLKKEGWRPRRT ILFASWDAEEF-GLLGSTEWAEENSRLLQERGVAYINADSSIEGNYTL-RVDCTPLMYSLVH NLTKELKSPDEGFEGKSLYESWTKKSPSPEFSGM-PRISKLGSGNDFEVFFQRLGIASGRAR YTKN-WETNKFSGYPLYHSVYETYELVEKFYDPMFKYHLT-VAQVRGGMVFELANSIVLPF DCRDYAVVLRKYADKIYSISMKHPQEMKTYSVSFD-SLFSAVKNFTEIASKFSERLQDFDK SKHVI-YAPSSHNKYAGESFPGIYDALFDIESKVDPSKAW-GEVKRQIYVAAFTVQAAAETL SEVA (SEQ ID No: 41; GenBank Accession No. BCO25672). In another embodiment, the FOLH1 protein is a homologue of SEQ ID No: 41. In another embodiment, the FOLH1 protein is a variant of SEQ ID No: 41. In another embodiment, the FOLH1 protein is an isomer of SEQ ID No: 41. In another embodiment, the FOLH1 protein is a fragment of SEQ ID No: 41. Each possibility represents a separate embodiment of the present invention.

In another embodiment, the FOLH1 protein is encoded by a nucleotide molecule having the sequence:

ctggaccccaggtctggagcgaattccagcctgcagggctgataagc gag-gcattagtgagattgagagagacataccccgccg tggtggaggagggcgcgca-gtagagcagcagcacaggcgcgggtccc gggaggccggctctgctcgcgc-cgagatgtggaatctccttc acgaaaccgactcggctgtggccaccgcgcgccgcccgcgctggctgtg cgctggggcgctggtgctggcgggtggcnctactcctcgg cacctcacgggtg-gntataaaatcctccaatgaagctactaacattactccaa agcataatat-gaaagcantaggatgaattgaaagctgaga acatcaagaagncttatataattna-cacagataccacantagcaggaacaga acaaaacatcagcngcaaagcaaattcaatcccagtgga aagaatttggcctg-gattctgttgagctagcacattatgatgtcctgttgtcctac ccaaataagactcatc-ccaactacatctcaataattaatgaa gatggaaatgagatatcaacacatcattant-gaaccacctcctccaggatatga aaatgatcggatattgtaccacctacagtgctactctcctc aaggaatgcca-gagggcgatctagtgtatgnaactatgcacgaactgaaga cttattaaattg-gaacgggacatgaaaatcaattgctctggg aaaattgtaattgccaga-tatgggaaagttttcagaggaaataaggttaaaaat gcccagctggcaggggccaaaggagtcattctctactccg accctgctgac-tactagctcctggggtgaagtcctatccagatggaggaatc acctggaggtggt-gtccagcgtggaaatatcctaaatctga atggtgcaggagaccctctcacaccag-gnacccagcaaatgaatatgcttat aggcgtggaattgcagaggctgaggtcaccaagtattcct gttcatccaattgga-tactatgatgcacagaagctcctagaaaaaatgggtg gctcagcaccaccaga-tagcagctggagaggaagtctcaaa gtgccctacaatgaggacctggcntactg-gaaacanctacacaaaaagtcaa gatgcacatccactctaccaatgaagtgacaagaantac aatgtgatagg-tactctcagaggagcagtggaaccagacagatatgtcanct gggaggtcac-cgggactcatgggtgatggtggtattgacc ctcagagtggagcagctgttgttcat-gaaattgtgaggagctttggaacactga aaaaggaagggtggagacctagaagaacaattttgtttgc aagctgggatgca-gaagaatttggtcttcttggttctactgagtgggcagagga gaattcaagactcct-tcaagagcgtggcgtggcttatatta atgctgactcatctatagaaggaaacta-cactctgagagagangtacaccgct gatgtacagcaggtacacaacctaacaaaagagctgaaa agccctgat-gaaggctttgaaggcaaatctctttatgaaagttggactaaaaa aagtccttcccca-gagttcagtggcatgcccaggataagca aattgggatctggaaatgattttgaggt-gttcttccaacgacttggaattgcttca ggcagagcacggtatactaaaaattgggaaacaaacaaat tcagcggctatc-cactgtatcacagtgtctatgaaacatatgagaggtggaa aagattatgatccaat-gataaatatcacctcactgtggccca ggttcgaggagggatggtgttt-gagctagccaattccatagtgctccctttga ttgtcgagattatgctgtagttttaagaaagtatgctgacaaa atctacagtatactat-gaaacatccacaggaaatgaagacatacagtgtatca tttgattcacttanctgca-gtaaagaatatacagaaattgat ccaagttcagtgagagactccaggacttt-gacaaaagcaagcatgtcatctat gctccaagcagccacaacaagtatgcaggggagtcattcc caggaantatgat-gctctgtagatattgaaagcaaagtggacccaccaaggc ctggggagaagt-gaagagacagatttatgagcagccac acagtgcaggcagctgcagagacta-gagtgaagtagcctaagaggatt catagagaatccgtattgaatagtgtggtatgtcactcagaaag aatcgtaatggg-tatattgataaattttaaaattggtatatttgaaataaagttg aatat-tatatataaaaaaaaaaaaaaaaaaaaaaaaaaaaaa aa (SEQ ID No: 42; GenBank Accession No. BCO25672). In another embodiment, the FOLH1 protein is encoded by residues 160-2319 of SEQ ID No: 42. In another embodiment, the FOLH1 protein is encoded by a homologue of SEQ ID No: 42. In another embodiment, the FOLH1 protein is encoded by a variant of SEQ ID No: 42. In another embodiment, the FOLH1 protein is encoded by an isomer of SEQ ID No: 42. In another embodiment, the FOLH1 protein is encoded by a fragment of SEQ ID No: 42. Each possibility represents a separate embodiment of the present invention.

In another embodiment, the FOLH1 protein has the sequence:

MWNLLHETDSAVATARRPRWLCAGALVLAGGF-FLLGFLFGWFIKSSNEATNITPK HNMKAFLDELKAE-NIKKFLYNFTQIPHLAGTEQNFQLAKQIQSQWKEF-GLDSVELAHYD VLLSYPNKTHPNYISIINEDGNEIFNTSLFEPPPPGY-ENVSDIVPPFSAFSPQGMPEGDLVYV NYARTED-FFKLERDMKINCSGKIVIARYGKVFRGNK-VKNAQLAGAKGVILYSDPADYFA PGVKSYPDGWNLPGGGVQRGNILNLNGAGDPLTP-GYPANEYAYRRGIAEAVGLPSIPVHP IGYYDAQKLLE-KMGGSAPPDSSWRGSLKVPYNVGPGFTGNFSTQK-VKMHIHSTNEVTRI YNVIGTLRGAVEPDRYVILGGHRDSWVFGGIDPQS-GAAVVHEIVRSFGTLKKEGWRPRRT ILFASWDAEEF-GLLGSTEWAEENSRLLQERGVAYINADSSIEGNYTL-RVDCTPLMYSLVH NLTKELKSPDEGFEGKSLYESWTKKSPSPEFSGM-PRISKLGSGNDFEVFFQRLGIASGRAR YTKN-WETNKFSGYPLYHSVYETYELVEKFYDPMFKYHLT-VAQVRGGMVFELANSIVLPF DCRDYAVVLRKYADKIYSISMKHPQEMKTYSVSFD-SLFSAVKNFTEIASKFSERLQDFDK SKHVI-YAPSSHNKYAGESFPGIYDALFDIESKVDPSKAW-GEVKRQIYVAAFTVQAAAETL SEV (SEQ ID No: 43; GenBank Accession No. NM_001014986). In another embodiment, the FOLH1 protein is a homologue of SEQ ID No: 43. In another embodiment, the FOLH1 protein is a variant of SEQ ID No: 43. In another embodiment, the FOLH1 protein is an isomer of SEQ ID No: 43. In another embodiment, the FOLH1 protein is a fragment of SEQ ID No: 43. Each possibility represents a separate embodiment of the present invention.

In another embodiment, the FOLH1 protein has the sequence:

MWNLLHETDSAVATARRPRWLCAGALVLAGGF-FLLGFLFGWFIKSSNEATNITPK HNMKAFLDELKAE-NIKKFLYNFTQIPHLAGTEQNFQLAKQIQSQWKEF-GLDSVELAHYD VLLSYPNKTHPNYISIINEDGNEIFNTSLFEPPPPGY-ENVSDIVPPFSAFSPQGMPEGDLVYV NYARTED-FFKLERDMKINCSGKIVIARYGKVFRGNK-VKNAQLAGAKGVILYSDPADYFA PGVKSYPDGWNLPGGGVQRGNILNLNGAGDPLTP-GYPANEYAYRRGIAEAVGLPSIPVHP IGYYDAQKLLE-KMGGSAPPDSSWRGSLKVPYNVGPGFTGNFSTQK-

VKMHIHSTNEVTRI YNVIGTLRGAVEPDRYVILGGHRDSWVFGGIDPQSGAAVVHEIVRSFGTLKKEGWRPRRT ILFASWDAEEFGLLGSTEWAEENSRLLQERGVAYINADSSIEGNYTLRVDCTPLMYSLVH NLTKELKSPDEGFEGKSLYESWTKKSPSPEFSGMPRISKLGSGNDFEVFFQRLGIASGRAR YTKNWETNKFSGYPLYHSVYETYELVEKFYDPMFKYHLTVAQVRGGMVFELANSIVLPF DCRDYAVVLRKYADKIYSISMKHPQEMKTYSVSFDSLFSAVKNFTEIASKFSERLQDFDK SNPIVLRMMNDQLMFLERAFIDPLGLPDRPFYRHVIYAPSSHNKYAGESFPGIYDALFDIES KVDPSKAWGEVKRQIYVAAFTVQAAAETLSEVA (SEQ ID No: 44; GenBank Accession No. NM_004476). In another embodiment, the FOLH1 protein is a homologue of SEQ ID No: 44. In another embodiment, the FOLH1 protein is a variant of SEQ ID No: 44. In another embodiment, the FOLH1 protein is an isomer of SEQ ID No: 44. In another embodiment, the FOLH1 protein is a fragment of SEQ ID No: 44. Each possibility represents a separate embodiment of the present invention.

In another embodiment, the FOLH1 protein has the sequence:

IPHLAGTEQNFQLAKQIQSQWKEFGLDSVELAHYDVLLSYPNKTHPNYISIINEDGN EIFNTSLFEPPPPGYENVSDIVPPFSAFSPQGMPEGDLVYVNYARTEDFFKLERDMKINCSG KIVIARYGKVFRGNKVKNAQLAGAKGVILYSDPADYFAPGVKSYPDGWNLPGGGVQRG NILNLNGAGDPLTPGYPANEYAYRRGIAEAVGLPSIPVHPIGYYDAQKLLEKMGGSAPPD SSWRGSLKVPYNVGPGFTGNFSTQKVKMHIHSTNEVTRIYNVIGTLRGAVEPDRYVILGG HRDSWVFGGIDPQSGAAVVHEIVRSFGTLKKEGWRPRRTILFASWDAEEFGLLGSTEWAE ENSRLLQERGVAYINADSSIEGNYTLRVDCTPLMYSLVHNLTKELKSPDEGFEGKSLYES WTKKSPSPEFSGMPRISKLGSGNDFEVFFQRLGIASGRARYTKNWETNKFSGYPLYHSVY ETYELVEKFYDPMFKYHLTVAQVRGGMVFELANSIVLPFDCRDYAVVLRKYADKIYSIS MKHPQEMKTYSVSFDSLFSAVKNFTEIASKFSERLQDFDKSNPIVLRMMNDQLMFLERAF IDPLGLPDRPFYRHVIYAPSSHNKYAGESFPGIYDALFDIESKVDPSKAWGEVKRQIYVAA FTVQAAAETLSEVA (SEQ ID No: 45; GenBank Accession No. BC108719). In another embodiment, the FOLH1 protein is a homologue of SEQ ID No: 45. In another embodiment, the FOLH1 protein is a variant of SEQ ID No: 45. In another embodiment, the FOLH1 protein is an isomer of SEQ ID No: 45. In another embodiment, the FOLH1 protein is a fragment of SEQ ID No: 45. Each possibility represents a separate embodiment of the present invention.

In another embodiment, the FOLH1 protein is encoded by a sequence set forth in one of the following GenBank Accession Numbers: NM_001014986, NM_004476, BC108719. Each possibility represents a separate embodiment of the present invention.

In another embodiment, the FOLH1 protein has the sequence that comprises a sequence set forth in one of the above GenBank Accession Numbers. Each possibility represents a separate embodiment of the present invention.

In another embodiment, the FOLH1 protein is any other FOLH1 protein known in the art. Each FOLH1 protein represents a separate embodiment of the present invention.

In another embodiment, the present invention provides a vaccine comprising a recombinant *Listeria* strain of the present invention and an adjuvant.

In another embodiment, the present invention provides an immunogenic composition comprising a recombinant *Listeria* strain of the present invention.

In another embodiment, the recombinant *Listeria* strain expresses a recombinant polypeptide that comprises a KLK3 peptide. In another embodiment, the recombinant *Listeria* strain comprises a recombinant polypeptide, wherein the recombinant peptide comprises a KLK3 peptide. In another embodiment, the recombinant *Listeria* strain comprises a recombinant nucleotide encoding the recombinant polypeptide. Each possibility represents a separate embodiment of the present invention.

In another embodiment, the recombinant *Listeria* strain expresses a recombinant polypeptide that comprises an FOLH1 peptide. In another embodiment, the recombinant *Listeria* strain comprises a recombinant polypeptide, wherein the recombinant peptide comprises an FOLH1 peptide. In another embodiment, the recombinant *Listeria* strain comprises a recombinant nucleotide encoding the recombinant polypeptide. Each possibility represents a separate embodiment of the present invention.

The KLK3 peptide expressed by the recombinant *Listeria* strain is, in another embodiment, in the form of a fusion peptide. In another embodiment, the fusion peptide further comprises a non-KLK3 peptide. In another embodiment, the non-KLK3 peptide enhances the immunogenicity of the KLK3 peptide. Each possibility represents a separate embodiment of the present invention.

In another embodiment, an FOLH1 peptide expressed by the recombinant *Listeria* strain is in the form of a fusion peptide. In another embodiment, the fusion peptide further comprises a non-FOLH1 peptide. In another embodiment, the non-FOLH1 peptide enhances the immunogenicity of the FOLH1 peptide. Each possibility represents a separate embodiment of the present invention.

In another embodiment, the non-KLK3/non-FOLH1 peptide of methods and compositions of the present invention is a non-hemolytic LLO peptide. In another embodiment, the non-KLK3/non-FOLH1 peptide is an ActA peptide. In another embodiment, the non-KLK3/non-FOLH1 peptide is a PEST-like sequence-containing peptide. In another embodiment, the non-KLK3/non-FOLH1 peptide is any other non-KLK3/non-FOLH1 peptide known in the art. Each possibility represents a separate embodiment of the present invention.

In another embodiment, the present invention provides a recombinant *Listeria* strain comprising a recombinant polypeptide of the present invention. In another embodiment, the present invention provides a recombinant *Listeria* strain comprising a recombinant nucleotide encoding a recombinant polypeptide of the present invention. In another embodiment, the *Listeria* vaccine strain is a strain of the species *Listeria monocytogenes* (LM). In another embodiment, the present invention provides a composition comprising the *Listeria* strain. In another embodiment, the present invention provides an immunogenic composition comprising the *Listeria* strain. Each possibility represents a separate embodiment of the present invention.

In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. Each possibility represents a separate embodiment of the present invention.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the KLK3 peptide-containing recombinant peptide. In another embodiment, the *Listeria* strain contains a genomic insertion of the gene encoding the FOLH1 peptide-containing recombinant peptide. In another embodiment, the *Listeria* strain carries a plasmid comprising the gene encoding the KLK3 peptide-containing recombinant peptide. In another embodiment, the *Listeria* strain carries a plasmid comprising the gene encoding the FOLH1 peptide-containing recombinant peptide. Methods for passaging a recombinant *Listeria* strain through an animal host are well known in the art, and are described, for example, in United States Patent Application No. 2006/0233835, which is incorporated herein by reference. In another embodiment, the passaging is performed by any other method known in the art. Each possibility represents a separate embodiment of the present invention.

In another embodiment, the recombinant *Listeria* strain utilized in methods of the present invention has been stored in a frozen cell bank. In another embodiment, the recombinant *Listeria* strain has been stored in a lyophilized cell bank. Each possibility represents a separate embodiment of the present invention.

In another embodiment, the cell bank of methods and compositions of the present invention is a master cell bank. In another embodiment, the cell bank is a working cell bank. In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art. Each possibility represents a separate embodiment of the present invention.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States. Each possibility represents a separate embodiment of the present invention.

In another embodiment, a recombinant *Listeria* strain utilized in methods of the present invention is from a batch of vaccine doses.

In another embodiment, a recombinant *Listeria* strain utilized in methods of the present invention is from a frozen stock produced by a method disclosed herein.

In another embodiment, a recombinant *Listeria* strain utilized in methods of the present invention is from a lyophilized stock produced by a method disclosed herein.

In another embodiment, a cell bank, frozen stock, or batch of vaccine doses of the present invention exhibits viability upon thawing of greater than 90%. In another embodiment, the thawing follows storage for cryopreservation or frozen storage for 24 hours. In another embodiment, the storage is for 2 days. In another embodiment, the storage is for 3 days. In another embodiment, the storage is for 4 days. In another embodiment, the storage is for 1 week. In another embodiment, the storage is for 2 weeks. In another embodiment, the storage is for 3 weeks. In another embodiment, the storage is for 1 month. In another embodiment, the storage is for 2 months. In another embodiment, the storage is for 3 months. In another embodiment, the storage is for 5 months. In another embodiment, the storage is for 6 months. In another embodiment, the storage is for 9 months. In another embodiment, the storage is for 1 year. Each possibility represents a separate embodiment of the present invention.

In another embodiment, a cell bank, frozen stock, or batch of vaccine doses of the present invention is cryopreserved by a method that comprises growing a culture of the *Listeria* strain in a nutrient media, freezing the culture in a solution comprising glycerol, and storing the *Listeria* strain at below −20 degrees Celsius. In another embodiment, the temperature is about −70 degrees Celsius. In another embodiment, the temperature is about $^{-}70$-$^{-}80$ degrees Celsius.

In another embodiment, a cell bank, frozen stock, or batch of vaccine doses of the present invention is cryopreserved by a method that comprises growing a culture of the *Listeria* strain in a defined media of the present invention (as described below), freezing the culture in a solution comprising glycerol, and storing the *Listeria* strain at below −20 degrees Celsius. In another embodiment, the temperature is about −70 degrees Celsius. In another embodiment, the temperature is about $^{-}70$-$^{-}80$ degrees Celsius. In another embodiment, any defined microbiological media of the present invention may be used in this method. Each defined microbiological media represents a separate embodiment of the present invention.

In another embodiment of methods and compositions of the present invention, the culture (e.g. the culture of a *Listeria* vaccine strain that is used to produce a batch of *Listeria* vaccine doses) is inoculated from a cell bank. In another embodiment, the culture is inoculated from a frozen stock. In another embodiment, the culture is inoculated from a starter culture. In another embodiment, the culture is inoculated from a colony. In another embodiment, the culture is inoculated at mid-log growth phase. In another embodiment, the culture is inoculated at approximately mid-log growth phase. In another embodiment, the culture is inoculated at another growth phase. Each possibility represents a separate embodiment of the present invention.

In another embodiment, the solution used for freezing contains another colligative additive or additive with anti-freeze properties, in place of glycerol. In another embodiment, the solution used for freezing contains another colligative additive or additive with anti-freeze properties, in addition to glycerol. In another embodiment, the additive is mannitol. In another embodiment, the additive is DMSO. In another embodiment, the additive is sucrose. In another embodiment, the additive is any other colligative additive or additive with anti-freeze properties that is known in the art. Each possibility represents a separate embodiment of the present invention.

In another embodiment, the nutrient media utilized for growing a culture of a *Listeria* strain is LB. In another embodiment, the nutrient media is TB. In another embodiment, the nutrient media is a modified, animal-product free Terrific Broth. In another embodiment, the nutrient media is a defined media. In another embodiment, the nutrient media is a defined media of the present invention. In another embodiment, the nutrient media is any other type of nutrient media known in the art. Each possibility represents a separate embodiment of the present invention.

In another embodiment of methods and compositions of the present invention, the step of growing is performed with a shake flask. In another embodiment, the flask is a baffled shake flask. In another embodiment, the growing is performed with a batch fermenter. In another embodiment, the growing is performed with a stirred tank or flask. In another embodiment, the growing is performed with an airflit fermenter. In another embodiment, the growing is performed with a fed batch. In another embodiment, the growing is performed with a continuous cell reactor. In another embodiment, the growing is performed with an immobilized cell reactor. In another embodiment, the growing is performed with any other means of growing bacteria that is known in the art. Each possibility represents a separate embodiment of the present invention.

In another embodiment, a constant pH is maintained during growth of the culture (e.g. in a batch fermenter). In another embodiment, the pH is maintained at about 7.0. In another embodiment, the pH is about 6. In another embodiment, the pH is about 6.5. In another embodiment, the pH is about 7.5. In another embodiment, the pH is about 8. In another embodiment, the pH is 6.5-7.5. In another embodiment, the pH is 6-8. In another embodiment, the pH is 6-7. In another embodiment, the pH is 7-8. Each possibility represents a separate embodiment of the present invention.

In another embodiment, a constant temperature is maintained during growth of the culture. In another embodiment, the temperature is maintained at about 37° C. In another embodiment, the temperature is 37° C. In another embodiment, the temperature is 25° C. In another embodiment, the temperature is 27° C. In another embodiment, the temperature is 28° C. In another embodiment, the temperature is 30° C. In another embodiment, the temperature is 32° C. In another embodiment, the temperature is 34° C. In another embodiment, the temperature is 35° C. In another embodiment, the temperature is 36° C. In another embodiment, the temperature is 38° C. In another embodiment, the temperature is 39° C. Each possibility represents a separate embodiment of the present invention.

In another embodiment, a constant dissolved oxygen concentration is maintained during growth of the culture. In another embodiment, the dissolved oxygen concentration is maintained at 20% of saturation. In another embodiment, the concentration is 15% of saturation. In another embodiment, the concentration is 16% of saturation. In another embodiment, the concentration is 18% of saturation. In another embodiment, the concentration is 22% of saturation. In another embodiment, the concentration is 25% of saturation. In another embodiment, the concentration is 30% of saturation. In another embodiment, the concentration is 35% of saturation. In another embodiment, the concentration is 40% of saturation. In another embodiment, the concentration is 45% of saturation. In another embodiment, the concentration is 50% of saturation. In another embodiment, the concentration is 55% of saturation. In another embodiment, the concentration is 60% of saturation. In another embodiment, the concentration is 65% of saturation. In another embodiment, the concentration is 70% of saturation. In another embodiment, the concentration is 75% of saturation. In another embodiment, the concentration is 80% of saturation. In another embodiment, the concentration is 85% of saturation. In another embodiment, the concentration is 90% of saturation. In another embodiment, the concentration is 95% of saturation. In another embodiment, the concentration is 100% of saturation. In another embodiment, the concentration is near 100% of saturation. Each possibility represents a separate embodiment of the present invention.

In another embodiment of methods and compositions of the present invention, the *Listeria* culture is flash-frozen in liquid nitrogen, followed by storage at the final freezing temperature. In another embodiment, the culture is frozen in a more gradual manner; e.g. by placing in a vial of the culture in the final storage temperature. In another embodiment, the culture is frozen by any other method known in the art for freezing a bacterial culture. Each possibility represents a separate embodiment of the present invention.

In another embodiment of methods and compositions of the present invention, the storage temperature of the culture is between −20 and −80 degrees Celsius (° C.). In another embodiment, the temperature is significantly below −20° C. In another embodiment, the temperature is not warmer than −70° C. In another embodiment, the temperature is −70° C. In another embodiment, the temperature is about −70° C. In another embodiment, the temperature is −20° C. In another embodiment, the temperature is about −20° C. In another embodiment, the temperature is −30° C. In another embodiment, the temperature is −40° C. In another embodiment, the temperature is −50° C. In another embodiment, the temperature is −60° C. In another embodiment, the temperature is −80° C. In another embodiment, the temperature is −30-−70° C. In another embodiment, the temperature is −40-−70° C. In another embodiment, the temperature is −50-−70° C. In another embodiment, the temperature is −60-−70° C. In another embodiment, the temperature is −30-−80° C. In another embodiment, the temperature is −40-−80° C. In another embodiment, the temperature is −50-−80° C. In another embodiment, the temperature is −60-−80° C. In another embodiment, the temperature is −70-−80° C. In another embodiment, the temperature is colder than −70° C. In another embodiment, the temperature is colder than −80° C. Each possibility represents a separate embodiment of the present invention.

Methods for lyophilization and cryopreservation of recombinant *Listeria* strains are well known to those skilled in the art. Each possibility represents a separate embodiment of the present invention.

The *Listeria*-containing composition of methods and compositions of the present invention is, in another embodiment, an immunogenic composition. In another embodiment, the composition is inherently immunogenic by virtue of its comprising a *Listeria* strain of the present invention. In another embodiment, the composition further comprises an adjuvant. Each possibility represents a separate embodiment of the present invention.

In another embodiment, the present invention provides a recombinant polypeptide, comprising a KLK3 peptide operatively linked to a non-KLK3 peptide. In another embodiment, the non-KLK3 peptide is an LLO peptide. In another embodiment, the non-KLK3 peptide is an ActA peptide. In another embodiment, the non-KLK3 peptide is a PEST-like sequence peptide. In another embodiment, the non-KLK3 peptide enhances the immunogenicity of the KLK3 peptide. In another embodiment, the non-KLK3 peptide is any other type of peptide known in the art. Each possibility represents a separate embodiment of the present invention.

In another embodiment, the present invention provides a recombinant polypeptide, comprising an FOLH1 peptide operatively linked to a non-FOLH1 peptide. In another embodiment, the non-FOLH1 peptide is an LLO peptide. In another embodiment, the non-FOLH1 peptide is an ActA peptide. In another embodiment, the non-FOLH1 peptide is a PEST-like sequence peptide. In another embodiment, the non-FOLH1 peptide enhances the immunogenicity of the FOLH1 peptide. In another embodiment, the non-FOLH1 peptide is any other type of peptide known in the art. Each possibility represents a separate embodiment of the present invention.

As provided herein, a recombinant *Listeria* strain expressing an LLO-KLK3 fusion protects mice from tumors and elicits formation of antigen-specific CTL. Thus, *Listeria* strains expressing prostate-specific antigens (e.g. prostate-specific antigen/KLK3 and prostate-specific membrane antigen/FOLH1) are antigenic and efficacious in vaccination methods. Further, fusions of LLO and fragments thereof to prostate-specific antigens (e.g. prostate-specific antigen/KLK3 and prostate-specific membrane antigen/FOLH1) are antigenic and efficacious in vaccination methods.

Further, as provided herein, Lm-LLO-E7 induces regression of established subcutaneous HPV-16 immortalized tumors from C57B1/6 mice (Example 1). Further, as provided herein, Lm-LLO-NP protects mice from RENCA-NP, a renal cell carcinoma (Example 3). Further, as provided herein, fusion of antigens to ActA and PEST-like sequences produces similar results. Thus, non-hemolytic LLO, ActA, and PEST-like sequences are all efficacious at enhancing the immunogenicity of KLK3 and FOLH1 peptides.

In another embodiment, the present invention provides a vaccine comprising a recombinant polypeptide of the present invention and an adjuvant.

In another embodiment, the present invention provides an immunogenic composition comprising a recombinant polypeptide of the present invention.

In another embodiment, the present invention provides a recombinant vaccine vector encoding a recombinant polypeptide of the present invention.

In another embodiment, the present invention provides a nucleotide molecule encoding a recombinant polypeptide of the present invention.

In another embodiment, the present invention provides a vaccine comprising a nucleotide molecule of the present invention and an adjuvant.

In another embodiment, the present invention provides an immunogenic composition comprising a nucleotide molecule of the present invention.

In another embodiment, the present invention provides a recombinant vaccine vector comprising a nucleotide molecule of the present invention.

In other embodiments, the adjuvant of methods and compositions of the present invention is Montanide ISA 51. Montanide ISA 51 contains a natural metabolizable oil and a refined emulsifier. In another embodiment, the adjuvant is GM-CSF. In another embodiment, the adjuvant is KLH. Recombinant GM-CSF is a human protein grown, in another embodiment, in a yeast (*S. cerevisiae*) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum. In another embodiment, the adjuvant is an interleukin. In another embodiment, the adjuvant is an unmethylated CpG oligonucleotide. In another embodiment, the adjuvant is quill glycosides. In another embodiment, the adjuvant is monophosphoryl lipid A. In another embodiment, the adjuvant is liposomes. In another embodiment, the adjuvant is a bacterial mitogen. In another embodiment, the adjuvant is a bacterial toxin. In another embodiment, the adjuvant is a chemokine. In another embodiment, the adjuvant is any other type of adjuvant known in the art. In another embodiment, the vaccine of methods and compositions of the present invention comprises 2 of the above adjuvants. In another embodiment, the vaccine comprises more than 2 of the above adjuvants. Each possibility represents a separate embodiment of the present invention.

In another embodiment, the present invention provides a method of inducing an anti-KLK3 immune response in a subject, comprising administering to the subject a composition comprising a recombinant *Listeria* strain of the present invention, thereby inducing an anti-KLK3 immune response in a subject.

In another embodiment, the present invention provides a method of treating a KLK3-expressing tumor in a subject, the method comprising the step of administering to the subject a composition comprising a recombinant *Listeria* strain of the present invention, whereby the subject mounts an immune response against the KLK3-expressing tumor, thereby treating a KLK3-expressing tumor in a subject. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. In another embodiment, the KLK3-expressing tumor is a KLK3-expressing prostate adenocarcinoma. Each possibility represents a separate embodiment of the present invention.

In another embodiment, the present invention provides a method of protecting a human subject against a KLK3-expressing tumor, the method comprising the step of administering to the human subject a composition comprising a recombinant *Listeria* strain of the present invention, whereby the subject mounts an immune response against the KLK3-expressing tumor, thereby protecting a human subject against a KLK3-expressing tumor. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of inducing an anti-FOLH1 immune response in a subject, comprising administering to the subject a composition comprising a recombinant *Listeria* strain of the present invention, thereby inducing an anti-FOLH1 immune response in a subject.

In another embodiment, the present invention provides a method of treating an FOLH1-expressing tumor in a subject, the method comprising the step of administering to the subject a composition comprising a recombinant *Listeria* strain of the present invention, whereby the subject mounts an immune response against the FOLH1-expressing tumor, thereby treating an FOLH1-expressing tumor in a subject. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. In another embodiment, the FOLH1-expressing tumor is an FOLH1-expressing prostate adenocarcinoma. Each possibility represents a separate embodiment of the present invention.

In another embodiment, the present invention provides a method of protecting a human subject against an FOLH1-expressing tumor, the method comprising the step of administering to the human subject a composition comprising a recombinant *Listeria* strain of the present invention, whereby the subject mounts an immune response against the FOLH1-expressing tumor, thereby protecting a human subject against an FOLH1-expressing tumor. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

Methods for assessing efficacy of prostate cancer vaccines are well known in the art, and are described, for example, in Dzojic H et al (Adenovirus-mediated CD40 ligand therapy induces tumor cell apoptosis and systemic immunity in the TRAMP-C2 mouse prostate cancer model. Prostate. 2006 Jun. 1; 66(8):831-8), Naruishi K et al (Adenoviral vector-mediated RTVP-1 gene-modified tumor cell-based vaccine suppresses the development of experimental prostate cancer. Cancer Gene Ther. 2006 July; 13(7):658-63), Sehgal I et al (Cancer Cell Int. 2006 Aug. 23; 6:21), and Heinrich J E et al (Vaccination against prostate cancer using a live tissue factor deficient cell line in Lobund-Wistar rats. Cancer Immunol Immunother 2007; 56(5):725-30). Each possibility represents a separate embodiment of the present invention.

In another embodiment, the prostate cancer model used to test methods and compositions of the present invention is the TRAMP-C2 mouse model. In another embodiment, the prostate cancer model is a 178-2 BMA cell model. In another embodiment, the prostate cancer model is a PAIII adenocarcinoma cells model. In another embodiment, the prostate cancer model is a PC-3M model. In another embodiment, the prostate cancer model is any other prostate cancer model known in the art. Each possibility represents a separate embodiment of the present invention.

In another embodiment, the vaccine is tested in human subjects, and efficacy is monitored using methods well known in the art, e.g. directly measuring $CD4^+$ and $CD8^+$ T cell responses, or measuring disease progression, e.g. by determining the number or size of tumor metastases, or monitoring disease symptoms (cough, chest pain, weight loss, etc). Methods for assessing the efficacy of a prostate cancer vaccine in human subjects are well known in the art, and are described, for example, in Uenaka A et al (T cell immunomonitoring and tumor responses in patients immunized with a complex of cholesterol-bearing hydrophobized pullulan (CHP) and NY-ESO-1 protein. Cancer Immun. 2007 Apr. 19; 7:9) and Thomas-Kaskel A K et al (Vaccination of advanced prostate cancer patients with PSCA and PSA peptide-loaded dendritic cells induces DTH responses that correlate with superior overall survival. Int J Cancer. 2006 Nov. 15; 119(10):2428-34). Each method represents a separate embodiment of the present invention.

In another embodiment, the present invention provides a method of inducing an anti-KLK3 immune response in a subject, comprising administering to the subject an immunogenic composition comprising a recombinant polypeptide of the present invention, thereby inducing an anti-KLK3 immune response in a subject.

In another embodiment, the present invention provides a method of treating a KLK3-expressing tumor in a subject, the method comprising the step of administering to the subject an immunogenic composition comprising a recombinant polypeptide of the present invention, whereby the subject mounts an immune response against the KLK3 expressing tumor, thereby treating a KLK3 expressing tumor in a subject. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of protecting a human subject against a KLK3 expressing tumor, the method comprising the step of administering to the human subject an immunogenic composition comprising a recombinant polypeptide of the present invention, whereby the subject mounts an immune response against the KLK3 expressing tumor, thereby protecting a human subject against a KLK3 expressing tumor. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of inducing an anti-KLK3 immune response in a subject, comprising administering to the subject an immunogenic composition comprising a nucleotide molecule of the present invention, thereby inducing an anti-KLK3 immune response in a subject.

In another embodiment, the present invention provides a method of treating a KLK3 expressing tumor in a subject, the method comprising the step of administering to the subject an immunogenic composition comprising a nucleotide molecule of the present invention, whereby the subject mounts an immune response against the KLK3 expressing tumor, thereby treating a KLK3 expressing tumor in a subject. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of protecting a human subject against a KLK3 expressing tumor, the method comprising the step of administering to the human subject an immunogenic composition comprising a nucleotide molecule of the present invention whereby the subject mounts an immune response against the KLK3 expressing tumor, thereby protecting a human subject against a KLK3 expressing tumor. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of inducing an anti-KLK3 immune response in a subject, comprising administering to the subject a composition comprising a recombinant *Listeria* strain, wherein the strain comprises a recombinant polypeptide of the present invention, thereby inducing an anti-KLK3 immune response in a subject.

In another embodiment, the present invention provides a method of treating a KLK3 expressing tumor in a subject, the method comprising the step of administering to the subject a composition comprising a recombinant *Listeria* strain, wherein the strain comprises a recombinant polypeptide of the present invention, whereby the subject mounts an immune response against the KLK3 expressing tumor, thereby treating a KLK3 expressing tumor in a subject. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of protecting a human subject against a KLK3 expressing tumor, the method comprising the step of administering to the human subject a composition comprising a recombinant *Listeria* strain, wherein the strain comprises a recombinant polypeptide of the present invention whereby the subject mounts an immune response against the KLK3 expressing tumor, thereby protecting a human subject against a KLK3 expressing tumor. In another embodiment, the KLK3 expressing tumor is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the present invention provides a method of impeding a growth of a KLK3-expressing prostate cancer tumor in a subject, comprising administering to the subject a composition comprising a recombinant *Listeria* strain of the present invention, thereby impeding a growth of a KLK3-expressing prostate cancer tumor in a subject.

In another embodiment, the present invention provides a method of overcoming an immune tolerance of a subject to a KLK3-expressing prostate cancer tumor, comprising administering to the subject a composition comprising a recombinant *Listeria* strain of the present invention, thereby overcoming an immune tolerance of a subject to a KLK3-expressing prostate cancer tumor.

In another embodiment, the present invention provides a method of impeding a growth of a KLK3-expressing prostate cancer tumor in a subject, comprising administering to the subject an immunogenic composition comprising a recombinant polypeptide of the present invention, thereby impeding a growth of a KLK3-expressing prostate cancer tumor in a subject.

In another embodiment, the present invention provides a method of overcoming an immune tolerance of a subject to a KLK3-expressing prostate cancer tumor, comprising administering to the subject an immunogenic composition comprising a recombinant polypeptide of the present invention, thereby overcoming an immune tolerance of a subject to a KLK3-expressing prostate cancer tumor.

In another embodiment, the present invention provides a method of impeding a growth of a KLK3-expressing prostate cancer tumor in a subject, comprising administering to the subject an immunogenic composition comprising a nucleotide molecule of the present invention, thereby impeding a growth of a KLK3-expressing prostate cancer tumor in a subject.

In another embodiment, the present invention provides a method of overcoming an immune tolerance of a subject to a KLK3-expressing prostate cancer tumor, comprising administering to the subject an immunogenic composition comprising a nucleotide molecule of the present invention, thereby overcoming an immune tolerance of a subject to a KLK3-expressing prostate cancer tumor.

In another embodiment, the present invention provides a method of inducing an anti-FOLH1 immune response in a subject, comprising administering to the subject an immunogenic composition comprising a recombinant polypeptide of the present invention, thereby inducing an anti-FOLH1 immune response in a subject.

In another embodiment, the present invention provides a method of treating an FOLH1-expressing tumor in a subject, the method comprising the step of administering to the subject an immunogenic composition comprising a recombinant polypeptide of the present invention, whereby the subject mounts an immune response against the FOLH1-expressing tumor, thereby treating an FOLH1-expressing tumor in a subject. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the present invention provides a method of protecting a human subject against an FOLH1-expressing tumor, the method comprising the step of administering to the human subject an immunogenic composition comprising a recombinant polypeptide of the present invention, whereby the subject mounts an immune response against the FOLH1-expressing tumor, thereby protecting a human subject against an FOLH1-expressing tumor. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the present invention provides a method of inducing an anti-FOLH1 immune response in a subject, comprising administering to the subject an immunogenic composition comprising a nucleotide molecule of the present invention, thereby inducing an anti-FOLH1 immune response in a subject.

In another embodiment, the present invention provides a method of treating an FOLH1-expressing tumor in a subject, the method comprising the step of administering to the subject an immunogenic composition comprising a nucleotide molecule of the present invention, whereby the subject mounts an immune response against the FOLH1-expressing tumor, thereby treating an FOLH1-expressing tumor in a subject. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the present invention provides a method of protecting a human subject against an FOLH1-expressing tumor, the method comprising the step of administering to the human subject an immunogenic composition comprising a nucleotide molecule of the present invention whereby the subject mounts an immune response against the FOLH1-expressing tumor, thereby protecting a human subject against an FOLH1-expressing tumor. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the present invention provides a method of inducing an anti-FOLH1 immune response in a subject, comprising administering to the subject a composition comprising a recombinant *Listeria* strain, wherein the strain comprises a recombinant polypeptide of the present invention, thereby inducing an anti-FOLH1 immune response in a subject.

In another embodiment, the present invention provides a method of treating an FOLH1-expressing tumor in a subject, the method comprising the step of administering to the subject a composition comprising a recombinant *Listeria* strain, wherein the strain comprises a recombinant polypeptide of the present invention, whereby the subject mounts an immune response against the FOLH1-expressing tumor, thereby treating an FOLH1-expressing tumor in a subject. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the present invention provides a method of protecting a human subject against an FOLH1-expressing tumor, the method comprising the step of administering to the human subject a composition comprising a recombinant *Listeria* strain, wherein the strain comprises a recombinant polypeptide of the present invention whereby the subject mounts an immune response against the FOLH1-expressing tumor, thereby protecting a human subject against an FOLH1-expressing tumor. In another embodiment, the FOLH1-expressing tumor is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the present invention provides a method of impeding a growth of an FOLH1-expressing prostate cancer tumor in a subject, comprising administering to the subject a composition comprising a recombinant *Listeria* strain of the present invention, thereby impeding a growth of an FOLH1-expressing prostate cancer tumor in a subject.

In another embodiment, the present invention provides a method of overcoming an immune tolerance of a subject to an FOLH1-expressing prostate cancer tumor, comprising administering to the subject a composition comprising a recombinant *Listeria* strain of the present invention, thereby overcoming an immune tolerance of a subject to an FOLH1-expressing prostate cancer tumor.

In another embodiment, the present invention provides a method of impeding a growth of an FOLH1-expressing prostate cancer tumor in a subject, comprising administering to the subject an immunogenic composition comprising a recombinant polypeptide of the present invention, thereby impeding a growth of an FOLH1-expressing prostate cancer tumor in a subject.

In another embodiment, the present invention provides a method of overcoming an immune tolerance of a subject to an FOLH1-expressing prostate cancer tumor, comprising administering to the subject an immunogenic composition comprising a recombinant polypeptide of the present invention, thereby overcoming an immune tolerance of a subject to an FOLH1-expressing prostate cancer tumor.

In another embodiment, the present invention provides a method of impeding a growth of an FOLH1-expressing prostate cancer tumor in a subject, comprising administering to the subject an immunogenic composition comprising a nucleotide molecule of the present invention, thereby impeding a growth of an FOLH1-expressing prostate cancer tumor in a subject.

In another embodiment, the present invention provides a method of overcoming an immune tolerance of a subject to an FOLH1-expressing prostate cancer tumor, comprising administering to the subject an immunogenic composition comprising a nucleotide molecule of the present invention, thereby overcoming an immune tolerance of a subject to an FOLH1-expressing prostate cancer tumor.

"Tolerance" refers, in another embodiment, to a lack of responsiveness of the host to an antigen. In another embodiment, the term refers to a lack of detectable responsiveness of the host to an antigen. In another embodiment, the term refers to a lack of immunogenicity of an antigen in a host. In another embodiment, tolerance is measured by lack of responsiveness in an in vitro CTL assay. In another embodiment, tolerance is measured by lack of responsiveness in a delayed-type hypersensitivity assay. In another embodiment, tolerance is measured by lack of responsiveness in any other suitable assay known in the art. In another embodiment, tolerance is determined or measured as depicted in the Examples herein. Each possibility represents another embodiment of the present invention.

"Overcome" refers, in another embodiment, to a reversible of tolerance by a vaccine. In another embodiment, the term refers to conferment of detectable immune response by a vaccine. In another embodiment, overcoming of immune tolerance is determined or measured as depicted in the Examples herein. Each possibility represents another embodiment of the present invention.

In another embodiment, the present invention provides a method of treating benign prostate hyperplasia (BPH) in a subject, the method comprising the step of administering to the subject a KLK3-expressing *Listeria* strain of the present invention, thereby treating BPH in a subject. In another embodiment, the present invention provides a method of impeding the progression of BPH in a subject, the method comprising the step of administering to the subject a KLK3-expressing *Listeria* strain of the present invention, thereby impeding the progression of BPH in a subject.

In another embodiment, the present invention provides a method of treating BPH in a subject, the method comprising the step of administering to the subject an FOLH1-expressing *Listeria* strain of the present invention, thereby treating BPH in a subject. In another embodiment, the present invention provides a method of impeding the progression of BPH in a subject, the method comprising the step of administering to the subject an FOLH1-expressing *Listeria* strain of the present invention, thereby impeding the progression of BPH in a subject.

In another embodiment, the present invention provides a method of treating Prostatic Intraepithelial Neoplasia (PIN) in a subject, the method comprising the step of administering to the subject a KLK3-expressing *Listeria* strain of the present invention, thereby treating PIN in a subject. In another embodiment, the present invention provides a method of impeding the progression of PIN in a subject, the method comprising the step of administering to the subject a KLK3-expressing *Listeria* strain of the present invention, thereby impeding the progression of PIN in a subject.

In another embodiment, the present invention provides a method of treating Prostatic Intraepithelial Neoplasia (PIN) in a subject, the method comprising the step of administering to the subject an FOLH1-expressing *Listeria* strain of the present invention, thereby treating PIN in a subject. In another embodiment, the present invention provides a method of impeding the progression of PIN in a subject, the method comprising the step of administering to the subject an FOLH1-expressing *Listeria* strain of the present invention, thereby impeding the progression of PIN in a subject.

In another embodiment, the present invention provides a method of treating BPH in a subject, the method comprising the step of administering to the subject a KLK3-containing peptide of the present invention, thereby treating BPH in a subject. In another embodiment, the present invention provides a method of impeding the progression of BPH in a subject, the method comprising the step of administering to the subject a KLK3-containing peptide of the present invention, thereby impeding the progression of BPH in a subject.

In another embodiment, the present invention provides a method of treating BPH in a subject, the method comprising the step of administering to the subject an FOLH1-containing peptide of the present invention, thereby treating BPH in a subject. In another embodiment, the present invention provides a method of impeding the progression of BPH in a subject, the method comprising the step of administering to the subject an FOLH1-containing peptide of the present invention, thereby impeding the progression of BPH in a subject.

In another embodiment, the present invention provides a method of treating Prostatic Intraepithelial Neoplasia (PIN) in a subject, the method comprising the step of administering to the subject a KLK3-containing peptide of the present invention, thereby treating PIN in a subject. In another embodiment, the present invention provides a method of impeding the progression of PIN in a subject, the method comprising the step of administering to the subject a KLK3-containing peptide of the present invention, thereby impeding the progression of PIN in a subject.

In another embodiment, the present invention provides a method of treating Prostatic Intraepithelial Neoplasia (PIN) in a subject, the method comprising the step of administering to the subject an FOLH1-containing peptide of the present invention, thereby treating PIN in a subject. In another embodiment, the present invention provides a method of impeding the progression of PIN in a subject, the method comprising the step of administering to the subject an FOLH1-containing peptide of the present invention, thereby impeding the progression of PIN in a subject.

In another embodiment, the present invention provides a method of treating BPH in a subject, the method comprising the step of administering to the subject a KLK3-encoding nucleotide molecule of the present invention, thereby treating BPH in a subject. In another embodiment, the present invention provides a method of impeding the progression of BPH in a subject, the method comprising the step of administering to the subject a KLK3-encoding nucleotide molecule of the present invention, thereby impeding the progression of BPH in a subject.

In another embodiment, the present invention provides a method of treating BPH in a subject, the method comprising the step of administering to the subject an FOLH1-encoding nucleotide molecule of the present invention, thereby treating BPH in a subject. In another embodiment, the present invention provides a method of impeding the progression of BPH in a subject, the method comprising the step of administering to the subject an FOLH1-encoding nucleotide molecule of the present invention, thereby impeding the progression of BPH in a subject.

In another embodiment, the present invention provides a method of treating Prostatic Intraepithelial Neoplasia in a subject, the method comprising the step of administering to the subject a KLK3-encoding nucleotide molecule of the present invention, thereby treating Prostatic Intraepithelial Neoplasia in a subject. In another embodiment, the present invention provides a method of impeding the progression of Prostatic Intraepithelial Neoplasia in a subject, the method comprising the step of administering to the subject a KLK3-encoding nucleotide molecule of the present invention, thereby impeding the progression of Prostatic Intraepithelial Neoplasia in a subject.

In another embodiment, the present invention provides a method of treating Prostatic Intraepithelial Neoplasia in a subject, the method comprising the step of administering to the subject an FOLH1-encoding nucleotide molecule of the present invention, thereby treating Prostatic Intraepithelial Neoplasia in a subject. In another embodiment, the present invention provides a method of impeding the progression of Prostatic Intraepithelial Neoplasia in a subject, the method comprising the step of administering to the subject an FOLH1-encoding nucleotide molecule of the present invention, thereby impeding the progression of Prostatic Intraepithelial Neoplasia in a subject.

In another embodiment, fusion proteins of the present invention need not be expressed by LM, but rather can be expressed and isolated from other vectors and cell systems used for protein expression and isolation.

As provided herein, LLO-E7 fusions exhibit significant therapeutic efficacy. In these experiments, a vaccinia vector that expresses E7 as a fusion protein with a non-hemolytic truncated form of LLO was constructed. Expression of the LLO-E7 fusion product by plaque purified vaccinia was verified by Western blot using an antibody directed against the LLO protein sequence. Vac-LLO-E7 was demonstrated to produce $CD8^+$ T cells specific to LLO and E7 as determined using the LLO (91-99) and E7 (49-57) epitopes of Balb/c and C57/BL6 mice, respectively. Results were confirmed by a CTL assay (Example 4).

Thus, expression of an antigen, e.g. KLK3 or FOLH1, as a fusion protein with a non-hemolytic truncated form of LLO, ActA, or a PEST-like sequence in host cell systems in *Listeria* and host cell systems other than *Listeria* results in enhanced immunogenicity of the antigen. While comparative experiments were performed with vaccinia, a multitude of other plasmids and expression systems which can be used to express these fusion proteins are known. For example, bacterial vectors useful in the present invention include, but are not limited to *Salmonella* sp., *Shigella* sp., BCG, *L. monocytogenes* and *S. gordonii*. In addition the fusion proteins can be delivered by recombinant bacterial vectors modified to escape phagolysosomal fusion and live in the cytoplasm of the cell. Viral vectors useful in the present invention include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. Naked DNA vectors can also be used.

In another embodiment, a KLK3 protein expressed by the target tumor cell shares complete homology with the KLK3 peptide (throughout the length of the peptide) expressed by the Listerial vector. In another embodiment, the KLK3 protein is highly homologous (throughout the length of the peptide) to the KLK3 peptide expressed by the Listerial vector. "Highly homologous" refers, in another embodiment, to a homology of greater than 90%. In another embodiment, the term refers to a homology of greater than 92%. In another embodiment, the term refers to a homology of greater than 93%. In another embodiment, the term refers to a homology of greater than 94%. In another embodiment, the term refers to a homology of greater than 95%. In another embodiment, the term refers to a homology of greater than 96%. In another embodiment, the term refers to a homology of greater than 97%. In another embodiment, the term refers to a homology of greater than 98%. In another embodiment, the term refers to a homology of greater than 99%. In another embodiment, the term refers to a homology of 100%. Each possibility represents a separate embodiment of the present invention.

In another embodiment, an FOLH1 protein expressed by the target tumor cell shares complete homology with the FOLH1 peptide (throughout the length of the peptide) expressed by the Listerial vector. In another embodiment, the FOLH1 protein is highly homologous (throughout the length of the peptide) to the FOLH1 peptide expressed by the Listerial vector. "Highly homologous" refers, in another embodiment, to a homology of greater than 90%. In another embodiment, the term refers to a homology of greater than 92%. In another embodiment, the term refers to a homology of greater than 93%. In another embodiment, the term refers to a homology of greater than 94%. In another embodiment, the term refers to a homology of greater than 95%.

In another embodiment, the term refers to a homology of greater than 96%. In another embodiment, the term refers to a homology of greater than 97%. In another embodiment, the term refers to a homology of greater than 98%. In another embodiment, the term refers to a homology of greater than 99%. In another embodiment, the term refers to a homology of 100%. Each possibility represents a separate embodiment of the present invention.

The KLK3 peptide of methods and compositions of the present invention is, in another embodiment, 200-261 amino acids (AA) in length. In another embodiment, the KLK3 peptide is about 100-261 AA long. In another embodiment, the length is 100-261 AA. In another embodiment, the length is 110-261 AA. In another embodiment, the length is 120-261 AA. In another embodiment, the length is 130-261 AA. In another embodiment, the length is 140-261 AA. In another embodiment, the length is 150-261 AA. In another embodiment, the length is 160-261 AA. In another embodiment, the length is 175-261 AA. In another embodiment, the length is 190-261 AA. In another embodiment, the length is 200-261 AA. In another embodiment, the length is 210-261 AA. In another embodiment, the length is 220-261 AA. In another embodiment, the length is 230-261 AA. In another embodiment, the length is 240-261 AA. In another embodiment, the length is 250-261 AA. In another embodiment, the length is 100-150 AA. In another embodiment, the length is 100-160 AA. In another embodiment, the length is 100-170 AA. In another embodiment, the length is 100-180 AA. In another embodiment, the length is 100-190 AA. In another embodiment, the length is 100-200 AA. In another embodiment, the length is 100-210 AA. In another embodiment, the length is 100-220 AA. In another embodiment, the length is 100-240 AA. In another embodiment, the length is 50-150 AA. In another embodiment, the length is 50-160 AA. In another embodiment, the length is 50-170 AA. In another embodiment, the length is 50-180 AA. In another embodiment, the length is 50-190 AA. In another embodiment, the length is 50-200 AA.

In another embodiment, the length is about 175 AA. In another embodiment, the length is about 200 AA. In another embodiment, the length is about 220 AA. In another embodiment, the length is about 240 AA. In another embodiment, the length is about 260 AA.

Each length represents a separate embodiment of the present invention.

In another embodiment, the KLK3 peptide consists of about one-third to one-half of the KLK3 protein. In another embodiment, the fragment consists of about one-tenth to one-fifth thereof. In another embodiment, the fragment consists of about one-fifth to one-fourth thereof. In another embodiment, the fragment consists of about one-fourth to one-third thereof. In another embodiment, the fragment consists of about one-third to one-half thereof. In another embodiment, the fragment consists of about one-half to three quarters thereof. In another embodiment, the fragment consists of about three quarters to the KLK3 protein. In another embodiment, the fragment consists of about 5-10% thereof. In another embodiment, the fragment consists of about 10-15% thereof. In another embodiment, the fragment consists of about 15-20% thereof. In another embodiment, the fragment consists of about 20-25% thereof. In another embodiment, the fragment consists of about 25-30% thereof. In another embodiment, the fragment consists of about 30-35% thereof. In another embodiment, the fragment consists of about 35-40% thereof. In another embodiment, the fragment consists of about 45-50% thereof. In another embodiment, the fragment consists of about 50-55% thereof. In another embodiment, the fragment consists of about 55-60% thereof. In another embodiment, the fragment consists of about 5-15% thereof. In another embodiment, the fragment consists of about 10-20% thereof. In another embodiment, the fragment consists of about 15-25% thereof. In another embodiment, the fragment consists of about 20-30% thereof. In another embodiment, the fragment consists of about 25-35% thereof. In another embodiment, the fragment consists of about 30-40% thereof. In another embodiment, the fragment consists of about 35-45% thereof. In another embodiment, the fragment consists of about 45-55% thereof. In another embodiment, the fragment consists of about 50-60% thereof. In another embodiment, the fragment consists of about 55-65% thereof. In another embodiment, the fragment consists of about 60-70% thereof. In another embodiment, the fragment consists of about 65-75% thereof. In another embodiment, the fragment consists of about 70-80% thereof. In another embodiment, the fragment consists of about 5-20% thereof. In another embodiment, the fragment consists of about 10-25% thereof. In another embodiment, the fragment consists of about 15-30% thereof. In another embodiment, the fragment consists of about 20-35% thereof. In another embodiment, the fragment consists of about 25-40% thereof. In another embodiment, the fragment consists of about 30-45% thereof.

In another embodiment, the fragment consists of about 35-50% thereof. In another embodiment, the fragment consists of about 45-60% thereof. In another embodiment, the fragment consists of about 50-65% thereof. In another embodiment, the fragment consists of about 55-70% thereof. In another embodiment, the fragment consists of about 60-75% thereof. In another embodiment, the fragment consists of about 65-80% thereof. In another embodiment, the fragment consists of about 70-85% thereof. In another embodiment, the fragment consists of about 75-90% thereof. In another embodiment, the fragment consists of about 80-95% thereof. In another embodiment, the fragment consists of about 85-100% thereof. In another embodiment, the fragment consists of about 5-25% thereof. In another embodiment, the fragment consists of about 10-30% thereof. In another embodiment, the fragment consists of about 15-35% thereof. In another embodiment, the fragment consists of about 20-40% thereof. In another embodiment, the fragment consists of about 30-50% thereof. In another embodiment, the fragment consists of about 40-60% thereof. In another embodiment, the fragment consists of about 50-70% thereof. In another embodiment, the fragment consists of about 60-80% thereof. In another embodiment, the fragment consists of about 70-90% thereof. In another embodiment, the fragment consists of about 80-100% thereof. In another embodiment, the fragment consists of about 5-35% thereof. In another embodiment, the fragment consists of about 10-40% thereof. In another embodiment, the fragment consists of about 15-45% thereof. In another embodiment, the fragment consists of about 20-50% thereof. In another embodiment, the fragment consists of about 30-60% thereof. In another embodiment, the fragment consists of about 40-70% thereof. In another embodiment, the fragment consists of about 50-80% thereof. In another embodiment, the fragment consists of about 60-90% thereof. In another embodiment, the fragment consists of about 70-100% thereof. In another embodiment, the fragment consists of about 5-45% thereof. In another embodiment, the fragment consists of about 10-50% thereof. In another embodiment, the fragment consists of about 20-60% thereof. In another embodiment, the fragment consists of about 30-70% thereof. In another embodiment, the fragment consists of about 40-80% thereof. In another embodiment, the fragment consists of about 50-90% thereof. In another embodiment, the fragment consists of about 60-100% thereof. In another embodiment, the fragment consists of about 5-55% thereof. In another embodiment, the fragment consists of about 10-60% thereof. In another embodiment, the fragment consists of about 20-70% thereof. In another embodiment, the fragment consists of about 30-80% thereof. In another embodiment, the fragment consists of about 40-90% thereof. In another embodiment, the fragment consists of about 50-100% thereof. In another embodiment, the fragment consists of about 5-65% thereof. In another embodiment, the fragment consists of about 10-70% thereof. In another embodiment, the fragment consists of about 20-80% thereof. In another embodiment, the fragment consists of about 30-90% thereof. In another embodiment, the fragment consists of about 40-100% thereof. In another embodiment, the fragment consists of about 5-75% thereof. In another embodiment, the fragment consists of about 10-80% thereof. In another embodiment, the fragment consists of about 20-90% thereof. In another embodiment, the fragment consists of about 30-100% thereof. In another embodiment, the fragment consists of about 10-90% thereof. In another embodiment, the fragment consists of about 20-100% thereof. In another embodiment, the fragment consists of about 10-100% thereof.

In another embodiment, the fragment consists of about 5% of the KLK3 protein. In another embodiment, the fragment consists of about 6% thereof. In another embodiment, the fragment consists of about 8% thereof. In another embodiment, the fragment consists of about 10% thereof. In another embodiment, the fragment consists of about 12% thereof. In another embodiment, the fragment consists of about 15% thereof. In another embodiment, the fragment consists of about 18% thereof. In another embodiment, the fragment consists of about 20% thereof. In another embodiment, the fragment consists of about 25% thereof. In another embodiment, the fragment consists of about 30% thereof. In another embodiment, the fragment consists of about 35% thereof. In another embodiment, the fragment consists of about 40% thereof. In another embodiment, the fragment consists of about 45% thereof. In another embodiment, the fragment consists of about 50% thereof. In another embodiment, the fragment consists of about 55% thereof. In another embodiment, the fragment consists of about 60% thereof. In another embodiment, the fragment consists of about 65% thereof. In another embodiment, the fragment consists of about 70% thereof. In another embodiment, the fragment consists of about 75% thereof. In another embodiment, the fragment consists of about 80% thereof. In another embodiment, the fragment consists of about 85% thereof. In another embodiment, the fragment consists of about 90% thereof. In another embodiment, the fragment consists of about 95% thereof. In another embodiment, the fragment consists of about 100% thereof. Each possibility represents a separate embodiment of the present invention.

In another embodiment, a KLK3 peptide or FOLH1 peptide of methods and compositions of the present invention is an immunogenic peptide. "Immunogenic" refers, in another embodiment, to an ability to induce an immune response when administered to a subject. In another embodiment, the subject is a human subject. In another embodiment, the immune response elicited is a T-cell response. In another embodiment, the immune response elicited is a cytotoxic T lymphocyte (CTL) response. In another embodiment, the immune response elicited is detectable. In another embodiment, the immune response elicited is detectable by an in vitro assay. In another embodiment, the assay is a cytokine release assay (e.g. fluorescence-activated cell sorting; or FACS). In another embodiment, the assay is a chromium-release assay or other in vitro cytotoxicity assay. Each possibility represents a separate embodiment of the present invention.

In another embodiment, the immunogenic fragment of a sequence selected from the sequences set forth in SEQ ID No: 25, 27, 29-32, 34, and 36-39, which is contained in a KLK3 peptide of methods and compositions of the present invention, is about 10-150 AA long. In another embodiment, the length is 15-150 AA. In another embodiment, the length is 20-150 AA. In another embodiment, the length is 30-150 AA. In another embodiment, the length is 40-150 AA. In another embodiment, the length is 50-150 AA. In another embodiment, the length is 60-150 AA. In another embodiment, the length is 70-150 AA. In another embodiment, the length is 80-150 AA. In another embodiment, the length is 90-150 AA. In another embodiment, the length is 100-150 AA. In another embodiment, the length is 10-100 AA. In another embodiment, the length is 15-100 AA. In another embodiment, the length is 20-100 AA. In another embodiment, the length is 30-100 AA. In another embodiment, the length is 40-100 AA. In another embodiment, the length is 50-100 AA. In another embodiment, the length is 60-100 AA. In another embodiment, the length is 70-100 AA. In another embodiment, the length is 10-80 AA. In another embodiment, the length is 15-80 AA. In another embodiment, the length is 20-80 AA. In another embodiment, the length is 30-80 AA. In another embodiment, the length is 40-80 AA. In another embodiment, the length is 50-80 AA. In another embodiment, the length is 60-80 AA. In another embodiment, the length is 70-80 AA. In another embodiment, the length is 10-60 AA. In another embodiment, the length is 15-60 AA. In another embodiment, the length is 20-60 AA. In another embodiment, the length is 30-60 AA. In another embodiment, the length is 40-60 AA. In another embodiment, the length is 50-60 AA. In another embodiment, the length is 10-50 AA. In another embodiment, the length is 15-50 AA. In another embodiment, the length is 20-50 AA. In another embodiment, the length is 30-50 AA. In another embodiment, the length is 40-50 AA. In another embodiment, the length is 10-40 AA. In another embodiment, the length is 15-40 AA. In another embodiment, the length is 20-40 AA. In another embodiment, the length is 30-40 AA. In another embodiment, the length is 10-30 AA. In another embodiment, the length is 15-30 AA. In another embodiment, the length is 20-30 AA. In another embodiment, the length is 5-20 AA. In another embodiment, the length is 10-20 AA. In another embodiment, the length is 15-20 AA.

In another embodiment, the length of the immunogenic fragment is about 10 AA. In another embodiment, the length is about 15 AA. In another embodiment, the length is about 20 AA. In another embodiment, the length is about 30 AA. In another embodiment, the length is about 40 AA. In another embodiment, the length is about 50 AA. In another embodiment, the length is about 60 AA. In another embodiment, the length is about 70 AA. In another embodiment, the length is about 80 AA. In another embodiment, the length is about 90 AA. In another embodiment, the length is about 100 AA.

Each length of the immunogenic fragment represents a separate embodiment of the present invention.

The FOLH1 peptide of methods and compositions of the present invention is, in another embodiment, 200-750 AA in length. In another embodiment, the FOLH1 peptide is about 100-750 AA long. In another embodiment, the length is 100-750 AA. In another embodiment, the length is 110-750 AA. In another embodiment, the length is 120-750 AA. In another embodiment, the length is 130-750 AA. In another embodiment, the length is 140-750 AA. In another embodiment, the length is 150-750 AA. In another embodiment, the length is 160-750 AA. In another embodiment, the length is 175-750 AA. In another embodiment, the length is 190-750 AA. In another embodiment, the length is 200-750 AA. In another embodiment, the length is 210-750 AA. In another embodiment, the length is 220-750 AA. In another embodiment, the length is 230-750 AA. In another embodiment, the length is 240-750 AA. In another embodiment, the length is 250-750 AA. In another embodiment, the length is 280-750 AA. In another embodiment, the length is 300-750 AA. In another embodiment, the length is 350-750 AA. In another embodiment, the length is 400-750 AA. In another embodiment, the length is 450-750 AA. In another embodiment, the length is 500-750 AA. In another embodiment, the length is 550-750 AA. In another embodiment, the length is 600-750 AA. In another embodiment, the length is 650-750 AA. In another embodiment, the length is 700-750 AA. In another embodiment, the length is 100-150 AA. In another embodiment, the length is 100-160 AA. In another embodiment, the length is 100-170 AA. In another embodiment, the length is 100-180 AA. In another embodiment, the length is 100-190 AA. In another embodiment, the length is 100-200 AA. In another embodiment, the length is 100-220 AA. In another embodiment, the length is 100-240 AA. In another embodiment, the length is 100-260 AA. In another embodiment, the length is 100-280 AA. In another embodiment, the length is 100-300 AA. In another embodiment, the length is 100-350 AA. In another embodiment, the length is 100-400 AA. In another embodiment, the length is 100-450 AA. In another embodiment, the length is 100-500 AA. In another embodiment, the length is 100-600 AA. In another embodiment, the length is 100-700 AA. In another embodiment, the length is 50-150 AA. In another embodiment, the length is 50-160 AA. In another embodiment, the length is 50-170 AA. In another embodiment, the length is 50-180 AA. In another embodiment, the length is 50-190 AA. In another embodiment, the length is 50-200 AA. In another embodiment, the length is 50-220 AA. In another embodiment, the length is 50-240 AA. In another embodiment, the length is 50-260 AA. In another embodiment, the length is 50-280 AA. In another embodiment, the length is 50-300 AA. In another embodiment, the length is 50-350 AA. In another embodiment, the length is 50-400 AA. In another embodiment, the length is 50-450 AA. In another embodiment, the length is 50-500 AA.

In another embodiment, the length is about 175 AA. In another embodiment, the length is about 200 AA. In another embodiment, the length is about 220 AA. In another embodiment, the length is about 240 AA. In another embodiment, the length is about 260 AA.

Each length represents a separate embodiment of the present invention.

In another embodiment, the FOLH1 peptide consists of about one-third to one-half of the FOLH1 protein. In another embodiment, the fragment consists of about one-tenth to one-fifth thereof. In another embodiment, the fragment consists of about one-fifth to one-fourth thereof. In another embodiment, the fragment consists of about one-fourth to one-third thereof. In another embodiment, the fragment consists of about one-third to one-half thereof. In another embodiment, the fragment consists of about one-half to three quarters thereof. In another embodiment, the fragment consists of about three quarters to the FOLH1 protein. In another embodiment, the fragment consists of about 5-10% thereof. In another embodiment, the fragment consists of about 10-15% thereof. In another embodiment, the fragment consists of about 15-20% thereof. In another embodiment, the fragment consists of about 20-25% thereof. In another embodiment, the fragment consists of about 25-30% thereof. In another embodiment, the fragment consists of about 30-35% thereof. In another embodiment, the fragment consists of about 35-40% thereof. In another embodiment, the fragment consists of about 45-50% thereof. In another embodiment, the fragment consists of about 50-55% thereof. In another embodiment, the fragment consists of about 55-60% thereof. In another embodiment, the fragment consists of about 5-15% thereof. In another embodiment, the fragment consists of about 10-20% thereof. In another embodiment, the fragment consists of about 15-25% thereof. In another embodiment, the fragment consists of about 20-30% thereof. In another embodiment, the fragment consists of about 25-35% thereof. In another embodiment, the fragment consists of about 30-40% thereof. In another embodiment, the fragment consists of about 35-45% thereof.

In another embodiment, the fragment consists of about 45-55% thereof. In another embodiment, the fragment consists of about 50-60% thereof. In another embodiment, the fragment consists of about 55-65% thereof. In another embodiment, the fragment consists of about 60-70% thereof. In another embodiment, the fragment consists of about 65-75% thereof. In another embodiment, the fragment consists of about 70-80% thereof. In another embodiment, the fragment consists of about 5-20% thereof. In another embodiment, the fragment consists of about 10-25% thereof. In another embodiment, the fragment consists of about 15-30% thereof. In another embodiment, the fragment consists of about 20-35% thereof. In another embodiment, the fragment consists of about 25-40% thereof. In another embodiment, the fragment consists of about 30-45% thereof. In another embodiment, the fragment consists of about 35-50% thereof. In another embodiment, the fragment consists of about 45-60% thereof. In another embodiment, the fragment consists of about 50-65% thereof. In another embodiment, the fragment consists of about 55-70% thereof. In another embodiment, the fragment consists of about 60-75% thereof. In another embodiment, the fragment consists of about 65-80% thereof. In another embodiment, the fragment consists of about 70-85% thereof. In another embodiment, the fragment consists of about 75-90% thereof. In another embodiment, the fragment consists of about 80-95% thereof. In another embodiment, the fragment consists of about 85-100% thereof. In another embodiment, the fragment consists of about 5-25% thereof. In another embodiment, the fragment consists of about 10-30% thereof. In another embodiment, the fragment consists of about 15-35% thereof. In another embodiment, the fragment consists of about 20-40% thereof. In another embodiment, the fragment consists of about 30-50% thereof. In another embodiment, the fragment consists of about 40-60% thereof. In another embodiment, the fragment consists of about 50-70% thereof. In another embodiment, the fragment consists of about 60-80% thereof. In another embodiment, the fragment consists of about 70-90% thereof. In another embodiment, the fragment consists of about 80-100% thereof. In another embodiment, the fragment consists of about 5-35% thereof. In another embodiment, the fragment consists of about 10-40% thereof. In another embodiment, the fragment consists of about 15-45% thereof. In another embodiment, the fragment consists of about 20-50% thereof. In another embodiment, the fragment consists of about 30-60% thereof. In another embodiment, the fragment consists of about 40-70% thereof. In another embodiment, the fragment consists of about 50-80% thereof. In another embodiment, the fragment consists of about 60-90% thereof. In another embodiment, the fragment consists of about 70-100% thereof. In another embodiment, the fragment consists of about 5-45% thereof. In another embodiment, the fragment consists of about 10-50% thereof. In another embodiment, the fragment consists of about 20-60% thereof. In another embodiment, the fragment consists of about 30-70% thereof. In another embodiment, the fragment consists of about 40-80% thereof. In another embodiment, the fragment consists of about 50-90% thereof. In another embodiment, the fragment consists of about 60-100% thereof. In another embodiment, the fragment consists of about 5-55% thereof. In another embodiment, the fragment consists of about 10-60% thereof. In another embodiment, the fragment consists of about 20-70% thereof. In another embodiment, the fragment consists of about 30-80% thereof. In another embodiment, the fragment consists of about 40-90% thereof. In another embodiment, the fragment consists of about 50-100% thereof. In another embodiment, the fragment consists of about 5-65% thereof. In another embodiment, the fragment consists of about 10-70% thereof. In another embodiment, the fragment consists of about 20-80% thereof. In another embodiment, the fragment consists of about 30-90% thereof. In another embodiment, the fragment consists of about 40-100% thereof. In another embodiment, the fragment consists of about 5-75% thereof. In another embodiment, the fragment consists of about 10-80% thereof. In another embodiment, the fragment consists of about 20-90% thereof. In another embodiment, the fragment consists of about 30-100% thereof. In another embodiment, the fragment consists of about 10-90% thereof. In another embodiment, the fragment consists of about 20-100% thereof. In another embodiment, the fragment consists of about 10-100% thereof.

In another embodiment, the fragment consists of about 5% of the FOLH1 protein. In another embodiment, the fragment consists of about 6% thereof. In another embodiment, the fragment consists of about 8% thereof. In another embodiment, the fragment consists of about 10% thereof. In another embodiment, the fragment consists of about 12% thereof. In another embodiment, the fragment consists of about 15% thereof. In another embodiment, the fragment consists of about 18% thereof. In another embodiment, the fragment consists of about 20% thereof. In another embodiment, the fragment consists of about 25% thereof. In another embodiment, the fragment consists of about 30% thereof. In another embodiment, the fragment consists of about 35% thereof. In another embodiment, the fragment consists of about 40% thereof. In another embodiment, the fragment consists of about 45% thereof. In another embodiment, the fragment consists of about 50% thereof. In another embodiment, the fragment consists of about 55% thereof. In another embodiment, the fragment consists of about 60% thereof. In another embodiment, the fragment consists of about 65% thereof. In another embodiment, the fragment consists of about 70% thereof. In another embodiment, the fragment consists of about 75% thereof. In another embodiment, the fragment consists of about 80% thereof. In another embodiment, the fragment consists of about 85% thereof. In another embodiment, the fragment consists of about 90% thereof. In another embodiment, the fragment consists of about 95% thereof. In another embodiment, the fragment consists of about 100% thereof. Each possibility represents a separate embodiment of the present invention.

In another embodiment, the immunogenic fragment of a sequence selected from the sequences set forth in SEQ ID No: 41, 43, 44, and 45, which is contained in an FOLH1 peptide of methods and compositions of the present invention, is about 10-150 AA long. In another embodiment, the length is 15-150 AA. In another embodiment, the length is 20-150 AA. In another embodiment, the length is 30-150 AA. In another embodiment, the length is 40-150 AA. In another embodiment, the length is 50-150 AA. In another embodiment, the length is 60-150 AA. In another embodiment, the length is 70-150 AA. In another embodiment, the length is 80-150 AA. In another embodiment, the length is 90-150 AA. In another embodiment, the length is about 10-200 AA long. In another embodiment, the length is 15-200 AA. In another embodiment, the length is 20-200 AA. In another embodiment, the length is 30-200 AA. In another embodiment, the length is 40-200 AA. In another embodiment, the length is 50-200 AA. In another embodiment, the length is 60-200 AA. In another embodiment, the length is 70-200 AA. In another embodiment, the length is 80-200 AA. In another embodiment, the length is 90-200

AA. In another embodiment, the length is 100-200 AA. In another embodiment, the length is 50-300 AA. In another embodiment, the length is 60-300 AA. In another embodiment, the length is 70-300 AA. In another embodiment, the length is 80-300 AA. In another embodiment, the length is 90-300 AA. In another embodiment, the length is 100-300 AA. In another embodiment, the length is 90-300 AA. In another embodiment, the length is 200-300 AA. In another embodiment, the length is 50-400 AA. In another embodiment, the length is 60-400 AA. In another embodiment, the length is 70-400 AA. In another embodiment, the length is 80-400 AA. In another embodiment, the length is 90-400 AA. In another embodiment, the length is 100-400 AA. In another embodiment, the length is 200-400 AA. In another embodiment, the length is 300-400 AA. In another embodiment, the length is 100-150 AA. In another embodiment, the length is 10-100 AA. In another embodiment, the length is 15-100 AA. In another embodiment, the length is 20-100 AA. In another embodiment, the length is 30-100 AA. In another embodiment, the length is 40-100 AA. In another embodiment, the length is 50-100 AA. In another embodiment, the length is 60-100 AA. In another embodiment, the length is 70-100 AA. In another embodiment, the length is 10-80 AA. In another embodiment, the length is 15-80 AA. In another embodiment, the length is 20-80 AA. In another embodiment, the length is 30-80 AA. In another embodiment, the length is 40-80 AA. In another embodiment, the length is 50-80 AA. In another embodiment, the length is 60-80 AA. In another embodiment, the length is 70-80 AA. In another embodiment, the length is 10-60 AA. In another embodiment, the length is 15-60 AA. In another embodiment, the length is 20-60 AA. In another embodiment, the length is 30-60 AA. In another embodiment, the length is 40-60 AA. In another embodiment, the length is 50-60 AA. In another embodiment, the length is 10-50 AA. In another embodiment, the length is 15-50 AA. In another embodiment, the length is 20-50 AA. In another embodiment, the length is 30-50 AA. In another embodiment, the length is 40-50 AA. In another embodiment, the length is 10-40 AA. In another embodiment, the length is 15-40 AA. In another embodiment, the length is 20-40 AA. In another embodiment, the length is 30-40 AA. In another embodiment, the length is 10-30 AA. In another embodiment, the length is 15-30 AA. In another embodiment, the length is 20-30 AA. In another embodiment, the length is 5-20 AA. In another embodiment, the length is 10-20 AA. In another embodiment, the length is 15-20 AA.

In another embodiment, the length of the immunogenic fragment is about 10 AA. In another embodiment, the length is about 15 AA. In another embodiment, the length is about 20 AA. In another embodiment, the length is about 30 AA. In another embodiment, the length is about 40 AA. In another embodiment, the length is about 50 AA. In another embodiment, the length is about 60 AA. In another embodiment, the length is about 70 AA. In another embodiment, the length is about 80 AA. In another embodiment, the length is about 90 AA. In another embodiment, the length is about 100 AA.

Each length of the immunogenic fragment represents a separate embodiment of the present invention.

In another embodiment, the present invention provides a method of reducing a size of a KLK3-expressing tumor, comprising administering a vaccine, immunogenic composition, or vector comprising a recombinant *Listeria* strain of the present invention, thereby reducing a size of a KLK3-expressing tumor. In another embodiment, a cell of the tumor expresses KLK3. Each possibility represents a separate embodiment of the present invention.

In another embodiment, the present invention provides a method of suppressing a formation of a KLK3-expressing tumor, comprising administering an effective amount of a vaccine comprising either: (a) a recombinant *Listeria* strain comprising an N-terminal fragment of a protein fused to a KLK3 peptide; or (b) a recombinant nucleotide encoding the recombinant polypeptide, whereby the subject mounts an immune response against the KLK3-expressing tumor, thereby suppressing a formation of a KLK3-expressing tumor.

In another embodiment, the present invention provides a method of reducing a size of a KLK3-expressing tumor, comprising administering a vaccine, immunogenic composition, or vector comprising a recombinant polypeptide of the present invention, thereby reducing a size of a KLK3-expressing tumor. In another embodiment, a cell of the tumor expresses KLK3. Each possibility represents a separate embodiment of the present invention.

In another embodiment, the present invention provides a method of suppressing a formation of a KLK3-expressing tumor, comprising administering an effective amount of a vaccine comprising either: (a) a recombinant polypeptide comprising an N-terminal fragment of a protein fused to a KLK3 peptide; or (b) a recombinant nucleotide encoding the recombinant polypeptide, whereby the subject mounts an immune response against the KLK3-expressing tumor, thereby suppressing a formation of a KLK3-expressing tumor.

In another embodiment, the present invention provides a method of reducing a size of a KLK3-expressing tumor, comprising administering a vaccine, immunogenic composition, or vector comprising a recombinant nucleotide molecule of the present invention, thereby reducing a size of a KLK3-expressing tumor. In another embodiment, a cell of the tumor expresses KLK3. Each possibility represents a separate embodiment of the present invention.

In another embodiment, the present invention provides a method of suppressing a formation of a KLK3-expressing tumor, comprising administering an effective amount of a vaccine comprising either: (a) a recombinant nucleotide molecule comprising an N-terminal fragment of a protein fused to a KLK3 peptide; or (b) a recombinant nucleotide encoding the recombinant polypeptide, whereby the subject mounts an immune response against the KLK3-expressing tumor, thereby suppressing a formation of a KLK3-expressing tumor.

The non-KLK3/non-FOLH1 peptide of methods and compositions of the present invention is, in another embodiment, a listeriolysin (LLO) peptide. In another embodiment, the non-KLK3/non-FOLH1 peptide is an ActA peptide. In another embodiment, the non-KLK3/non-FOLH1 peptide is a PEST-like sequence peptide. In another embodiment, the non-KLK3/non-FOLH1 peptide is any other peptide capable of enhancing the immunogenicity of a KLK3 or FOLH1 peptide. Each possibility represents a separate embodiment of the present invention.

In another embodiment, a recombinant fusion peptide of methods and compositions of the present invention is an LLO-KLK3 fusion peptide. In another embodiment, the fusion peptide has the sequence set forth in SEQ ID No: 54. In another embodiment, the fusion peptide is homologous to the sequence set forth in SEQ ID No: 54. In another embodiment, the fusion peptide is a variant of the sequence set forth in SEQ ID No: 54. In another embodiment, "homology" refers to identity to one of SEQ ID No: 54 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

The sequence of the LLO protein utilized to construct vaccines of the present invention is, in another embodiment:

MKKIMLVFITLILVSLPIAQQTEAKDASAFNKENSISSMAPPASPPASPKTPIEKKHADEIDK YIQGLDYNKNNVLVYHGDAVTNVPPRKGYKDGNEYIVVEKKKKSINQNNADIQVVNAIS SLTYPGALVKANSELVENQPDVLPVKRDSLTLSIDLPGMTNQDNKIVVKNATKSNVNNA VNTLVERWNEKYAQAYPNVSAKIDYDDEMAYSESQLIAKFGTAFKAVNNSLNVNFGAIS EGKMQEEVISFKQIYYNVNVNEPTRPSRFFGKAVTKEQLQALGVNAENPPAYISSVAYGR QVYLKLSTNSHSTKVKAAFDAAVSGKSVSGDVELTNIIKNSSFKAVIYGGSAKDEVQIIDG NLGDLRDILKKGATFNRETPGVPIAYTTNFLKDNELAVIKNNSEYIETTSKAYTDGKINIDH SGGYVAQFNISWDEVNYDPEGNEIVQHKNWSENNKSKLAHFTSSIYLPGNARNINVYAKE CTGLAWEWWRTVIDDRNLPLVKNRNISIWGTTLYPKYSNKVDNPIE (GenBank Accession No. P13128; SEQ ID NO: 17; nucleic acid sequence is set forth in GenBank Accession No. X15127). The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein is a homologue of SEQ ID No: 17. In another embodiment, the LLO protein is a variant of SEQ ID No: 17. In another embodiment, the LLO protein is an isomer of SEQ ID No: 17. In another embodiment, the LLO protein is a fragment of SEQ ID No: 17. Each possibility represents a separate embodiment of the present invention.

In another embodiment, "LLO peptide" and "LLO fragment" refer to an N-terminal fragment of an LLO protein. In another embodiment, the terms refer to a full-length but non-hemolytic LLO protein. In another embodiment, the terms refer to a non-hemolytic protein containing a point mutation in cysteine 484 of sequence ID No: 17 or a corresponding residue thereof in a homologous LLO protein. Each possibility represents a separate embodiment of the present invention.

In another embodiment, the N-terminal fragment of an LLO protein utilized in compositions and methods of the present invention has the sequence:

MKKIMLVFITLILVSLPIAQQTEAKDASAFNKENSISSVAPPASPPASPKTPIEKKHADEIDK YIQGLDYNKNNVLVYHGDAVTNVPPRKGYKDGNEYIVVEKKKKSINQNNADIQVVNAIS SLTYPGALVKANSELVENQPDVLPVKRDSLTLSIDLPGMTNQDNKIVVKNATKSNVNNA VNTLVERWNEKYAQAYSNVSAKIDYDDEMAYSESQLIAKFGTAFKAVNNSLNVNFGAIS EGKMQEEVISFKQIYYNVNVNEPTRPSRFFGKAVTKEQLQALGVNAENPPAYISSVAYGR QVYLKLSTNSHSTKVKAAFDAAVSGKSVSGDVELTNIIKNSSFKAVIYGGSAKDEVQIIDG NLGDLRDILKKGATFNRETPGVPIAYTTNFLKDNELAVIKNNSEYIETTSKAYTDGKINIDH SGGYVAQFNISWDEVNYD (SEQ ID NO: 18). In another embodiment, the LLO fragment is a homologue of SEQ ID No: 18. In another embodiment, the LLO fragment is a variant of SEQ ID No: 18. In another embodiment, the LLO fragment is an isomer of SEQ ID No: 18. In another embodiment, the LLO fragment is a fragment of SEQ ID No: 18. Each possibility represents a separate embodiment of the present invention.

In another embodiment, the LLO fragment has the sequence:

MKKIMLVFITLILVSLPIAQQTEAKDASAFNKENSISSVAPPASPPASPKTPIEKKHADEIDK YIQGLDYNKNNVLVYHGDAVTNVPPRKGYKDGNEYIVVEKKKKSINQNNADIQVVNAIS SLTYPGALVKANSELVENQPDVLPVKRDSLTLSIDLPGMTNQDNKIVVKNATKSNVNNA VNTLVERWNEKYAQAYSNVSAKIDYDDEMAYSESQLIAKFGTAFKAVNNSLNVNFGAIS EGKMQEEVISFKQIYYNVNVNEPTRPSRFFGKAVTKEQLQALGVNAENPPAYISSVAYGR QVYLKLSTNSHSTKVKAAFDAAVSGKSVSGDVELTNIIKNSSFKAVIYGGSAKDEVQIIDG NLGDLRDILKKGATFNRETPGVPIAYTTNFLKDNELAVIKNNSEYIETTSKAYTD (SEQ ID NO: 19). In another embodiment, the LLO fragment is a homologue of SEQ ID No: 19. In another embodiment, the LLO fragment is a variant of SEQ ID No: 19. In another embodiment, the LLO fragment is an isomer of SEQ ID No: 19. In another embodiment, the LLO fragment is a fragment of SEQ ID No: 19. Each possibility represents a separate embodiment of the present invention.

In another embodiment, the LLO fragment is any other LLO fragment known in the art. Each possibility represents a separate embodiment of the present invention.

"ActA peptide" refers, in another embodiment, to a full-length ActA protein. In another embodiment, the term refers to an ActA fragment. Each possibility represents a separate embodiment of the present invention.

The ActA fragment of methods and compositions of the present invention is, in another embodiment, an N-terminal ActA fragment. In another embodiment, the fragment is any other type of ActA fragment known in the art. Each possibility represents a separate embodiment of the present invention.

In another embodiment, the N-terminal fragment of an ActA protein has the sequence: MRAMMVVFITANCITINPDIIFAATDSEDSSLNTDEWEEEKTEEQPSEVNTGPRYETAREV SSRDIKELEKSNKVRNTNKADLIAMLKEKAEKGPNINNNNSEQTENAAINEEASGADRPAI QVERRHPGLPSDSAAEIKKRRKAIASSDSELESLTYPDKPTKVNKKKVAKESVADASESDL DSSMQSADESSPQPLKANQQPFFPKVFKKIKDAGKWVRDKIDENPEVKKAIVDKSAGLID QLLTKKKSEEVNASDFPPPPTDEELRLALPETPMLLGFNAPATSEPSSFEFPPPPTDEELRLA LPETPMLLGFNAPATSEPSSFEFPPPPTEDELEIIR ETASSLDSSF- TRGDLASLRNAINRHSQN FSDFPPIPTEEELNGRGGRP (SEQ ID No: 15). In another embodiment, the ActA fragment comprises SEQ ID No: 15. In another embodiment, the ActA fragment is a homologue of SEQ ID No: 15. In another embodiment, the ActA fragment is a variant of SEQ ID No: 15. In another embodiment, the ActA fragment is an isomer of SEQ ID No: 15. In another embodiment, the ActA fragment is a fragment of SEQ ID No: 15. Each possibility represents a separate embodiment of the present invention.

In another embodiment, the N-terminal fragment of an ActA protein has the sequence: MRAMMVVFITANCITINPDIIFAATDSEDSSLNTDEWEEEKTEEQPSEVNTGPRYETAREV SSRDIKELEKSNKVRNTNKADLIAMLKEKAEKGPNINNN (SEQ ID No: 14). In another embodiment, the ActA fragment is a homologue of SEQ ID No: 14. In another embodiment, the ActA fragment is a variant of SEQ ID No: 14. In another embodiment, the ActA fragment is an isomer of SEQ ID No: 14. Each possibility represents a separate embodiment of the present invention.

In another embodiment, the ActA fragment of methods and compositions of the present invention comprises a PEST-like sequence. In another embodiment, the PEST-like sequence contained in the ActA fragment is selected from SEQ ID No: 2-5. In another embodiment, the ActA fragment comprises at least 2 of the PEST-like sequences set forth in SEQ ID No: 2-5. In another embodiment, the ActA fragment comprises at least 3 of the PEST-like sequences set forth in SEQ ID No: 2-5. In another embodiment, the ActA fragment comprises the 4 PEST-like sequences set forth in SEQ ID No: 2-5. Each possibility represents a separate embodiment of the present invention.

In another embodiment, the N-terminal ActA fragment is encoded by a nucleotide molecule having the sequence SEQ ID NO: 16:

atgcgtgcgatgatggtggttttcattactgccaattgcattacgattaaccc cgacataatatttgcagcgacagatagcgaagattct agtctaaacacagatgaatgggaagaagaaaaacagaagagcaaccaa cgaggtaaatacgggaccaagatacgaaactgcacgtga agtaagttcacgtgatattaaagaactagaaaaatcgaataaagtgagaaata cgaacaaagcagacctaatagcaatgttgaaagaaaaagc agaaaaaggtccaaatatcaataataacaacagtgaacaaactgagaatgegg ctataaatgaagaggcncaggagccgaccgaccagct atacaagtggagcgtcgtcatccaggattgccatcggatagcgcagcggaaa ttaaaaaaagaaggaaagccatagcatcatcggatagtga gettgaaagccttacttatccggataaaccaacaaaagtaaataagaaaaaa gtggcgaaagagtcagagcggatgcnctgaaagtgactta ganctagcatgcagtcagcagatgagtcncaccacaaccataaaagcaaac caacaaccatattccctaaagtatttaaaaaaataaaagat gcggggaaatgggtacgtgataaaatcgacgaaaatcctgaagtaaagaaagc gattgttgataaaagtgcagggttaattgaccaattattaa ccaaaaagaaaagtgaagaggtaaatgcncggacacccgccaccacct acggatgaagagnaagacttgctagccagagacaccaatg Menggttttaatgctcctgctacatcagaaccgagctcattcgaatttccacca ccacctacggatgaagagnaagacttgattgccagaga cgccaatgatcaggattaatgctcctgctacatcggaaccgagctcgacgaata ccaccgcctccaacagaagatgaactagaaatcatcc gggaaacagcatcctcgctagattctagttttacaagaggggatttagctag tttgagaaatgctattaatcgccatagtcaaaatttctctgatttc ccaccaatcccaacagaagaagagttgaacgggagaggcggtagacca (SEQ No: 16). In another embodiment, the ActA fragment is encoded by a nucleotide molecule that comprises SEQ ID No: 16. In another embodiment, the ActA fragment is encoded by a nucleotide molecule that is a homologue of SEQ ID No: 16. In another embodiment, the ActA fragment is encoded by a nucleotide molecule that is a variant of SEQ ID No: 16. In another embodiment, the ActA fragment is encoded by a nucleotide molecule that is an isomer of SEQ ID No: 16. In another embodiment, the ActA fragment is encoded by a nucleotide molecule that is a fragment of SEQ ID No: 16. Each possibility represents a separate embodiment of the present invention.

In another embodiment, a recombinant nucleotide of the present invention comprises any other sequence that encodes a fragment of an ActA protein. Each possibility represents a separate embodiment of the present invention.

In another embodiment, the ActA fragment is any other ActA fragment known in the art. Each possibility represents a separate embodiment of the present invention.

In another embodiment of methods and compositions of the present invention, a PEST-like AA sequence is fused to the KLK3 peptide or FOLH1 peptide. In another embodiment, the PEST-like AA sequence has a sequence selected from SEQ ID NO: 2-7 and 20. In another embodiment, the PEST-like sequence is any other PEST-like sequence known in the art. Each possibility represents a separate embodiment of the present invention.

In another embodiment, the PEST-like AA sequence is KENSISSMAPPASPPASPKTPIEKKHADEIDK (SEQ ID NO: 1). In another embodiment, the PEST-like sequence is KENSISSMAPPASPPASPK (SEQ ID No: 21). In another embodiment, fusion of a KLK3 peptide or FOLH1 peptide to any LLO sequence that includes the 1 of the PEST-like AA sequences enumerated herein is efficacious for enhancing cell-mediated immunity against KLK3 or FOLH1.

The present invention also provides methods for enhancing cell mediated and anti-tumor immunity and compositions with enhanced immunogenicity which comprise a PEST-like amino acid sequence derived from a prokaryotic organism fused to a KLK3 or FOLH1 antigen. In another embodiment, the PEST-like sequence is embedded within an antigen. In another embodiment, the PEST-like sequence is fused to either the amino terminus of the antigen. In another embodiment, the PEST-like sequence is fused to the carboxy terminus. As demonstrated herein, fusion of an antigen to the PEST-like sequence of LM enhanced cell mediated and anti-tumor immunity of the antigen. Thus, fusion of an antigen to other PEST-like sequences derived from other prokaryotic organisms will also enhance immunogenicity of KLK3 or FOLH1. PEST-like sequence of other prokaryotic organism can be identified routinely in accordance with methods such as described by, for example Rechsteiner and Rogers (1996, Trends Biochem. Sci. 21:267-271) for LM. In another embodiment, PEST-like AA sequences from other prokaryotic organisms are identified based by this method. In another embodiment, the PEST-like AA sequence is from another *Listeria* species. For example, the LM protein ActA contains 4 such sequences.

In another embodiment, the PEST-like AA sequence is a PEST-like sequence from a *Listeria* ActA protein. In another embodiment, the PEST-like sequence is KTEEQPSEVNTGPR (SEQ ID NO: 2), KASVTDTSEGDLDSSMQSADESTPQPLK (SEQ ID NO: 3), KNEEVNASDFPPPPTDEELR (SEQ ID NO: 4), or RGGIPTSEEFSSLNSGDFTDDENSETTEEEIDR (SEQ ID NO: 5). In another embodiment, the PEST-like sequence is from *Listeria seeligeri* cytolysin, encoded by the lso gene. In another embodiment, the PEST-like sequence is RSEVTISPAETPESPPATP (SEQ ID NO: 20). In another embodiment, the PEST-like sequence is from Streptolysin O protein of *Streptococcus* sp. In another embodiment, the PEST-like sequence is from *Streptococcus pyogenes* Streptolysin 0, e.g. KQNTASTETTTTNEQPK (SEQ ID NO: 6) at AA 35-51. In another embodiment, the PEST-like sequence is from *Streptococcus equisimilis* Streptolysin 0, e.g. KQNTANTETTTTNEQPK (SEQ ID NO: 7) at AA 38-54. In another embodiment, the PEST-like sequence has a sequence selected from SEQ ID NO: 1-7 and 20-21. In another embodiment, the PEST-like sequence has a sequence selected from SEQ ID NO: 2-7 and 20. In another embodiment, the PEST-like sequence is another PEST-like AA sequence derived from a prokaryotic organism.

PEST-like sequences of other prokaryotic organism are identified, in another embodiment, in accordance with methods such as described by, for example Rechsteiner and Rogers (1996, Trends Biochem. Sci. 21:267-271) for LM. Alternatively, PEST-like AA sequences from other prokaryotic organisms can also be identified based by this method. Other prokaryotic organisms wherein PEST-like AA sequences would be expected to include, but are not limited to, other *Listeria* species. In another embodiment, the PEST-like sequence is embedded within the antigenic protein. Thus, in another embodiment, "fusion" refers to an antigenic protein comprising a KLK3 peptide and a PEST-like amino acid sequence linked at one end of the KLK3 peptide. In another embodiment, the term refers to an antigenic protein comprising an FOLH1 peptide and a PEST-like amino acid sequence linked at one end of the FOLH1 peptide. In another embodiment, the term refers to an antigenic protein comprising PEST-like amino acid sequence embedded within the KLK3 peptide. In another embodiment, the term refers to an antigenic protein comprising PEST-like amino acid sequence embedded within the FOLH1 peptide. Each possibility represents a separate embodiment of the present invention.

In another embodiment, the PEST-like sequence is identified using the PEST-find program. In another embodiment, a PEST-like sequence is defined as a hydrophilic stretch of at least 12 AA in length with a high local concentration of proline (P), aspartate (D), glutamate (E), serine (S), and/or threonine (T) residues. In another embodiment, a PEST-like sequence contains no positively charged AA, namely arginine (R), histidine (H) and lysine (K).

In another embodiment, identification of PEST motifs is achieved by an initial scan for positively charged AA R, H, and K within the specified protein sequence. All AA between the positively charged flanks are counted and only those motifs are considered further, which contain a number of AA equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical AA as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Dootlittle, RF. J. Mol. Biol. 157, 105 (1982). For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine.

Hydropathy index=10*Kyte-Doolittle hydropathy index+45

In another embodiment, a potential PEST motif's hydrophobicity is calculated as the sum over the products of mole percent and hydrophobicity index for each AA species. The desired PEST score is obtained as combination of local enrichment term and hydrophobicity term as expressed by the following equation:

PEST score=0.55*DEPST−0.5*hydrophobicity index.

In another embodiment, "PEST-like sequence," "PEST-like sequence peptide," or "PEST-like sequence-containing peptide" refers to a peptide having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST-like sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each stretch of appropriate length (e.g. a 30-35 AA stretch) by assigning a value of 1 to the AA Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, "PEST-like sequence peptide" or "PEST-like sequence-containing peptide" refers to a peptide containing a PEST-like sequence, as defined hereinabove.

"Fusion to a PEST-like sequence" refers, in another embodiment, to fusion to a protein fragment comprising a PEST-like sequence. In another embodiment, the term includes cases wherein the protein fragment comprises surrounding sequence other than the PEST-like sequence. In another embodiment, the protein fragment consists of the PEST-like sequence. Each possibility represents a separate embodiment of the present invention.

As provided herein, recombinant *Listeria* strains expressing PEST-like sequence-antigen fusions induce anti-tumor immunity (Example 5) and generate antigen-specific, tumor-infiltrating T cells (Example 6).

In another embodiment, "homology" refers to identity greater than 70% to a KLK3 sequence set forth in a sequence selected from SEQ ID No: 25-40. In another embodiment, "homology" refers to identity to one of SEQ ID No: 25-40 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

In another embodiment, "homology" refers to identity greater than 70% to an FOLH1 sequence set forth in a sequence selected from SEQ ID No: 41-45. In another embodiment, "homology" refers to identity to one of SEQ ID No: 41-45 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

In another embodiment, "homology" refers to identity greater than 70% to an LLO sequence set forth in a sequence selected from SEQ ID No: 17-19. In another embodiment, "homology" refers to identity to one of SEQ ID No: 17-19 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

In another embodiment, "homology" refers to identity greater than 70% to an ActA sequence set forth in a sequence selected from SEQ ID No: 14-16. In another embodiment, "homology" refers to identity to one of SEQ ID No: 14-16 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

In another embodiment, "homology" refers to identity greater than 70% to a PEST-like sequence set forth in a sequence selected from SEQ ID No: 1-7 and 20-21. In another embodiment, "homology" refers to identity to one of SEQ ID No: 1-7 and 20-21 of greater than 72%. In another embodiment, the homology is greater than 75%. In another embodiment, "homology" refers to identity to a sequence of greater than 78%. In another embodiment, the homology is greater than 80%. In another embodiment, the homology is greater than 82%. In another embodiment, "homology" refers to identity to a sequence of greater than 83%. In another embodiment, the homology is greater than 85%. In another embodiment, the homology is greater than 87%. In another embodiment, "homology" refers to identity to a sequence of greater than 88%. In another embodiment, the homology is greater than 90%. In another embodiment, the homology is greater than 92%. In another embodiment, "homology" refers to identity to a sequence of greater than 93%. In another embodiment, the homology is greater than 95%. In another embodiment, "homology" refers to identity to a sequence of greater than 96%. In another embodiment, the homology is greater than 97%. In another embodiment, the homology is greater than 98%. In another embodiment, the homology is greater than 99%. Each possibility represents a separate embodiment of the present invention.

Methods of identifying corresponding sequences in related proteins are well known in the art, and include, for example, AA sequence alignment. Each method represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

In another embodiment, the ActA or LLO fragment is attached to the KLK3 or FOLH1 peptide by chemical conjugation. In another embodiment, paraformaldehyde is used for the conjugation. In another embodiment, the conjugation is performed using any suitable method known in the art. Each possibility represents another embodiment of the present invention.

In another embodiment, the KLK3 expressing tumor targeted by methods and compositions of the present invention is a KLK3-expressing prostate cancer. In another embodiment, the KLK3-expressing tumor is a KLK3-expressing prostate carcinoma. In another embodiment, the KLK3-expressing tumor is a KLK3-expressing adenocarcinoma. Each possibility represents a separate embodiment of the present invention.

In another embodiment, the FOLH1-expressing tumor targeted by methods and compositions of the present invention is an FOLH1-expressing prostate cancer. In another embodiment, the FOLH1-expressing tumor is an FOLH1-expressing prostate carcinoma. In another embodiment, the FOLH1-expressing tumor is an FOLH1-expressing adenocarcinoma. Each possibility represents a separate embodiment of the present invention.

In another embodiment, the KLK3- or FOLH1-expressing tumor is a breast cancer. In another embodiment, the cancer is a melanoma. In another embodiment, the cancer is a glioma tumor. In another embodiment, the cancer is an ovarian neoplasm. In another embodiment, the cancer is a mammary carcinoma. In another embodiment, the cancer is an ependymoma.

In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is mesothelioma. In another embodiment, the cancer is a glioma. In another embodiment, the cancer is a germ cell tumor. In another embodiment, the cancer is a choriocarcinoma. Each possibility represents a separate embodiment of the present invention.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma. Each possibility represents a separate embodiment of the present invention.

In another embodiment, the cancer is any other KLK3 or FOLH1-expressing cancer known in the art. Each type of cancer represents a separate embodiment of the present invention.

As provided herein, enhanced cell mediated immunity was demonstrated for fusion proteins comprising an antigen and truncated LLO containing the PEST-like amino acid sequence, SEQ ID NO: 1. The ΔLLO used in some of the Examples was 416 amino acids long (following cleavage of the signal peptide), as 88 residues from the carboxy terminus which is inclusive of the activation domain containing cysteine 484 were truncated. However, it is apparent from the present disclosure that other ΔLLO without the activation domain, and in particular cysteine 484, are efficacious in methods of the present invention. In another embodiment fusion of KLK3 or FOLH1 to any non-hemolytic LLO protein or fragment thereof, ActA protein or fragment thereof, or PEST-like amino AA enhances cell-mediated and anti-tumor immunity of the resulting vaccine.

As provided herein, fusion of an antigen to a non-hemolytic truncated form of listeriolysin O (LLO) enhanced immunogenicity. An LM vector that expresses and secretes a fusion product of Human Papilloma Virus (HPV) strain 16 E7 and LLO was a more potent cancer immunotherapeutic for HPV-immortalized tumors than LM secreting the E7 protein alone. Further, a recombinant vaccinia virus that carries the gene for the fusion protein LLO-E7 is a more potent cancer immunotherapeutic for HPV-immortalized tumors than an isogenic strain of vaccinia that carries the gene for E7 protein alone. In comparison, a short fusion protein Lm-AZ/-E7 comprising the E7 antigen fused to the promoter, signal sequence and the first 7 AA residues of LLO was an ineffective anti-tumor immunotherapeutic. This short fusion protein terminates directly before the PEST-like sequence and does not contain it.

"Fusion protein" refers, in another embodiment, to a protein comprising 2 or more proteins linked together by peptide bonds or other chemical bonds. In another embodiment, the proteins are linked together directly by a peptide or other chemical bond. In another embodiment, the proteins are linked together with one or more amino acids (e.g. a "spacer") between the two or more proteins. Each possibility represents a separate embodiment of the present invention.

Fusion proteins comprising a KLK3 or FOLH1 peptide are, in another embodiment, prepared by any suitable method. In another embodiment, a fusion protein is prepared by cloning and restriction of appropriate sequences or direct chemical synthesis by methods discussed below. In another embodiment, subsequences are cloned and the appropriate subsequences cleaved using appropriate restriction enzymes. The fragments are then ligated, in another embodiment, to produce the desired DNA sequence. In another embodiment, DNA encoding the KLK3 or FOLH1 peptide is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the 2 fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The KLK3 or FOLH1 peptide-encoding gene is then ligated into a plasmid.

In another embodiment, the KLK3 or FOLH1 peptide is conjugated to the truncated ActA protein, truncated LLO protein, or PEST-like sequence by any of a number of means well known to those of skill in the art. In another embodiment, the KLK3 or FOLH1 peptide is conjugated, either directly or through a linker (spacer), to the ActA protein or LLO protein. In another embodiment, wherein both the KLK3 or FOLH1 peptide and the ActA protein or LLO protein are polypeptides, the chimeric molecule is recombinantly expressed as a single-chain fusion protein.

In another embodiment, wherein the KLK3 or FOLH1 peptide and/or the ActA protein, LLO protein, or PEST-like sequence is relatively short (i.e., less than about 50 AA), they are synthesized using standard chemical peptide synthesis techniques. Where both molecules are relatively short, in another embodiment, the chimeric molecule is synthesized as a single contiguous polypeptide. In another embodiment, the KLK3 or FOLH1 peptide and the ActA protein, LLO protein, or PEST-like sequence are synthesized separately and then fused by condensation of the amino terminus of one molecule with the carboxyl terminus of the other molecule thereby forming a peptide bond. In another embodiment, the KLK3 or FOLH1 peptide and the ActA protein, LLO protein, or PEST-like sequence are each condensed with one end of a peptide spacer molecule, thereby forming a contiguous fusion protein.

In another embodiment, the peptides and proteins of the present invention are readily prepared by standard, well-established solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin coupled peptide can be treated with 20% acetic anhydride in acetonitrile. The N-blocked peptide product can then be cleaved from the resin, deprotected and subsequently isolated.

In another embodiment, to ensure that the peptide obtained from either chemical or biological synthetic techniques is the desired peptide, analysis of the peptide composition is conducted. In another embodiment, amino acid composition analysis is conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

In another embodiment, prior to its use, the peptide is purified to remove contaminants. In this regard, it will be appreciated that the peptide will be purified so as to meet the standards set out by the appropriate regulatory agencies and guidelines. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Solid phase synthesis in which the C-terminal AA of the sequence is attached to an insoluble support followed by sequential addition of the remaining amino acids in the sequence is used, in another embodiment, for the chemical synthesis of the polypeptides of this invention. Techniques for solid phase synthesis are described by Barany and Merrifield in Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

In another embodiment, peptides of the present invention can incorporate AA residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

In another embodiment, blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkyl amino groups such as methyl amino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

In another embodiment, other modifications are incorporated without adversely affecting the activity. In another embodiment, such modifications include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

In another embodiment, acid addition salts peptides of the present invention are utilized as functional equivalents thereof. In another embodiment, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

In another embodiment, modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

In another embodiment polypeptides are modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In another embodiment, the chimeric fusion proteins of the present invention are synthesized using recombinant DNA methodology. Generally this involves creating a DNA sequence that encodes the fusion protein, placing the DNA in an expression cassette, such as the plasmid of the present invention, under the control of a particular promoter/regulatory element, and expressing the protein.

DNA encoding a fusion protein of the present invention are prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

Chemical synthesis produces a single stranded oligonucleotide. This is converted, in another embodiment, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences may be obtained by the ligation of shorter sequences.

In another embodiment, "isolated nucleic acid" includes an RNA or a DNA sequence encoding a fusion protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Such modifications are detailed elsewhere herein. Any and all combinations of modifications of the nucleotide sequences are contemplated in the present invention.

In another embodiment, the present invention provides an isolated nucleic acid encoding a KLK3 or FOLH1 peptide operably linked to a non-hemolytic LLO, truncated ActA protein, or PEST-like sequence, wherein the isolated nucleic acid further comprises a promoter/regulatory sequence, such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, a nucleotide of the present invention is operably linked to a promoter/regulatory sequence that drives expression of the encoded peptide in the *Listeria* strain. Promoter/regulatory sequences useful for driving constitutive expression of a gene are well known in the art and include, but are not limited to, for example, the $P_{hlyA}$, $P_{ActA}$, and p60 promoters of *Listeria*, the *Streptococcus* bac promoter, the *Streptomyces griseus* sgiA promoter, and the *B. thuringiensis* phaZ promoter. Thus, it will be appreciated that the invention includes the use of any promoter/regulatory sequence that is capable of driving expression of the desired protein operably linked thereto.

Expressing a KLK3 or FOLH1 peptide operably linked to a non-hemolytic LLO, truncated ActA protein, or PEST-like sequence using a vector allows the isolation of large amounts of recombinantly produced protein. It is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides a vector comprising an isolated nucleic acid encoding a KLK3 or FOLH1 peptide operably linked to a non-hemolytic LLO, truncated ActA protein, or PEST-like sequence. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the present invention provides cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the nucleic acids encoding a KLK3 or FOLH1 peptide operably linked to a non-hemolytic LLO, truncated ActA protein, or PEST-like sequence are cloned into a plasmid vector. In another embodiment, a recombinant *Listeria* strain is transformed with the plasmid vector. Each possibility represents a separate embodiment of the present invention.

Once armed with the present invention, it is readily apparent to one skilled in the art that other nucleic acids encoding a KLK3 or FOLH1 peptide operably linked to a non-hemolytic LLO, truncated ActA protein, or PEST-like sequence can be obtained by following the procedures described herein in the experimental details section for the generation of other fusion proteins as disclosed herein (e.g., site-directed mutagenesis, frame shift mutations, and the like), and procedures in the art.

Methods for the generation of derivative or variant forms of fusion proteins are well known in the art, and include, inter alia, using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York), and elsewhere herein.

In another embodiment, the present invention provides a nucleic acid encoding a KLK3 or FOLH1 peptide operably linked to a non-hemolytic LLO, truncated ActA protein, or PEST-like sequence, wherein a nucleic acid encoding a tag polypeptide is covalently linked thereto. That is, the invention encompasses a chimeric nucleic acid wherein the nucleic acid sequence encoding a tag polypeptide is covalently linked to the nucleic acid encoding a KLK3 or FOLH1 peptide-containing protein. Such tag polypeptides are well known in the art and include, for instance, green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The present invention also provides for analogs of ActA, LLO, and PEST-like sequences of the present invention, fragments thereof, proteins, or peptides. Analogs differ, in another embodiment, from naturally occurring proteins or peptides by conservative amino acid sequence differences, by modifications which do not affect sequence, or by both.

In another embodiment, the present invention provides a KLK3 peptide with enhanced immunogenicity. In another embodiment, the present invention provides an FOLH1 peptide with enhanced immunogenicity. That is, as the data disclosed herein demonstrate, a KLK3 or FOLH1 peptide fused to a truncated ActA protein, non-hemolytic LLO protein, or PEST-like sequence, when administered to an animal, results in a clearance of existing tumors and the induction of antigen-specific cytotoxic lymphocytes capable of infiltrating tumor or infected cells. When armed with the present disclosure, and the methods and compositions disclosed herein, the skilled artisan will readily realize that the present invention in amenable to treatment and/or prevention of a multitude of diseases.

In another embodiment, a commercially available plasmid is used in the present invention. Such plasmids are available from a variety of sources, for example, Invitrogen (Carlsbad, Calif.), Stratagene (La Jolla, Calif.), Clontech (Palo Alto, Calif.), or can be constructed using methods well known in the art. A commercially available plasmid such as pCR2.1 (Invitrogen, Carlsbad, Calif.), which is a prokaryotic expression vector with a prokaryotic origin of replication and promoter/regulatory elements to facilitate expression in a prokaryotic organism.

The present invention further comprises transforming such a *Listeria* strain with a plasmid comprising (a) a KLK3 or FOLH1 peptide; and (b) an isolated nucleic acid encoding a truncated ActA protein, truncated LLO protein, or PEST-like sequence. In another embodiment, if an LM vaccine strain comprises a deletion in the prfA gene or the actA gene, the plasmid comprises a prfA or actA gene in order to complement the mutation, thereby restoring function to the *L. monocytogenes* vaccine strain. As described elsewhere herein, methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.).

The plasmid of the present invention comprises, in another embodiment, a promoter/regulatory sequence operably linked to a gene encoding a fusion protein.

Plasmids and other expression vectors useful in the present invention are described elsewhere herein, and can include such features as a promoter/regulatory sequence, an origin of replication for gram negative and/or gram positive bacteria, and an isolated nucleic acid encoding a fusion protein. Further, the isolated nucleic acid encoding a fusion protein will have its own promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of bacteriophage lambda ($P_L$ and $P_R$), the trp, recA, lacZ, lacd, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter (GenBank Acc. No. Y07639), the Listerial hly promoter (GenBank Acc. No. X15127), and the Listerial p60 promoter (GenBank Acc. No. AY126342), or fragments thereof.

In another embodiment, a *Listeria* strain of methods and compositions of the present invention contains an integrated gene encoding a peptide that comprises a KLK3 peptide. In another embodiment, the *Listeria* strain contains an integrated gene encoding a peptide that comprises a FOLH1 peptide.

In another embodiment, a *Listeria* strain of methods and compositions of the present invention is created using a site-specific integration vector. In another embodiment, a *Listeria* strain containing an integrated gene is created using homologous recombination. In another embodiment, a *Listeria* strain containing an integrated gene is created using any other method known in the art of integrating a gene into the *Listeria* chromosome. Each possibility represents a separate embodiment of the present invention.

In another embodiment, the integration vector comprises a PSA attPP' site. In another embodiment, the integration vector comprises a gene encoding a PSA integrase. In another embodiment, the integration vector comprises a U153 attPP' site. In another embodiment, the integration vector comprises a gene encoding a U153 integrase. In another embodiment, the integration vector comprises an A118 attPP' site. In another embodiment, the integration vector comprises a gene encoding an A118 integrase. In another embodiment, the integration vector comprises any other attPP' site known in the art. In another embodiment, the integration vector comprises any other phage integrase known in the art. Each possibility represents a separate embodiment of the present invention.

In another embodiment, a *Listeria* strain of methods and compositions of the present invention contains a mutation or auxotrophy in a metabolic gene. In another embodiment, a plasmid carrying a KLK3 peptide or FOLH1 peptide contains a metabolic gene that complements the mutation or auxotrophy. In another embodiment, a KLK3 peptide- or FOLH1 peptide-encoding integration vector or construct used for integration into the *Listeria* chromosome contains a gene that complements the mutation or auxotrophy. In another embodiment, the metabolic gene is used for selection instead of an antibiotic resistance gene. In another embodiment, the metabolic gene is used for selection in addition to an antibiotic resistance gene. Each possibility represents a separate embodiment of the present invention.

In another embodiment, the metabolic gene is a gene encoding an amino acid metabolism enzyme. In another embodiment, the metabolic enzyme is an alanine racemase (dal) enzyme. In another embodiment, the metabolic enzyme is D-amino acid transferase enzyme (dat).

In another embodiment, the metabolic enzyme metabolizes an amino acid (AA) that is used for a bacterial growth process. In another embodiment, the product AA is used for a replication process. In another embodiment, the product AA is used for cell wall synthesis. In another embodiment, the product AA is used for protein synthesis. In another embodiment, the product AA is used for metabolism of a fatty acid. In another embodiment, the product AA is used for any other growth or replication process known in the art. Each possibility represents a separate embodiment of the present invention.

In another embodiment, the metabolic enzyme catalyzes the formation of an AA used in cell wall synthesis. In another embodiment, the metabolic enzyme catalyzes synthesis of an AA used in cell wall synthesis. In another embodiment, the metabolic enzyme is involved in synthesis of an AA used in cell wall synthesis. In another embodiment, the AA is used in cell wall biogenesis. Each possibility represents a separate embodiment of the present invention.

In another embodiment, the metabolic enzyme is a synthetic enzyme for D-glutamic acid, a cell wall component.

In another embodiment, the metabolic enzyme is encoded by an alanine racemase gene (dal) gene. D-glutamic acid synthesis is controlled in part by the dal gene, which is involved in the conversion of D-glu+pyr to alpha-ketoglutarate+D-ala, and the reverse reaction.

In another embodiment, the dal protein of methods and compositions of the present invention has the sequence:

MVTGWHRPTWIEIDRAAIRENIKNEQNKLPES-VDLWAVVKANAYGHGIIEVARTAKE AGAKG-FCVAILDEALALREAGFQDDFILVLGATRKEDAN-LAAKNHISLTVFREDWLENLTLE ATLRIHLKVDSGMGRLGIRTTEEARRIEATSTND HQLQLEGIYTHFATADQLETSYFEQQLAKF QTILT-SLKKRPTYVHTANSAASLLQPQIGFDAIRF GISMYGLTPSTEIKTSLPFELKPALALYTE MVHVKELAPGDSVSYGATYTATEREWVATLPIG-YADGLIRHYSGFHVLVDGEPAPIIGRVCM DQTIIKL-PREFQTGSKVTIIGKDHGNTVTADDAAQYLDTI-NYEVTCLLNERIPRKYIH (SEQ ID No: 56; GenBank Accession No: AF038438). In another embodiment, the dal protein is homologous to SEQ ID No: 56. In another embodiment, the dal protein is a variant of SEQ ID No: 56. In another embodiment, the dal protein is an isomer of SEQ ID No: 56. In another embodiment, the dal protein is a fragment of SEQ ID No: 56. In another embodiment, the dal protein is a fragment of a homologue of SEQ ID No: 56. In another embodiment, the dal protein is a fragment of a variant of SEQ ID No: 56. In another embodiment, the dal protein is a fragment of an isomer of SEQ ID No: 56.

In another embodiment, the dal protein any other *Listeria* dal protein known in the art. In another embodiment, the dal protein is any other gram-positive dal protein known in the art. In another embodiment, the dal protein any other dal protein known in the art. Each possibility represents a separate embodiment of the present invention.

The dat protein of methods and compositions of the present invention is encoded, in another embodiment, by the sequence:

MKVLVNNHLVEREDATVDIEDRGYQFGDGVYEV-VRLYNGKFFTYNEHIDRLYASAA KIDLVIPYSKEEL-RELLEKLVAENNINTGNVYLQVTRGVQNPRN-HVIPDDFPLEGVLTAAARE VPRNERQFVEGGTAITEEDVRWLRCDIKSLNLLG-NILAKNKAHQQNALEAILHRGEQVTECSA SNVSIIKDGVLWTHAADNLILNGITRQVIIDVAKK NGIPVKEADFTLTDLREADEVFISSTTIEIT PITH-IDGVQVADGKRGPITAQLHQYFVEEITRACGELEFAK (SEQ ID No: 57; GenBank Accession No: AF038439). In another embodiment, the dat protein is homologous to SEQ ID No: 57. In another embodiment, the dat protein is a variant of SEQ ID No: 57. In another embodiment, the dat protein is an isomer of SEQ ID No: 57. In another embodiment, the dat protein is a fragment of SEQ ID No: 57. In another embodiment, the dat protein is a fragment of a homologue of SEQ ID No: 57. In another embodiment, the dat protein is a fragment of a variant of SEQ ID No: 57. In another embodiment, the dat protein is a fragment of an isomer of SEQ ID No: 57.

In another embodiment, the dat protein any other *Listeria* dat protein known in the art. In another embodiment, the dat protein is any other gram-positive dat protein known in the art. In another embodiment, the dat protein any other dat protein known in the art. Each possibility represents a separate embodiment of the present invention.

In another embodiment, the metabolic enzyme is a D-glutamic acid synthesis gene. In another embodiment, the metabolic enzyme is encoded by dga. In another embodiment, the metabolic enzyme is encoded by an alr (alanine racemase) gene. In another embodiment, the metabolic enzyme is any other enzyme known in the art that is involved in alanine synthesis.

In another embodiment, the metabolic enzyme is encoded by serC, a phosphoserine aminotransferase. In another embodiment, the metabolic enzyme is encoded by asd (aspartate beta-semialdehyde dehydrogenase), involved in synthesis of the cell wall constituent diaminopimelic acid. In another embodiment, the metabolic enzyme is encoded by gsaB-glutamate-1-semialdehyde aminotransferase, which catalyzes the formation of 5-aminolevulinate from (S)-4-amino-5-oxopentanoate. In another embodiment, the metabolic enzyme is encoded by HemL, which catalyzes the formation of 5-aminolevulinate from (S)-4-amino-5-oxopentanoate. In another embodiment, the metabolic enzyme is encoded by aspB, an aspartate aminotransferase that catalyzes the formation of oxalozcetate and L-glutamate from L-aspartate and 2-oxoglutarate. In another embodiment, the metabolic enzyme is encoded by argF-1, involved in arginine biosynthesis. In another embodiment, the metabolic enzyme is encoded by aroE, involved in amino acid biosynthesis. In another embodiment, the metabolic enzyme is encoded by aroB, involved in 3-dehydroquinate biosynthesis. In another embodiment, the metabolic enzyme is encoded by aroD, involved in amino acid biosynthesis. In another embodiment, the metabolic enzyme is encoded by aroC, involved in amino acid biosynthesis. In another embodiment, the metabolic enzyme is encoded by hisB, involved in histidine biosynthesis. In another embodiment, the metabolic enzyme is encoded by hisD, involved in histidine biosynthesis. In another embodiment, the metabolic enzyme is encoded by hisG, involved in histidine biosynthesis. In another embodiment, the metabolic enzyme is encoded by metX, involved in methionine biosynthesis. In another embodiment, the metabolic enzyme is encoded by proB, involved in proline biosynthesis. In another embodiment, the metabolic enzyme is encoded by argR, involved in arginine biosynthesis. In another embodiment, the metabolic enzyme is encoded by argJ, involved in arginine biosynthesis. In another embodiment, the metabolic enzyme is encoded by thiI, involved in thiamine biosynthesis. In another embodiment, the metabolic enzyme is encoded by LMOf2365_1652, involved in tryptophan biosynthesis. In another embodiment, the metabolic enzyme is encoded by aroA, involved in tryptophan biosynthesis. In another embodiment, the metabolic enzyme is encoded by ilvD, involved in valine and isoleucine biosynthesis. In another embodiment, the metabolic enzyme is encoded by ilvC, involved in valine and isoleucine biosynthesis. In another embodiment, the metabolic enzyme is encoded by leuA, involved in leucine biosynthesis. In another embodiment, the metabolic enzyme is encoded by dapF, involved in lysine biosynthesis. In another embodiment, the metabolic enzyme is encoded by thrB, involved in threonine biosynthesis (all GenBank Accession No. NC_002973).

In another embodiment, the metabolic enzyme is a tRNA synthetase. In another embodiment, the metabolic enzyme is encoded by the trpS gene, encoding tryptophanyltRNA synthetase. In another embodiment, the metabolic enzyme is any other tRNA synthetase known in the art. Each possibility represents a separate embodiment of the present invention.

In another embodiment, the host strain bacteria is Δ(trpS aroA), and both markers are contained in the integration vector.

In another embodiment, the metabolic enzyme is encoded by murE, involved in synthesis of diaminopimelic acid (GenBank Accession No: NC_003485).

In another embodiment, the metabolic enzyme is encoded by LMOf2365_2494, involved in teichoic acid biosynthesis.

In another embodiment, the metabolic enzyme is encoded by WecE (Lipopolysaccharide biosynthesis protein rffA; GenBank Accession No: AE014075.1). In another embodiment, the metabolic enzyme is encoded by amiA, an N-acetylmuramoyl-L-alanine amidase. In another embodiment, the metabolic enzyme is aspartate aminotransferase. In another embodiment, the metabolic enzyme is histidinol-phosphate aminotransferase (GenBank Accession No. NP_466347). In another embodiment, the metabolic enzyme is the cell wall teichoic acid glycosylation protein GtcA.

In another embodiment, the metabolic enzyme is a synthetic enzyme for a peptidoglycan component or precursor. In another embodiment, the component is UDP-N-acetylmuramyl-pentapeptide. In another embodiment, the component is UDP-N-acetylglucosamine. In another embodiment, the component is MurNAc-(pentapeptide)-pyrophosphoryl-undecaprenol. In another embodiment, the component is GlcNAc-β-(1,4)-MurNAc-(pentapeptide)-pyrophosphoryl-undecaprenol. In another embodiment, the component is any other peptidoglycan component or precursor known in the art. Each possibility represents a separate embodiment of the present invention.

In another embodiment, the metabolic enzyme is encoded by murG. In another embodiment, the metabolic enzyme is encoded by murD. In another embodiment, the metabolic enzyme is encoded by murA-1. In another embodiment, the metabolic enzyme is encoded by murA-2 (all set forth in GenBank Accession No. NC_002973). In another embodiment, the metabolic enzyme is any other synthetic enzyme for a peptidoglycan component or precursor. Each possibility represents a separate embodiment of the present invention.

In another embodiment, the metabolic enzyme is a trans-glycosylase. In another embodiment, the metabolic enzyme is trans-peptidase. In another embodiment, the metabolic enzyme is a carboxy-peptidase. In another embodiment, the metabolic enzyme is any other class of metabolic enzyme known in the art. Each possibility represents a separate embodiment of the present invention.

In another embodiment, the metabolic enzyme is any other *Listeria monocytogenes* metabolic enzyme known in the art.

In another embodiment, the metabolic enzyme is any other *Listeria* metabolic enzyme known in the art.

In another embodiment, the metabolic enzyme is any other gram-positive bacteria metabolic enzyme known in the art.

In another embodiment, the metabolic enzyme is any other metabolic enzyme known in the art. Each possibility represents a separate embodiment of the present invention.

In another embodiment, the integration vector is any other site-specific integration vector known in the art that is capable of infecting *Listeria*. Each possibility represents a separate embodiment of the present invention.

In another embodiment, the present invention provides methods for enhancing the immunogenicity of a KLK3 or FOLH1 antigen via fusion of the antigen to a non-hemolytic truncated form of LLO ("ΔLLO"). In another embodiment, the antigen is fused to a PEST-like sequence. In another embodiment, the PEST-like amino acid sequence is SEQ ID NO: 1, of LLO. The present invention further provides methods and compositions for enhancing the immunogenicity of a KLK3 or FOLH1 antigen by fusing the antigen to a truncated ActA protein, truncated LLO protein, or fragment thereof. As demonstrated by the data disclosed herein, an antigen fused to an ActA protein elicits an immune response that clears existing tumors and results in the induction of antigen-specific cytotoxic lymphocytes.

In another embodiment, fusion proteins of the present invention are produced recombinantly via transcription and translation, in a bacterium, of a plasmid or nucleotide molecule that encodes both a KLK3 peptide and a non-KLK3 peptide. In another embodiment, a fusion protein is produced recombinantly via transcription and translation, in a bacterium, of a plasmid or nucleotide molecule that encodes both a FOLH1 peptide and a non-FOLH1 peptide/In another embodiment, the plasmid or nucleotide is transcribed and/or translated in vitro. In another embodiment, the antigen is chemically conjugated to the truncated form of LLO comprising the PEST-like AA sequence of *L. monocytogenes* or a PEST-like AA sequence derived from another prokaryotic organism. "Antigen" refers, in another embodiment, to the native KLK3 or FOLH1 gene product or truncated versions of these that include identified T cell epitopes. In another embodiment, these fusion proteins are then incorporated into vaccines for administration to a subject, to invoke an enhanced immune response against the antigen of the fusion protein. In other embodiments, the fusion proteins of the present invention are delivered as DNA vaccines, RNA vaccines or replicating RNA vaccines. As will be apparent to those of skill in the art upon this disclosure, vaccines comprising the fusion proteins of the present invention are particularly useful in the prevention and treatment of infectious and neoplastic diseases.

The present invention further comprises a method of administering to an animal or human an effective amount of a composition comprising a vaccine of the present invention. The composition comprises, among other things, a pharmaceutically acceptable carrier. In another embodiment, the composition includes a *Listeria* vaccine strain comprising a truncated ActA protein, truncated LLO protein, or fragment thereof, fused to a KLK3 or FOLH1 peptide, and a pharmaceutically acceptable carrier.

In another embodiment, the present invention provides a kit that comprises a composition, including a KLK3 or FOLH1 peptide fused to a truncated LLO protein, truncated ActA protein, or a PEST-like sequence and/or a *Listeria* vaccine strain comprising same, an applicator, and an instructional material which describes use of the compound to perform the methods of the invention. Although model kits are described below, the contents of other useful kits will be apparent to the skilled artisan in light of the present disclosure. Each of these kits is contemplated within the present invention.

In another embodiment, the present invention provides a kit for eliciting an enhanced immune response to an antigen, the kit comprising a KLK3 or FOLH1 peptide fused to a truncated ActA protein, truncated LLO protein, or PEST-like sequence, and a pharmaceutically acceptable carrier, said kit further comprising an applicator, and an instructional material for use thereof.

In another embodiment, the present invention provides a kit for eliciting an enhanced immune response to an antigen. The kit is used in the same manner as the methods disclosed herein for the present invention. In another embodiment, the kit is used to administer a *Listeria* vaccine strain comprising a KLK3 or FOLH1 peptide fused to a truncated ActA protein, LLO protein, or PEST-like sequence. In another embodiment, the kit comprises an applicator and an instructional material for the use of the kit. These instructions simply embody the examples provided herein.

In another embodiment, the invention includes a kit for eliciting an enhanced immune response to an antigen. The kit is used in the same manner as the methods disclosed herein for the present invention. Briefly, the kit may be used to administer an antigen fused to an ActA protein, LLO protein, or PEST-like sequence. Additionally, the kit comprises an applicator and an instructional material for the use of the kit. These instructions simply embody the examples provided herein.

EXPERIMENTAL DETAILS SECTION

Example 1

LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1 expresses low levels of E6 and E7 and is highly tumorigenic. TC-1 was grown in RPMI 1640, 10% FCS, 2 mM L-glutamine, 100 U/ml penicillin, 100 μg/ml streptomycin, 100 μM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

*L. monocytogenes* Strains and Propagation

*Listeria* strains used were Lm-LLO-E7 (hly-E7 fusion gene in an episomal expression system; FIG. 1A), Lm-E7 (single-copy E7 gene cassette integrated into *Listeria* genome), Lm-LLO-NP ("DP-L2028"; hly-NP fusion gene in an episomal expression system), and Lm-Gag ("ZY-18"; single-copy HIV-1 Gag gene cassette integrated into the chromosome).

To generate pGG-55, the LLO-E7 plasmid, E7 was amplified by PCR using the primers 5'-GGCTCGAGCATGGAGATACACC-3' (SEQ ID No: 8; XhoI site is underlined) and 5'-GGGGACTAGTTTATGGTTTCTGAGAACA-3' (SEQ ID No: 9; SpeI site is underlined) and ligated into pCR2.1 (Invitrogen, San Diego, Calif.). E7 was excised from pCR2.1 by XhoI/SpeI digestion and ligated into pDP-2028 (Ikonomidis G et al. Delivery of a viral antigen to the class I processing and presentation pathway by *Listeria monocytogenes*. J Exp Med. 1994 Dec. 1; 180(6):2209-18). The hly-E7 fusion gene and the pluripotential transcription factor prfA were amplified and subcloned into pAM401, a multicopy shuttle plasmid (Wirth R et al, J Bacteriol, 165: 831, 1986), generating pGG-55. The hly promoter and gene fragment were amplified using primers 5'-GGGGGCTAGCCCTCCTTTGATTAGTATATTC-3' (SEQ ID No: 10; NheI site is underlined) and 5'-CTCCCTCGAGATCATAATTTACTTCATC-3' (SEQ ID No: 11; XhoI site is underlined). The prfA gene was PCR amplified using primers 5'-GACTACAAGGACGATGACCGACAAGTGATAACCCGGGATCTAAATAAATCCGTTT-3' (SEQ ID No: 12; XbaI site is underlined) and 5'-CCCGTCGACCAGCTCTTCTTGGTGAAG-3' (SEQ ID No: 13; SalI site is underlined).

In the resulting plasmid, pGG-55, the hly promoter drives the expression of the first 441 AA of the hly gene product, including the subsequently cleaved signal sequence, which is joined by the XhoI site to the E7 gene, yielding a hly-E7 fusion gene that is transcribed and secreted as LLO-E7. This LLO fragment lacks the hemolytic C-terminus and has the sequence set forth in SEQ ID No: 18. It is referred to below as "ΔLLO," and is merely an exemplary ΔLLO of many that could be used with methods and compositions of the present invention. Transformation of a prfA-negative strain of *Listeria*, XFL-7 (provided by Dr. Hao Shen, University of Pennsylvania), with pGG-55 selected for the retention of the plasmid in vivo (FIGS. 1A-B).

Figure 2:
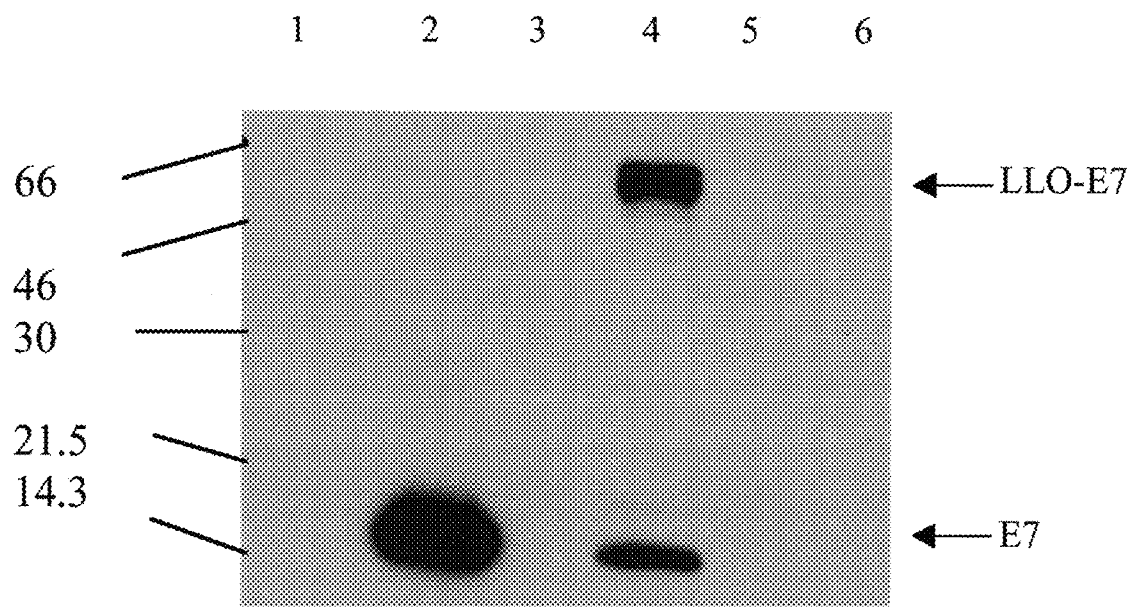
FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

Lm-E7 was generated by introducing an expression cassette containing the hly promoter and signal sequence driving the expression and secretion of E7 into the orfZ domain of the LM genome. E7 was amplified by PCR using the primers 5'-GCGGATCCCATGGAGATACACCTAC-3' (SEQ ID No: 22; BamHI site is underlined) and 5'-GCTCTAGATTATGGTTTCTGAG-3' (SEQ ID No: 23; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 μg/ml). Bacteria were frozen in aliquots at −80° C. Expression was verified by Western blotting (FIG. 2)

Western Blotting

*Listeria* strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm Tumor measurements for each time point are shown only for surviving mice.

Effects of *Listeria* Recombinants on Established Tumor Growth

Six- to 8-wk-old C57BL/6 mice (Charles River) received $2\times10^5$ TC-1 cells s.c. on the left flank. One week following tumor inoculation, the tumors had reached a palpable size of 4-5 mm in diameter. Groups of 8 mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5\times10^5$ CFU) on days 7 and 14.

$^{51}$Cr Release Assay

C57BL/6 mice, 6-8 wk old, were immunized i.p. with 0.1$LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF). E:T cell ratios, performed in triplicate, were 80:1, 40:1, 20:1, 10:1, 5:1, and 2.5:1. Following a 4-h incubation at 37° C., cells were pelleted, and 50 μl supernatant was removed from each well. Samples were assayed with a Wallac 1450 scintillation counter (Gaithersburg, Md.). The percent specific lysis was determined as [(experimental counts per minute−spontaneous counts per minute)/(total counts per minute−spontaneous counts per minute)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5\times10^5$/well in flat-bottom 96-well plates with $2.5\times10^4$, $1.25\times10^4$, $6\times10^3$, or $3\times10^3$ irradiated TC-1 cells/well as a source of E7 Ag, or without TC-1 cells or with 10 μg/ml Con A. Cells were pulsed 45 h later with 0.5 μCi [$^3$H]thymidine/well. Plates were harvested 18 h later using a Tomtec harvester 96 (Orange, Conn.), and proliferation was assessed with a Wallac 1450 scintillation counter. The change in counts per minute was calculated as experimental counts per minute—no Ag counts per minute.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2Db tetramer was performed using a FACSCalibur® flow cytometer with CellQuest® software (Becton Dickinson, Mountain View, Calif.). Splenocytes harvested 5 days after the boost were stained at room temperature (rt) with H-2Db tetramers loaded with the E7 peptide (RAHYNIVTF) or a control (HIV-Gag) peptide. Tetramers were used at a 1/200 dilution and were provided by Dr. Larry R. Pease (Mayo Clinic, Rochester, Minn.) and by the National Institute of Allergy and Infectious Diseases Tetramer Core Facility and the National Institutes of Health AIDS Research and Reference Reagent Program. Tetramer$^+$, CD8$^+$, CD62L$^{low}$ cells were analyzed.

Depletion of Specific Immune Components

CD8$^+$ cells, CD4$^+$ cells and IFN were depleted in TC-1-bearing mice by injecting the mice with 0.5 mg per mouse of mAb: 2.43, GK1.5, or xmg1.2, respectively, on days 6, 7, 8, 10, 12, and 14 post-tumor challenge. CD4$^+$ and CD8$^+$ cell populations were reduced by 99% (flow cytometric analysis). CD25$^+$ cells were depleted by i.p. injection of 0.5 mg/mouse anti-CD25 mAb (PC61, provided by Andrew J. Caton) on days 4 and 6. TGF was depleted by i.p. injection of the anti-TGF-mAb (2G7, provided by H. I. Levitsky), into TC-1-bearing mice on days 6, 7, 8, 10, 12, 14, 16, 18, and 20. Mice were treated with $10^7$ Lm-LLO-E7 or Lm-E7 on day 7 following tumor challenge.

Adoptive Transfer

Donor C57BL/6 mice were immunized and boosted 7 days later with 0.1 $LD_{50}$ Lm-E7 or Lm-Gag. The donor splenocytes were harvested and passed over nylon wool columns to enrich for T cells. CD8$^+$ T cells were depleted in vitro by incubating with 0.1 μg 2.43 anti-CD8 mAb for 30 min at rt. The labeled cells were then treated with rabbit complement. The donor splenocytes were >60% CD4$^+$ T cells (flow cytometric analysis). TC-1 tumor-bearing recipient mice were immunized with 0.1 $LD_{50}$ 7 days post-tumor challenge. CD4$^+$-enriched donor splenocytes ($10^7$) were transferred 9 days after tumor challenge to recipient mice by i.v. injection.

B16F0-Ova Experiment

24 C57BL/6 mice were inoculated with $5\times10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p<0.05$ was considered significant.

Results

Figure 3A:
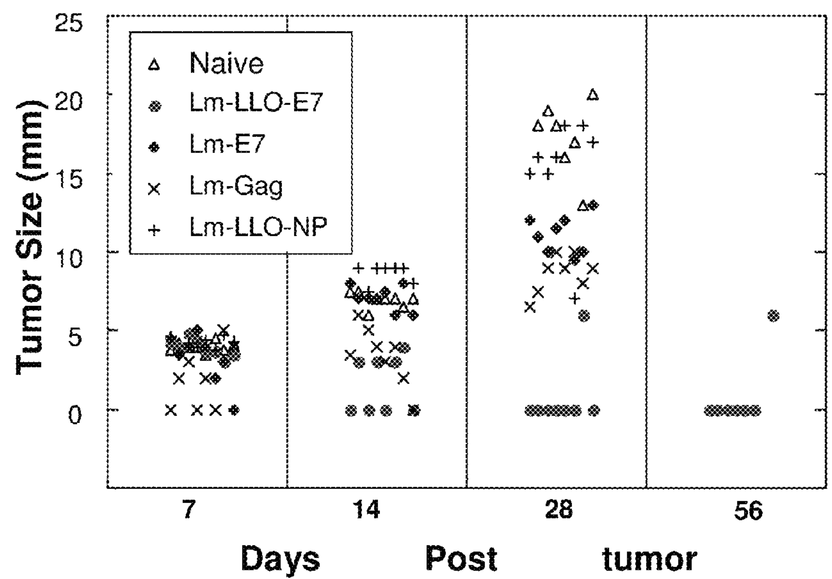
FIG. 3A-B.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm) Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while the other 2 mice in the group controlled their tumor growth (FIG. 3A). By contrast, immunization Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7remained tumor free until termination of the experiment (day 124 in the case of TC-1 and day 54 for EL-4/E7).

Figure 3B:
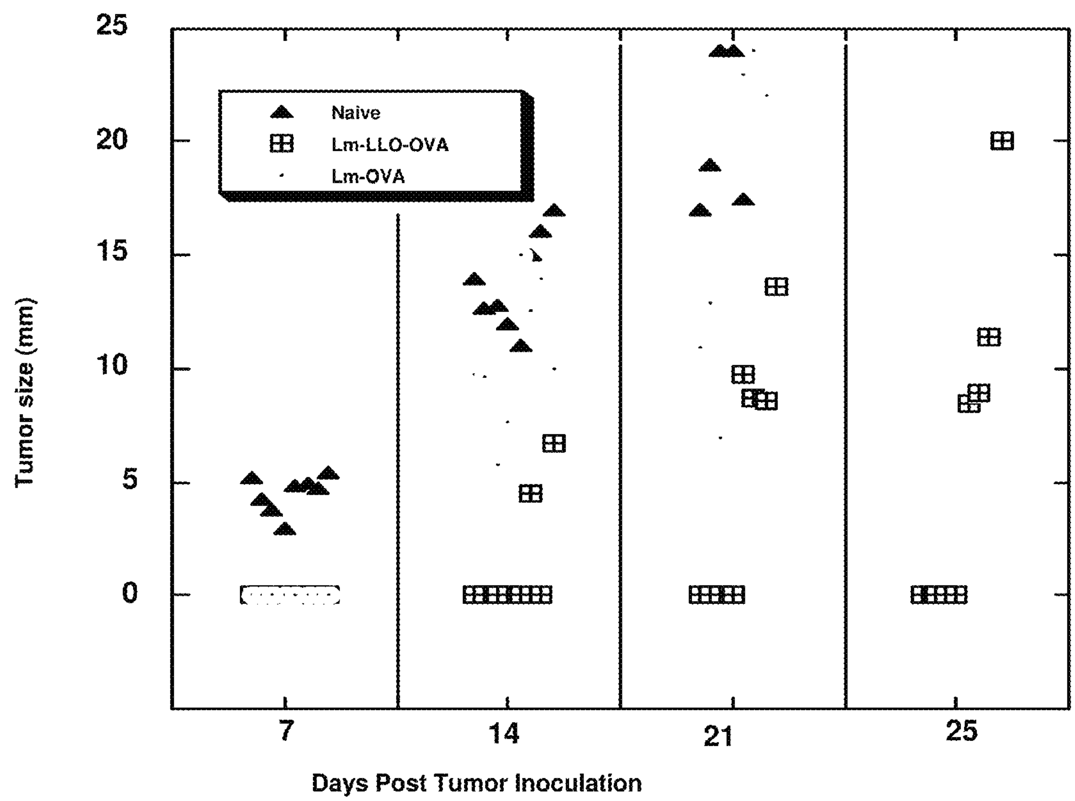

A similar experiment was performed with the chicken ovalbumin antigen (OVA). Mice were immunized with either Lm-OVA or Lm-LLO-OVA, then challenged with either an EL-4 thymoma engineered to express OVA or the very aggressive murine melanoma cell line B16F0-Ova, which has very low MHC class I expression. In both cases, Lm-LLO-OVA, but not Lm-OVA, induced the regression of established tumors. For example, at the end of the B16F0 experiment (day 25), all the mice in the naive group and the Lm-OVA group had died. All the Lm-LLO-OVA mice were alive, and 50% of them were tumor free. (FIG. 3B).

Thus, expression of an antigen gene as a fusion protein with ΔLLO enhances the immunogenicity of the antigen.

Example 2

LM-LLO-E7 Treatment Elicits TC-1 Specific Splenocyte Proliferation

Figure 4:
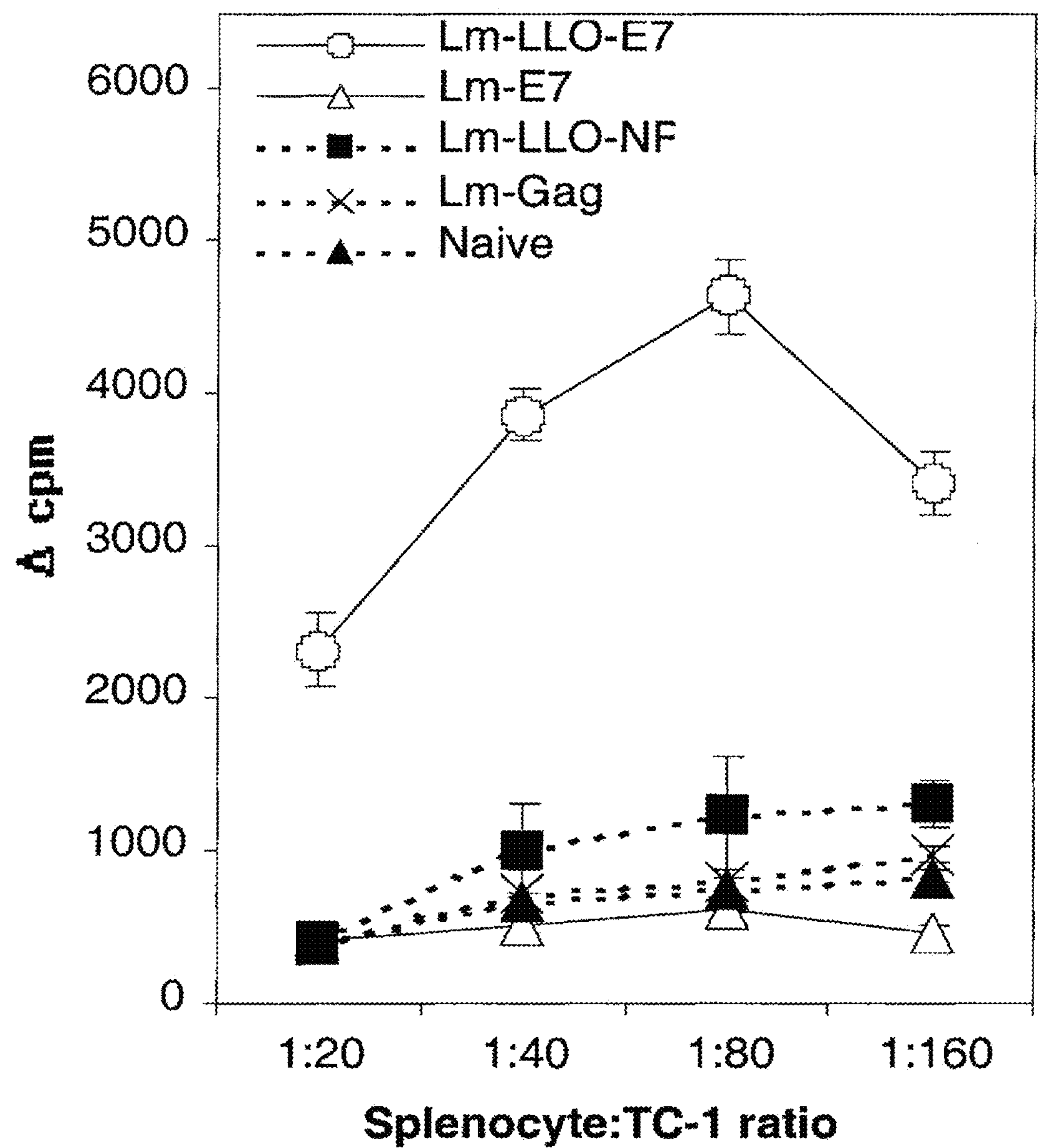
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)−(no-TC-1 control).

To measure induction of T cells by Lm-E7 with Lm-LLO-E7, TC-1-specific proliferative responses of splenocytes from rLm-immunized mice, a measure of antigen-specific immunocompetence, were assessed. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control immunized mice exhibited only background levels of proliferation.

Example 3

Fusion of NP to LLO Enhances its Immunogenicity

Materials and Experimental Methods

Figure 1:
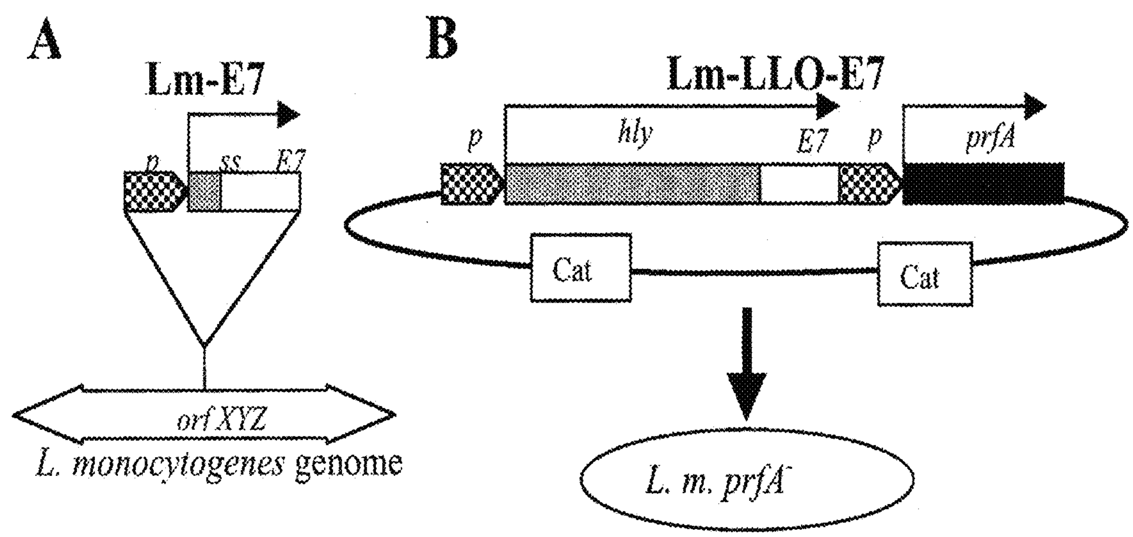
FIG. 1. Lm-E7 and Lm-LLO-E7 use different expression systems to express and secrete E7. Lm-E7 was generated by introducing a gene cassette into the orfZ domain of the *L. monocytogenes* genome (A). The hly promoter drives expression of the hly signal sequence and the first five amino acids (AA) of LLO followed by HPV-16 E7. B), Lm-LLO-E7 was generated by transforming the prfA$^-$ strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

Lm-LLO-NP was prepared as depicted in FIG. 1, except that influenza nucleoprotein (NP) replaced E7 as the antigen. 32 BALB/c mice were inoculated with $5\times10^5$ RENCA-NP tumor cells. RENCA-NP is a renal cell carcinoma retrovirally transduced with influenza nucleoprotein NP (described in U.S. Pat. No. 5,830,702, which is incorporated herein by reference). After palpable macroscopic tumors had grown on day 10, 8 animals in each group were immunized i.p. with 0.1 $LD_{50}$ of the respective *Listeria* vector. The animals received a second immunization one week later.

Results

Figure 5:
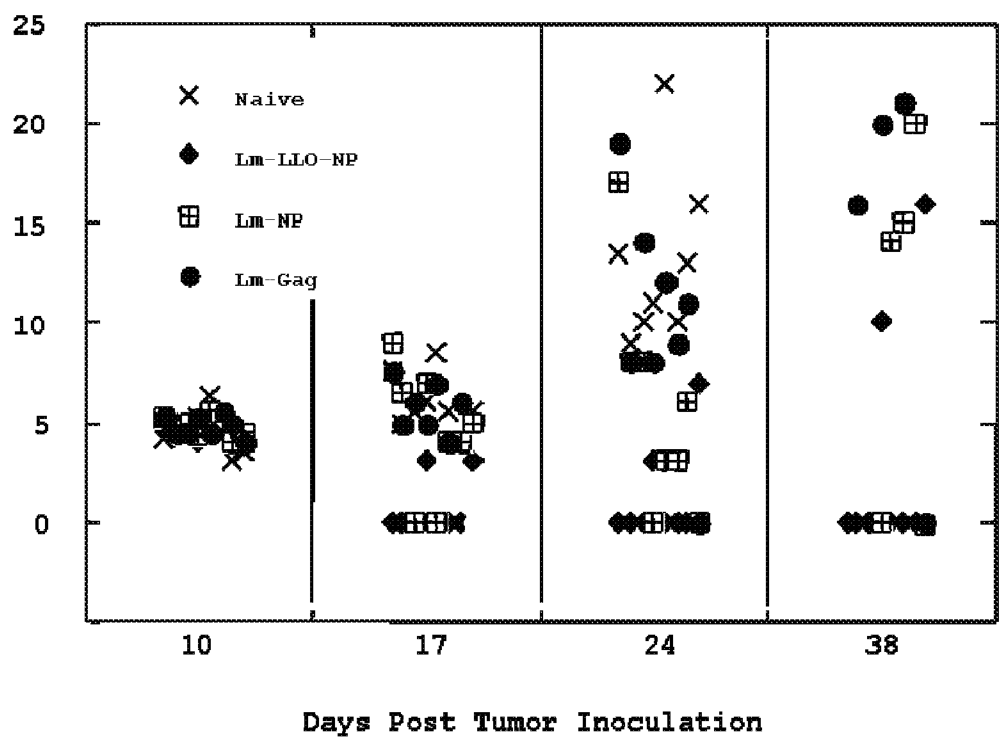
FIG. 5. Tumor immunotherapeutic efficacy of NP antigen expressed in LM. Tumor size in millimeters in mice is shown at 10, 17, 24, and 38 days post tumor-inoculation. Naive mice: X's; mice administered Lm-LLO-NP: filled diamonds; Lm-NP: squares; Lm-Gag: open circles.

In order to confirm the generality of the finding that fusing LLO to an antigen confers enhanced immunity, Lm-LLO-NP and Lm-NP (isogenic with the Lm-E7 vectors, but expressing influenza antigen) were constructed, and the vectors were compared for ability to induce tumor regression, with Lm-Gag (isogenic with Lm-NP except for the antigen expressed) as a negative control. As depicted in FIG. 5, 6/8 of the mice that received Lm-LLO-NP were tumor free. By contrast, only 1/8 and 2/8 mice in the Lm-Gag and Lm-NP groups, respectively, were tumor free. All the mice in the naive group had large tumors or had died by day 40. Thus, LLO strains expressing NP and LLO-NP fusions are immunogenic. Similar results were achieved for Lm-LLO-E7 under different immunization protocols. Further, just a single immunization was demonstrated to cure mice of established TC-1 of 5 mm diameter.

Example 4

Enhancement of Immunogenicity by Fusion of an Antigen to LLO does not Require a *Listeria* Vector

Materials and Experimental Methods

Construction of Vac-SigE7Lamp

Figure 6:
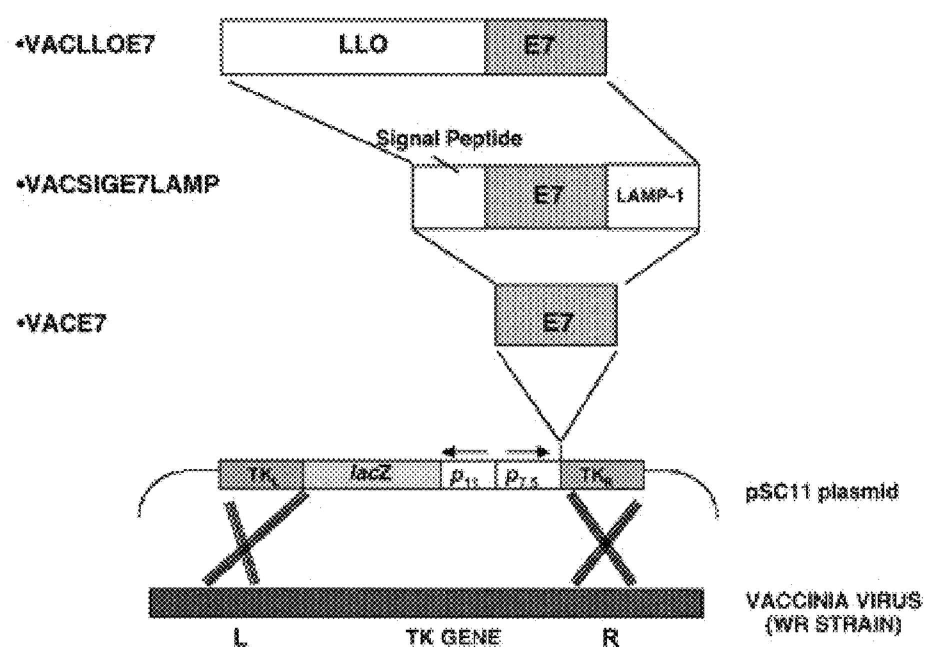
FIG. 6. Depiction of vaccinia virus constructs expressing different forms of HPV16 E7 protein.

The WR strain of vaccinia was used as the recipient and the fusion gene was excised from the Listerial plasmid and inserted into pSC11 under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same early/late compound promoter p7.5. In addition, SC11 allows the selection of recombinant viral plaques to TK selection and beta-galactosidase screening. FIG. 6 depicts the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1. It was designed to facilitate the targeting of the antigen to the MHC class II pathway.

The following modifications were made to allow expression of the gene product by vaccinia: (a) the TSXT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSCl 1-E7 construct was used to transfect the TK-ve cell line CV1 that had been infected with the wild-type vaccinia strain, WR. Cell lysates obtained from this co-infection/transfection step contain vaccinia recombinants that were plaque-purified 3 times. Expression of the LLO-E7 fusion product by plaque purified vaccinia was verified by Western blot using an antibody directed against the LLO protein sequence. In addition, the ability of Vac-LLO-E7 to produce $CD8^+$ T cells specific to LLO and E7 was determined using the LLO (91-99) and E7 (49-57) epitopes of Balb/c and C57/BL6 mice, respectively. Results were confirmed in a chromium release assay.

Results

Figure 7:
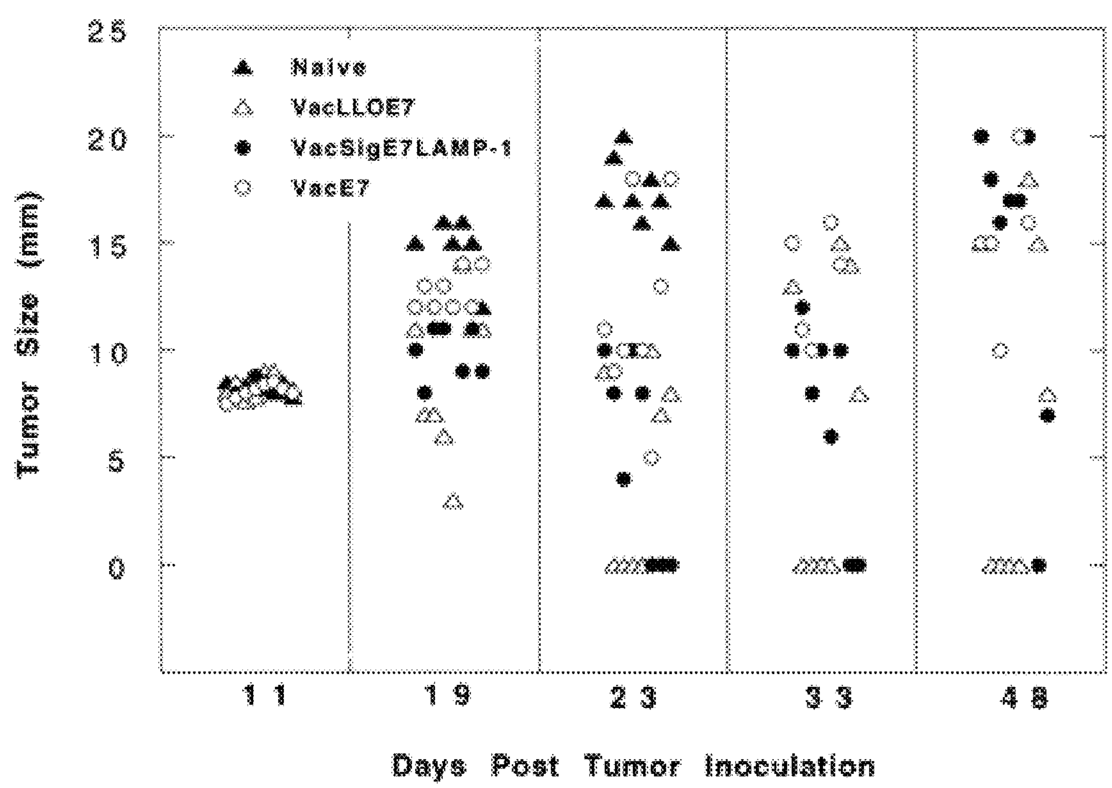
FIG. 7. VacLLOE7 causes long-term regression of tumors established from 2×10$^5$ TC-1 cells injected s.c. into C57BL/6 mice. Mice were injected 11 and 18 days after tumor challenge with 10$^7$ PFU of VacLLOE7, VacSigE7LAMP-1, or VacE7/mouse i.p. or were left untreated (naive). 8 mice per treatment group were used, and the cross section for each tumor (average of 2 measurements) is shown for the indicated days after tumor inoculation.

To determine whether enhancement of immunogenicity by fusion of an antigen to LLO requires a *Listeria* vector, a vaccinia vector expressing E7 as a fusion protein with a non-hemolytic truncated form of LLO (ΔLLO) was constructed. Tumor rejection studies were performed with TC-1 following the protocol described for Example 1. Two experiments were performed with differing delays before treatment was started. In one experiment, treatments were initiated when the tumors were about 3 mm in diameter (FIG. 7). As of day 76, 50% of the Vac-LLO-E7 treated mice were tumor free, while only 25% of the Vac-SigE7Lamp mice were tumor free. In other experiments, ΔLLO-antigen fusions were more immunogenic than E7 peptide mixed with SBAS2 or unmethylated CpG oligonucleotides in a side-by-side comparison.

These results show that (a) fusion of ΔLLO-antigen fusions are immunogenic not only in the context of *Listeria*, but also in other contexts; and (b) the immunogenicity of ΔLLO-antigen fusions compares favorably with other accepted vaccine approaches.

Example 5

ActA-Antigen and Pest-Antigen Fusions Confer Anti-Tumor Immunity

Materials and Experimental Methods

Figure 8A:
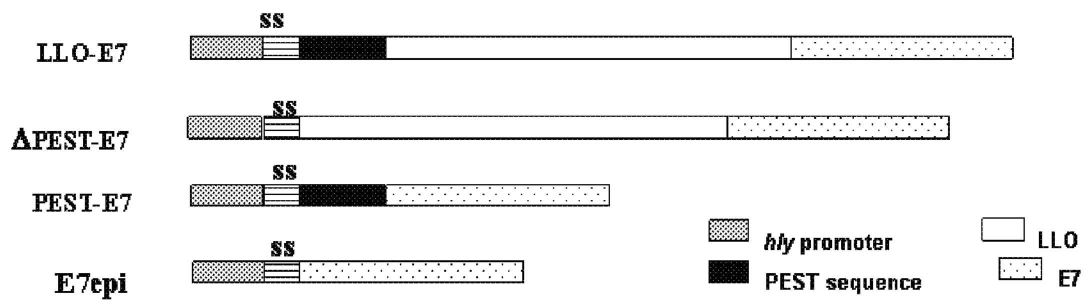
FIG. 8A-E.

Construction of Lm-PEST-E7, Lm-ΔPEST-E7, and Lm-E7epi (FIG. 8A)

Lm-PEST-E7 is identical to Lm-LLO-E7, except that it contains only the promoter and PEST sequence of the hly gene, specifically the first 50 AA of LLO. To construct Lm-PEST-E7, the hly promoter and PEST regions were fused to the full-length E7 gene using the SOE (gene splicing by overlap extension) PCR technique. The E7 gene and the hly-PEST gene fragment were amplified from the plasmid pGG-55, which contains the first 441 AA of LLO, and spliced together by conventional PCR techniques. To create a final plasmid, pVS16.5, the hly-PEST-E7 fragment and the prfA gene were subcloned into the plasmid pAM401, which includes a chloramphenicol resistance gene for selection in vitro, and the resultant plasmid was used to transform XFL-7.

Lm-ΔPEST-E7 is a recombinant *Listeria* strain that is identical to Lm-LLO-E7 except that it lacks the PEST sequence. It was made essentially as described for Lm-PEST-E7, except that the episomal expression system was constructed using primers designed to remove the PEST-containing region (bp 333-387) from the hly-E7 fusion gene. Lm-E7epi is a recombinant strain that secretes E7 without the PEST region or LLO. The plasmid used to transform this strain contains a gene fragment of the hly promoter and signal sequence fused to the E7 gene. This construct differs from the original Lm-E7, which expressed a single copy of the E7 gene integrated into the chromosome. Lm-E7epi is completely isogenic to Lm-LLO-E7, Lm-PEST-E7, and Lm-ΔPEST-E7 except for the form of the E7 antigen expressed.

Construction of Lm-actA-E7

Figure 8B:
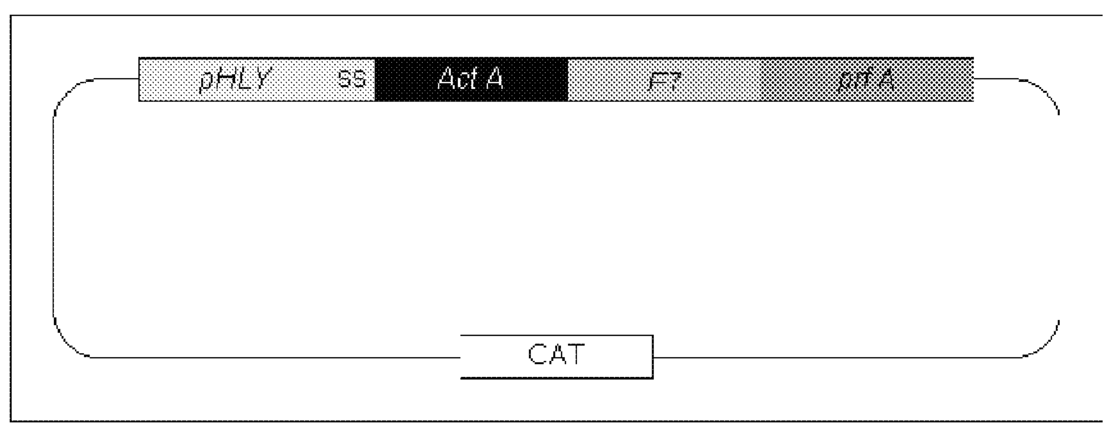

Lm-actA-E7 is a recombinant strain of LM, comprising a plasmid that expresses the E7 protein fused to a truncated version of the actA protein. Lm-actA-E7 was generated by introducing a plasmid vector pDD-1 constructed by modifying pDP-2028 into LM. pDD-1 comprises an expression cassette expressing a copy of the 310 bp hly promoter and the hly signal sequence (ss), which drives the expression and secretion of actA-E7; 1170 bp of the actA gene that comprises 4 PEST sequences (SEQ ID No: 16) (the truncated ActA polypeptide consists of the first 390 AA of the molecule, SEQ ID No: 15); the 300 bp HPV E7* gene; the 1019 bp prfA* gene (controls expression of the virulence genes); and the CAT gene (chloramphenicol resistance gene) for selection of transformed bacteria clones. (FIG. 8B).

The hly promoter (pHly) and gene fragment were PCR amplified from pGG-55 (Example 1) using the primers 5'-GGGGTCTAGACCTCCTTTGATTAGTATATTC-3' (Xba I site is underlined; SEQ ID NO: 46) and 5'-ATCTTCGCTATCTGTCGC CGCGGCGCGTGCTTCAGTTTGTTGCGC-'3 (Not I site is underlined; the first 18 nucleotides are the ActA gene overlap; SEQ ID NO: 47). The actA gene was PCR amplified from the LM 10403s wildtype genome using primer 5'-GCGCAACAAACTGAAGCAGC GGCCGCGGCGACAGATAGCGAAGAT-3' (NotI site is underlined; SEQ ID NO: 48) and primer 5'-TGTAGGTGTATCTCCATGCTCGAGAGCTAGGCGATCAATTTC-3' (XhoI site is underlined; SEQ ID NO: 49). The E7 gene was PCR amplified from pGG55 (pLLO-E7) using primer 5'-GGAATTGATCGCCTAGCT CTCGAGCATGGAGATACACCTACA-3' (XhoI site is underlined; SEQ ID NO: 50) and primer 5'-AAACGGATTTATTTAGATCCCGGGTTATGGTTTCTGAGAACA-3' (XmaI site is underlined; SEQ ID NO: 51). The prfA gene was PCR amplified from the LM 10403s wild-type genome using primer 5'-TGTTCTCAGAAACCATAA CCCGGGATCTAAATAAATCCGTTT-3' (XmaI site is underlined; SEQ ID NO: 52) and primer 5'-GGGGGTCGACCAGCTCTTCTTGGTGAAG-3' (SalI site is underlined; SEQ ID NO: 53). The hly promoter was fused to the actA gene (pHly-actA) was PCR generated and amplified from purified pHly DNA and purified actA DNA using the upstream pHly primer (SEQ ID NO: 46) and downstream actA primer (SEQ ID NO: 49).

The E7 gene fused to the prfA gene (E7-prfA) was PCR generated and amplified from purified E7 DNA and purified prfA DNA using the upstream E7 primer (SEQ ID NO: 50) and downstream prfA gene primer (SEQ ID NO: 53).

The pHly-actA fusion product fused to the E7-prfA fusion product was PCR generated and amplified from purified fused pHly-actA DNA product and purified fused E7-prfA DNA product using the upstream pHly primer (SEQ ID NO: 46) and downstream prfA gene primer (SEQ ID NO: 53) and ligated into pCRII (Invitrogen, La Jolla, Calif.). Competent *E. coli* (TOP10'F, Invitrogen, La Jolla, Calif.) were transformed with pCRII-*ActAE*7. After lysis and isolation, the plasmid was screened by restriction analysis using BamHI (expected fragment sizes 770 bp and 6400 bp (or when the insert was reversed into the vector: 2500 bp and 4100 bp)) and B stXI (expected fragment sizes 2800 bp and 3900 bp) and also screened with PCR analysis using the upstream pHly primer (SEQ ID NO: 46) and the downstream prfA gene primer (SEQ ID NO: 53).

The pHly-ActA-E7-PrfA DNA insert was excised from pCRII by double digestion with Xba I and Sal I and ligated into pDP-2028 also digested with Xba I and Sal I. After transforming TOP10'F competent *E. coli* (Invitrogen, La Jolla, Calif.) with expression system pActAE7, chloramphenicol resistant clones were screened by PCR analysis using the upstream pHly primer (SEQ ID NO: 46) and the downstream PrfA gene primer (SEQ ID NO: 53). A clone carrying pHly-ActA-E7 was grown in brain heart infusion medium with 20 mcg (microgram)/ml (milliliter) chloramphenicol (Difco, Detroit, Mich.), and pActAE7 was isolated from the bacteria cell using a midiprep DNA purification system kit (Promega, Madison, Wis.). Penicillin-treated

*Listeria* strain XFL-7 was transformed with pActAE7, and clones were selected for the retention of the plasmid in vivo. Clones were grown in brain heart infusion with chloramphenicol (20 mcg/ml) at 37° C. Bacteria were frozen in aliquots at −80° C.

Results

Figure 9:
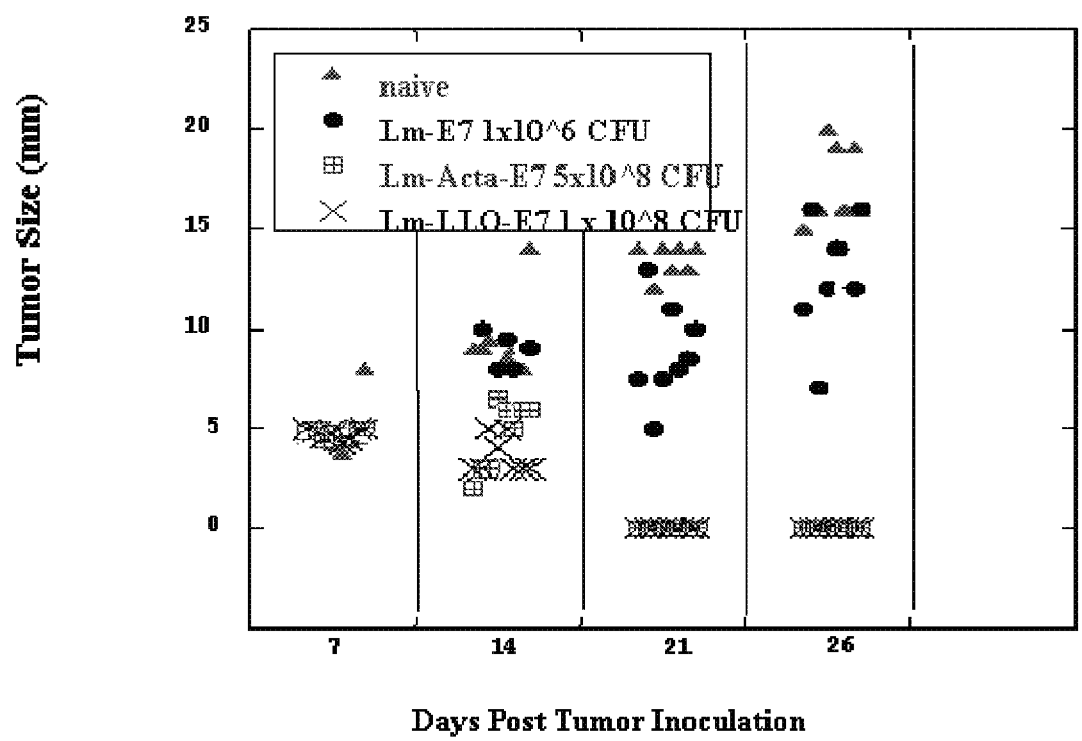
FIG. 9. Tumor size in mice administered Lm-ActA-E7 (rectangles), Lm-E7 (ovals), Lm-LLO-E7 (X), and naive mice (non-vaccinated; solid triangles).

To compare the anti-tumor immunity induced by Lm-ActA-E7 versus Lm-LLO-E7, $2\times10^5$ TC-1 tumor cells were implanted subcutaneously in mice and allowed to grow to a palpable size (approximately 5 millimeters [mm]) Mice were immunized i.p. with one $LD_{50}$ of either Lm-ActA-E7 ($5\times10^8$ CFU), (crosses) Lm-LLO-E7 ($10^8$ CFU) (squares) or Lm-E7 ($10^6$ CFU) (circles) on days 7 and 14. By day 26, all of the animals in the Lm-LLO-E7 and Lm-ActA-E7 were tumor free and remained so, whereas all of the naive animals (triangles) and the animals immunized with Lm-E7 grew large tumors (FIG. 9). Thus, vaccination with ActA-E7 fusions causes tumor regression.

Figure 8C:
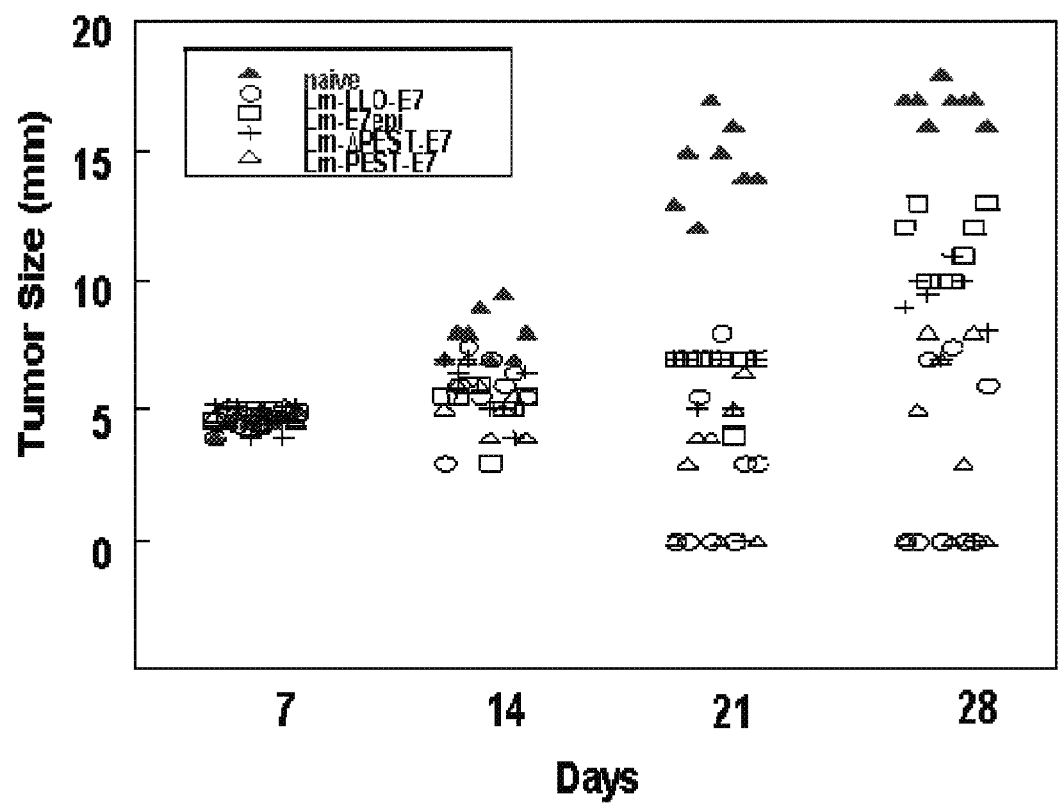
Figure 8D:
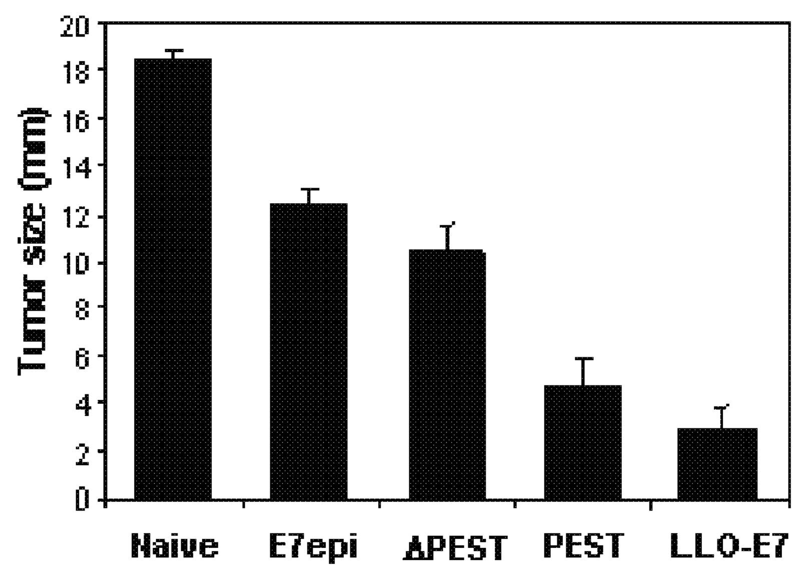
Figure 8E:
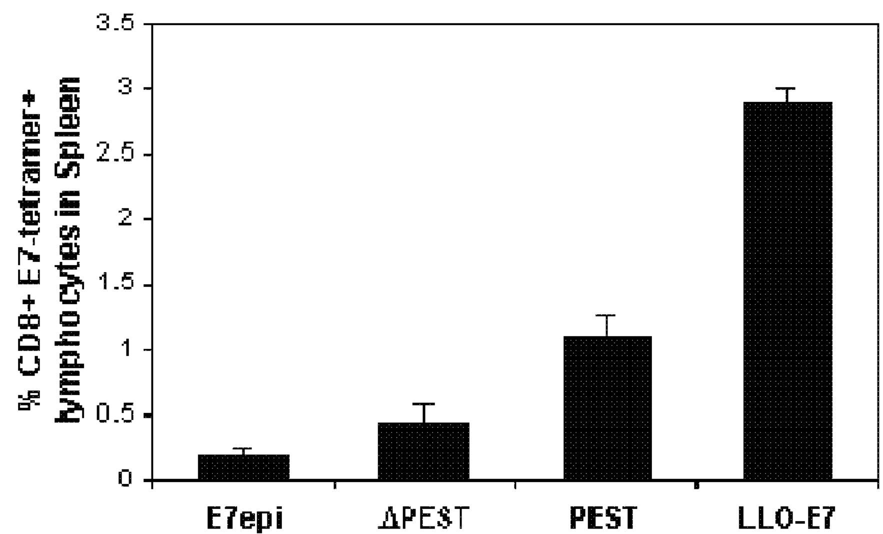

In addition, Lm-LLO-E7, Lm-PEST-E7, Lm-ΔPEST-E7, and Lm-E7epi were compared for their ability to cause regression of E7-expressing tumors. S.c. TC-1 tumors were established on the left flank of 40 C57BL/6 mice. After tumors had reached 4-5 mm, mice were divided into 5 groups of 8 mice. Each groups was treated with 1 of 4 recombinant LM vaccines, and 1 group was left untreated. Lm-LLO-E7 and Lm-PEST-E7 induced regression of established tumors in 5/8 and 3/8 cases, respectively. There was no statistical difference between the average tumor size of mice treated with Lm-PEST-E7 or Lm-LLO-E7 at any time point. However, the vaccines that expressed E7 without the PEST sequences, Lm-ΔPEST-E7 and Lm-E7epi, failed to cause tumor regression in all mice except one (FIG. 8C, top panel). This was representative of 2 experiments, wherein a statistically significant difference in mean tumor sizes at day 28 was observed between tumors treated with Lm-LLO-E7 or Lm-PEST-E7 and those treated with Lm-E7epi or Lm-ΔPEST-E7; $P<0.001$, Student's t test; FIG. 8C, bottom panel). In addition, increased percentages of tetramer-positive splenocytes were seen reproducibly over 3 experiments in the spleens of mice vaccinated with PEST-containing vaccines (FIG. 8D). Thus, vaccination with PEST-E7 fusions causes tumor regression.

Example 6

Fusion of E7 to LLO, ActA, or a Pest-Like Sequence Enhances Antigen-Specific Immunity and Generates Tumor-Infiltrating E7-Specific $CD8^+$ Cells Materials and Experimental Methods 500 mcl (microliter) of MATRIGEL®, comprising 100 mcl of $2\times10^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-Stop® or Golgi-Plug® (Pharmingen, San Diego, Calif.), and stained for IFN-gamma. 500,000 events were acquired using two-laser flow cytometer FACSCalibur and analyzed using Cellquest Software (Becton Dickinson, Franklin Lakes, N.J.). Percentages of IFN-gamma secreting cells within the activated ($CD62L^{low}$) $CD8^+$ T cells were calculated.

For tetramer staining, H-$2D^b$ tetramer was loaded with phycoerythrin (PE)-conjugated E7 peptide (RAHYNIVTF, SEQ ID NO: 24), stained at rt for 1 hour, and stained with anti-allophycocyanin (APC) conjugated MEL-14 (CD62L) and FITC-conjugated CD8β at 4° C. for 30 min. Cells were analyzed comparing $tetramer^+CD8^+$ $CD62L^{low}$ cells in the spleen and in the tumor.

Results

Figure 10B:
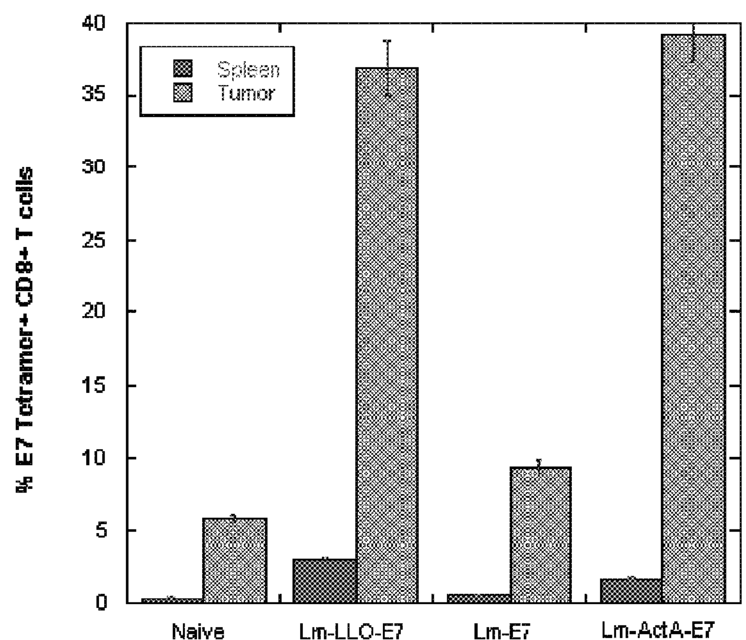

To analyze the ability of Lm-ActA-E7 to enhance antigen specific immunity, mice were implanted with TC-1 tumor cells and immunized with either Lm-LLO-E7 ($1\times10^7$ CFU), Lm-E7 ($1\times10^6$ CFU), or Lm-ActA-E7 ($2\times10^8$ CFU), or were untreated (naïve). Tumors of mice from the Lm-LLO-E7 and Lm-ActA-E7 groups contained a higher percentage of IFN-gamma-secreting $CD8^+$ T cells (FIG. 10A) and tetramer-specific $CD8^+$ cells (FIG. 10B) than in Lm-E7 or naive mice.

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 $LD_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 11A). This result was reproducible over three experiments (FIG. 11B).

Thus, Lm-LLO-E7, Lm-ActA-E7, and Lm-PEST-E7 are each efficacious at induction of tumor-infiltrating $CD8^+$ T cells and tumor regression.

Example 7

Creation and Verification of *Listeria*-LLO-PSA Constructs

Materials and Experimental Methods

Subcloning of LLO-PSA

A truncated PSA open reading frame (GenBank Accession Number NM_001648), lacking its secretory signal sequence, the first 24 AA, was amplified using the primers: Adv60-PSA(XhoI-no ATG)F: gtgCTCGAGattgtgggaggctgggagtg (SEQ ID No: 58) and Adv61-PSA(SpeI-Stop)R: gatACTAGTttaggggttggccacgatgg (SEQ ID No: 59) and was subcloned in-frame with the first 441 amino acids of LLO (FIG. 12). The plasmid backbone, pGG55 (Example 1) also has a copy of the *Listeria* virulence gene prfA, and 2 chloramphenicol acetyl-transferase genes that render chloramphenicol resistance in both gram-positive and gram negative bacterial strains. The AA sequence of LLO-PSA is as follows:

```
MKKIMLVFITLILVSLPIAQQTEAKDASAFNKENSISSMAPPASPPASPK
TPIEKKHADEIDKYIQGLDYNKNNVLVYHGDAVTNVPPRKGYKDGNEYIV
VEKKKKSINQNNADIQVVNAISSLTYPGALVKANSELVENQPDVLPVKRD
SLTLSIDLPGMTNQDNKIVVKNATKSNVNNAVNTLVERWNEKYAQAYPNV
SAKIDYDDEMAYSESQLIAKFGTAFKAVNNSLNVNFGAISEGKMQEEVIS
FKQIYYNVNVNEPTRPSRFFGKAVTKEQLQALGVNAENPPAYISSVAYGR
QVYLKLSTNSHSTKVKAAFDAAVSGKSVSGDVELTNIIKNSSFKAVIYGG
SAKDEVQIIDGNLGDLRDILKKGATENRETPGVPIAYTTNELKDNELAVI
KNNSEYIETTSKAYTDGKINIDHSGGYVAQFNISWDEVNYDLEIVGGWEC
EKHSQPWQVLVASRGRAVCGGVLVHPQWVLTAAHCIRNKSVILLGRHSLF
HPEDTGQVFQVSHSFPHPLYDMSLLKNRFLRPGDDSSHDLMLLRLSEPAE
LTDAVKVMDLPTQEPALGTTCYASGWGSIEPEEFLTPKKLQCVDLHVISN
DVCAQVHPQKVTKFMLCAGRWTGGKSTCSGDSGGPLVCYGVLQGITSWGS
EPCALPERPSLYTKVVHYRKWIKDTIVANP
(SEQ ID No: 54; PSA sequence is underlined)
```

There is one AA difference between this PSA and the sequence in NM_001648, at position N 221 Y). pGG55-LLO-PSA was electroporated into *L. monocytogenes* XFL-7 (Example 1).

Growth and Storage of Bacterial Vaccine Strains

Recombinant *Listeria*-PSA was grown in an animal product free medium (Modified Terrific Broth), in the presence of 34 μg/ml chloramphenicol and 250 μg/ml streptomycin at 37° C. in a shaker incubator. After reaching an optical density ($OD_{600}$) of 0.5, which indicated a logarithmic growth phase, bacteria were collected by centrifugation, and the pellet was washed 2 times in Phosphate Buffered Saline (PBS) and resuspended in PBS containing 2% glycerol, then aliquoted and stored at −80° C. One aliquot was thawed 1 day later and titrated to determine bacterial titer (Colony Forming Units/ml). *Listeria* vaccines stored in this manner are stable for up to 1 year. These aliquots were then thawed, diluted at $1\times10^7$ CFU/dose and used for the immunogenicity studies as follows.

Verification of Expression and Secretion of LLO-PSA

Four colonies of Lm-PSA were grown in Brain Heart infusion broth in the presence of 34 μg/ml chloramphenicol for 8 hours. Proteins in the culture broth were precipitated with 10% TCA, separated by SDS-PAGE, transferred to PVDF membranes, and blotted as indicated in the legend to FIG. 13.

Testing Stability of Lm-PSA Construct

Lm-PSA was grown and passaged for 7 consecutive days in modified terrific broth containing 34 μg/ml chloramphenicol. Plasmid DNA was purified from the bacteria at different time points during passaging and tested for integrity and the presence of PSA gene by amplification of PSA gene by PCR or EcoRI/HindIII restriction mapping of the plasmid.

Results

A *Listeria* strain was created that expresses a non-hemolytic LLO fused to a truncated PSA (kallikrein-related peptidase 3). The resulting recombinant *Listeria* strain secretes a protein of the predicted size for LLO-PSA (75 Kd), which is detected by both anti-LLO and anti-PSA antibodies, showing that LLO-PSA protein was expressed and secreted (FIG. 13).

To test the in vitro stability of Lm-PSA, the strain was grown and passaged for 7 consecutive days in modified terrific broth. After this time, the bacteria retained the plasmid, the plasmid contained the PSA gene and there were no deletions or re-arrangements in the plasmid, indicating plasmid stability (FIG. 14).

To test the in vivo stability of Lm-PSA, the strain was passaged twice through mice. The plasmid was then sequenced by Genewiz™ and found to have the following sequence:

```
                                    (SEQ ID No: 55)
AATTCCGGATGAGCATTCATCAGGCGGGCAAGAATGTGAATAAAGGCCGG
ATAAAACTTGTGCTTATTTTTCTTTACGGTCTTTAAAAAGGCCGTAATAT
CCAGCTGAACGGTCTGGTTATAGGTACATTGAGCAACTGACTGAAATGCC
TCAAAATGTTCTTTACGATGCCATTGGGATATATCAACGGTGGTATATCC
AGTGATTTTTTTCTCCATTTTAGCTTCCTTAGCTCCTGAAAATCTCGATA
ACTCAAAAAATACGCCCGGTAGTGATCTTATTTCATTATGGTGAAAGTTG
GAACCTCTTACGTGCCGATCAACGTCTCATTTTCGCCAAAAGTTGGCCCA
GGGCTTCCCGGTATCAACAGGGACACCAGGATTTATTTATTCTGCGAAGT
GATCTTCCGTCACAGGTATTTATTCGGCGCAAAGTGCGTCGGGTGATGCT
GCCAACTTACTGATTTAGTGTATGATGGTGTTTTTGAGGTGCTCCAGTGG
CTTCTGTTTCTATCAGCTGTCCCTCCTGTTCAGCTACTGACGGGGTGGTG
CGTAACGGCAAAAGCACCGCCGGACATCAGCGCTAGCGGAGTGTATACTG
GCTTACTATGTTGGCACTGATGAGGGTGTCAGTGAAGTGCTTCATGTGGC
AGGAGAAAAAAGGCTGCACCGGTGCGTCAGCAGAATATGTGATACAGGAT
ATATTCCGCTTCCTCGCTCACTGACTCGCTACGCTCGGTCGTTCGACTGC
GGCGAGCGGAAATGGCTTACGAACGGGGCGGAGATTTCCTGGAAGATGCC
AGGAAGATACTTAACAGGGAAGTGAGAGGGCCGCGGCAAAGCCGTTTTTC
CATAGGCTCCGCCCCCCTGACAAGCATCACGAAATCTGACGCTCAAATCA
GTGGTGGCGAAACCCGACAGGACTATAAAGATACCAGGCGTTTCCCCCTG
GCGGCTCCCTCGTGCGCTCTCCTGTTCCTGCCTTTCGGTTTACCGGTGTC
ATTCCGCTGTTATGGCCGCGTTTGTCTCATTCCACGCCTGACACTCAGTT
CCGGGTAGGCAGTTCGCTCCAAGCTGGACTGTATGCACGAACCCCCCGTT
CAGTCCGACCGCTGCGCCTTATCCGGTAACTATCGTCTTGAGTCCAACCC
GGAAAGACATGCAAAAGCACCACTGGCAGCAGCCACTGGTAATTGATTTA
GAGGAGTTAGTCTTGAAGTCATGCGCCGGTTAAGGCTAAACTGAAAGGAC
AAGTTTTGGTGACTGCGCTCCTCCAAGCCAGTTACCTCGGTTCAAAGAGT
TGGTAGCTCAGAGAACCTTCGAAAAACCGCCCTGCAAGGCGGTTTTTTCG
TTTTCAGAGCAAGAGATTACGCGCAGACCAAAACGATCTCAAGAAGATCA
TCTTATTAATCAGATAAAATATTTCTAGCCCTCCTTTGATTAGTATATTC
CTATCTTAAAGTTACTTTTATGTGGAGGCATTAACATTTGTTAATGACGT
CAAAAGGATAGCAAGACTAGAATAAAGCTATAAAGCAAGCATATAATATT
```

-continued

GCGTTTCATCTTTAGAAGCGAATTTCGCCAATATTATAATTATCAAAAGA
GAGGGGTGGCAAACGGTATTTGGCATTATTAGGTTAAAAAATGTAGAAGG
AGAGTGAAACCCATGAAAAAAATAATGCTAGTTTTTATTACACTTATATT
AGTTAGTCTACCAATTGCGCAACAAACTGAAGCAAAGGATGCATCTGCAT
TCAATAAAGAAAATTCAATTTCATCCATGGCACCACCAGCATCTCCGCCT
GCAAGTCCTAAGACGCCAATCGAAAAGAAACACGCGGATGAAATCGATAA
GTATATACAAGGATTGGATTACAATAAAAACAATGTATTAGTATACCACG
GAGATGCAGTGACAAATGTGCCGCCAAGAAAAGGTTACAAAGATGGAAAT
GAATATATTGTTGTGGAGAAAAAGAAGAAATCCATCAATCAAAATAATGC
AGACATTCAAGTTGTGAATGCAATTTCGAGCCTAACCTATCCAGGTGCTC
TCGTAAAAGCGAATTCGGAATTAGTAGAAAATCAACCAGATGTTCTCCCT
GTAAAACGTGATTCATTAACACTCAGCATTGATTTGCCAGGTATGACTAA
TCAAGACAATAAAATAGTTGTAAAAAATGCCACTAAATCAAACGTTAACA
ACGCAGTAAATACATTAGTGGAAAGATGGAATGAAAAATATGCTCAAGCT
TATCCAAATGTAAGTGCAAAAATTGATTATGATGACGAAATGGCTTACAG
TGAATCACAATTAATTGCGAAATTTGGTACAGCATTTAAAGCTGTAAATA
ATAGCTTGAATGTAAACTTCGGCGCAATCAGTGAAGGGAAAATGCAAGAA
GAAGTCATTAGTTTTAAACAAATTTACTATAACGTGAATGTTAATGAACC
TACAAGACCTTCCAGATTTTTCGGCAAAGCTGTTACTAAAGAGCAGTTGC
AAGCGCTTGGAGTGAATGCAGAAAATCCTCCTGCATATATCTCAAGTGTG
GCGTATGGCCGTCAAGTTTATTTGAAATTATCAACTAATTCCCATAGTAC
TAAAGTAAAAGCTGCTTTTGATGCTGCCGTAAGCGGAAAATCTGTCTCAG
GTGATGTAGAACTAACAAATATCATCAAAAATTCTTCCTTCAAAGCCGTA
ATTTACGGAGGTTCCGCAAAAGATGAAGTTCAAATCATCGACGGCAACCT
CGGAGACTTACGCGATATTTTGAAAAAAGGCGCTACTTTTAATCGAGAAA
CACCAGGAGTTCCCATTGCTTATACAACAAACTTCCTAAAAGACAATGAA
TTAGCTGTTATTAAAAACAACTCAGAATATATTGAAACAACTTCAAAAGC
TTATACAGATGGAAAAATTAACATCGATCACTCTGGAGGATACGTTGCTC
AATTCAACATTTCTTGGGATGAAGTAAATTATGATCTCGAGattgtggga
ggctgggagtgcgagaagcattcccaaccctggcaggtgcttgtggcctc
tcgtggcagggcagtctgcggcggtgttctggtgcacccccagtgggtcc
tcacagctgcccactgcatcaggaacaaaagcgtgatcttgctgggtcgg
cacagcctgtttcatcctgaagacacaggccaggtatttcaggtcagcca
cagcttcccacacccgctctacgatatgagcctcctgaagaatcgattcc
tcaggccaggtgatgactccagccacgacctcatgctgctccgcctgtca
gagcctgccgagctcacggatgctgtgaaggtcatggacctgcccaccca
ggagccagcactggggaccacctgctacgcctcaggctggggcagcattg
aaccagaggagttcttgaccccaaagaaacttcagtgtgtggacctccat
gttatttccaatgacgtgtgtgcgcaagttcacccctcagaaggtgacca
agttcatgctgtgtgctggacgctggacagggggcaaaagcacctgctcg
ggtgattctgggggcccacttgtctgttatggtgtgcttcaaggtatcac
gtcatggggcagtgaaccatgtgccctgcccgaaaggccttccctgtaca
ccaaggtggtgcattaccggaagtggatcaaggacaccatcgtggccaac
cccTAAACTAGTGACTACAAGGACGATGACGACAAGTGATACCCGGGATC
TAAATAAATCCGTTTTTAAATATGTATGCATTTCTTTTGCGAAATCAAAA
TTTGTATAATAAAATCCTATATGTAAAAAACATCATTTAGCGTGACTTTC
TTTCAACAGCTAACAATTGTTGTTACTGCCTAATGTTTTTAGGGTATTTT
AAAAAAGGGCGATAAAAAACGATTGGGGGATGAGACATGAACGCTCAAGC
AGAAGAATTCAAAAAATATTTAGAAACTAACGGGATAAAACCAAAACAAT
TTCATAAAAAAGAACTTATTTTTAACCAATGGGATCCACAAGAATATTGT
ATTTTCCTATATGATGGTATCACAAAGCTCACGAGTATTAGCGAGAACGG
GACCATCATGAATTTACAATACTACAAAGGGGCTTTCGTTATAATGTCTG
GCTTTATTGATACAGAAACATCGGTTGGCTATTATAATTTAGAAGTCATT
AGCGAGCAGGCTACCGCATACGTTATCAAAATAAACGAACTAAAAGAACT
ACTGAGCAAAAATCTTACGCACTTTTTCTATGTTTTCCAAACCCTACAAA
AACAAGTTTCATACAGCCTAGCTAAATTTAATGATTTTTCGATTAACGGG
AAGCTTGGCTCTATTTGCGGTCAACTTTTAATCCTGACCTATGTGTATGG
TAAAGAAACTCCTGATGGCATCAAGATTACACTGGATAATTTAACAATGC
AGGAGTTAGGATATTCAAGTGGCATCGCACATAGCTCAGCTGTTAGCAGA
ATTATTTCCAAATTAAAGCAAGAGAAAGTTATCGTGTATAAAAATTCATG
CTTTTATGTACAAAATCGTGATTATCTCAAAAGATATGCCCCTAAATTAG
ATGAATGGTTTTATTTAGCATGTCCTGCTACTTGGGGAAAATTAAATTAA
ATCAAAAACAGTATTCCTCAATGAGGAATACTGTTTTATATTTTATTCGA
ATAAAGAACTTACAGAAGCATTTTCATGAACGCGTACGATTGCTTCACCA
AGAAGAGCTGGTCGACCGATGCCCTTGAGAGCCTTCAACCCAGTCAGCTC
CTTCCGGTGGGCGCGGGGCATGACTATCGTCGCCGCACTTATGACTGTCT
TCTTTATCATGCAACTCGTAGGACAGGTGCCGGCAGCGCTCTGGGTCATT
TTCGGCGAGGACCGCTTTCGCTGGAGCGCGACGATGATCGGCCTGTCGCT
TGCGGTATTCGGAATCTTGCACGCCCTCGCTCAAGCCTTCGTCACTGGTC
CCGCCACCAAACGTTTCGGCGAGAAGCAGGCCATTATCGCCGGCATGGCG
GCCGACGCGCTGGGCTACGTCTTGCTGGCGTTCGCGACGCGAGGCTGGAT
GGCCTTCCCCATTATGATTCTTCTCGCTTCCGGCGGCATCGGGATGCCCG
CGTTGCAGGCCATGCTGTCCAGGCAGGTAGATGACGACCATCAGGGACAG
CTTCAAGGATCGCTCGCGGCTCTTACCAGCCTAACTTCGATCATTGGACC
GCTGATCGTCACGGCGATTTATGCCGCCTCGGCGAGCACATGGAACGGGT
TGGCATGGATTGTAGGCGCCGCCCTATACCTTGTCTGCCTCCCCGCGTTG
CGTCGCGGTGCATGGAGCCGGGCCACCTCGACCTGAATGGAAGCCGGCGG
CACCTCGCTAACGGATTCACCACTCCAAGAATTGGAGCCAATCAATTCTT
GCGGAGAACTGTGAATGCGCAAACCAACCCTTGGCAGAACATATCCATCG
CGTCCGCCATCTCCAGCAGCCGCACGCGGCGCATCTCGGCTTTCGATTTG
TTTTTGAATGGTTTATCCGATAAAGAAGTTGAAGAACAAACTGGAATCAA TCGCCGAACGTTTAGAAGGTATCGAGCAAGATATAACGTGACAGTCGATC
AAAGAAAAAACAATGAAAAGAGGGATAGTTAATGAGTACGGTTATTTTAG
CTGAAAAACCAAGCCAGGCATTAGCCTACGCAAGTGCTTTAAAACAAAGC
ACCAAAAAAGACGGTTATTTTGAGATCAAAGACCCACTATTTACAGATGA
AACGTTTATCACCTTTGGTTTTGGGCATTTAGTGGAATTAGCAGAACCAG
GTCATTATGACGAAAAGTGGCAAAATTGGAAACTTGAATCTTTGCCGATT
TTTCCTGATCGATACGATTTTGAAGTTGCAAAAGATAAGGGAAAGCAGTT
TAAAATTGTTGCAGAACTTCTCAAAAAGGCAAATACAATTATTGTTGCAA
CAGATAGCGACAGAGAAGGTGAAAATATCGCCTGGTCGATTATCCATAAA
GCAAATGCCTTTTCAAAAGATAAAACATTTAAAAGACTATGGATCAATAG
CTTAGAAAAAGATGTAATCCGAAGCGGTTTTCAAAATTTGCAACCTGGAA
TGAATTACTATCCCTTTTATCAAGAAGCGCAAACACGCCAAATTGCCGAT
TGGTTGATCGGCATGAACGCAAGCCCTTTGTATACGTTAAATTTACAACA
GAAGGGCGTACAAGGTACATTTTCACTAGGACGTGTTCAAACGCCCACCT
TATACCTTATTTTTCAGCGCCAGGAAGCCATAGAGAATTTTAAAAAAGAA
CCTTTTTTCGAGGTGGAAGCTAGTATAAAAGTAAACCAAGGGTCGTTTAA
GGGCGTTCTAAGCCCCACACAGCGTTTTAAAACCCAAGAGGAGCTTTTAG
CTTTTGTTTCTTCTAAACAAGCTAAAATAGGCAATCAAGAGGGGATAATT
GCTGATGTTCAAACCAAAGAGAAGAAAACGAATAGTCCGAGTTTGTTTTC
TTTAAGTAGTTTGCAATCAAAAGTCAATCAGCTTTATAAAGCGACAGCGA
GCCAAACTTTAAAAGCTATTTCTTTTTTAATAACTTAAAAATAAACTTAA
TGTAACAGCAAGCACAGTCAAGGTATACACCTTTGACAAAAAATAGCACA
TTCTCTATCGAAAATTTTTGCTTATTTTTTAAATTATTTTGGGAAATTTT
CCCAATCCCTTTTTCTAACTCAAAAAATATAATCACTCAAAATTTAAAAG
GGCGCACTTATACATCATTTTAAAAAATTGATGTAACGTGCTAAGTTCAA
AACAAAGGGCGCACTTATACACGATTTTCAATCTTGTATATTTCTAACGA
AAAGCGTGCGCCAAAAAACCCCCTTCGTCAATTTTGACAGGGGGCTTTTT
GATGTAAAAATTTCTATCGAAATTTAAAAATTCGCTTCACTCATGTTATA
AAGACTTAAAATAAAATAACTCTTTAAAATCTTTTGCTAGTTGTTCTTCA
ATATTTTTTATTCGGTGCATCTTCCAAGTAAAGTATAACACACTAGACTT
ATTTACTACGTTTCATAAGTCATTAATGCGTGTGCTCTGCGAGGCTAGTT
TTTGTGCAAGCACAAAAAATGGACTGAATAAATCAGTCCATAAGTTCAAA
ACCAAATTCAAAATCAAAACCACAAGCAACCAAAAAATGTGGTTGTTATA
CGTTCATAAATTTTATGATCACTTACGTGTATAAAATTAAATTCACTTTC
AAAATCTAAAAACTAAATCCAATCATCTACCCTATGAATTATATCTTGAA
ATTCATTCATAAATAGTGAAGCATGGTAACCATCACATACAGAATGATGA
AGTTGCAGAGCAACTGGTATATAAATTTTATTATTCTCACTATAAAATTT
ACCTATCGTAATAATAGGCAATAAAAAGCTGCTATTGTTACCAATATTTA
AATTAAATGAACTAAAATCAATCCAAGGAATCATTGAAATCGGTATGGTG
TTTTCAGGTATCGGTTTTTTAGGAAACATTTCTTCTTTATCTTTATATTC AAGCAAGTCATTTTTATAATTATTATAAAAAGAAATGAAGTTTTTATCAG
ATTCAGTCCAAATGTTAGTAAATTTTTCAGTTTGCTTATTAAAAACTGTA
TACAAAGGATTTAACTTATCCCAATAACCTAATTTATTCTCACTATTAAT
TCCTGTTCTAAACACTTTATTTTTATTTACAACTTCCATAATTGCATAAA
TTAAAGAGGGATAAATTTCATATCCTTTCTTTTTTATCATATCTTTAAAC
AAAGTAATATCAATTTCTTTAGTAATGCTATAAGTAGTTTGCTGATTAAA
ATAGTGTTCAAAATATTCTTTTCTATCCCAATTTTCTAATTCAATAATAT
TAAAAGTCATATATAACTTCCTCCTAAATTTTAAATTTTTATATTTAGGA
GGAATAATCCTCTGATTTTTTCATACGTTATGTCACCTCGTAAATATTAA
TTATACTGAATTAGCAATTTTTATCAAATAAAACTTATTTTACTTCCAAA
ACCTAAATTCACGTTGCCAAAAATCAATCTGCTTTTGCAATTGTTTTTCG
TTCGCTTTTAAAGTCGATTTCATTAATTCCGTTAAATCAATTGGAGATAT
TTCTCTAATCAATTTTTTAAATTTAGTCTTAGTATTCTTACTTAGCTTTC
CCCACATACTTTCTTCATGCAACAAAGTATAAACCATAGCTTGCTCATTA
ATTTTTTCTAAAGTAGCCCACGCAGGTTTCAAGATGTGTAAATCATTAAA
ACAATCATTCCAGTAATCAACCATATCTCTTTTTAATTCAACTTCTACAC
GCCATAAATGTTCAGACACAACTTCAACATCTGCGTTATCTTTACGTTCT
TGTTTTTTATTATAAATTCTAATAAATCTATCACTATCACGGACACCAAA
ATATTTTGTTTCTGGCTTGCCATTACGACCATAAAAAACAGTTTTCTTAA
CTGCTTTATCAGTCATTGCATAGTAATCGCTCAAATCATCTTCAAAATCA
AAAGCTAAGTCTAATCTTGTAAAACCGTCATCTTCCATGTAGTCGATAAT
ATTTTGTTTTAACCAAATCATTTCTTCATGTGTGAGTTTATTGGGATTAA
ATTCAACACGCATATTACGTCTATCCCAAGTATCTGCTTTTACTTTGTCA
TATTCGATATAAACTTTTTCTTGAAGTGCCTTAGCTTTAAACTTTGTTTG
AAGTATATCCCAAAGTCGTATTTGTGGCTCTACACTCATAAAGTCAGATA
GCTTTTTAGCATTAGTTTTGTTCAAATTTCCAACGATTGTCATGGCATCA
AAACTTAATGCGGGTTGAGATTTTCCCAAAGTTTGACCACTTAACCGGCT
ATTACTTAACCGGCTATTAGAGACGGAACTAACTCAACGCTAGTAGTGGA
TTTAATCCCAAATGAGCCAACAGAACCAGAACCAGAAACAGAACAAGTAA
CATTGGAGTTAGAAATGGAAGAAGAAAAAAGCAATGATTTCGTGTGAATA
ATGCACGAAATCATTGCTTATTTTTTTAAAAAGCGATATACTAGATATAA
CGAAACAACGAACTGAATAAAGAATACAAAAAAAGAGCCACGACCAGTTA
AAGCCTGAGAAACTTTAACTGCGAGCCTTAATTGATTACCACCAATCAAT
TAAAGAAGTCGAGACCCAAAATTTGGTAAAGTATTTAATTACTTTATTAA
TCAGATACTTAAATATCTGTAAACCCATTATATCGGGTTTTTGAGGGGAT
TTCAAGTCTTTAAGAAGATACCAGGCAATCAATTAAGAAAAACTTAGTTG
ATTGCCTTTTTTGTTGTGATTCAACTTTGATCGTAGCTTCTAACTAATTA
ATTTTCGTAAGAAAGGAGAACAGCTGAATGAATATCCCTTTTGTTGTAGA
AACTGTGCTTCATGACGGCTTGTTAAAGTACAAATTTAAAAATAGTAAAA
TTCGCTCAATCACTACCAAGCCAGGTAAAGTAAAGGGGCTATTTTTGCG -continued

```
TATCGCTCAAAAAAAAGCATGATTGGCGGACGTGGCGTTGTTCTGACTTC
CGAAGAAGCGATTCACGAAAATCAAGATACATTTACGCATTGGACACCAA
ACGTTTATCGTTATGGTACGTATGCAGACGAAAACCGTTCATACACTAAA
GGACATTCTGAAAACAATTTAAGACAAATCAATACCTTCTTTATTGATTT
TGATATTCACACGGAAAAAGAAACTATTTCAGCAAGCGATATTTTAACAA
CAGCTATTGATTTAGGTTTTATGCCTACGTTAATTATCAAATCTGATAAA
GGTTATCAAGCATATTTTGTTTTAGAAACGCCAGTCTATGTGACTTCAAA
ATCAGAATTTAAATCTGTCAAAGCAGCCAAAATAATCTCGCAAAATATCC
GAGAATATTTTGGAAAGTCTTTGCCAGTTGATCTAACGTGCAATCATTTT
GGGATTGCTCGTATACCAAGAACGGACAATGTAGAATTTTTTGATCCCAA
TTACCGTTATTCTTTCAAAGAATGGCAAGATTGGTCTTTCAAACAAACAG
ATAATAAGGGCTTTACTCGTTCAAGTCTAACGGTTTTAAGCGGTACAGAA
GGCAAAAAACAAGTAGATGAACCCTGGTTTAATCTCTTATTGCACGAAAC
GAAATTTTCAGGAGAAAAGGGTTTAGTAGGGCGCAATAGCGTTATGTTTA
CCCTCTCTTTAGCCTACTTTAGTTCAGGCTATTCAATCGAAACGTGCGAA
TATAATATGTTTGAGTTTAATAATCGATTAGATCAACCCTTAGAAGAAAA
AGAAGTAATCAAAATTGTTAGAAGTGCCTATTCAGAAAACTATCAAGGGG
CTAATAGGGAATACATTACCATTCTTTGCAAAGCTTGGGTATCAAGTGAT
TTAACCAGTAAAGATTTATTTGTCCGTCAAGGGTGGTTTAAATTCAAGAA
AAAAAGAAGCGAACGTCAACGTGTTCATTTGTCAGAATGGAAAGAAGATT
TAATGGCTTATATTAGCGAAAAAAGCGATGTATACAAGCCTTATTTAGCG
ACGACCAAAAAAGAGATTAGAGAAGTGCTAGGCATTCCTGAACGGACATT
AGATAAATTGCTGAAGGTACTGAAGGCGAATCAGGAAATTTTCTTTAAGA
TTAAACCAGGAAGAAATGGTGGCATTCAACTTGCTAGTGTTAAATCATTG
TTGCTATCGATCATTAAATTAAAAAAAGAAGAACGAGAAAGCTATATAAA
GGCGCTGACAGCTTCGTTTAATTTAGAACGTACATTTATTCAAGAAACTC
TAAACAAATTGGCAGAACGCCCCAAAACGGACCCACAACTCGATTTGTTT
AGCTACGATACAGGCTGAAAATAAAACCCGCACTATGCCATTACATTTAT
ATCTATGATACGTGTTTGTTTTTCTTTGCTGTTTAGTGAATGATTAGCAG
AAATATACAGAGTAAGATTTTAATTAATTATTAGGGGGAGAAGGAGAGAG
TAGCCCGAAAACTTTTAGTTGGCTTGGACTGAACGAAGTGAGGGAAAGGC
TACTAAAACGTCGAGGGGCAGTGAGAGCGAAGCGAACACTTGATCTTTTA
AGTTGCTATCATTTATAGGTCAATAGAGTATACCTATTTGTCCTAATATG
ATTTTAGCAGTATAATTGACTTGGTGAATAGGTCATTTAAGTTGGGCATA
ATAGGAGGAGTAAAATGAAAAAATTTATTTATCGAGTTTTAGAAAATGAC
GAAGTGGTGGCTATTTTTAATGAGCAACAATATGCGCAAGATTTTATCGC
TTACGAAAAGACAATTTCTGATAAGCAATTTGAAATTGAAAAAGTAGATA
TTGCTGATTGGTTATTGCAACCGAGAGAATTTTAGAGGTTGGTTGAAAAT
GGCTAAAATTGGTTATGCACGTGTCAGTAGCAAAGAACAGAACTTAGATC
GGCAATTACAAGCGTTACAGGGCGTTTCTAAGGTCTTTTCAGACAAATTA
AGCGGTCAATCGGTCGAACGCCCACAATTACAAGCTATGCTTAACTATAT
TCGTGAAGGGGATATTGTTATTGTTACTGAATTAGATCGATTAGGACGAA
ATAATAAAGAATTAACAGAATTGATGAATCAAATTCAAATTAAGGGGGCA
ACCCTGGAAGTCTTAAATTTACCCTCAATGAATGGTATTGAAGATGAAAA
TTTAAGGCGTTTGATTAATAGCCTTGTCATTGAATTGTACAAGTATCAAG
CAGAATCAGAACGAAAAAAAATTAAGGAACGTCAGGCACAAGGAATCGAA
ATTGCTAAGAAAAAAGGCAAATTCAAAGGTCGTCAGCATAAATTTAAAGA
AAATGATCCACGTTTAAAGTCGGGCAGCGTTGGGTCCTGGCCACGGGTGC
GCATGATCGTGCTCCTGTCGTTGAGGACCCGGCTAGGCTGGCGGGGTTGC
CTTACTGGTTAGCAGAATGAATCACCGATACGCGAGCGAACGTGAAGCGA
CTGCTGCTGCAAAACGTCTGCGACCTGAGCAACAACATGAATGGTCTTCG
GTTTCCGTGTTTCGTAAAGTCTGGAAACGCGGAAGTCCCCTACGTGCTGC
TGAAGTTGCCCGCAACAGAGAGTGGAACCAACCGGTGATACCACGATACT
ATGACTGAGAGTCAACGCCATGAGCGGCCTCATTTCTTATTCTGAGTTAC
AACAGTCCGCACCGCTGCCGGTAGCTCCTTCCGGTGGGCGCGGGGCATGA
CTATCGTCGCCGCACTTATGACTGTCTTCTTTATCATGCAACTCGTAGGA
CAGGTGCCGGCAGCGCCCAACAGTCCCCCGGCCACGGGGCCTGCCACCAT
ACCCACGCCGAAACAAGCGCCCTGCACCATTATGTTCCGGATCTGCATCG
CAGGATGCTGCTGGCTACCCTGTGGAACACCTACATCTGTATTAACGAAG
CGCTAACCGTTTTTATCAGGCTCTGGGAGGCAGAATAAATGATCATATCG
TCAATTATTACCTCCACGGGGAGAGCCTGAGCAAACTGGCCTCAGGCATT
TGAGAAGCACACGGTCACACTGCTTCCGGTAGTCAATAAACCGGTAAACC
AGCAATAGACATAAGCGGCTATTTAACGACCCTGCCCTGAACCGACGACC
GGGTCGAATTTGCTTTCGAATTTCTGCCATTCATCCGCTTATTATCACTT
ATTCAGGCGTAGCAACCAGGCGTTTAAGGGCACCAATAACTGCCTTAAAA
AAATTACGCCCCGCCCTGCCACTCATCGCAGTACTGTTGTAATTCATTAA
GCATTCTGCCGACATGGAAGCCATCACAAACGGCATGATGAACCTGAATC
GCCAGCGGCATCAGCACCTTGTCGCCTTGCGTATAATATTTGCCCATGGT
GAAAACGGGGGCGAAGAAGTTGTCCATATTGGCCACGTTTAAATCAAAAC
TGGTGAAACTCACCCAGGGATTGGCTGAGACGAAAAACATATTCTCAATA
AACCCTTTAGGGAAATAGGCCAGGTTTTCACCGTAACACGCCACATCTTG
CGAATATATGTGTAGAAACTGCCGGAAATCGTCGTGGTATTCACTCCAGA
GCGATGAAAACGTTTCAGTTTGCTCATGGAAAACGGTGTAACAAGGGTGA
ACACTATCCCATATCACCAGCTCACCGTCTTTCATTGCCATACGG.
```

The sequence matches exactly the predicted sequence of the PSA cloned into pGG55. LLO-PSA open reading frame is underlined; lower case letters indicate the sequence of PSA alone.

Example 8

*Listeria*-LLO-PSA Constructs Elicit Antigen-Specific Cytotoxic T Lymphocytes

Materials and Experimental Methods

CTL assays

Male C57BL/6 mice were immunized i.p. with either 0.1 LD50 of Lm-PSA or 0.1 LD50 of Lm-HPV16E7E6TM and boosted 1 time after 2 weeks. Spleens were harvested 6 days after the boost. Isolated splenocytes were prepared and stimulated for 5 days with mitomycin-treated, PSA-vaccinia infected, MC57G cells as feeders. In the first experiment, a CTL assay was performed using PSA H2Db peptide (1 μM, HCIRNKSVIL; SEQ ID No: 60)-pulsed EL4 cells as targets labeled with 100 μM of europium (Sigma), using the following E:T ratios: 25:1, 8:1, 2.8:1, 0.9:1, 0.3:1, 0.1:1 and 0.03:1. After 4 hour incubation of mixed targets and effectors, cells were separated from the culture supernatant by centrifugation. Released europium from lysed cells in the supernatant was determined as follows: 10 μl of the supernatant was added to 100 μl Europium enhancement solution (Delfia). Absorbance was read at 590 nm using Victor II spectrophotometer (Perkin Elmer). Maximum release of Europium was determined from the supernatant of labeled target cells with 1% triton X-100 and the spontaneous release was determined from the target cells incubated in the absence of effector cells. In the second experiment, E:T ratio was kept constant at 25:1, and the peptide concentrations was varied as indicated. Percent specific lysis was determined as [(experimental release−spontaneous release)/(maximum release−spontaneous release)]×100.

Cytokine secretion assays

Male C57BL/6 mice were immunized with either Lm-PSA or *Listeria* expressing different fragments of Wilm's tumor antigen (negative control) or left un-immunized. Mice were boosted 1 time after two weeks and the spleens were harvested 6 days after the boost. Isolated splenocytes were prepared and stimulated in vitro overnight in the presence of 1 μM PSA H2Db peptide. IFN-γ secretion by isolated splenocytes was determined by ELISpot assay.

Results

To test the immunogenicity of LLO-PSA, 6-8 weeks old C57BL/6 mice (Jackson laboratories) were immunized i.p. with either Lm-PSA (0.1 $LD_{50}$, $1\times10^7$ CFU/dose) or Lm-HPV16E7E6TM (negative control, 0.1 $LD_{50}$, $1\times10^6$ CFU/dose) or left un-immunized. Splenocytes from vaccinated mice were tested for ability to recognize and lyse PSA peptide presenting cells in vitro in a CTL assay. Splenocytes from the immunized mice were able to recognize and lyse PSA-peptide pulsed tumor cells with high efficiency (FIG. 15A). Further, the response was dose-dependent with regard to the amount of antigen presented by the target cells (FIG. 15B).

In additional assays, mice were immunized with Lm-PSA or strains expressing fragments of Wilm's tumor antigen (negative control), and cytokine secretion was determined, in response to incubation with the PSA peptide. Splenocytes from the vaccinated mice exhibited high levels of IFN-γ secretion (FIG. 16).

Thus, PSA-expressing LM strains and LLO-PSA fusions are efficacious in the induction of antigen-specific CTL that are capable of target cell lysis and IFN-γ secretion. Accordingly, PSA-expressing LM strains and LLO-PSA fusions are efficacious in therapeutic and prophylactic vaccination against PSA-expressing prostate cancer.

Example 9

*Listeria*-LLO-PSA Constructs Provide Tumor Protection

Materials and Experimental Methods

Cell Culture, Materials, and Reagents

TRAMP-C1 mouse prostate adenocarcinoma cells derived from a C57BL/6 mouse prostate tumor was purchased from ATCC. This cell line is negative for PSA expression. Cells were maintained in Dulbecco's modified Eagle's medium with 4 mM L-glutamine adjusted to contain 1.5 g/L sodium bicarbonate and 4.5 g/L glucose supplemented with 0.005 mg/ml bovine insulin and 10 nM dehydroisoandrosterone, 90%; fetal bovine serum, 5%; Nu-Serum IV, 5%. The gene encoding the full-length human PSA protein, including its signal sequence, was subcloned into a pUV6/v5 plasmid (Invitrogen). After confirmation of the correct sequence, the plasmid was linearized and transfected into TRAMP-C1 cells using Lipofectamine 2000 ™ (Invitrogen). Positive clones were selected in the presence of 10 μg/ml blasticidin. Several stably expressing PSA clones were isolated and tested for the secretion of human PSA into the cell culture medium.

Subcutaneous tumor inoculation

Two different clones of PSA-expressing TRAMP-C1 cells were resuspended at $5\times10^6$ cells per 200 mcl dose. Male C57BL/6 mice (8 per group, 6-8 weeks old) were inoculated s.c. in the left flank.

Tumor regression studies 7 days after tumor inoculation, mice are immunized with either 0.1 $LD_{50}$ of Lm-PSA ($10^7$ CFU), 0.1 $LD_{50}$ of Lm-HPV16E7, or PBS. Two boosts are administered on days 15 and 25 post-tumor inoculation. Tumors are monitored for 90 days. Tumor size is defined as the mean of two perpendicular diameters.

Orthotopic Injection of Prostate Tumor Cells

Six-week-old male C57BL/6 mice are anesthetized with 2% isoflurane. In a sterile field, a lower midline incision is made to access the prostate. The left lobe of the dorsal prostate is injected with $1\times10^5$ TRAMPC-1/PSA tumor cells from a single-cell suspension in PBS, using a 27-gauge needle fitted on a 50-μl Hamilton syringe. Mice are sutured, and sutures are removed 10 days after surgery. Seven days later, mice are immunized i.v. with Lm-PSA, LmHPV16E7 or PBS. Mice are sacrificed at different time points, prostates are removed surgically and weighed for determination of the tumor growth.

Tumor protection studies

C57BL/6 mice are immunized and boosted with Lm-PSA, LmHPV16E7, or PBS, as described in the previous Example. Seven days after the boost, mice are injected s.c. with $5\times10^6$ TRAMPC-1/PSA tumor cells. Growth of the tumors is monitored by measuring with a caliper for 90 days.

Inhibition of prostate cancer metastases

For orthotopic tumor inoculation, 8-10 week old C57BL/6 male mice (Jackson labs) are anesthetized with isoflurane. A low abdominal skin incision cranial to the prepucial glands is made, and the seminal vesicles are carefully exteriorized to expose the dorso-lateral prostate. Using a 29 gauge insulin syringe, $5\times10^5$ TRAMPC-1/PSA cells suspended in PBS are injected into the dorso-lateral prostate in a 20 μL volume.

The seminal vesicles and prostate are held for one minute to allow the injected cells to settle into the gland and then gently replaced into the abdominal cavity. Body wall and skin wounds closed are closed with 5-0 PDS and 5-0 nylon, respectively.

Tumors are allowed to develop for 50 days. The primary tumor is removed during necropsy and fixed in formalin, and then paraffin embedded, sectioned and stained with H&E. Enlarged lymph nodes from the paralumbar region are visualized under surgical microscopy and then dissected out, fixed, embedded, and histologically analyzed for prostate cancer cells.

Tissue immunostaining

Formalin-fixed prostate tumor tissues are paraffin embedded, sectioned, applied to Plus Slides™ (VWR Corp), and then stained using a Dako autostainer system. Slides are pre-treated with 3.0% hydrogen peroxide for 10 minutes, then rinsed and treated with a 10 μg/mL solution of proteinase K solution for 3 minutes to enhance antigen retrieval. Non-specific binding sites are blocked by addition of normal goat serum for 30 minutes, and then a 10 μg/mL solution of rabbit anti-human PSA antibody (Sigma) or rabbit anti-human Proliferating Cell Nuclear Antigen (AB15497, AbCam antibodies) is applied to the tissue for 30 minutes. Primary antibody is removed by washing, and appropriate horseradish peroxidase-labeled secondary antibody is applied for a 30-minute period and detected using NovaRed™ substrate (Vector Labs, Burlingame, Calif.) in an 8-minute incubation. Slides are counter-stained with hematoxylin before drying.

Cells from slides of primary and lymph node sections are scored as either positive or negative for human PSA. Four regions of each slide were randomly selected, and 20 cells from each region are scored. PSA staining in tumors is compared to lymph node metastases from the same mouse.

*Listeria* strains

*Listeria* vaccines are prepared and stored as described in the previous Example.

Results

*Listeria* vaccines described in the previous Example are used in tumor protection experiments in an orthotopic prostate carcinoma animal model. Mice are immunized with either Lm-PSA, LmHPV16E7, or PBS, then injected with TRAMPC-1 Lm-PSA protects mice from tumor formation.

In additional experiments, mice are first injected with TRAMPC-1/PSAprostate cancer cells, vaccinated with Lm-PSA, LmHPV16E7, or PBS 4 days later, and boosted with the same vaccine. Lm-PSA impedes growth of prostate metastases.

Thus, PSA-producing LM strains and LLO-PSA fusions induce tumor protection.

Example 10

*Listeria*-LLO-Folate Hydrolase 1 (FOLH1) Constructs Elicit Antigen-Specific Cytotoxic T Lymphocytes Materials and Experimental Methods Growth and storage of bacterial vaccine strains Recombinant *Listeria*-LLO-FOLH1 is grown and maintained as described for *Listeria*-PSA in Example 7 above.

Results

A gene encoding a truncated FOLH1, which contains the complete open reading frame of FOLH1, except for its secretion signal sequence, is fused to a gene encoding a truncated non-hemolytic fragment of Listeriolysin 0, in a similar manner to that described for KLK3 in Example 7 above. The gene is cloned into *Listeria* plasmid pGG55 and electroporated into LM XFL-7. LLO-FOLH1 protein is thus expressed and secreted episomally from this recombinant *Listeria* strain.

To test the immunogenicity of LLO-FOLH1, mice re immunized with either Lm-LLO-FOLH1 or LmWT1A (irrelevant antigen control) or PBS (negative control), as described for LLO-KLK3 in Example 7 above. Following culture with vaccinia-PSA infected stimulator cells with for 5 days, splenocytes from the vaccinated mice are able to recognize and lyse FOLH1-peptide pulsed tumor cells with high efficiency in a CTL assay. In addition, the splenocytes exhibit high levels of IFN-γ secretion, in response to incubation with the FOLH1 peptide.

Thus, FOLH1-expressing LM strains and LLO-FOLH1 fusions are efficacious in the induction of antigen-specific CTL that are capable of target cell lysis and IFN-γ secretion. Accordingly, FOLH1-expressing LM strains and LLO-FOLH1 fusions are efficacious in therapeutic and prophylactic vaccination against PSA-expressing prostate cancer.

Example 11

*Listeria*-LLO-FOLH1 Constructs Provide Tumor Protection

*Listeria* vaccines described in the previous Example are used in tumor protection experiments in the orthotopic prostate carcinoma animal model described in Example 9 above. Mice are immunized with either Lm-FOLH1, LmWT1A, or PBS, then injected with PC3M-LN4 or 22Rv1 cells. Lm-FOLH1 protects mice from tumor formation.

In additional experiments, mice are first injected with PC-3M prostate cancer cells, as described for Example 9 above, vaccinated with Lm-FOLH1, LmWT1A, or PBS 4 days later, and boosted with the same vaccine. Lm-FOLH1 impedes growth of prostate metastases.

Thus, FOLH1-producing LM strains and Lm-FOLH1 fusions induce tumor protection.

What is claimed:

1. A method of inducing an anti-KLK3 immune response in a subject, comprising administering to said subject a composition comprising a recombinant *Listeria* strain encoding a recombinant fusion peptide consisting of a KLK3 peptide operatively linked to a non-KLK3 peptide, wherein said non-KLK3 peptide is a N-terminal non-hemolytic listeriolysin (LLO) peptide, said fusion peptide consisting of the sequence of SEQ ID NO: 54 or a sequence at least 99% homologous (throughout the length of the peptide) thereto, wherein said N-terminal LLO peptide enhances the immunogenicity of the fusion peptide, thereby inducing an anti-KLK3 immune response in a subject.

2. The method of claim 1, wherein said recombinant *Listeria* strain is an auxotrophic *Listeria*.

3. The method of claim 2, wherein said auxotrophic *Listeria* strain is a dal/dat mutant.

4. The method of claim 2, wherein said auxotrophic *Listeria* further comprises a deletion in the endogenous ActA gene.

5. The method of claim 2, wherein said auxotrophic *Listeria* strain further comprises a deletion in the endogenous ActA gene and is a dal/dat mutant.

6. The method of claim 2, wherein said auxotrophic *Listeria* strain comprises an episomal expression vector comprising a metabolic enzyme that complements the auxotrophy of said auxotrophic *Listeria* strain.

7. The method of claim 6 wherein said metabolic enzyme is an alanine racemase enzyme.

8. The method of claim 6, wherein said metabolic enzyme is a D-amino acid transferase enzyme.

9. The method of claim 1, wherein said recombinant *Listeria* is a recombinant *Listeria monocytogenes* strain.

10. A method of treating a kallikrein-related peptidase 3 (KLK3)-expressing prostate cancer in a subject, the method comprising the step of administering to said subject a composition comprising a recombinant *Listeria* strain encoding a recombinant fusion peptide consisting of a KLK3 peptide operatively linked to a non-KLK3 peptide, wherein said non-KLK3 peptide is a N-terminal non-hemolytic listeriolysin (LLO) peptide, said fusion peptide consisting of the sequence of SEQ ID NO: 54 or a sequence at least 99% homologous (throughout the length of the peptide) thereto, wherein said N-terminal LLO peptide enhances the immunogenicity of the fusion peptide, whereby said subject mounts an immune response against said KLK3 protein-expressing prostate cancer, thereby treating a KLK3 protein-expressing prostate cancer in a subject.

11. The method of claim 10, wherein said recombinant *Listeria* strain is an auxotrophic *Listeria*.

12. The method of claim 11, wherein said auxotrophic *Listeria* strain is a dal/dat mutant.

13. The method of claim 11, wherein said auxotrophic *Listeria* further comprises a deletion in the endogenous ActA gene.

14. The method of claim 11, wherein said auxotrophic *Listeria* strain further comprises a deletion in the endogenous ActA gene and is a dal/dat mutant.

15. The method of claim 11, wherein said auxotrophic *Listeria* strain comprises an episomal expression vector comprising a metabolic enzyme that complements the auxotrophy of said auxotrophic *Listeria* strain.

16. The method of claim 15 wherein said metabolic enzyme is an alanine racemase enzyme.

17. The method of claim 15, wherein said metabolic enzyme is a D-amino acid transferase enzyme.

18. The method of claim 10, wherein said recombinant *Listeria* is a recombinant *Listeria monocytogenes* strain.

19. A method of protecting a human subject against a kallikrein-related peptidase 3 (KLK3) protein-expressing prostate cancer, the method comprising the step of administering to said human subject a composition comprising a recombinant *Listeria* strain encoding a recombinant fusion peptide consisting of a KLK3 peptide operatively linked to a non-KLK3 peptide, wherein said non-KLK3 peptide is a N-terminal non-hemolytic listeriolysin (LLO) peptide, said fusion peptide consisting of the sequence of SEQ ID NO: 54 or a sequence at least 99% homologous (throughout the length of the peptide) thereto, wherein said N-terminal LLO peptide enhances the immunogenicity of the fusion peptide, whereby said subject mounts an immune response against said KLK3protein, thereby protecting a human subject against a KLK3 protein-expressing prostate cancer.

20. The method of claim 19, wherein said recombinant *Listeria* strain is an auxotrophic *Listeria.*

21. The method of claim 20, wherein said auxotrophic *Listeria* strain is a dal/dat mutant.

22. The method of claim 20, wherein said auxotrophic *Listeria* further comprises a deletion in the endogenous ActA gene.

23. The method of claim 20, wherein said auxotrophic *Listeria* strain further comprises a deletion in the endogenous ActA gene and is a dal/dat mutant.

24. The method of claim 20, wherein said auxotrophic *Listeria* strain comprises an episomal expression vector comprising a metabolic enzyme that complements the auxotrophy of said auxotrophic *Listeria* strain.

25. The method of claim 24 wherein said metabolic enzyme is an alanine racemase enzyme.

26. The method of claim 24, wherein said metabolic enzyme is a D-amino acid transferase enzyme.

27. The method of claim 19, wherein said recombinant *Listeria* is a recombinant *Listeria monocytogenes* strain.

28. A recombinant fusion peptide comprising a KLK3 peptide operatively linked to a non-KLK3 peptide, wherein said non-KLK3 peptide is a N-terminal non-hemolytic listeriolysin (LLO) peptide, said fusion peptide consisting of the sequence of SEQ ID NO: 54 or a sequence at least 99% homologous (throughout the length of the peptide) thereto.

29. The recombinant fusion peptide of claim 28, wherein said KLK3peptide does not contain a KLK3 signal sequence.

30. A vaccine comprising the composition of claim 28 and an adjuvant.

31. The vaccine of claim 30, wherein said adjuvant comprises Montanide ISA 51, GM-CSF, KLH, a cytokine, a growth factor, a cell population, QS21, Freund's incomplete adjuvant, aluminum phosphate, aluminum hydroxide, BCG, alum, an interleukin, an unmethylated CpG oligonucleotide, quill glycosides, monophosphoryl lipid A, a liposomes, a bacterial mitogen, a bacterial toxin, or a chemokine, or any combination thereof.

* * * * *